US006323244B1

(12) United States Patent
Chen et al.

(10) Patent No.: US 6,323,244 B1

(45) **Date of Patent: *Nov. 27, 2001**

(54) METHODS AND COMPOSITIONS FOR THE DIAGNOSIS AND TREATMENT OF NEUROPSYCHIATRIC DISORDERS

(75) Inventors: Hong Chen, Brookline, MA (US); Nelson B. Freimer, San Francisco, CA (US)

(73) Assignees: Millennium Pharmaceuticals, Inc., Cambridge, MA (US); The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/965,048

(22) Filed: Nov. 5, 1997

(51) Int. Cl.[7] .......................... A01N 25/00; A61K 47/00; C12N 9/10

(52) U.S. Cl. ................................ 514/789; 435/6; 435/7.1; 435/15; 435/193; 435/69.2

(58) Field of Search ................................ 435/7.1, 6, 193, 435/15, 69.2; 514/789

(56) References Cited

PUBLICATIONS

GenBank Accession No. D63813.

M. Baron, "Genetic Linkage and Bipolar Affective Disorder: Progress and Pitfalls," Molecular Psychiatry, 2, 200–210 (1997).

H. Ewald et al., "Susceptibility Loci for Bipolar Affective Disorder on Chromosome 18? A Review and Study of Danish Families," Psychiatric Genetics, 7, 1–12 (1997).

D.F. MacKinnon et al., "Genetics of Manic Depressive Illness", Annu. Rev. Neurosci., 20, 355–373 (1997).

A. Shimizu–Matsumoto et al., Isolation and Chromosomal Localization of the Human Conge cGMP Phosphodiesterase Gamma cDNA (PDE6H), Genomics, 121–124 (1996).

A. Shimizu–Matsumoto, et al., "An Expression Profile of Genes in Human Retina and Isolation of a Company DNA for a Novel Rod Photoreceptor Protein", Investigative Opthamology & Visual Sci, 38:2576–2585 (1997).

D18S1140 Chromosomal MNW (Database ID:AFM287WE1).

D18S59 Chromosomal MNW (Database ID: AFM178XC3).a.

Dolnick, B. Proteins encoded by antisense strand gene (rTS) of thymidylate synthase interact with thymidylate synthase and dihydrofolate reductase. Proceedings of the American Association for Cancer Research Annual Meeting 37(0): 652–653, Mar. 1996.*

Dolnick et al.rTS Gene Expression is Associated With Altered Cell Sensitivity to Thymidylate Synthase Inhibitors. Advances in Enzyme Regulation 36: 165–80, Aug. 23, 1996.*

Altschul, 1990, "Basic Local Alignment Search Tool", J. Mol. Biol. 215:403–410.

Baron et al., 1993 "Diminished Support for Linkage between Manic Depressive Illness and X–Chromosome Markers in Three Israeli Pedigrees", Nature Genet. 3:49–55.

Baron et al., 1987, "Genetic Linkage between X–Chromosome Markers and Bipolar Affective Illness", Nature 326:289–292.

Berrettini et al., 1994, "Chromosome 18 DNA Markers and Manic Depressive Illness: Evidence for a Susceptibility Gene", Proc. Natl. Acad. Sci. USA 91:5918–5921.

Bertelson et al., 1977, "A Danish Twin Study of Manic–Depressive Disorders", Br. J. Psychiat. 130:330–351.

Black and Dolnick, 1996, "Expression of rTS Correlates with Altered Growth Regulation of Thymidylate Synthase", Cancer Res. 56:700–705.

Dolnick and Black, 1996, "Alternate Splicing of the rTS Gene Product and Its Overexpression in a 5–Fluorouracil––Resistant Cell Line", Cancer Res. 56:3207–3210.

Dolnick et al., 1993, "Cloning and Characterization of a Naturally Occurring Antisense RNA to Human Thymidylate Synthase mRNA", Nucl. Acids Res.21:1747–1752.

Egeland et al., 1987, "Bipolar Affective Disorders Linked to DNA Markers on Chromosome 11", Nature 325:783–787.

Freimer et al., 1996, "An Approach to Investigating Linkage for Bipolar Disorder Using Large Costa Rican Pedigrees", Neuropsychiatric Genetics 67:254–263.

Freimer et al., 1996, "Genetic Mapping Using Haplotype, Association and Linkage Methods Suggests a Locus for Severe Bipolar Disorder (BPI) at 18q22–q23", Nature Genetics 12:436–441.

Freimer and Reus, 1992, "The Genetics of Bipolar Disorder and Schizophrenia", in: *The Molecular and Genetic Basis of Neurological Disease*, Rosenberg et al., eds., Butterworths, NY, pp. 951–965.

Kelsoe et al., 1989, "Re–Evaluation of the Linkage relationship between Chromosome 11p Loci and the Gene for Bipolar Affective Disorder in the Old Amish", Nature 342:238–243.

(List continued on next page.)

*Primary Examiner*—Rebecca E. Prouty
*Assistant Examiner*—Richard Hutson

(57) ABSTRACT

The present invention relates to the mammalian rTS gene, a gene associated with bipolar affective disorder (BAD) in humans. The invention relates to methods for the identification of compounds that modulate the expression of rTS and to using such compounds as therapeutic agents in the treatment of rTS disorders and neuropsychiatric disorders. The invention also relates to methods for the diagnostic evaluation, genetic testing and prognosis of rTS neuropsychiatric disorders including schizophrenia, attention deficit disorder, a schizoaffective disorder, a bipolar affective disorder or a unipolar affective disorder, and to methods and compositions for the treatment these disorders.

4 Claims, 43 Drawing Sheets

OTHER PUBLICATIONS

Levinson and Levitt, 1987, "Schizoaffective Mania Reconsidered", Am. J. Psychiatry 144:415–426.

Maier et al., 1995, "Linkage Analysis between Pericentromeric Markers on Chromosome 18 and Bipolar Disorder: A Replication Test", Psychiatry Res. 59:7–15.

McInnes and Freimer, 1995, "Mapping Genes for Psychiatric Disorders and Behavioral Traits", Curr. Opin. Genet. Devel. 5:376–381.

Murray et al., 1994, "A Comprehensive Human Linkage Map with Centimorgan Density", Science 265:2049–2054.

Pauls et al., 1995, "Linkage Analyses of Chromosome 18 Markers Do Not Identify a Major Susceptibility Locus for Bipolar Affective Disorder in the Old Order Amish", Am. J. Hum. Genet. 57:636–643.

Pauls et al., 1992, "Risks of Affective Illness Among First-Degree Relatives of Bipolar 1 Old–Order Amish Probands", Arch. Gen. Psychiatry 49:703–708.

Rosenthal et al., 1980, "Toward the Validation of RDC Schizoaffective Disorder", Arch. Gen. Psychiatry 37:804–810.

Ruther and Muller–Hill, 1983, "Easy Identification of cDNA Clones", EMBO J. 2:1791–1794.

Straub et al., 1994, "A Possible Vulnerability Locus for Bipolar Affective Disorder on Chromosome 21q22.3", Nature Genetics 8:291–296.

* cited by examiner-

```
gccacggcgc ggacgccatg cacacggacc ctgactactc ggctgcctat gtcgtcatag 60
aaactg atg cag aag atg gaa tca agg ggt gtg gaa tta cct tca ctc   108
       Met Gln Lys Met Glu Ser Arg Gly Val Glu Leu Pro Ser Leu
         1               5                  10
tgg gaa aag gca ctg aag ttg att ggt cca gaa aag ggc gtg gtg cac   156
Trp Glu Lys Ala Leu Lys Leu Ile Gly Pro Glu Lys Gly Val Val His
 15                  20                  25                  30
ctg gcg aca gcg gcc gtc cta aac gcg gtg tgg gac ttg tgg gcc aag   204
Leu Ala Thr Ala Ala Val Leu Asn Ala Val Trp Asp Leu Trp Ala Lys
                 35                  40                  45
cag gag gga aag cct gtc tgg aag tta ctt gtg gac atg gat ccc agg   252
Gln Glu Gly Lys Pro Val Trp Lys Leu Leu Val Asp Met Asp Pro Arg
             50                  55                  60
atg ctg gta tcc tgc ata gat ttc agg tac atc act gat gtc ctg act   300
Met Leu Val Ser Cys Ile Asp Phe Arg Tyr Ile Thr Asp Val Leu Thr
         65                  70                  75
gag gag gat gcc cta gaa ata ctg cag aaa ggt caa att ggt aaa aaa   348
Glu Glu Asp Ala Leu Glu Ile Leu Gln Lys Gly Gln Ile Gly Lys Lys
     80                  85                  90
gaa aga gag aag caa atg ctg gca caa gga tac cct gct tac acg aca   396
Glu Arg Glu Lys Gln Met Leu Ala Gln Gly Tyr Pro Ala Tyr Thr Thr
 95                 100                 105                 110
tcg tgc gcc tgg ctg ggg tac tca gat gac acg ttg aag cag ctc tgt   444
Ser Cys Ala Trp Leu Gly Tyr Ser Asp Asp Thr Leu Lys Gln Leu Cys
                115                 120                 125
gcc cag gcg ctg aag gat ggc tgg acc agg ttt aaa gta aag gtg ggt   492
Ala Gln Ala Leu Lys Asp Gly Trp Thr Arg Phe Lys Val Lys Val Gly
            130                 135                 140
gct gat ctc cag gat gac atg cga aga tgc caa atc atc cga gac atg   540
Ala Asp Leu Gln Asp Asp Met Arg Arg Cys Gln Ile Ile Arg Asp Met
        145                 150                 155
att gga ccg gaa aag act ttg atg atg gat gcc aac cag cgc tgg gat   588
Ile Gly Pro Glu Lys Thr Leu Met Met Asp Ala Asn Gln Arg Trp Asp
    160                 165                 170
gtg cct gag gcg gtg gag tgg atg tcc aag ctg gcc aag ttc aag cca   636
Val Pro Glu Ala Val Glu Trp Met Ser Lys Leu Ala Lys Phe Lys Pro
175                 180                 185                 190
ttg tgg att gag gag cca acc tcc cct gat gac att ctg ggg cac gcc   684
Leu Trp Ile Glu Glu Pro Thr Ser Pro Asp Asp Ile Leu Gly His Ala
                195                 200                 205
acc att tcc aag gca ctg gtc cca tta gga att ggc att gcc aca gga   732
Thr Ile Ser Lys Ala Leu Val Pro Leu Gly Ile Gly Ile Ala Thr Gly
            210                 215                 220
```

FIG.1A

```
gaa cag tgc cac aat aga gtg ata ttt aag caa ctc cta cag gcg aag   780
Glu Gln Cys His Asn Arg Val Ile Phe Lys Gln Leu Leu Gln Ala Lys
        225                 230                 235
gcc ctg cag ttc ctc cag att gac agt tgc aga ctg ggc agt gtc aat   828
Ala Leu Gln Phe Leu Gln Ile Asp Ser Cys Arg Leu Gly Ser Val Asn
    240                 245                 250
gag aac ctc tca gta ttg ctg atg gcc aaa aag ttt gaa att cct gtt   876
Glu Asn Leu Ser Val Leu Leu Met Ala Lys Lys Phe Glu Ile Pro Val
255                 260                 265                 270
tgc ccc cat gct ggt gga gtt ggc ctc tgt gaa ctg gtg cag cac ctg   924
Cys Pro His Ala Gly Gly Val Gly Leu Cys Glu Leu Val Gln His Leu
                275                 280                 285
att ata ttt gac tac ata tca gtt tct gca agc ctt gaa aat agg gtg   972
Ile Ile Phe Asp Tyr Ile Ser Val Ser Ala Ser Leu Glu Asn Arg Val
            290                 295                 300
tgt gag tat gtt gac cac ctg cat gag cat ttc aag tat ccc gtg atg   1020
Cys Glu Tyr Val Asp His Leu His Glu His Phe Lys Tyr Pro Val Met
        305                 310                 315
atc cag cgg gct tcc tac atg cct ccc aag gat ccc ggc tac tca aca   1068
Ile Gln Arg Ala Ser Tyr Met Pro Pro Lys Asp Pro Gly Tyr Ser Thr
    320                 325                 330
gaa atg aag gag gaa tct gta aag aaa cac cag tat cca gat ggt gaa   1116
Glu Met Lys Glu Glu Ser Val Lys Lys His Gln Tyr Pro Asp Gly Glu
335                 340                 345                 350
gtt tgg aag aaa ctc ctt cct gct caa gaa aat taagtgctca gccccaacaa 1169
Val Trp Lys Lys Leu Leu Pro Ala Gln Glu Asn
                355                 360
ctttttcttt tctgaagtga aagggcttaa aatttcttgg aaatagtttt acaaaaatgg 1229
atttaaaaaa tcctaccgat caagatgagt tcagctagaa gtcataccac cctcaggaat 1289
cagctaaagc aaaaagaact tttacctcgg catccagccc aacccctaaa gactgacaat 1349
atccttcaag ctcctttgaa agcaccctaa acagccattt ccattttaat agttggatgc 1409
ggattgtacc cttcaatctg aaagtcttca gctttgaagt catcaatttt ctcaactttt 1469
cgaagaatcc tgagctttgg gaaaggtctg ggttctcgct gaagctaaaa acaaaataag 1529
gccattattt tgccataatt gtacgacctg ttgtaattgc tcctcatgtc catgaaacaa 1589
gtacacagga tgtgatcaac aaagttctat tttacaggag tatgatcctg tcgatacctt 1649
gccgtagtta tgtaacatga ttggagcgca accagctgtt ctcttgacca cagatcgaga 1709
gtgaggggta ttttgtgaca ttacacagca tcaggagcct ggtgcctcat caggtgtaag 1769
ttcttataac cactcttggc aaatttatta aagacaggaa cacagtca
```

FIG. 1B

```
                   M   H   T   D   P   D   Y   S   A   A   Y   V   V   I   E      15
GCCACGGCGCGGACGCC ATG CAC ACG GAC CCT GAC TAC TCG GCT GCC TAT GTC GTC ATA GAA     62

 T   D   A   E   D   G   I   K   G   C   G   I   T   F   T   L   G   K   G   T    35
ACT GAT GCA GAA GAT GGA ATC AAG GGG TGT GGA ATT ACC TTC ACT CTG GGA AAA GGC ACT  122

 E   V   V   V   C   A   V   N   A   L   A   H   H   V   L   N   K   D   L   K    55
GAA GTT GTT GTC TGT GCT GTG AAT GCC CTC GCC CAC CAT GTG CTC AAC AAG GAC CTC AAG  182

 D   I   V   G   D   F   R   G   F   Y   R   Q   L   T   S   D   G   Q   L   R    75
GAC ATT GTT GGT GAC TTC AGA GGC TTC TAT AGG CAG CTC ACA AGT GAT GGG CAG CTC AGA  242

 W   I   G   P   E   K   G   V   V   H   L   A   T   A   A   V   L   N   A   V    95
TGG ATT GGT CCA GAA AAG GGC GTG GTG CAC CTG GCG ACA GCG GCC GTC CTA AAC GCG GTG  302

 W   D   L   W   A   K   Q   E   G   K   P   V   W   K   L   L   V   D   M   D   115
TGG GAC TTG TGG GCC AAG CAG GAG GGA AAG CCT GTC TGG AAG TTA CTT GTG GAC ATG GAT  362

 P   R   M   L   V   S   C   I   D   F   R   Y   I   T   D   V   L   T   E   E   135
CCC AGG ATG CTG GTA TCC TGC ATA GAT TTC AGG TAC ATC ACT GAT GTC CTG ACT GAG GAG  422

 D   A   L   E   I   L   Q   K   G   Q   I   G   K   K   E   R   E   K   Q   M   155
GAT GCC CTA GAA ATA CTG CAG AAA GGT CAA ATT GGT AAA AAA GAA AGA GAG AAG CAA ATG  482

 L   A   Q   G   Y   P   A   Y   T   T   S   C   A   W   L   G   Y   S   D   D   175
CTG GCA CAA GGA TAC CCT GCT TAC ACG ACA TCG TGC GCC TGG CTG GGG TAC TCA GAT GAC  542

 T   L   K   Q   L   C   A   Q   A   L   K   D   G   W   T   R   F   K   V   K   195
ACG TTG AAG CAG CTC TGT GCC CAG GCG CTG AAG GAT GGC TGG ACC AGG TTT AAA GTA AAG  602
```

FIG.2A

```
 V   G   A   D   L   Q   D   D   M   R   R   C   Q   I   I   R   D   M   I   G    215
GTG GGT GCT GAT CTG CAG GAT GAC ATG CGA AGA TGC CAA ATC ATC CGA GAC ATG ATT GGA   662

 P   E   K   T   L   M   M   D   A   N   Q   R   W   D   V   P   E   A   V   E    235
CCG GAA AAG ACT TTG ATG ATG GAT GCC AAC CAG CGC TGG GAT GTG CCT GAG GCG GTG GAG   722

 W   M   S   K   L   A   K   F   K   P   L   W   I   E   E   P   T   S   P   D    255
TGG ATG TCC AAG CTG GCC AAG TTC AAG CCA TTG TGG ATT GAG GAG CCA ACC TCC CCT GAT   782

 P   I   L   G   H   A   T   I   S   K   A   L   V   P   L   G   I   G   I   A    275
GAC ATT CTG GGG CAC GCC ACC ATT TCC AAG GCA CTG GTC CCA TTA GGA ATT GGC ATT GCC   842

 T   G   E   Q   C   H   N   R   V   I   F   K   Q   L   L   Q   A   K   A   L    295
ACA GGA GAA CAG TGC CAC AAT AGA GTG ATA TTT AAG CAA CTC CTA CAG GCG AAG GCC CTG   902

 Q   F   L   Q   I   D   S   C   R   L   G   S   V   N   E   N   L   S   V   L    315
CAG TTC CTC CAG ATT GAC AGT TGC AGA CTG GGC AGT GTC AAT GAG AAC CTC TCA GTA TTG   962

 L   M   A   K   K   F   E   I   P   V   C   P   H   A   G   G   V   G   L   C    335
CTG ATG GCC AAA AAG TTT GAA ATT CCT GTT TGC CCC CAT GCT GGT GGA GTT GGC CTC TGT  1022

 E   L   V   Q   H   L   I   I   F   D   Y   I   S   V   S   A   S   L   E   N    355
GAA CTG GTG CAG CAC CTG ATT ATA TTT GAC TAC ATA TCA GTT TCT GCA AGC CTT GAA AAT  1082

 R   V   C   E   Y   V   D   H   L   H   E   H   F   K   Y   P   V   M   I   Q    375
AGG GTG TGT GAG TAT GTT GAC CAC CTG CAT GAG CAT TTC AAG TAT CCC GTG ATG ATC CAG  1142

 R   A   S   Y   M   P   P   K   D   P   G   Y   S   T   E   M   K   E   E   S    395
CGG GCT TCC TAC ATG CCT CCC AAG GAT CCC GGC TAC TCA ACA GAA ATG AAG GAG GAA TCT  1202
```

FIG.2B

```
 V   K   K   H   Q   Y   P   D   G   E   V   W   K   K   L   L   P   A   Q   E      415
GTA AAG AAA CAC CAG TAT CCA GAT GGT GAA GTT TGG AAG AAA CTC CTT CCT GCT CAA GAA    1262

 N   *                                                                              417
AAT TAA                                                                            1268

GTGCTCAGCCCCAACAACTTTTTTCTTTCTGAAGTGAAAGGGCTTAAAATTTCTTGGAAATAGTTTTACAAAAATGGAT    1347

TTAAAAAATCCTACCGATCAAGATGAGTTCAGCTAGAAGTCATACCACCCTCAGGAATCAGCTAAGTAATTATTACTTG    1426

ATTCTTTTAGCAAATCAATGCACGTTATCCTACTTAATCCTTAAATAAGTTTAGATTTAACTAACCCAAAGTCCAGGAG    1505

GATGTTCTTACAAAAATAGCTATATCAAGGGCTGGCACCTAGACATTAAACTGTACTTTGAAAATAAAAAAAAAAAAAA    1584

AAAAAAAAAAAAAAAAAAAAAAAAAAAAA                                                      1613
```

FIG.2C

```
ctgggtgcag tggctcatgc ctgtaatccc aacactttgg gagcctggtc tggaggatcg 60
cttgagccca ggagttcaag ataagcctgg gcagcaagac gaaaccccat ctgtacaaaa 120
attagctggg catggtggtg cgtacctgtg gtcccaacta ctaaggaggc tgaggtggga 180
taactgtttg agtccaggag gtagaaactg cagtgaactg tgattgcacc actgcactcc 240
aatctgggtg acagaatgag accctgtctc aaaaaaaaaa ttagaaataa gacttagtaa 300
aacaataaaa gctaaataga taatatgtga aatttatcca gtagcaggaa tggtccctgg 360
gacctttaag aagcagatgg cggtattcaa ttttaagttg cttgcagagt ccttgctacc 420
ccaaaccttc ctgcaaatca gctacacata acggtgagtc agtgaccttt aggaaagaaa 480
agggattggg gtcacggcca gaggtacaat gacaaggtac aaacaaggat agggatggat 540
ttcataacct agtttaaacg cagtggggaa ataaattcag gaaataaatc aggtaagtag 600
gagaaaagtt caccaagtac ttggagagac actggatttc acagggacat ggcgtagggg 660
ttcaatccag cttcacttct atcttaaagg tcaagttaac gagtaagttg gaggactttg 720
aaaatccaag taaaaaattg tcactagcct gtgacaatag ggatgagaga aataaaaact 780
tcgcagttgg ccaaaaaggt tgacagtgat tctaataact gaattaaagt ggtgtggccc 840
ttaaagttta tcaaattcca tttattcact cataattgca ctattttcat ggaaagtctt 900
agtctcctaa aacattgaga ggatatacca cggaactaga tggcaaactt ggtttggttg 960
gtttttgtaa tctttaccat tgctagaaag ttagaaaagg gtggcttcac ttcagcagaa 1020
attttgaaaa attcgtggaa ccagaagaaa cccaatctaa aagaaataca agagaacatt 1080
ttcgcagagt tttaagtgca atttcaaaga aaattcaaac ttagaatcaa attcaaagag 1140
gaggcagcac cccaaagcaa catttttgt tttattgagg tataatttac atacaacaaa 1200
gctcaccatt ttaagtgtac cactagatga gttgttgaca aatgtagaca gccatgaaac 1260
caccatgaaa ccagaatcat agaacatttc catcatttca gaaaattcca ttatgccctt 1320
ttacagtcaa tctcttccat tcacccctga cctctgtcaa ccactgagtg ttttctgtca 1380
ctataattgt acatttctag ggctttatat aaatggaatc atatgtagtc actgtgtctg 1440
atgtctttcg tttagcataa tgcttttgag atctttttat ggctcagtaa tattccattg 1500
tgtggatgtg tactacatct tggttttgtc ctttaccaat tgatggatgt ttaggttgtt 1560
actagtttta ggctatcaca aataaagctg ctatgaacat tcaaatacaa gtttttattt 1620
taaacatagg ttttaaattc tcttggataa ttacctatga gtaggattac tgagttgtat 1680
gatacatgaa tgcttaactt tctaagaaac tgataaccta tttccaaaga agatgtaccc 1740
tttcataccc ctccagcaat gtatgagagt tccagctgct tcacatcctt gccaatactt 1800
ggtattgcca gtcactttaa ttgcagccat cctggtgcgt gttagtagta catcattgtg 1860
gttttagtgt gcatttccct aatgactaat aatgttgagt cttttcataa gcttatttca 1920
aattcatatg tctgcttagg tggaatgtct attagaaagt cttttgccca ttttttatat 1980
caagttgcca tcttactgag ttgtaatttt ttcagtattc tgcatacaag tccttttaac 2040
agatatgttt tgcaaatatt tttcttccaa tctgcagctt gcattttcat ttctttaatg 2100
gttttcatca aagagaaaac atttttaatg ttgataattt aattggcaat gtttttcttt 2160
tatgattcat gcttttagtg tcctaagaaa gtttgcttta tccaagtaca aaaagatttt 2220
ctcctgtgtt ttctttagaa gttttgtaat tctagctctt aaaatttaga tctatattcc 2280
acttcgagat gatttttgtg tatgatataa ggtaatgatc caggattgtt ctgtttgttc 2340
ttatggatat tcaattgttc gagcaccagt tgttggaaag actagcttac tcgttgaatt 2400
ttcttggccc ctgttttttt tttgttgttt ttattttgta gacggagtct cgctttgtcg 2460
cccagcctgg agggcagtgg cgcgatctca gctcaccgca acctccgcct cccgggttca 2520
```

FIG.3A

```
aatgattctc ctgcctcagc ctcccgagta gctgggacta caggcgcgtg ctaccacgcc 2580
tggctaattt tttgtatttt tactatttca agacctcttc tgttccattg atctacttgt 2640
ctgtctttat gtcaatttca cattgactcg attagtgtat agcaagtctt aaaaccaagt 2700
agtttaagtt cttcagcctt gttctttttt aggattattt tggctattca aatttccata 2760
taaattttag aatcaacttg gtccaatttc ttcaaaaaaa tcctgctagt gatttagatt 2820
agattgcatt gaatttgtag ttcgatttgg gaagaactgc tattttaaca atattgagtc 2880
ttccaatcca agaatatgaa tttctctaca tttctacatt tctttagatc tttttttctc 2940
agcaatgttt tatagttcag tgtgcaaatc ttgcatattt ttgttaaact tgtcctgttt 3000
tatattttca atgcaattgt tttaagagat acngttttct aatttgtttc caatttttta 3060
ttactagcac atcaactata gattttaaat tgaccttgta tcctacaaac ttgctaagct 3120
caatattagt tccagtagct tttttcgtta agtccaatga agacagtttt caacaaagat 3180
gaataatcat gtcatccaag aataaacagg tttacttcct tttcaatctg ccttttattt 3240
cttttcttat tatattaccc taactagaac ctgcagtact atgttgaata gaagtggtgg 3300
aagcagacat cctttccttg ttccaaatct taaggagaaa gcatcaatca ttcaccataa 3360
agtcagtttg tggctgtttc tatcttctga aatagattat agagaattgt tgtaatttct 3420
tccttaaatg tttggtgtaa aattcaccag tgaaaccatg gacctggtgc tttttgtttt 3480
tggaaggcta ttatttattc aagttattta atagatatag gcctattcag attgtccatt 3540
tcttctcgtg tgaattttgg cagattgtgt ctttcaagga attggtttat ttcatcncag 3600
gttatcaaat ttgtggacat agaattcata gtattccttt attatcattt taatgtccgt 3660
cggatctgta gtaatgttcc ttattncact tttgatatta gttatttgcg ttctcttttc 3720
ttgcctggnt agaggcttat tgattttatc aatgttttca aagaaccagc tttkgttttc 3780
attgattttt ctttgttgct ttcctgtttt caatttcaca ggtttctgct ttaattttta 3840
ttatttcttc tcttctgctt actttggatt ttctttttat ttctttttat ttatttattt 3900
ttgagacaca gtctcactct gtcgcccagg ctggagtgca gtggtgcgat ctcggctcac 3960
tgcaacctcc gcctcctggg ttgaagcgat tctcctgcct cagcctcccg agtagctggg 4020
actgcaggcg cccgccacca cgcccggcta atttttgta tttttagtag agacggggtt 4080
tcaccgtgtt agccaggatg gtctcgatct cctgactcgc catctgcccg ccttggcctc 4140
ccaaactgct gggattacag gcgtgagccg cccagcatyt tttttttttt gagtcggagt 4200
cttgctctgt cgcccgggct gcagtgcagt ggcgcgatct cagttcactg caagctccac 4260
ctcccgggtt caggcagttc tgcctcagcc tcccgagtag ccgggactac gggcgcgcac 4320
caccacgccc tgctaatttt tgtttttagt agaggcggga tttcgccgta ttggccaggc 4380
tgatttcaaa cgcctgacct caggtgatcc gcccgcctcg gcctcccgaa ktctggatta 4440
caggctgagg cacggtacgg gacctcatct gcatcagtac gggtgtaatc aatgatgacc 4500
tgcctcttaa tttatcaggt ggcaaactga ggctgtgggc actgaaagag acctagcatt 4560
ttctagggca ccgctctcct gggtacgctg gcgacaacca gcggcctcgg cttgggagct 4620
gagccactgg ccggaatctg ccgctgagcg aatgcactcg ctcagacccg acttctccct 4680
ctagggcgcg gctcccgggc aggtcccttc acgagtcttc catccgagca gagcagggtc 4740
ccgcggaggc gccgaccggg cgcgaggcct cctgcctgcc caggttcccc ggcgaccctg 4800
agcgaaccct ctcggggtca gctccgtcta ggctgagaag ggaacggcgg aaggcggagt 4860
gcgcccccgg gagcccggag ctgggactgc agctcccatg gggccaagtt cacggggtgc 4920
ggccgcgcgg ccaatgagcg ccctctatgc cctgacggtg ccccgcctcg cggcgctgcc 4980
ggctcccgcc ctcccgccct cccgccgcgc gctcgggatc ccgaccagtc ctgaccgcac 5040
```

FIG.3B

```
gggggccgcg gccacggggc gcaggggcca tggtgcgcgg caggatctcc cggctctcgg 5100
tccgggacgt gcgcttcccc acgtcgcttg ggggccacgg cgcggacgcc atggtaagcg 5160
cggacgccat ggtaagcgcg gacgccatgg taagcgcgga cgccatggta agcgcggacg 5220
ccatggtaag cgcggacgcc atggtaagcg cggacgccat ggtaagcgcg gacgccatgg 5280
taagcgcgga cgccatggta agcgcggacg ccatggtaag cgcggacgcc atggtaagcg 5340
cggcttgcgg cccgggtccc tcccgccccg actgcagctc tgcgggcccc gggcagcttc 5400
ccgacttcga acccattgct tctgtaaagt gggaggcgcg cctgggggag acactcgctt 5460
ttcatgcctt ggagcaattg tataagtatc cagaaacttt ccactctcct gggtttttc 5520
tttgctggag tttagaatat cctggtttta cttttacgac tcacattttg ctggaaatgg 5580
tagaatgcat aataggcaat agcagcaaaa tgattttgtt gggttcccgc cagtggaaac 5640
cctagagcac agtgctcgct ggcttcctct gtaccctgaa cgcgacgggg ttggcgctga 5700
gggagaacgg gaagcccggg gctgggagtt ttgagtggtg atcccgcttc cacaacttgc 5760
tgtgtgactt ggagaagttc cagacctctc tgggtctctt ggacccgtct gtgtaatgaa 5820
ggtgtcacag tcgggttgag aaaccaagcg cgtgctaact gcgtcacatg agagggcgct 5880
ctcgtgaaat tacccgcaaa cacgcttaga aaggactgat gcaaatgtca gttcgtctta 5940
agagatgtaa taaagtaagg gcaggaactc tgactcctac ctaaatattg aaggtctttt 6000
ttgcttactg agggtgttag aatgtcaggc cttccctccc ctgccccgt ctagagcggt 6060
gtttcccaaa tacagtgggt tctgtgcagg gttttcaggg agcctgttcc ccactgggtc 6120
ctcactgccc gtcgtagtcc actgatgaga ttggccgcgc tagaaaagca gagttgtatg 6180
ggtatgtagt gaatgtgtga aagtatgctg ggaagtgagg aacggcaatg ttaggaaaat 6240
ggttaccagt agggagggaa ggaaatgggg tcacggaggg gaccacgagg tctctaattc 6300
ccattgtaat gttttacttc ctaaattggg tggatggcaa gctggtgtcc attacattat 6360
ctatactctt tttgtacctg aaatgtttta taaaaataga tctctcgtta aagttattaa 6420
atgcaaaaca atgtcctttt tgagattaag ttcatcctgc atttttaaat ttttatttta 6480
ttctatttta tgttttaaat ttatttattt atttattttg aggcagggtc tcttatctgt 6540
tgcccaagct ggagtgcagt ggtactatca tggctcacag cagccttgac ctccctgact 6600
caaccaatcc tcccacctca gcctcccaag tagctgggac tacaggtgtg caccatgatg 6660
cccagctact ttctgtattt tttgtagaga cagggcccag gctgtcatcc tctttaaaat 6720
cttcatgttt cctttcttac atgatgttgg taaataactt aaacacccag caggcaatcc 6780
tttatggaac tcaaaataaa tgttggaaat tttactggct tatagaatcc aaacactcga 6840
tctcatgcaa ctgcctttgc ctctgtgaag ctttagcagc tgtggctaag tcacacaatc 6900
tttctaagcc taggtttctc atctgtaaaa tgggtataat aatattcact ttatacatgt 6960
aaatgagata cctgtaaaga gcctggctca gagaaggccg tcagtaaagt tggctatagg 7020
ccaggcatga gggctcacac ctctaatcct aagtggaggc ctaggcaggg ggatcacttg 7080
agcccaggaa ttcaattaca tgagctatga tcatgccact gcattccagc ctgggcactg 7140
gatgacacag tgagaccctg tttctaaaga aaaaaggagg ggtggctgta attactattc 7200
actctgagga aactgaagca gaaggaatcc ctaatctaga cttgactttg aatttgtgaa 7260
atgttaagac agcctggttt ggctgagacg tggtggttca agcctataat cccagcactt 7320
tggaaggcca aggcaggtgg atcgcttgag cccaggagtt cgagaccagc ctgagcaaca 7380
tagtgagacc tcgtctcaac aaaaaaatac aaaaattagc tgggcgtagt tgcatgcacc 7440
tgtggtccca gccactcagg aggctgagkt gggaggatct cttgagtcca ggaggtcgag 7500
gctgcagtga gctgtaattg tgtcactgca ctccagcctg ggtgagagag agagaccctg 7560
```

FIG.3C

```
tctcaaaaga cagcctggtt tactgtagaa taattcaaga aatggaattt gcctctgggc 7620
ctgagtgatg tctaacacag ggtaaggaga cattatctaa cacctgtatt gcaagctcat 7680
aaatacttaa gcattttatc ttggggagat agggtgtatg ttgtgtgcca gctctcaagt 7740
gccttcttat tagaatgagc tgttttgcag ttcaccatgg agatggcttc acatgccctc 7800
gaggcatgct ggaccatcag cacttagcaa agtgagcctc cctgatcaga agtaggatat 7860
tttcaagaaa gagcaataaa gctgtcctcc aaaatctgct aaagactcct gctttttttt 7920
tttagacaga gtctcgcttg ttgcnccagc ctggagtgca gtggtgcaat ctcatctcac 7980
tgcaacctct gcctcccata tgcaaatgat tstsgtacct cagmctctgg agtagctgtg 8040
attacaggtg tgcaccacca cacctggcta atttttgtat ttttggtaga gacggggttt 8100
caacatgttg tccaggctgg tctcgaactc ctgagctcag gtgatccacc tgcctcggcc 8160
tcccaaagtg ccggattaca ggcatgagcc actactccgg gcttacctcc ttcttaatct 8220
gaaatctact tctgttcctt tcttctctgt gaattgccct tgttatttct ccttcagctg 8280
tccttaccct cagatacgtt ttccgctgtc ggccgcctct tcttcgtgtg ctctctcccc 8340
tcgtggcctc ctgcctttct gacagctcct tcttcctcca ctggcccctt cttccctctc 8400
tgaggctcag gcctcagtgt ctttccggtc tccctacaca ctcccatgaa gaccctctcc 8460
acattctgac ttcggtgcca ccctttatgc cggagactcc cagatctcat ttccggatct 8520
gcctccttaa cttataggtc tggatacttc ctgtttggtt tttcaccttc atgctaaacg 8580
cagtttgtct aaatcggaag tcaacttcca ttctctgccg cccctccctc ctgacccatg 8640
ttggatcatt ccgctaatca cagggaccca aaagcttcga gtcacttttg gctcatctcg 8700
tcctgttgac cctcatctga ggcttcagtg caaggtttcc tttttccatt gcttcctctt 8760
cttggaaccc agaaactgcc gatgggtctt taattcttgg agtctccttc tcagcctcat 8820
cgctcaactc cttcaggaac ccaatggctc agccaaccca ggtgggcacc aacacttgaa 8880
tacactccag tctctccctc ttctgacccc tttactttct gcactgctgc tgctgctacc 8940
ttgcctgaga tattcctccc tcccagactc ttcactcccc ttcccactgc tgaggagctc 9000
cccttccttg accggccagc tcacattctg tcttcatcat aaagcgctct ccctcttcaa 9060
gaagcacatt cagctaacag cgctctctgc cagtcgttca tagtttgcat ccctcccagg 9120
ccttagcatt ttctgcctta tattattaag gttttttttt aaccatgtct ttttatttat 9180
ttattttaga gatggggtct cgctttgttg cccaggctag tctcgaactc ctgggctcaa 9240
acaatcctcc tgtcttggcc tcccaaagtg ttgggattac aggtatgagc cagcatgccc 9300
gttctataag caggtcttct caaatgtaac ctcctcaagg gcagacgtat ctgtaacccc 9360
ctagcaagct gcaccagctc tgacacgtac ttggtgctca gcgatgcatc acactgattt 9420
cctgccactg gactgtgata ccagactcag ggctcccagc catcacatac agctccctca 9480
gccacgacac cccaatacag ggatttaaaa tctgccttca taatttactt gtggccgggc 9540
gtggtggctc acacctgtaa tcctagcact ttgggaggcc gaggcaagtg gatcacctga 9600
ggtcaggagt tcaagaccag cctggccaac atggcaaaat cccatcttta ctaaaaaaaa 9660
aaaaaaagct ggtcatagtg gtgggtgcct gtaatcccag ctacttggga ggctgaggca 9720
gaagaatcgc ttgaatccag gaggcagagg ttgcagtgag ccaagatcat gccactgcac 9780
tccagcctgg agaacagagt gagagtcagt ctcaaaaata ataataataa taataaaaca 9840
ttatttactt gtggtgtgac cttttgtaaa ttactaaagc tccttaaaac ttcatttcct 9900
ctttaataag gataagagca cctactttat aatattgtta taagattaaa ttaaaccatg 9960
tggagctctt agaatatagt gtgtctggca caataaatat tatagaataa taacagtaat 10020
aaattttcat agccttatgc acaattcttc tttatgaatg cattcacatc ttctgcctgg 10080
```

FIG.3D

```
cttttggag tctccattat tccatgacat agaacaaaac aaaaaatgag tgaattaatc 10140
tcgaagcttt acttcttcat tttcccccac tggtgtctga acttttgcca gtgtattttc 10200
agccctgcta taaactgcta taagtgagat cactccaatt ttatgcaaca gttttctgaa 10260
cctttggctt gttcaatttg aagctgcttg tgaatgtaac tttgttcaaa aagctgacag 10320
agatagctgc gagtgaaaac tccttggctt aaaattgagc cccttccggg catgatggct 10380
catgcctgta atcccagcac tttaagaggc ccaagcgggt ggatcactag agctctggag 10440
tttgagacca gcctgggtaa catgcaagac tccatctcta tttttttatt taaaaaataa 10500
ataagtaaat aaaattgagc ctcatttttt aacctaattg aaaatgggtg ataaaaatgt 10560
atacattgcg accaggtgcg gtggctcaca cttgtaatcc cagcactttg ggaggccaag 10620
gcaggtggat cacctgaggt caggagttca agaccagcct ggccaacatg gtgaaacttc 10680
gtctctatta aaaatacaaa aatcagccaa gtgtggtggc acatgcctgt aatcccagct 10740
acccgggagg ctgaggcagg agaatcgctt gaacttggga ggctgcagtt gcagtgagct 10800
gagatcgcac cattgcactc ctgcctaggt gacagagcaa gactctgtct caaaaaagaa 10860
aaaaaaaaaa atatatatat atatatatat atacatacat tgctcttgtt gaaacatttt 10920
ggatctttca ggaggacatt ccttttctcc attcagagcc ctttgttttc tttggggtat 10980
agcaacagtt ccttctatgg gagctcttgt ggcacggccc ctgtggcatt gtctgtcctc 11040
atgtgacatc attctcatgg ttcttttcgg gtttctcaca ctggcattgt ttcggcgggg 11100
aactcctctc ctgcagcaca cggaccctga ctactcggct gcctatgtcg tcatagaaac 11160
tgatgcagaa gatggaatca aggggtgtgg aattaccttc actctgggaa aaggcactga 11220
agttggtgag ttgaagattc tctcgaggtt ccagaatgct taattttcag atgagattct 11280
aatttagatt cttagattca ttagaatctt gatttagatt gagttctgat cttgttttta 11340
tctgtattta cactgctcaa agtgagtaaa aacagtgttt catggtttgt tacttgtttc 11400
actgggagaa atttaaaagt gacagaattt ggcctctctc cttgcaatca tctctagcct 11460
gttagaaaat ccttggctgt tagtctgttt ctctgtgtca aatgacagct acaagagtgc 11520
ttttcacctg cctttcaccc ggggccactg tcgagctttg acaacctgta gtgggcgagt 11580
aaccaagggc aatgagaggg aggagacatg agttcccata gcaaaaaagg ctcattgtga 11640
tgtgcacagc aagtctactc gcttttcaat atatatatgt atatattttt gagacagagt 11700
ctcactctgt cgcccaggct ggagtgcagt ggcacaatct cagctcactg caacctctgc 11760
ctcctgggtt caagcaattc tcctgcctca gcctcccgag aagctaggat tacaggctcc 11820
caccaccatg cccagccaat ttttgtattt ttagtagaga cagggtttca ccatgttggc 11880
caggctggtc tcgaactcct gacctcaaat gatccgcctg tctcagcctc gcaaagtgct 11940
gggattacag gtgtgagcca tcacacccgg ccttttcaaa atatttcaca ccaaatcggt 12000
ttcaagttca ctattttcat ggcgaaaagg gctttggccc cgcccaatct cggaggtctc 12060
ccttggggaa gagcagattc tttaagatgc atactgagcc gtgtatacgt cattcttttt 12120
ttatttgcat tttctatttt cttaaacaga agacacagaa cataactttt ttcagagctg 12180
gatgtgatct caaatggtga tcttgagccg tctcattttt tagagagaag aaaactgagg 12240
cacagacagc tacccagcaa gtcatggcag aaccacctga ctgcccagag cactttctct 12300
tcagaacttt taaatgcaac tctttttgaa tacataatac ttacacatgg tacaaaattc 12360
aagaagtcca aaacagtggc cttcgccaga tcaatttcag tggattatta gagcctgaag 12420
ccaaattatg atagattgaa gggtaagggt ctagaaggag ggaaaagagt ttctctaact 12480
tcggtggtag tgtgatacct ctcccttgga tatttgcacc atcagcgctc tcagtagttg 12540
tagaaaaaaa tcttggccca ttgagagatt ttaaattgtt aagcatataa aagaagtgtg 12600
```

FIG.3E

```
tgagtttgtg aatgtgtgta tgtgcgaatg gcaagggaac cttccttgaa ctttcaatgg 12660
acactgccca ggtggctgct gttactgctc ttcacagggc tggcggtcag ttgtccagca 12720
agtcagtcct tctgcagact tctcctgagt gctgccatgt atcaggcacc aaagtaattt 12780
taaaaagaga aagataggcc gggcgtggtg attcaggcct gtaatcccag cactttggga 12840
ggctgaggcg ggcagattgc ttgagtcaag cagttcgaga ccagcctggt caacatgctg 12900
aaaccctgtc tttactaaaa atacaaaaat tacctggccg tggtgatgca tggctgtaat 12960
ctcagctact caggaggctg aagcacgaga attgcttgaa cctgggagtt ggagtttgca 13020
gtgagccgag attgcgccgc tgcactccag cctgggtgaa aaagcgagac tccatcccaa 13080
aaaaaaaaaa aaaaaaagat acagaagaca gaatcccaca tacaaggagc acacgaactt 13140
attggggaag tagacataaa agaaatgatc atagtgcagt ctgagaatta ctgtttttta 13200
aaactatgta caagttttac agagagagga tatattaggc tgttcttttt tttttttttt 13260
tttttttctt ttctttttgg aaacaagagt cttgctctgt cgcccagcct ggagtgcagt 13320
ggcgcaatct cgctcactac aacctccacc tcccgggttc aagcaattct tatgcctcag 13380
cctcccgagt agctgggatt acaggcacac accaccacgc ccggctagkt tttatatttt 13440
tagtaaagat gaggtttcac cgtgtttsgt caggctggtc tcctgacttc aaatgatctg 13500
cccaccttgg cctctcaaag tgctaagatt ataggcatga accaccactc tgagccaggc 13560
tatttttgca ttgctataaa ggagtacgag agactggata atttataaag aaaaagaggt 13620
ttaattgcct catggttctg caggttttac agaaagcatg atgccagcta ctcagcttct 13680
agggaggctt caggacactt acaatcatgg tagaaggtga agggggagca ggcacgtcct 13740
atgtcgaaag gatcaagaga aagggaatgg ggaggtgcta cacactttta agtcaccaga 13800
tctcacgaga actcactcac tatctcaaag acagtaccaa tgggatagtg ctaaaccatt 13860
caggagaaat ccacctccaa gatctaataa tcacctccca ccaggcccca cctccaacac 13920
tggggattac acttcaacat gaaatttgtg cagaatgtct aaaccatctc agggggtaac 13980
ttcactctgt ccaaaaggct cagggaaggc ttcagagcag aagtaatgct ttgaggtgag 14040
tctcgaagag caaacaggaa tttgccaggc agagaaagac catgctgtga gtcagtcccg 14100
cttttctcca ttaagtaaac aatttactgt taaagttttc cccagagtag taaccactta 14160
ctaagacaga gctgtgagct gtttctgctt cttctgcaac tctaattgtc ccttgtttgt 14220
aagttgagta ctttatgaag ccgctgcctt tctccatact gcaaatccta cagcacagcc 14280
cccaaaggtt gcataaaact cagcgagctt acaagatatg ttaggccatt ggacccactc 14340
tctgttaaca gcccagactt taaactttgc tgacttgggc acacgtggag gggccctggg 14400
cactaagata gataagaagc ccttctggga tgggtgctga gctcagtgtt tagggccttc 14460
acttcccctc tcctcctcca ttcccagccc cacaccgctg tcttggtgga tgtctcaggc 14520
acggataaat caacttccat ctctccatga ctttaattaa tgactctttt gtgctaaggg 14580
ttttggcttc ctcctttttc agaccacaac atgacagaac ccattttaac tttaaccttg 14640
ctacatattt caggtgactc actgcagtct cactaaatgt gttacacagc actcacacta 14700
aagatgaaaa attccattag ctcatcctgg ttcttctgct tacttaccta atcatctgtt 14760
tatgatttaa aaaaataggg ttactgtgaa gagagtgctt gtgtgtgaga cagagaggga 14820
gggttgtttt tcaaatgtat agaatatacc aatgtagttt ttggttgggt atttttttaa 14880
atcatgactt tattaaattt acttaattaa tattcatttt tatccttttt ttatgttttt 14940
aaagttttta ttatttatta atttatttga gataaggtct tgctctgtca cccaggctgg 15000
agtgcagtgg tgcaatcacg gctcatacag ccttgacctt ccagactcaa atgattgtcc 15060
cacctcacct tcccgagtag ctgggcccac aggcacaagc caccatgcct agctaatgtt 15120
```

FIG.3F tctttttttt gagagacaga gtctcgctct gttgcccagg ctggagtgga gtggcacatt 15180
cttggctcac tgcaacctcc acctccaagg ttcaaacgat tctcctgcct cagtttccca 15240
agtagctggg actacagatg tgtgccacca tgcccagcta atttttgtat ttttaggaga 15300
gacagggttt cactatatgt tggccaggct ggtctcaaac tcctgacctc aggtgatcca 15360
cccactttgg cctcccaaag tggtaggatt gcagatgtaa gccaccamac ctgacykggg 15420
tttttttttt tttttttttt gagatgtagt ttcgctcttg ttgcccaggc tggagtgcag 15480
tagcacaatc tctgctcact gcaacaacca cctcccaggt tcaagcgatt ctcctgcctc 15540
agcctcccag gtagctggga ctataggtgc ctgccaccat gctgggctga tttttgtatt 15600
ttttgtagag acaggatttc atcattttgc ccagactggt cttgaactcc tgagctcaag 15660
caatccgcct gcctcagcct cccaaagtga tgggattgca ggcataagct ataagccacc 15720
atgcctggcc tgtttctgtt tttatttatt tatttattta tttatctatg tatttattta 15780
tttttgagat agagtcccac tctgttgccc aggctggagt gcagtggtgt gatctcggct 15840
cactgcaacc tctgcctcct aggttcaagc aattctcctg cctcagcctc ccgagtagct 15900
gggattacag gtgcccacta tcacgccagc taattttttt tttttttgag atggagtctc 15960
gctctgtcac ccaggctgga gtacagtggc gcgatctcag ctcactgcaa gctctgcttc 16020
ctgggttcac gccattctcc tgcctcagcc tctccagtag ctggactaca ggcacctgcc 16080
accacgcccg gctaattttt tttttatttt tagtagagat ggggtttcac cgtgttagcc 16140
aggatggtct cgaactcctg acctcaggtg atccacccgc cttgacctcc caaagtgctg 16200
ggattacagg cgtgagccac cgtggccagc cttttttttt tttaagactt tatttttta 16260
gagtagtttt aggttcacag caaaactgaa tggaagttac aaagatttcc cacatacccc 16320
tgtccccaca caggcacagc ctccttcatt atcaacattc tgcccagagt ggcccacttg 16380
gtacaactga tgaacctgca ttggcacatc atgatcaccc aaagtctgta gtttacaata 16440
ggggtcactc ttaggtttgg acacatgtat aataatatgt acaatgtaga ctaagttagt 16500
tttttaaaaa atagaaaaag atgtacaaag aaagaatttt taaatagaca aaatttttaa 16560
aaatccagcc ttaagagttt atgacaccac tcttacttca gacacccaca agtcacccac 16620
agactttact caatgtcctt ccagtgctag aggctccaga gaattgaagt ccctgagcag 16680
atagaatcac aagagaaaac cccccgggtt tagttgccaa gaagctgctt tcaagggcct 16740
ttttttttctt ttccaagtca atttcctgcc acagccaaaa tttctctcgt tttttttttt 16800
tttttttttt ttgaggcaga gtttcgctct tgtcgcccag actggagtgc gatggcgtga 16860
tcttggctgg ctcactgcaa cctctgcctc ccaggttcaa gcgattctca tacctcagcc 16920
cccacaagta gctgggatta caggcatgtg ccaccacacc cagctaattt ttgtattttt 16980
agtagagaca gggtttcacc atgttgatca ggttggtctc atactcctga cctcaggtga 17040
tccgcccgcc tcagcctccc aaagtgctgg gattacaggc atgagccacc gtgcctggcc 17100
tcacaaccca aatttctatt gaatgcgaca aattctagtc tcctgttgag caagaaaaat 17160
ccatacactg tagatgaata cataagtgct gcttgtgcac tctgagagtc ataaaaatga 17220
gatcatcctt agcttttgtt aagtgcattt ggtattgtga catgaaccag aggtatgctt 17280
cagtcaatga tttatagcaa caatcaaatc cttgagacgg tggtttggtg tcgataataa 17340
cgtacctcac tgtgagtcac tgacttactt cagattttct ttaattcaag agcatcaacc 17400
ttcaagaagt gaggaggact ctgtcttctc acaattctag ggaatgaatg tctgaaccag 17460
aatgattgtg tatcccatta acaaaagccc tagagaacct ggaatggctg gttcagccct 17520
aaatgctaca tctgacctaa agtgtgcaat catccgagag ctgtttcacc cttagccagg 17580
catgtgctaa aagcttgggg catcactttc tttcttttc ttgagatgga gtttcgctct 17640

FIG.3G

```
tgttgcccag gctggagtgc aatggcatgg tcttggctca ctgcaacctc cacctcctgg 17700
gttcaagtga ttctcctccc tccgcttccc aagtagctgg gattacaggc acctgccacc 17760
atgcccagct aatttttgta tttttagtag agatggggtt tcaccatgtt ggccaagctg 17820
gtctcaaact cttgacctca ggcaatccac cggccttggc ctcccaaagt gctaggatta 17880
cagacgtgag ccaccgcgcc cagcctgggg caccactttc aaactgtcct tctcaagatc 17940
ttattgacag taaaactgta cccctacaac tgtcctatta aatgactaaa aacttttact 18000
attgaatcca cggcagcacc aaacaaatta atcaaaacgt tttggaatac attcctttct 18060
ttgaagctaa gttgatggct tgattcaatt attgtgtcca tttacacaac gtaggctaaa 18120
tgtttcctag aattggcaaa ggatcaaagg gttactttac ttattcatca tcttaaataa 18180
cccaagaaag cctttatatt attattatta ttattatttg agacagggcc cagctctgtc 18240
acctaggctg gagtgcagtg gcacaatctc agctcactgc aacctctgcc tccaaagcta 18300
aagtgatcct cctacctcaa gtgatcctcc tacctcagcc tcccgagagg cggggaccac 18360
aggcgcacca ccgcaaccgg ctaatttttg tatttttttgt agagatgatg tcttgccaca 18420
ctgcccaggc tggtctcaaa ttcctgagct caagtgatcc acccacctca gcctcccaaa 18480
gtgctggcat tacaggagtg agcgccaggt ccaagaaatc ctttcaaagt aaaataccac 18540
aggacatggt ggctcacacc tgtaatccca acacttcagg aggccgaggt gggaggattg 18600
cttgagccca gagttccaga acctccccac ccactgcccc atgcaacata gcaagacctt 18660
gtcactacaa aaaatttaaa aattagctgg tgtggtgttg cgtgtaggtc ctagctactc 18720
aggaggctga gacaaaaaga ttgcttgagg ctaggcattc aagattacag tgaggtgctg 18780
ggtgcagtgt ctcaggcctg taatcccagc aattttggtg gccgaggcag gtgtatcact 18840
tgagctcagg agctcgagac cagcctggga agcatggtga aaccctgtct ctaccaaaaa 18900
tacaagaaat tagctgggca tggcagctca agcctgtggt ctcagctact caggaggcgg 18960
aggtggaagg atcacttgag cccaggacgc agagattgca atgagcctag atcccgccac 19020
tgcactccag gctgggtgac agagtgaaac cctgtctcta aaaaataata attaaaggta 19080
ccaaaaataa ataattgatg gtaatgccga cccaaattaa atttaacctt caaattactt 19140
atgaaaaatg tagtatatca taagaaagtc aatagtaaga aatttcatgt taagacagtg 19200
ttttcatata ttttaacatt ttacatataa atagtatgct aattgcaaat tcattttatt 19260
taatgtttaa tagtttatgt tatgaattca aggcattttc tatacttgtc aataatgaaa 19320
aggcatttct ccttttaaaa attctatgaa gtcagccttc ttattcctta ggaacatgaa 19380
ctagtgtggt ttggttttga atctgattgt tcaaacactt tacaaagtga ataggaaaat 19440
aatttgggaa catttatatt taaacttgtc aatctatgat tctgtttttc atgtgacagc 19500
caatcacaat gtgttctcta ctcaggaagt ttagctcagt atatggatta acacgtgttc 19560
tacttgtgtg atatttctta tgacaaccac agaaaacata tggggctggg cacagtggct 19620
tatgcctgta atcccagaac tttgggaggc caaggcgggt ggatcacttg agcgcagtaa 19680
tttgacacca gcctgggcag catgtcgaaa ctgcgtctct acaaaaaata ccaaaattaa 19740
ccaggtgtgg cggcacatgc ctgtaatcct agcttctcga gaagctgagg tgggaggatt 19800
acctgagccg gggaggtcaa ggttgcggtg agccgtgatg gtgccactgc actcaagcct 19860
gggtgacaga gtgagaccct gcctaaaaaa gaaaagaraa gaaarraaaa catatttgat 19920
gcattttaaa aagaatatac ctttgagata gagtctcact cttgttgccc aggctggagt 19980
gcagtggtgc aatctcggct cactgcaacc tctgcctcct gggttcaagc gattctcctg 20040
cctcagcctc ctgagtagct gggattacag gtgcgcacca ctgtgccctg ctaatttttg 20100
tattttcagt agagacaggg ttttgccatt ttggccagac tggtctggag ctcctcatct 20160
```

FIG.3H

```
caagtggtcc tcctgccgtg gcctcccaaa gtgttgagat tacaggcatg agccaccgcg 20220
cctggcctag atttaatttt ttcataaaac tttcacattt gtttgtttgt gatgttttca 20280
ggtgctaatt tcttgaccta gtatagaagc ataaacaaga gttcaatcct ttttaaatag 20340
ggtaagggac ctattttgta aaatgcttac ataagtaata ttaccaaggt ctgagatgtc 20400
ctttgagtgc aacgaatgtg aaaatagaga tgggtttatt tatttgttta tttatttatt 20460
ttttgagatg gagtctcact ctgtcaccca cgttggagtg cagtgatgca atcttggctc 20520
actgcaacct ccgcctcctg ggttcaaaca gttctcctgc ttcagcctcc tgagtagctg 20580
ggactacagg catgcactag cacacctggc taatgtttgt aattttagta gagatggggt 20640
ttgaccacgt tggccaggct ggtctcgaac tcctgacctc aagtgatccg ccttcctcag 20700
cctcccaaag tgctgggatt acaggtgtga gccaccatgc ccatcctaga gatgtgttta 20760
taattttaaa gtaaaacatt ttattcagtt aaattcaggc ttgagtcatt tagatcatca 20820
gtattttgag gtaaacaact catttctgta agactgatga tctaaatgac tcaagactga 20880
atttagctga ataaaatgtt ctactaagga gatgaggtcc tgagatttgg gtcctaagag 20940
ctatctcttc tctaaggacc tcatctcctc ctccctgaat tggaaagtgc tctagaggat 21000
aaagtactaa atgggcaatc tctttatgga gaaataatgt gagtagtgtt agagatgtaa 21060
gagaaggtca ggccgggcgc ggtggctcac tcctgtaatc ccagcacttt gggaggccaa 21120
ggcaggcaga tcacgaggtc aggaggtcga gaccatcctg gctaacatgg tgaaaccccg 21180
tctctactaa aaatacaaaa aattagccgg gcatggtggc gggcgcctat agtcccagtt 21240
actcaggagg ctgaggcagg agaacggcgt gaacctggga ggcggagctt gcagtgagcc 21300
gagatcgcac cactgcactc cagcctgggc aacagagtga gactctgtct caaaacaaaa 21360
aaaaaaaaaa aaaaaaaaga gagagatkta aaagaaggkc attaaagaga aaacattaag 21420
agaagagcaa atttaaaaar rtggragacc atggtacctt ttatgggttt gggatttgac 21480
ctataaattc aaggcatgaa aaagttaggc yctggagaaa rgrttccaac acaataaggt 21540
gaattcaata ccctgacctt tgcctttgtc ccgtgatact ggattttgtc ttttcctaac 21600
ccggcttagt ctcccatcca tgcactgaga arggcacaag agaatgtact ttcaatagtg 21660
cctgggattt catcttttac tttatacaga gaatattaaa cttaccttga aagatgtcac 21720
cttgaagaag ttcccattgg ctgaatctgg gacaatttga acatccaaat aaatatgata 21780
gtaatggctt ataacccatt gaataaaatc catgagtcca ttcagataat gaacaatcag 21840
ctgggcacag tagctcacgc ctataatccc agcaccttgg ggctgaagca ggagaatcac 21900
ttaaggccag gagttcaaga ccagcctggg cagcatagtt gagacccccg tctgtacttt 21960
ttaaaaataa aaataatnaa atanaanatt tttaaggagg taataaacaa caaggtcaag 22020
cccattacag ctgattaana tctaataant ataaaaggaa tgataacatc agagaatcac 22080
cataactgtc atagctacaa ttaattgagg caagagtcat caagggatgc ccaaattttg 22140
ggacaataat aacctcctta cttggaaaat gaaatggtaa cttcacagtg gagaaagcaa 22200
atggacacta agttacccaa gtggtaaaag ttaacaatcc taataataaa acaaaatgac 22260
ataatcactt atgtagtatt gatgccaaaa aatgtattac ctgaatctag tcatgaagga 22320
actccagatc agcccagatt gaggaatgct gtacaaatca agtggcctgt actcttttaa 22380
aatgctaata acatttaaaa aagaagaaga aaaattattc caggtaaaaa gagactaaag 22440
aggcatggcg actaaatgta atacgtgatc ccagatggga tatggattag ggtaaaataa 22500
aatacattat tggaaaaaac tggtgacatt tgattatgga ctggccttta gacagcaata 22560
ttctatcaat gttatattcc ctgagtgtga ttattgtact acggttatgt aagaaaatat 22620
ccttgttttc aggaactata cactgatgta tttagggtta agagagcatg atatttgcaa 22680
```

FIG.3I

```
ctttattcaa atggttcaga aaaaagaagt acatatgtgt gtgtgttcat atgtatatac 22740
atacatatac ttaacatata tatagagaga gagaaagaag agaggaaaac acaggtgttt 22800
ttcctgctat tcttaaaact cttcaatagg ttagcaactg ttttttttaa acttaacctt 22860
taggtgggtt tctattgcta ccttttaatt cttgagatgt gtccctggac ggaagaccta 22920
aatatctttc tctctctctc tttttttttt tttttgagac agagtcttgc tctgttgccc 22980
aggctggagt gtagtggtgc gatcttggct cactgcaacc tccgccttct gggttcgaga 23040
gatcctcttg cctcagcctc ctgagtaggg actacaggca caaaccacca cacctggctc 23100
atttctctgt tttcagtaga gacggggttt caccatgttg gccaggctgg tcttggtccc 23160
aaagtcctgg gtttacaggc atgagccatc acacccagcc ctctttttca tttctaaaaa 23220
gtgcttttgt actttgcttc ctaaccagat tggtccagaa aagggcgtgg tgcacctggc 23280
gacagcggcc gtcctaaacg cggtgtggga cttgtgggcc aagcaggagg gaaaggtaac 23340
ccctctcaca aacgctcagg aggctcctgg gagctgcacg acactgactt tccctacgca 23400
cagaggaaag acagacacac tgcagccccc aaaaggaaat acagataatt gctttggtgt 23460
tttttctcc tctgagaggt tttggcagta ggtagggaac tgcaggagga ggagaaagag 23520
gagacaggat ggcggaaggc gcaggcagca gtagaggggg gtgtggggac ctggtggctg 23580
acagccagca ttagctgcca acgtgtttac tgtcaggaaa aaatggggac tttacacata 23640
tgtcttacaa atcctttctt ttttacttca agcctgtctg gaagttactt gtggacatgg 23700
tgagtagcat tgttaatgtt acaattgttt ctgtaaatga aatggatatc attgatgaca 23760
tgccttttga tgatcagtaa atatattcag gactatctgt tgatcactat agcgatgata 23820
aagcaaaaag ccaataaaat atgacattcc ttttctgata tctgacgtaa cagatggctg 23880
tgctcatgca ggcagggtgg catgagggga agcagtgagg gggtcctgcc tccccccactg 23940
tgcatgtgta acacacggtg ccagttctct gagcctccat tgcctgacta tgacaagagg 24000
atcatcctaa cttctctagg aacctcacaa aattaaagat caatgagaaa agcacctcat 24060
aaactctgaa aagccagatg ttataatatt atgaagatat tatccaggcc aggcatggtg 24120
gctcaagcct gtaatcccaa tactttggaa ggctggagga tggcttgagc ccaggagttt 24180
caggctgcag tgagctataa ttgcaccact gcactcaggt gacagagcaa gaccctgtct 24240
caaaaaaaga aaaaagaaaa gatactatcc agtcactttg acaccaagaa taagatcagg 24300
ccattgtagc ctctactgta caattccagc agggaaggag ctcaacactg aattctaaag 24360
ctatgcactt gactgttttc tttctccttg accttttcat agcaggggtg aacaactgga 24420
tgctgaggag gaaaaaactg ggcaaattaa aggggaatga gcttcagacc ccatgcagag 24480
ctggctgtga gtccgggttt cactgctcac cagctgcatg accttgagca tgtgacttcc 24540
ccactctgag ctgcggtggc ctcagtgcaa cacctgggtg gcggttaaaa acctcgtgat 24600
ccacaaatga aggcccttgt tattagttgg caaaaaatta aggaaaaaca aagaacacca 24660
tggccttgaa gagtgttggg caggagactg ctcctcctcc ggaggaaagt gaagacagga 24720
ggctgtcaca tcgtctctga catggagagt ggcttccggg ccatccgtag gggaaggaca 24780
cagagctctt gagccccctt ctagattcaa ggttggcgtt ttacggggat ggaggaggta 24840
gccaccaaaa gggaatgatt tgcaggccac cagaaatgtg cctgaggtcc cacctgtgga 24900
ccctccattt ttggatcctg ttccctttca atgccagtac tcttttcttt tttctttttt 24960
tctttctttc tttttttttt ttttagacgg agttttcttc ttgttgccca ggctacagta 25020
cagtggcatg atctcagctc actgcaactg attcaagcga ttctcctgtc tcagcctcct 25080
gagtagctgg gattacaggc acccgccacc atgcccagct aatttttttgt atttttagtg 25140
aaaacggggt ttcaccatgt tggtcagtct gagctcgaac tccggacctc aggtgatcca 25200
```

FIG. 3J

```
cccatctcag cctcccaaag tgctgggatt acagatgtga gccaccgaac ctggcccaga 25260
actcttagaa gtagaatctc agggttgaaa gagtttttcg gattttcgac agttatggta 25320
gagtattatt ggtcactata agatgttagt gggaatggaa ctactggctg ttttccaact 25380
gactgttccg tcagggtagg gagaggtctc agcacgaggc cccgccgaaa tgttggtaag 25440
tggtcagcca agtgggccgc tcactcccgg ttcgcccact gtgttcctgt cagtgaagca 25500
aacatcccca tttggcagga gaagaagctg ccggaggtca cactgctagt gattggtggc 25560
ccaggggtag ggcagccttc tttcctctgc agttcactgc tccagaacca tctccagcct 25620
catagctcac cgtggacagc cctgcggtgt ggcgctgatg tacagagtga tgccaggcgt 25680
tcatctcccc actgagctcc tgctgagtgt ttgcctgggg ccaggtcctc cttccgggaa 25740
gtcattttag ctggaaagaa cagggtgggg gcgggtggca agggatcaga gcatgagcgt 25800
ttgagggctt cgtcaggggc agtgaggagc ctctaaagga ctctacattt aggaatgaca 25860
gagtcaaaca atttaacaaa gccctaaagg tccctgccag gaaagaatga gccccatgta 25920
tcaccataag caacttctta gaaacataac ccacccctgt catcccagca ctttgggagg 25980
ccaaggaggg aggattgctt gaagccagga gctcaagatc aacctggtca acatagtgag 26040
accccatctc tacaaaaata aaaataaatt agccgggcat agtggcacat acctggagtc 26100
ccagctactc aggaggctga ggcaggagga tcacataagc cggggagact gaggctgcag 26160
tgagctatga tggcatcact gcactccagc ctgggcaaca gagtgagacc ttgtctctaa 26220
aaaaagaata ataaatttta aaaaacaaaa tataacccac cttataattg attcaggcct 26280
cttcccctcc tgtcacgttg ccaggatccc aggatgctgg tatcctgcat agatttcagg 26340
tacatcactg atgtcctgac tgaggaggat gccctaggtg agtttggaag ctttctggga 26400
tacacgatgt gcacacacag tagtggcatg ctttgtttcc taaaagagtg agtgatgctt 26460
tttatttctt ccagaaatac tgcagaaagg tcaaattggt aaaaaagaaa gaggtgggtt 26520
gtaagaaaat tttcttcatt gtttttgcta acattgtcca cttttgagtg cccctgtcct 26580
tttggggtac acattgtctt cccaaatgcc ctgtgctgag cagctaggcc ctcaaatcaa 26640
cattcaagtc tgcatggtga agcctgctgg gtatgacctc tgactgcaga gtttgcttca 26700
gccactgctg aaaggaagtt tggctttagg attacactgt agggagagcc ctgggggagc 26760
agggcagtcc gtgagagtat cctgatcacc tgggtttgac atcctagtaa tttgtggctg 26820
ggtgtgtgtg tgcagggccg gatcaggaga acagctggac tctccagggg aaacagctgg 26880
actctccagg ggaaacagct tagctacagg cacttccaat tccgaagggc cctggaaagt 26940
gcaaaatgtt gacggcgctg tgttttcaca gagaagcaaa tgctggcaca aggataccct 27000
gcttacacga catcgtgcgc ctggctgggg tactcagatg acacgttgaa gcaggtgggc 27060
attttaacct ggctttgtag acagctgaat ggggagaaac caacctgttt ttccttctgt 27120
cctcatacca ctactctcag tacctcactt ctgacaccag atgtgtgtgg ttttccttct 27180
cacgccaacc agttctccac ttctctgtgg acaccaactg ggtgtcctgc tattttactc 27240
aattctgaca gcacatacct ggaactagcc tcagacccca caggttaagg gctcagtctt 27300
acaggactgc cctatggcag atgccagtca caagtccacg ttgtcacctg tgcttctgac 27360
tggctttgcc tcagattaga ggttcccaca aaccccgctt tgagttgaat catttggtgg 27420
aatggctcac ggaattcagg gaaacactac ttatgtttac tcatttatta taaaggatgc 27480
aacttaagaa cagccaaact gaagagacac acagggcaag gtgtgaggag ggggtacaga 27540
gcttccatgt cccctccagg tgagccacac tcccagtacc tccacgtgtt caccaacctg 27600
gaagctctct gaaccctgtt ccttgggggt tttatggagg cttcagtatt tagatgtgat 27660
tcattatttg gccattggcc atcaattcag ccttcagccc cctcgcctcc ccagctatct 27720
```

FIG. 3K

```
gggaataggc taaagtttcc aaccccacca tcatgccttt caggtctttc tggtccccag 27780
ccccatcctg aagctacgta ggggacctca gcagggctct ctcgttcacg tacaaaagac 27840
ayycctatca ctcaggagat gccmarggkt ttwrgggstg tgtgttgtgt gttaggaaat 27900
agggggggcag cgatgggggc agagacaaaa tatatattcc ttcttatgtc acatgggctt 27960
ttgattccag cctctctggg agaaatttaa tactttcctg ttcacctctc taaatcattt 28020
tggctgaggg cagtggctca cgcctataat cctagcattt tgggaggctg aggtgggtgg 28080
atcacctgag gtcagaagtt caaaaccagc ctggccaaca tggtgaaacc ccgtctctac 28140
taaaaataca aaaaattatc tgggcgtggt aatgcgtatc tgtagtccca gccactcagg 28200
aggctgaggc aggagaatca cttgaaccca ggaggcaggg gttgcaatga gccgagatca 28260
cgccactgcc ctccaacctg ggtgacagaa caagagtccg tctcaaaaaa caacaaaaaa 28320
attattttgg atccaagccc tcgttctgaa agtacacaag gaaatgcaaa gccattcatt 28380
ttgtggaccg caggactctg tgacttagtg agtcaccttg ggctctggaa ggtgacagcc 28440
tagggtaaga ttcctgggca gcaccagcgg tagacccact gcgagattga gaagtaatgc 28500
ctatttcatg gggtggtttt gaggattcag atacatgctg taagttgcgt catgctcaag 28560
gcaccatggc tggcacatgg catgcagtcg gcacatggtg gatttattac tgtttctcct 28620
tacactgtgc ccacttctag agagtggaga gagaggctgg cttctgcatg ttactcttat 28680
atccactcat tctatggatg ccacagaata ttctagcttt aaaaagagag agatcagtgc 28740
tatcttcccc ttccgggaag gttgtgacca ttaaaaaaat ggttcccata gagatgagga 28800
aagaaagtca ccctacaagt aaaaagtgat ctctgtcagc caggctgttt ctgctgttaa 28860
tttcaacaac acatgggtgt tactctggtc tatgctataa ccgtaatgct tgtgaaacag 28920
atcagcaatg actgacttcc tggtcagacc aaggggctct ctccagtgtg tgaccctgtg 28980
ctcctttccc acagctctgt gcccaggcgc tgaaggatgg ctggaccagg tgagtgtgat 29040
gatggacctg actttcccag ttggcggcag gagagactca ggcagtaagt ctctcctggc 29100
agggagccaa ggagtaaaag gcacccacgg gctaggatca ccctggctca tagggatgca 29160
taagagaagt ttccccttag gccaggctct ttctctaaag gcaggatgtg agtcctcatt 29220
agaattatag gccatcagag ttgaaagagg cttgggagat tgtttatttc gggcactaac 29280
ctagagtaga aatccagtct ttactgtcag taacagcgtt gattcagttt ctgcatgaac 29340
atctccagag gcagcgagct taacttggtg aggcactttc cattctttga gggctttgag 29400
tattaggtgg gtcttttctt ctcttttttt ttttttgag atgaagtttc actctcgtca 29460
cccagactgg agtgcagtgg cgcaatctcg gctcagtgca acctccacct cccggattca 29520
agccattctc ctgcctcagc ctccctagca gctgggatta cagacacccg ccaccacacc 29580
tggctaattt ttgtattttt aatagagaca gggtttcgct atgttgatca ggctggtcct 29640
gaactcctga cctcaggtga tccgcctgcc tcagcctccc aaagtgctgg gattataggc 29700
gtgagccact gcacccagcc aggtgggtct ttaatatcag caaccctttg cttccatgta 29760
atttccagcc agaggtccca gttcccaaga gccaggctgt tcctcttcca cttgagtgcc 29820
ctcctctccc tccaggccac ctcctttcca cactgctcat ctgcacttct cccttctgac 29880
tctcgcctgt gcaggtaaag acctctggcc atcctaagac cttctctgga tgaacctcga 29940
tggttgatga ccctgcatcc tgaaacaggg caggatgcag agggaccatc atctcttttg 30000
acccagtcac tgtgtgtccc tcagcacagc tcacggtggc actttttgcc tgtgacatgt 30060
cacccaggct tcctatctga cttgcagcca ctctggtctc tgagcctcct gctactcagt 30120
gtgtcctgtg gagcaggagc tccagcatca cctgggagct tgtgagaaat gcagcctggg 30180
cctctcccca gacccgctgc ctgggaatct gcattggaac aagatcccct agtgaktcct 30240
```

FIG.3L atgcgttctt aagttggaga ggcactgaat tcttgttaat gcctcagcta aataaaggct 30300
tgaggagtga gaacttgaag gaggcagcat gaagcsgcgg aaagaggtgt tggcatctga 30360
tagaactgaa atcacatctt gccttttccc ctcatccgct gcaagtactt gctgtgtgat 30420
caattactca acctctctga acttcatttt ctctcagtag aaataatatg agctttggtc 30480
ctcctccaag ttgccatatc tcagaaggac cagcacaggg caggattcag agcagctgct 30540
gtaagtgctg tttgccctcc ctctgcatac ccgggggagg ctgcagcagt gtatctggtg 30600
agtcagagaa ggctgtgggg agatttaaag ggtctcttcc cagcacagga agcctggcac 30660
ccagagccta aggccagcca ccctctctgg agcatcacgg atcatgtagt tgaagcctcc 30720
agctggtaca gaagagaaca gcaggtgcct gagaatgtgc ggcactctgc aagctggggc 30780
tctttgcaaa gcagcagggg gacctcagcc aaggaggcgc acagggaggg taggctgctg 30840
ttcgaggggg cagatgctgg cctccccgtg gtggtgtccc ctcctccacc tgccagtgcc 30900
cacactgagg ccagcaacac actcttctga cagcagagtc atagggtgtg gacatagags 30960
cccatgtctc aagagaacag ctggacatcc acagagatta aggagctccc tacaagtgtc 31020
tggatgtggt gtaaaggaga cctctgcacg gaggctccag ccgcactctg ctattcccta 31080
gttacctgat ctcatcactt tccctcccgg aacctcaggc ccctgcactg caggggacag 31140
accatccctg tggccttcct ctcactgagt taattcaaga caaagctctc ctttgtaaac 31200
cagacccttt ccattcagtc tatcacagtg tggcttactc ggcacccctt ttcagccccg 31260
ctctcctctt cagttctcac tgtggctttt ttgttcttaa ttccttttca tggcccggca 31320
aaaacggagt taattatatt aaagacctga cttccctgtc tagctcctta actccaggtc 31380
agcagataat tgagagtcat tgccctgata ctgaatgaag agataaagtt cccaggttta 31440
tttcaagtga cttatctgaa gatgaggaaa gagcaagagg ttactaaaaa acatatctgt 31500
gaattgttga cagagacggt cacttctgca gaaactccag atgccccttgc caagtccagg 31560
tacaggtcta aactagcaaa ccaaatgcat tttctaggtt taaagtaaag gtgggtgctg 31620
atctccagga tgacatgcga agatgccaaa tcatccgaga catgattgga ccggaaaaga 31680
ctttggtaaa tatcctctca caccactaag aagcagtagc ctttgtccag ggctaaatac 31740
aactcgtttc aagattaaag aacattggga atttaaaaag ttaattgtca gaggaagtac 31800
acttctgtag tcttgcagta ggcgagctca aacaaaaata agcaaaggga ctaatagttt 31860
tacgtttttt aattctgcag aactagttaa gtaagtttgg ggttaaggat cctttcttac 31920
taacacagat gtacctgagc aaacagtttt cccattggtg ctctggtgtg tcaatcatgt 31980
aatctcccct cctagctcct caggtaggag ggtgtcaggg ggccattact gaagaaatgt 32040
tggaacttca gctgagataa atgtaaggat cagtcatttc tgatttgtat ttttataaac 32100
cagttcttac gtgtaaaata ttttcataaa gtcacagtaa gatgttttta tgaggctttg 32160
gaggcttttt tgcataagtt aaaatagaaa ttttgagttc ttgacccagg atcactattt 32220
atacatgaat taatgctgct tttttttttt aatgaagtca tctgtatcca aataacttat 32280
gataaaaatt gattctgggc tggccagatg ctgtggctca tgcctgtaat cctagcactt 32340
tgggatgcct aggtgagtgg attgccggag ctcaggagta caagatcagc ctggcaacat 32400
ggaaaaaccc catctgtacc gaaaaataca agaaaaaaaa gtgttagcat tatatggctc 32460
atgcctataa tcctaacact ttgggaggct gaagcaggtg gatcacttga ggccaggagt 32520
ttgggaccag cctgggctac atagcaagac tctctctcta aaagaaagaa gaaaaaaaaa 32580
ttaaccaggt gtggtggtgc atgtctgtaa tccctcctac tttggaagat ggggcaagag 32640
gatcactgag ctcaggagtt ggaggctgca gtgagctaca ataataccac tgcactccag 32700
catgggcaac agagtgagat ccagcctctt aaaaaaaaaa aatccattct gagcatactg 32760

FIG.3M tcctctggtt ttcatagtgt cctgggagag agctcttatc acttagcaca ttctgtagag 32820
atgtccattt ctccaagcac gataagatca gggatgaggg gctgtccctt aagctgggca 32880
cagccatcac ctggcttcca agaaggatag tggtacacag agagccaggg cctaggaggg 32940
agaggactgg acttgaactc accattcact agatttattg ttcttaagca agttactgaa 33000
tttctctgca tgacagtttt cttatttgta aaatgggtta atatgaactg cctcatgggg 33060
ttattattat tattttttga gatagggtct cactcagtca cccaggctag agtacagcag 33120
catgatcaca cctcactgca gccttgacct cccctggctc aggggatcct cccacctcaa 33180
ccccctgagt agctgggact acaagtgaga gccaccacac ccagctamtt twkgtatttt 33240
ttgtagagag aggattttgc tatgttgccc agcctggtct tgaactcctg ggctcaagaa 33300
atccacaggc tgggccagat gcagtggctc atggctgtaa tcccagcact ttgggaggcc 33360
gaggcgggcg gatcacaagg tcaggagatt gagaccatcc tggctaacat ggtgaaaccc 33420
cgtctctact aaaaatacaa aaaaaaatag cctggtgtgg tggtgggcgc ctgtagtccc 33480
agctactcgg gaggctgagg caggagaatg gcgtgaacct gggaggcaga ggttgcagtg 33540
agccgagata gcgccactac actccagcct tggtgacaga gcgagactct gtctcaaaaa 33600
aaaaaaagaa aaagaaaaga aatccacggg cttcagcctc ccagagtgtt gagattacag 33660
gcatgagcca ccatgcctgg ccagttatta taaatattaa atggaacaaa atccataaag 33720
tgcctagtgg agtaggtgtg ccattatggg agagttaagg ctacttatta ttgtgccaga 33780
cacacagtgg gcaatagtca ataaatgact attgaacaaa caatgttgat tgtgcatgat 33840
tcagaatgtg acaaaatggt ttctacgaac agaaccaaca ctgcaagaca catgtatttg 33900
ggtggcatct agatggagat tggaccagag cccagggcca gcgagcactt ctcatggccc 33960
agcccagggc actgctggac atccagtggc tcctcaagca attcacggct cctcctaaag 34020
actgtacctg gagccagagt ccccgtctca gcagctgctc tctggctctt tttgttaggg 34080
ccgtgtgctg ggcctcagca gaggcgttag gggtctcac tcagctgttg gtggcactga 34140
gtgacagcat ttcctccctg ggagccgcag ccctgctgtg aggttggctc agggctgacc 34200
tccctgtgaa gagtctcttt ttgcagatga tggatgccaa ccagcgctgg gatgtgcctg 34260
aggcggtgga gtggatgtcc aagctggcca agttcaagcc attgtggatt gaggagccaa 34320
cctcccctga tgacattctg ggcacgccca ccatttccaa ggtaggaaaa cggctgctgc 34380
tgctgtggca gcttattttt ctgtttagtt ttccagagtg ctggggacag atcctaaaat 34440
ttcttcactt gttccctctt gcatttcctg ttgaagtagc tgaaataatt gtaatgtgtg 34500
acaaatacag gggttacaga cctgacattc ctttttctac ttcagcttat actttgccct 34560
tatttctgtt tgttttagat aaagtaagct gctaaaagtt gaagggctac cagcaatttg 34620
aaggttaata gacatggttc ctatgctttg taaatacaga aatgtgacag catttttttt 34680
ttttgttttt tggtggtttt ttttgttttg ttttgttttg ttttgagata gagtcttact 34740
ctgttgccca ggctggagtg caatggcatg atctcggctc actgcaacct ctgcctcccg 34800
agttcaagca attcttctgc ctcagcctcc tgagtagctg ggactacaga tgtgtgccac 34860
catgcctggc tttttttttt tttttttttt tggtattttt agtagagatg aggtttcacc 34920
acattggcca ggcctgtctc gaactcctga cctcagacca tctgcccgcc ttggcctccc 34980
aaagtgctgg attacaggag tgagccaccg cgcccggcct tgtgttttca tctgataatt 35040
ttttttctcc tacacgctaa ctggtttggc acagtcatgt gccccataac aatgtttcag 35100
tcagtgaaag actgcctata taatggcgca gtatatataa tcccataagc ttataatgga 35160
gctgaaaaac tcattgccca gtgacgttgt agagattgta atgtggtgca acgcattacc 35220
tttcctatgt ttaagtatgt ttagatactg gccattgtgt tccaattgcc tgcagcgttc 35280

FIG.3N

```
agaacagtag catgctgtac aggtttgtag cctgggagca ataggccatg ccatatagcc 35340
tagggcgtgt agtagtctct accatctagg gtcatggacg tacactctat gatgttcaca 35400
caatgatgaa acagcccaac ggcacatttc tcagagggta accttgtcat tcagtgacac 35460
gactgtacat tcatgtggct tatagccaca tcctgcctgc ctaggaacat tttttcctga 35520
ggtgactttg catagctata cactccccat tttgtgttga tcttacacct ttaactctga 35580
tggagcagtc ttggttccag ttctaggagg gacaccttga tgcatcccac ataaattcat 35640
gggttgtact ggaggtgtgg agtcggggac tcagggacca gttctctgtt tctctcagca 35700
aatcagcaca tgatctacat tatgtgggat actctgccaa agcctgggtt tcagaaatgc 35760
cctccccttc cacattgcag cctcgctgga gagaacagcc gagatatgtg aaacaaagac 35820
cggaggatac tgggccaggg cactgaatgc caagcacagt agaaaagttc attgaggaga 35880
acgttgggtg tgggctggga cgagggagat ggccagagct gactccataa ggaaagctaa 35940
gcctcaggtg agggaagggt gagcaggagc catggagcga ccacagcctt cattatttaa 36000
acagagccca aattttctga ggaatcattc cacaatagga atctcaggtg aggagccccg 36060
gggaaacaag acttttcacc ttgggtccca cttgcttttt cctccttagg gctctttcag 36120
gttggctgtg ccctgctgaa tgccagctgg cctagcacca acctgatctc tgcctacctg 36180
aagcatctca caggaagctc ctcagggctc taaccctccc aggttttgct tacatgaggg 36240
aggccatccc cttaggagta tctgaggaag gagcagctgc agagcctgca ggtccaggcg 36300
ggggcagtgg agatgcccca gggagcacag ggcacatgcc agggacaggc tgccacgtgg 36360
ggctggatta tggggtctgt ccactcagag gatgcagcca gtcagagtga gccactgcag 36420
cttctccgat gaaagaacgg catagtggcc aggcatagtg gctcacacct gtaaccccag 36480
cactttggga ggccgaggtg ggtggatcac ctgaggtcag gagtttgaga ccagcctggc 36540
caacatggtg aaacctcgtc tctactaaaa atacaaaaat tagctggtct cgatcttctg 36600
acctcgtgat ccgcccacct atggtcccag ctactcggag aggctgaggc aggagaatgg 36660
cgtgaaccca ggaggaggag cttgcagtga gccaaaatcg caccactgca ctccagcctg 36720
ggtgacagag cgagactcca tctcagaaaa aaaaaaaaaa ttagcagggt gcggtgatgt 36780
gtgcctgtaa tcccagctac tcaggaggct gaggcaggag aatggcttga gcctgggaag 36840
tggaggttac ggtaagccaa gtttgcgcca ttgcactcca gcctgggcga cagagcaata 36900
ctccatctca aaaaaaaaaa aaaaaaaaac acaacagcat agtgacagct gaagcacaga 36960
taatgtgact ggtggctaca tgtagagtcc attgagacag agggtgtgtg ggaggtgagg 37020
aatgggcagg gagaaaccca ggcagggatg ggagcgagga ggcttttcca ggaatctgag 37080
agagagaaag ggagagggca gcttgaatag agcagattca ggaaatattg aaaaggagga 37140
aaaacatttg gcccctagtc tgccatatat gcttaaaatg gtagaacaaa taagtcaaat 37200
ggcctttcct cctccccctt cctccatttc tccctttctc ttctctttgg agataaataa 37260
ccaagagtac ttaaattaga aattttaaga agcataaaat gttggcttga aaaggtgcct 37320
tagagaccat ctgctcaaac taaggccttc tgcagatgag gaggccgagg ctttgggtgg 37380
cacaggcggg gcttgcccaa ggccacacat cccgtgagat gcggggccag caccggaatc 37440
agggatactt ggctgctgag tgaagggatt tttctgctga gaagttggct tagtctgatt 37500
attcagatgc ctcctctggc tctggaatca gtggagttcc aacccagtct ctaccacttt 37560
ctagctttgt gatccaggaa cagttcaaac ccggcacaca gttttatcat tttttataaa 37620
atggggataa cgctggctcc tctcccattg gattgagacc aggaatcatt taagtcagtg 37680
ttttgcacag cacctgacag gtactcagag ctccaaaaat gttagctgtc agtgtgatta 37740
ctattaccct aagcaaaggg aagggaagcc agggaggaac caaggctacc tgtgcggagt 37800
```

FIG.3O agctgtggag tcgcagtcac agtagaggat ggatgggagc gcccagagtc caggtggcag 37860
gtgacggagg tagtgttcag gggccaggtg agaggacaga gagcagcagg gctgtgttca 37920
ggtgcagagt ccagtacctc accaggtgag gactctacca ggtgagcaat ggtctcagcc 37980
taacctgcag attgaggtct gaggccaccc actgagctgg aaggaagagg attttttttt 38040
ttcatggatt tttcctgcct taaggaagag gattttggaa tcaacaaaga catgaggcca 38100
ggtgcagtgg ctcacacctg taatcccaac actttgggag gccgaggcgg gaggggatca 38160
tctgaggtca ggagtttgag accagcctgg ccaacatggc aaaaccctga ctctattaaa 38220
aatacaaaaa ttagccagca tggtggcgtg cacctctaat cccagctact cgggaggctg 38280
aggcacgaga atcgcttcag cctgggggt ggaggttgcg gtgarctaag atcatgccac 38340
tgcactccag cttgggtgac agagcaagac tcggtctcaa aaaaaaaaaa aaaaagatat 38400
gagagggttc tagaaggagg tttctcaggg aggcaagaag aagggaattg atggagtgat 38460
gacccacagg aaggagtcgt ccaaaggttg gaccctgtga gtccacaatg agccactccg 38520
aatagccctg tccttatgcc actgcgcagg ctggagaggg aggtgctgtc cacgttggga 38580
ggagcgcagc tggagcatgg gccgggacac cgcagaagga gatctgcaga gccctggtca 38640
ggaacggggc tggtggyggc agctcagcag tgctcacctt ctcctctgca gatacacaga 38700
gccctcccgc acgcatgtgt tcccctggac atcctttgcc agtcttgagc cttcacatgg 38760
cttaacagca gggccgtttc ctccttcagc tataaatgtt tttaaacatt aggagttgca 38820
gttcaaaact taggaaaata acaccaggct gccttctatt ttataggcac tggtcccatt 38880
aggaattggc attgccacag gagaacaggt gagtgacgcc cccaacaggt ggatgacgtc 38940
cccttggggt cagtacacgc tgaccagtga ccgaggacac agttgtgtgt taggctccat 39000
cacctgctgt actttgagtt gggaaatttt catcatctta gaaactgggt cattttatca 39060
gagtctagag tcagatatag aaaaagtttg tggctatttc tccaatttat atgactaagg 39120
tcaggtatct ttttcaaagt gtctaattga aattgaaaag gcagcaattt aaagttgcta 39180
ttgcaagggc agaaaatggt cttaagaaag ccagctttca aattgaataa acatgactgc 39240
gttcactttt tgagcttata aatgaagccc gagtgcctgc caaaacctgc tgcagtcagc 39300
ccacgagcag agcagcgtga ggagctgatt ctcagttttc ccggcaaaag gagcaatact 39360
gctctgccgt ggttccgtgt tgtcatctgt gccacctgct catcactgtc accgtatttc 39420
atcctgatgc ttcatctccc acttatcagt cgctgtgaca gtcattccct cataaatggc 39480
gagccagtgt gattttgacc tgactcacac tgttgcatta gcagatttgt aaagaagtga 39540
gcacaaggtc cctgcccacg ctataaaagc tcgcctcatg cccagcgaga acaaagaaga 39600
aatacagtct gggcttcctg acggccactg atgaataatt attggcatag agtggctgcg 39660
ttgccaggtt tagagatcct gaaggccaag gctgactctt ctgttggtgt tattttcaat 39720
tctatttcca gtgccacaat agagtgatat ttaagcaact cctacaggcg aaggccctgc 39780
agttcctcca gattgacagt tgcagactgg gcagtgtcaa tgagaacctc tcagtattgc 39840
tgatggccaa aaagtttgaa agtaagcgtg ctgcagcggc tgcagaccag accttcattt 39900
ccccactaat cagacacctc ccttgatggt ttgcaattca catgcatggg agtctgtagt 39960
ttgccatttc gattttttc taactctcat ttagctttaa tccgggaatt tttgatgatt 40020
ttcatcttgg aatttccttc ctaaatatta ataaatgatt taatcacctg tgggcaataa 40080
gaaaaaccag aaagttccct ttcacccctt cctctccctg ccctactctt ggtattaaat 40140
agaaacgatt tccttttagt tcctgtttgc ccccatgctg gtggagttgg cctctgtgaa 40200
ctggtgcagc acctgattat atttgactac atatcagttt ctgcaagcct tgaaaatagg 40260
tcagtaatgt ggcattaata ctttctgttt cagtagggtc cytcaatcca ggccagagct 40320

FIG.3P tgtaaattct gccttcatga ccagaacaca ctaagacctt gtctgctggc atgtcctata 40380
actctcaggt ggagttggtt ttgctttcac agagacccac caatgaacgg tcattttgcc 40440
tcctaagata gggtctggta gctgactcac tttatttttt aagtacattg aaggtaagct 40500
tgcagccaca ctactccctt aaccagctcc tgttttcatc acgtgtattc tgtacttctg 40560
tcccatctcc tcttcccagt actggagtct tccatggtct agacacacat ttatttcatc 40620
ttatttctca gaacgcccca ggtgggcttt taaattagga caatctcctt ccagtcatct 40680
gcacacgtag ggttttgctt attccacttt tcttgtctcc tggaattaaa tgtctcacag 40740
aaagatcact gcaagtatat agcaaaggca caaaagcatt cactgggaaa gggaaacacc 40800
aaattcagga ctgagagtga taaatgggac ccttgagggt acataggagg cttcagtaat 40860
aatggtaacc gtttttctct tcaggggggt agtgagtaga caggtgctgt cttttaatat 40920
agccgaacta ttttatactg tattagtcta ttcttgcact gctataaaga aatacctgag 40980
actgggtaat ttataamgaa aagaggttta attggcttac agttctgcag gctgcacggg 41040
aagcatagcg gcttctgctc agcttctgga aacttacaat catgatggaa ggtgaagggg 41100
gaacaagcac ttcttatggc caagagcagg aggaagagag agtgaggggg gaaggtgcta 41160
cacactttta aacaacagat cttgtgataa ctatctcgaa cagcaccaag gaacgggtgc 41220
caaaccattc atgaaggacc acttcccatg atccaatcac ctcccagcag gccctgctgc 41280
caacactggg gattacagtt caacatgaga tttgggcagg gacacaaatc caaaacaaat 41340
ccaaaccata tcagcctgcc tgtcacagct gttcaataac aggcgatgga agtcaggcag 41400
cagagctcgg tcacttgccc caagcctcag aactacaaag tggctgacgc agaacctgaa 41460
cacagattga cctgattcta aatcctctgc tcttcatcta aatcatttgt atagctgaaa 41520
ggaacctcat ttggtgattt tattttttgg gtggggagta tggaatgtat tttattgttc 41580
tgcatctggg tttgcttcct tagatgtctt ggttcttgga tggaggtggg tgtgtcccac 41640
ctccctcagt tgtggtccca tggacctgtt cggattgttt tccaggtaca aagtgtacca 41700
agaaagcctc acagtgctaa tgcttcctag atgcccagct gaggcagtga caaaatggcc 41760
ctcccaaccc tacctgcttt tttaaaaccc caagcccctg gcagctgctg cagccatatg 41820
aaaaaataca wacgcttctt gaaaaataga tcacaaaatg tggtgatttt aatctattca 41880
tctgactttt gaccagagga acccaaataa ttctggatat ttacagagtc tgaattgatc 41940
ccttttaaag ggcaccacaa aacctctaga gggacttcgt gtgttcatgt catcaaagtc 42000
cccacctcac attgctatat tttagaagaa aaggacctga ggcacagagg tttagggact 42060
tgcctagaaa cgcatggtaa cacagctaag ccttggccaa cactgtcaat tgagtggtac 42120
tcgctccttc tgctttaagt tagcaccacg tgaataatct gacttcaggc atcattgccc 42180
cgatctgatt ccctcctcct agggtgtgtg agtatgttga ccacctgcat gagcatttca 42240
agtatcccgt gatgatccag cgggcttcct acatgcctcc caaggtaagc tgtgcctgag 42300
ggcccctgtg agaagagatg ctgccagcca ctgccacgcc tgtctcgtga actagactgt 42360
ggagcaccaa gctttgactc ctgtttgttt gcaatatcca ctaacaaacg gttcttcagt 42420
ttgtctgtat caaaatcctc aggcctgagg gccagggctt ggaggttcaa ttgcctctga 42480
caaggcttct gtaatactag cctttcctca ctagtggaga tcttaacatt tgcactcctt 42540
gtgcaaaaaa acctggcacc atctagcaag ttagtgacct aaaaagtttg gactacaatt 42600
gtgtrgctgg ggccatttat tctgatcatg ttcaagagat catggctcat tttcaccaac 42660
agaggtcaaa ctattatcaa agagtttgat gagttaacta actctggcaa gtagccagta 42720
aaatatgttc ctctgcccta ttatttccaa cagtctccaa acttatttta aaaatattaa 42780
ttcagggctg ggcatggtgg cttacgcctg taatcccaac actttgggag gctgaggcag 42840

FIG.3Q gtggatcatt tgaggtcagg tgtttgagac cagcctggcc aacatggtga aaccctgtct 42900
ctacaaaaaa tacaaaaaat tagccgggca tggtggcagg tgcctgtgat cccagctaca 42960
tgggaggctg aggcaggaga atcacttgaa cctgggaggt ggaggttgca gtgagccaag 43020
attgcgccac tgcactgcag cctgggcaac ggacagtgac tccatgtcar aaaaaaaaaa 43080
attaattaat tgcctctggc ttagacgtaa aagcatttct tggagcagca taaatgcata 43140
aaatctgttt ttgttccagg tggtkgttaa caggactcat ttttttggtc tttgatagga 43200
tcccggctac tcaacagaaa tgaaggagga atctgtaaag aaacaccagt atccagatgg 43260
tgaagtttgg aagaaactcc ttcctgctca agaaaattaa gtgctcagcc ccaacaactt 43320
ttttctttct gaagtgaaag ggcttaaaat ttcttggaaa tagttttaca aaaatggatt 43380
taaaaaatcc taccgatcaa gatgagttca gctagaagtc ataccacccct caggaatcag 43440
ctaaagcaac atgttgcata acttgttgga ataattcctt gttctgttta acacttgtca 43500
taaattagca gaataaaaat agtcgtgcaa caccgggggt atctggtatg caacgaaggg 43560
aaaaatattt cactgattaa ccccgaagtg gttttgcatc ttttccttgc ttaatctaag 43620
catattatta gagaagtcac accatgctga agctaatgag ggcaaaatsg tagtccatag 43680
attattttaa aataaccctt taaggttata aaagtttaaa aaaaaaaaaa aaaaactcta 43740
tcctaaatgg tcattatatt ttgaggataa gatgcagtta aaatgagaaa aatagggcaa 43800
aatatattca ctattatttc taaaatatac tcttttaagt agcatccaaa ccagaataca 43860
gcacatgttt acttaaggag agttctttaa tctattttag gaaggaactg agcagataag 43920
tggcagtaca gaatgaacaa agcgtggacg aatgcagaac acttctttat tatagcaaca 43980
tataaaacaa ctataaagtt cataaccaca ctctacatca tgatcgatgg tgttactcag 44040
ctccctcaga tttgagggaa tagcttgtga aattcttaaa atattctaaa aatattccaa 44100
aaatagcttg tgaaattcac caaccttctt tataagtacg tgggattgaa atgcacatac 44160
atgtttttgc taagagcaca tacatttcat tctcctcact ttgttcataa cctcagcatt 44220
gtcagatacc ctcagtgagt taactcaaag ccttttatta tggaaagaac tggcacagtt 44280
acatttgcca gtggcaacat ccttaaaaat taataactga taggtcacgg acagattttt 44340
gacctagttc ctttttcttt tagagcaaaa agaactttta cctcggcatc cagcccaacc 44400
cctaaagact gacaatatcc ttcaagctcc tttgaaagca ccctaaacag ccatttccat 44460
tttaatagtt ggatgcggat tgtacccttc aatctgaaag tcttcagctt tgaagtcatc 44520
aattttctca acttttcgaa gaatcctgag ctttgggaaa ggtctgggtt ctcgctgaag 44580
ctaaaaacaa aataaggcca ttattttgcc ataattgtac gacctgttgt aattgctcct 44640
catgtccatg aaacaagtac acaggatgtg atcaacaaag ttctatttta caggagtatg 44700
atcctgtcga taccttgccg taggttatgt aacatgattg gagcgcaacc agctgttctc 44760
ttgcacagat cgagagtgag gggtattttg tgacattaca cagcatcagg agcctggtgc 44820
ctcatcaggt gtaagttctt ataaccacty ttggcaaatt tattaaagac aggaacacag 44880
tcaatctgta actcatagta gctctacgtt tacttgaatt ccacaatccc taacccatct 44940
gtccctggca gaaagaagga aagatgacat gcatggacag tgaacagaaa gggatgaaag 45000
ccaggattcc tgggatgaac agacagtggc aattaggatg tgaagacagg tcacaaccta 45060
ttactatgtc taaaaatgac cagagcagag agccagagag aataagcctg aagtcacctc 45120
cactcaaaag cagccaaact ccctcaaagg aataactttt aaaacctgga tctaacctgg 45180
aaggggctaa aaagtgtctg gttctgagtt tttttcctta aggctcatga agcagatgaa 45240
cttacatttt tattgccatt tcatatcaat tgttggctgc tataacttca gggatttcaa 45300
cagacttttg aagtttggac ctaaatattg tacttaatgt aaaattaaca aaaaatattt 45360

FIG.3R atggccaggg tggtggctta tgcctgtaat tccagaactt tcggaggctg aggcaggtgg 45420
wwcacttgaa gtcaggagtt tgagayyagc ctggccaaca tgacgaaacc ccatctctac 45480
taataataca aaaattagct gggtgtggtg gcatgtgcct gtaatcccag ctacctggga 45540
ggctgaggca gaagaattgc ttgaacccgg gaggtggagg ttgcagtgag ctgagatcgc 45600
accacggcac actccagcct ggccgacaga gaaagactcc atctcaaaaa aaaagaaaag 45660
gaaaaacatt tgcacttcaa ttctccttca agttaaaatg agttaaaatg cctcct

FIG.3S

```
ctgggtgcag tggctcatgc ctgtaatccc aacactttgg gagcctggtc tggaggatcg 60
cttgagccca ggagttcaag ataagcctgg gcagcaagac gaaaccccat ctgtacaaaa 120
attagctggg catggtggtg cgtacctgtg gtcccaacta ctaaggaggc tgaggtggga 180
taactgtttg agtccaggag gtagaaactg cagtgaactg tgattgcacc actgcactcc 240
aatctgggtg acagaatgag accctgtctc aaaaaaaaaa ttagaaataa gacttagtaa 300
aacaataaaa gctaaataga taatatgtga aatttatcca gtagcaggaa tggtccctgg 360
gacctttaag aagcagatgg cggtattcaa ttttaagttg cttgcagagt ccttgctacc 420
ccaaaccttc ctgcaaatca gctacacata acggtgagtc agtgaccttt aggaaagaaa 480
agggattggg gtcacggcca gaggtacaat gacaaggtac aaacaaggat agggatggat 540
ttcataacct agtttaaacg cagtggggaa ataaattcag gaaataaatc aggtaagtag 600
gagaaaagtt caccaagtac ttggagagac actggatttc acagggacat ggcgtagggg 660
ttcaatccag cttcacttct atcttaaagg tcaagttaac gagtaagttg gaggactttg 720
aaaatccaag taaaaaattg tcactagcct gtgacaatag ggatgagaga aataaaaact 780
tcgcagttgg ccaaaaaggt tgacagtgat tctaataact gaattaaagt ggtgtggccc 840
ttaaagttta tcaaattcca tttattcact cataattgca ctattttcat ggaaagtctt 900
agtctcctaa aacattgaga ggatatacca cggaactaga tggcaaactt ggtttggttg 960
gtttttgtaa tctttaccat tgctagaaag ttagaaaagg gtggcttcac ttcagcagaa 1020
attttgaaaa attcgtggaa ccagaagaaa cccaatctaa aagaaataca agagaacatt 1080
ttcgcagagt tttaagtgca atttcaaaga aaattcaaac ttagaatcaa attcaaagag 1140
gaggcagcac cccaaagcaa catttttgt tttattgagg tataatttac atacaacaaa 1200
gctcaccatt ttaagtgtac cactagatga gttgttgaca aatgtagaca gccatgaaac 1260
caccatgaaa ccagaatcat agaacatttc catcatttca gaaaattcca ttatgccctt 1320
ttacagtcaa tctcttccat tcacccctga cctctgtcaa ccactgagtg ttttctgtca 1380
ctataattgt acatttctag ggctttatat aaatggaatc atatgtagtc actgtgtctg 1440
atgtctttcg tttagcataa tgcttttgag atctttttat ggctcagtaa tattccattg 1500
tgtggatgtg tactacatct tggttttgtc ctttaccaat tgatggatgt ttaggttgtt 1560
actagtttta ggctatcaca aataaagctg ctatgaacat tcaaatacaa gtttttattt 1620
taaacatagg ttttaaattc tcttggataa ttacctatga gtaggattac tgagttgtat 1680
gatacatgaa tgcttaactt tctaagaaac tgataaccta tttccaaaga agatgtaccc 1740
tttcataccc ctccagcaat gtatgagagt tccagctgct tcacatcctt gccaatactt 1800
ggtattgcca gtcactttaa ttgcagccat cctggtgcgt gttagtagta catcattgtg 1860
gttttagtgt gcatttccct aatgactaat aatgttgagt cttttcataa gcttatttca 1920
aattcatatg tctgcttagg tggaatgtct attagaaagt cttttgccca tttttttatat 1980
caagttgcca tcttactgag ttgtaatttt ttcagtattc tgcatacaag tccttttaac 2040
agatatgttt tgcaaatatt tttcttccaa tctgcagctt gcattttcat ttctttaatg 2100
gttttcatca aagagaaaac atttttaatg ttgataattt aattggcaat gtttttcttt 2160
tatgattcat gcttttagtg tcctaagaaa gtttgcttta tccaagtaca aaaagatttt 2220
ctcctgtgtt ttctttagaa gttttgtaat tctagctctt aaaatttaga tctatattcc 2280
acttcgagat gatttttgtg tatgatataa ggtaatgatc caggattgtt ctgtttgttc 2340
ttatggatat tcaattgttc gagcaccagt tgttggaaag actagcttac tcgttgaatt 2400
ttcttggccc ctgttttttt tttgttgttt ttattttgta gacggagtct cgctttgtcg 2460
cccagcctgg agggcagtgg cgcgatctca gctcaccgca acctccgcct cccgggttca 2520
```

FIG.4A

```
aatgattctc ctgcctcagc ctcccgagta gctgggacta caggcgcgtg ctaccacgcc 2580
tggctaattt tttgtatttt tactatttca agacctcttc tgttccattg atctacttgt 2640
ctgtctttat gtcaatttca cattgactcg attagtgtat agcaagtctt aaaaccaagt 2700
agtttaagtt cttcagcctt gttctttttt aggattattt tggctattca aatttccata 2760
taaattttag aatcaacttg gtccaatttc ttcaaaaaaa tcctgctagt gatttagatt 2820
agattgcatt gaatttgtag ttcgatttgg gaagaactgc tattttaaca atattgagtc 2880
ttccaatcca agaatatgaa tttctctaca tttctacatt tctttagatc tttttttctc 2940
agcaatgttt tatagttcag tgtgcaaatc ttgcatattt ttgttaaact tgtcctgttt 3000
tatattttca atgcaattgt tttaagagat acngttttct aatttgtttc caatttttta 3060
ttactagcac atcaactata gattttaaat tgaccttgta tcctacaaac ttgctaagct 3120
caatattagt tccagtagct tttttcgtta agtccaatga agacagtttt caacaaagat 3180
gaataatcat gtcatccaag aataaacagg tttacttcct tttcaatctg ccttttattt 3240
cttttcttat tatattaccc taactagaac ctgcagtact atgttgaata gaagtggtgg 3300
aagcagacat cctttccttg ttccaaatct taaggagaaa gcatcaatca ttcaccataa 3360
agtcagtttg tggctgtttc tatcttctga aatagattat agagaattgt tgtaatttct 3420
tccttaaatg tttggtgtaa aattcaccag tgaaaccatg gacctggtgc tttttgtttt 3480
tggaaggcta ttatttattc aagttattta atagatatag gcctattcag attgtccatt 3540
tcttctcgtg tgaattttgg cagattgtgt ctttcaagga attggtttat ttcatcncag 3600
gttatcaaat ttgtggacat agaattcata gtattccttt attatcattt taatgtccgt 3660
cggatctgta gtaatgttcc ttattncact tttgatatta gttatttgcg ttctcttttc 3720
ttgcctggnt agaggcttat tgattttatc aatgttttca aagaaccagc tttkgttttc 3780
attgattttt ctttgttgct ttcctgtttt caatttcaca ggtttctgct ttaattttta 3840
ttatttcttc tcttctgctt actttggatt ttctttttat ttctttttat ttatttattt 3900
ttgagacaca gtctcactct gtcgcccagg ctggagtgca gtggtgcgat ctcggctcac 3960
tgcaacctcc gcctcctggg ttgaagcgat tctcctgcct cagcctcccg agtagctggg 4020
actgcaggcg cccgccacca cgcccggcta atttttgta tttttagtag agacggggtt 4080
tcaccgtgtt agccaggatg gtctcgatct cctgactcgc catctgcccg ccttggcctc 4140
ccaaactgct gggattacag gcgtgagccg cccagcatyt tttttttttt gagtcggagt 4200
cttgctctgt cgcccgggct gcagtgcagt ggcgcgatct cagttcactg caagctccac 4260
ctcccgggtt caggcagttc tgcctcagcc tcccgagtag ccgggactac gggcgcgcac 4320
caccacgccc tgctaatttt tgtttttagt agaggcggga tttcgccgta ttggccaggc 4380
tgatttcaaa cgcctgacct caggtgatcc gcccgcctcg gcctcccgaa ktctggatta 4440
caggctgagg cacggtacgg gacctcatct gcatcagtac gggtgtaatc aatgatgacc 4500
tgcctcttaa tttatcaggt ggcaaactga ggctgtgggc actgaaagag acctagcatt 4560
ttctagggca ccgctctcct gggtacgctg gcgacaacca gcggcctcgg cttgggagct 4620
gagccactgg ccggaatctg ccgctgagcg aatgcactcg ctcagacccg acttctccct 4680
ctagggcgcg gctcccgggc aggtcccttc acgagtcttc catccgagca gagcagggtc 4740
ccgcggaggc gccgaccggg cgcgaggcct cctgcctgcc caggttcccc ggcgaccctg 4800
agcgaaccct ctcggggtca gctccgtcta ggctgagaag ggaacggcgg aaggcggagt 4860
gcgcccccgg gagcccggag ctgggactgc agctcccatg ggccaagtt cacggggtgc 4920
ggccgcgcgg ccaatgagcg ccctctatgc cctgacggtg ccccgcctcg cggcgctgcc 4980
ggctcccgcc ctcccgccct cccgccgcgc gctcgggatc ccgaccagtc ctgaccgcac 5040
```

FIG.4B

```
gggggccgcg gccacggggc gcaggggcca tggtgcgcgg caggatctcc cggctctcgg 5100
tccgggacgt gcgcttcccc acgtcgcttg gggccacgg cgcggacgcc atggtaagcg 5160
cggacgccat ggtaagcgcg gacgccatgg taagcgcgga cgccatggta agcgcggacg 5220
ccatggtaag cgcggacgcc atggtaagcg cggacgccat ggtaagcgcg gacgccatgg 5280
taagcgcgga cgccatggta agcgcggacg ccatggtaag cgcggacgcc atggtaagcg 5340
cggcttgcgg cccgggtccc tcccgccccg actgcagctc tgcgggcccc gggcagcttc 5400
ccgacttcga acccattgct tctgtaaagt gggaggcgcg cctgggggag acactcgctt 5460
ttcatgcctt ggagcaattg tataagtatc cagaaacttt ccactctcct gggtttttc 5520
tttgctggag tttagaatat cctggtttta cttttacgac tcacattttg ctggaaatgg 5580
tagaatgcat aataggcaat agcagcaaaa tgattttgtt gggttcccgc cagtggaaac 5640
cctagagcac agtgctcgct ggcttcctct gtaccctgaa cgcgacgggg ttggcgctga 5700
gggagaacgg gaagcccggg gctgggagtt ttgagtggtg atcccgcttc cacaacttgc 5760
tgtgtgactt ggagaagttc cagacctctc tgggtctctt ggacccgtct gtgtaatgaa 5820
ggtgtcacag tcgggttgag aaaccaagcg cgtgctaact gcgtcacatg agagggcgct 5880
ctcgtgaaat tacccgcaaa cacgcttaga aaggactgat gcaaatgtca gttcgtctta 5940
agagatgtaa taaagtaagg gcaggaactc tgactcctac ctaaatattg aaggtctttt 6000
ttgcttactg agggtgttag aatgtcaggc cttccctccc ctgcccccgt ctagagcggt 6060
gtttcccaaa tacagtgggt tctgtgcagg gttttcaggg agcctgttcc ccactgggtc 6120
ctcactgccc gtcgtagtcc actgatgaga ttggccgcgc tagaaaagca gagttgtatg 6180
ggtatgtagt gaatgtgtga aagtatgctg ggaagtgagg aacggcaatg ttaggaaaat 6240
ggttaccagt agggagggaa ggaaatgggg tcacggaggg gaccacgagg tctctaattc 6300
ccattgtaat gttttacttc ctaaattggg tggatggcaa gctggtgtcc attacattat 6360
ctatactctt tttgtacctg aaatgtttta taaaaataga tctctcgtta aagttattaa 6420
atgcaaaaca atgtcctttt tgagattaag ttcatcctgc atttttaaat ttttatttta 6480
ttctatttta tgttttaaat ttatttattt atttattttg aggcagggtc tcttatctgt 6540
tgcccaagct ggagtgcagt ggtactatca tggctcacag cagccttgac ctccctgact 6600
caaccaatcc tcccacctca gcctcccaag tagctgggac tacaggtgtg caccatgatg 6660
cccagctact ttctgtattt tttgtagaga cagggcccag gctgtcatcc tctttaaaat 6720
cttcatgttt cctttcttac atgatgttgg taaataactt aaacacccag caggcaatcc 6780
tttatggaac tcaaaataaa tgttggaaat tttactggct tatagaatcc aaacactcga 6840
tctcatgcaa ctgcctttgc ctctgtgaag ctttagcagc tgtggctaag tcacacaatc 6900
tttctaagcc taggtttctc atctgtaaaa tgggtataat aatattcact ttatacatgt 6960
aaatgagata cctgtaaaga gcctggctca gagaaggccg tcagtaaagt tggctatagg 7020
ccaggcatga gggctcacac ctctaatcct aagtggaggc ctaggcaggg ggatcacttg 7080
agcccaggaa ttcaattaca tgagctatga tcatgccact gcattccagc ctgggcactg 7140
gatgacacag tgagaccctg tttctaaaga aaaaaggagg ggtggctgta attactattc 7200
actctgagga aactgaagca gaaggaatcc ctaatctaga cttgactttg aatttgtgaa 7260
atgttaagac agcctggttt ggctgagacg tggtggttca agcctataat cccagcactt 7320
tggaaggcca aggcaggtgg atcgcttgag cccaggagtt cgagaccagc ctgagcaaca 7380
tagtgagacc tcgtctcaac aaaaaaatac aaaaattagc tgggcgtagt tgcatgcacc 7440
tgtggtccca gccactcagg aggctgagkt gggaggatct cttgagtcca ggaggtcgag 7500
gctgcagtga gctgtaattg tgtcactgca ctccagcctg ggtgagagag agagaccctg 7560
```

FIG.4C tctcaaaaga cagcctggtt tactgtagaa taattcaaga aatggaattt gcctctgggc 7620
ctgagtgatg tctaacacag ggtaaggaga cattatctaa cacctgtatt gcaagctcat 7680
aaatacttaa gcattttatc ttggggagat agggtgtatg ttgtgtgcca gctctcaagt 7740
gccttcttat tagaatgagc tgttttgcag ttcaccatgg agatggcttc acatgccctc 7800
gaggcatgct ggaccatcag cacttagcaa agtgagcctc cctgatcaga agtaggatat 7860
tttcaagaaa gagcaataaa gctgtcctcc aaaatctgct aaagactcct gctttttttt 7920
tttagacaga gtctcgcttg ttgcnccagc ctggagtgca gtggtgcaat ctcatctcac 7980
tgcaacctct gcctcccata tgcaaatgat tstsgtacct cagmctctgg agtagctgtg 8040
attacaggtg tgcaccacca cacctggcta atttttgtat ttttggtaga gacggggttt 8100
caacatgttg tccaggctgg tctcgaactc ctgagctcag gtgatccacc tgcctcggcc 8160
tcccaaagtg ccggattaca ggcatgagcc actactccgg gcttacctcc ttcttaatct 8220
gaaatctact tctgttcctt tcttctctgt gaattgccct tgttatttct ccttcagctg 8280
tccttaccct cagatacgtt ttccgctgtc ggccgcctct tcttcgtgtg ctctctcccc 8340
tcgtggcctc ctgcctttct gacagctcct tcttcctcca ctggcccctt cttccctctc 8400
tgaggctcag gcctcagtgt ctttccggtc tccctacaca ctcccatgaa gaccctctcc 8460
acattctgac ttcggtgcca ccctttatgc cggagactcc cagatctcat ttccggatct 8520
gcctccttaa cttataggtc tggatacttc ctgtttggtt tttcaccttc atgctaaacg 8580
cagtttgtct aaatcggaag tcaacttcca ttctctgccg cccctccctc ctgacccatg 8640
ttggatcatt ccgctaatca cagggaccca aaagcttcga gtcacttttg gctcatctcg 8700
tcctgttgac cctcatctga ggcttcagtg caaggtttcc tttttccatt gcttcctctt 8760
cttggaaccc agaaactgcc gatgggtctt taattcttgg agtctccttc tcagcctcat 8820
cgctcaactc cttcaggaac ccaatggctc agccaaccca ggtgggcacc aacacttgaa 8880
tacactccag tctctccctc ttctgacccc tttactttct gcactgctgc tgctgctacc 8940
ttgcctgaga tattcctccc tcccagactc ttcactcccc ttcccactgc tgaggagctc 9000
cccttccttg accggccagc tcacattctg tcttcatcat aaagcgctct ccctcttcaa 9060
gaagcacatt cagctaacag cgctctctgc cagtcgttca tagtttgcat ccctcccagg 9120
ccttagcatt ttctgcctta tattattaag gttttttttt aaccatgtct ttttatttat 9180
ttattttaga gatggggtct cgctttgttg cccaggctag tctcgaactc ctgggctcaa 9240
acaatcctcc tgtcttggcc tcccaaagtg ttgggattac aggtatgagc cagcatgccc 9300
gttctataag caggtcttct caaatgtaac ctcctcaagg gcagacgtat ctgtaacccc 9360
ctagcaagct gcaccagctc tgacacgtac ttggtgctca gcgatgcatc acactgattt 9420
cctgccactg gactgtgata ccagactcag ggctcccagc catcacatac agctccctca 9480
gccacgacac cccaatacag ggatttaaaa tctgccttca taatttactt gtggccgggc 9540
gtggtggctc acacctgtaa tcctagcact ttgggaggcc gaggcaagtg gatcacctga 9600
ggtcaggagt tcaagaccag cctggccaac atggcaaaat cccatcttta ctaaaaaaaa 9660
aaaaaaagct ggtcatagtg gtgggtgcct gtaatcccag ctacttggga ggctgaggca 9720
gaagaatcgc ttgaatccag gaggcagagg ttgcagtgag ccaagatcat gccactgcac 9780
tccagcctgg agaacagagt gagagtcagt ctcaaaaata ataataataa taataaaaca 9840
ttatttactt gtggtgtgac cttttgtaaa ttactaaagc tccttaaaac ttcatttcct 9900
ctttaataag gataagagca cctactttat aatattgtta taagattaaa ttaaaccatg 9960
tggagctctt agaatatagt gtgtctggca caataaatat tatagaataa taacagtaat 10020
aaattttcat agccttatgc acaattcttc tttatgaatg cattcacatc ttctgcctgg 10080

FIG.4D

```
cttttggag tctccattat tccatgacat agaacaaaac aaaaaatgag tgaattaatc 10140
tcgaagcttt acttcttcat tttcccccac tggtgtctga acttttgcca gtgtattttc 10200
agccctgcta taaactgcta taagtgagat cactccaatt ttatgcaaca gttttctgaa 10260
cctttggctt gttcaatttg aagctgcttg tgaatgtaac tttgttcaaa aagctgacag 10320
agatagctgc gagtgaaaac tccttggctt aaaattgagc cccttccggg catgatggct 10380
catgcctgta atcccagcac tttaagaggc ccaagcgggt ggatcactag agctctggag 10440
tttgagacca gcctgggtaa catgcaagac tccatctcta ttttttttatt taaaaaataa 10500
ataagtaaat aaaattgagc ctcatttttt aacctaattg aaaatgggtg ataaaaatgt 10560
atacattgcg accaggtgcg gtggctcaca cttgtaatcc cagcactttg ggaggccaag 10620
gcaggtggat cacctgaggt caggagttca agaccagcct ggccaacatg gtgaaacttc 10680
gtctctatta aaaatacaaa aatcagccaa gtgtggtggc acatgcctgt aatcccagct 10740
acccgggagg ctgaggcagg agaatcgctt gaacttggga ggctgcagtt gcagtgagct 10800
gagatcgcac cattgcactc ctgcctaggt gacagagcaa gactctgtct caaaaaagaa 10860
aaaaaaaaaa atatatatat atatatatat atacatacat tgctcttgtt gaaacatttt 10920
ggatctttca ggaggacatt ccttttctcc attcagagcc ctttgttttc tttggggtat 10980
agcaacagtt ccttctatgg gagctcttgt ggcacggccc ctgtggcatt gtctgtcctc 11040
atgtgacatc attctcatgg ttcttttcgg gtttctcaca ctggcattgt ttcggcgggg 11100
aactcctctc ctgcagcaca cggaccctga ctactcggct gcctatgtcg tcatagaaac 11160
tgatgcagaa gatggaatca aggggtgtgg aattaccttc actctgggaa aaggcactga 11220
agttggtgag ttgaagattc tctcgaggtt ccagaatgct taattttcag atgagattct 11280
aatttagatt cttagattca ttagaatctt gatttagatt gagttctgat cttgttttta 11340
tctgtattta cactgctcaa agtgagtaaa aacagtgttt catggtttgt tacttgtttc 11400
actgggagaa atttaaaagt gacagaattt ggcctctctc cttgcaatca tctctagcct 11460
gttagaaaat ccttggctgt tagtctgttt ctctgtgtca aatgacagct acaagagtgc 11520
ttttcacctg cctttcaccc ggggccactg tcgagctttg acaacctgta gtgggcgagt 11580
aaccaagggc aatgagaggg aggagacatg agttcccata gcaaaaaagg ctcattgtga 11640
tgtgcacagc aagtctactc gcttttcaat atatatatgt atatattttt gagacagagt 11700
ctcactctgt cgcccaggct ggagtgcagt ggcacaatct cagctcactg caacctctgc 11760
ctcctgggtt caagcaattc tcctgcctca gcctcccgag aagctaggat tacaggctcc 11820
caccaccatg cccagccaat ttttgtattt ttagtagaga cagggtttca ccatgttggc 11880
caggctggtc tcgaactcct gacctcaaat gatccgcctg tctcagcctc gcaaagtgct 11940
gggattacag gtgtgagcca tcacacccgg ccttttcaaa atatttcaca ccaaatcggt 12000
ttcaagttca ctattttcat ggcgaaaagg gctttggccc cgcccaatct cggaggtctc 12060
ccttggggaa gagcagattc tttaagatgc atactgagcc gtgtatacgt cattcttttt 12120
ttatttgcat tttctatttt cttaaacaga agacacagaa cataactttt ttcagagctg 12180
gatgtgatct caaatggtga tcttgagccg tctcattttt tagagagaag aaaactgagg 12240
cacagacagc tacccagcaa gtcatggcag aaccacctga ctgcccagag cactttctct 12300
tcagaacttt taaatgcaac tctttttgaa tacataatac ttacacatgg tacaaaattc 12360
aagaagtcca aaacagtggc cttcgccaga tcaatttcag tggattatta gagcctgaag 12420
ccaaattatg atagattgaa gggtaagggt ctagaaggag ggaaaagagt ttctctaact 12480
tcggtggtag tgtgatacct ctcccttgga tatttgcacc atcagcgctc tcagtagttg 12540
tagaaaaaaa tcttggccca ttgagagatt ttaaattgtt aagcatataa aagaagtgtg 12600
```

FIG.4E

```
tgagtttgtg aatgtgtgta tgtgcgaatg gcaagggaac cttccttgaa ctttcaatgg 12660
acactgccca ggtggctgct gttactgctc ttcacagggc tggcggtcag ttgtccagca 12720
agtcagtcct tctgcagact tctcctgagt gctgccatgt atcaggcacc aaagtaattt 12780
taaaaagaga aagataggcc gggcgtggtg attcaggcct gtaatcccag cactttggga 12840
ggctgaggcg ggcagattgc ttgagtcaag cagttcgaga ccagcctggt caacatgctg 12900
aaaccctgtc tttactaaaa atacaaaaat tacctggccg tggtgatgca tggctgtaat 12960
ctcagctact caggaggctg aagcacgaga attgcttgaa cctgggagtt ggagtttgca 13020
gtgagccgag attgcgccgc tgcactccag cctgggtgaa aaagcgagac tccatcccaa 13080
aaaaaaaaaa aaaaaaagat acagaagaca gaatcccaca tacaaggagc acacgaactt 13140
attggggaag tagacataaa agaaatgatc atagtgcagt ctgagaatta ctgtttttta 13200
aaactatgta caagttttac agagagagga tatattaggc tgttcttttt tttttttttt 13260
tttttttctt ttctttttgg aaacaagagt cttgctctgt cgcccagcct ggagtgcagt 13320
ggcgcaatct cgctcactac aacctccacc tcccgggttc aagcaattct tatgcctcag 13380
cctcccgagt agctgggatt acaggcacac accaccacgc ccggctagkt tttatatttt 13440
tagtaaagat gaggtttcac cgtgtttsgt caggctggtc tcctgacttc aaatgatctg 13500
cccaccttgg cctctcaaag tgctaagatt ataggcatga accaccactc tgagccaggc 13560
tatttttgca ttgctataaa ggagtacgag agactggata atttataaag aaaaagaggt 13620
ttaattgcct catggttctg caggttttac agaaagcatg atgccagcta ctcagcttct 13680
agggaggctt caggacactt acaatcatgg tagaaggtga agggggagca ggcacgtcct 13740
atgtcgaaag gatcaagaga aagggaatgg ggaggtgcta cacactttta agtcaccaga 13800
tctcacgaga actcactcac tatctcaaag acagtaccaa tgggatagtg ctaaaccatt 13860
caggagaaat ccacctccaa gatctaataa tcacctccca ccaggcccca cctccaacac 13920
tggggattac acttcaacat gaaatttgtg cagaatgtct aaaccatctc aggggggtaac 13980
ttcactctgt ccaaaaggct cagggaaggc ttcagagcag aagtaatgct ttgaggtgag 14040
tctcgaagag caaacaggaa tttgccaggc agagaaagac catgctgtga gtcagtcccg 14100
cttttctcca ttaagtaaac aatttactgt taaagttttc cccagagtag taaccactta 14160
ctaagacaga gctgtgagct gtttctgctt cttctgcaac tctaattgtc ccttgtttgt 14220
aagttgagta ctttatgaag ccgctgcctt tctccatact gcaaatccta cagcacagcc 14280
cccaaaggtt gcataaaact cagcgagctt acaagatatg ttaggccatt ggacccactc 14340
tctgttaaca gcccagactt taaactttgc tgacttgggc acacgtggag gggccctggg 14400
cactaagata gataagaagc ccttctggga tgggtgctga gctcagtgtt tagggccttc 14460
acttcccctc tcctcctcca ttcccagccc cacaccgctg tcttggtgga tgtctcaggc 14520
acggataaat caacttccat ctctccatga ctttaattaa tgactctttt gtgctaaggg 14580
ttttggcttc ctcctttttc agaccacaac atgacagaac ccattttaac tttaaccttg 14640
ctacatattt caggtgactc actgcagtct cactaaatgt gttacacagc actcacacta 14700
aagatgaaaa attccattag ctcatcctgg ttcttctgct tacttaccta atcatctgtt 14760
tatgatttaa aaaaataggg ttactgtgaa gagagtgctt gtgtgtgaga cagagaggga 14820
gggttgtttt tcaaatgtat agaatatacc aatgtagttt ttggttgggt atttttttaa 14880
atcatgactt tattaaattt acttaattaa tattcatttt tatccttttt ttatgttttt 14940
aaagttttta ttatttatta atttatttga gataaggtct tgctctgtca cccaggctgg 15000
agtgcagtgg tgcaatcacg gctcatacag ccttgacctt ccagactcaa atgattgtcc 15060
cacctcacct tcccgagtag ctgggcccac aggcacaagc caccatgcct agctaatgtt 15120
```

FIG.4F

```
tctttttttt gagagacaga gtctcgctct gttgcccagg ctggagtgga gtggcacatt 15180
cttggctcac tgcaacctcc acctccaagg ttcaaacgat tctcctgcct cagtttccca 15240
agtagctggg actacagatg tgtgccacca tgcccagcta atttttgtat ttttaggaga 15300
gacagggttt cactatatgt tggccaggct ggtctcaaac tcctgacctc aggtgatcca 15360
cccactttgg cctcccaaag tggtaggatt gcagatgtaa gccaccamac ctgacykggg 15420
tttttttttt tttttttttt gagatgtagt ttcgctcttg ttgcccaggc tggagtgcag 15480
tagcacaatc tctgctcact gcaacaacca cctcccaggt tcaagcgatt ctcctgcctc 15540
agcctcccag gtagctggga ctataggtgc ctgccaccat gctgggctga tttttgtatt 15600
ttttgtagag acaggatttc atcattttgc ccagactggt cttgaactcc tgagctcaag 15660
caatccgcct gcctcagcct cccaaagtga tgggattgca ggcataagct ataagccacc 15720
atgcctggcc tgtttctgtt tttatttatt tatttattta tttatctatg tatttattta 15780
tttttgagat agagtcccac tctgttgccc aggctggagt gcagtggtgt gatctcggct 15840
cactgcaacc tctgcctcct aggttcaagc aattctcctg cctcagcctc ccgagtagct 15900
gggattacag gtgcccacta tcacgccagc taattttttt tttttttgag atggagtctc 15960
gctctgtcac ccaggctgga gtacagtggc gcgatctcag ctcactgcaa gctctgcttc 16020
ctgggttcac gccattctcc tgcctcagcc tctccagtag ctggactaca ggcacctgcc 16080
accacgcccg gctaattttt tttttatttt tagtagagat ggggtttcac cgtgttagcc 16140
aggatggtct cgaactcctg acctcaggtg atccacccgc cttgacctcc caaagtgctg 16200
ggattacagg cgtgagccac cgtggccagc cttttttttt tttaagactt tattttttta 16260
gagtagtttt aggttcacag caaaactgaa tggaagttac aaagatttcc cacatacccc 16320
tgtccccaca caggcacagc ctccttcatt atcaacattc tgcccagagt ggcccacttg 16380
gtacaactga tgaacctgca ttggcacatc atgatcaccc aaagtctgta gtttacaata 16440
ggggtcactc ttaggtttgg acacatgtat aataatatgt acaatgtaga ctaagttagt 16500
tttttaaaaa atagaaaaag atgtacaaag aaagaatttt taaatagaca aaatttttaa 16560
aaatccagcc ttaagagttt atgacaccac tcttacttca gacacccaca agtcacccac 16620
agactttact caatgtcctt ccagtgctag aggctccaga gaattgaagt ccctgagcag 16680
atagaatcac aagagaaaac cccccgggtt tagttgccaa gaagctgctt tcaagggcct 16740
tttttttctt ttccaagtca atttcctgcc acagccaaaa tttctctcgt tttttttttt 16800
tttttttttt ttgaggcaga gtttcgctct tgtcgcccag actggagtgc gatggcgtga 16860
tcttggctgg ctcactgcaa cctctgcctc ccaggttcaa gcgattctca tacctcagcc 16920
cccacaagta gctgggatta caggcatgtg ccaccacacc cagctaattt ttgtattttt 16980
agtagagaca gggtttcacc atgttgatca ggttggtctc atactcctga cctcaggtga 17040
tccgcccgcc tcagcctccc aaagtgctgg gattacaggc atgagccacc gtgcctggcc 17100
tcacaaccca aatttctatt gaatgcgaca aattctagtc tcctgttgag caagaaaaat 17160
ccatacactg tagatgaata cataagtgct gcttgtgcac tctgagagtc ataaaaatga 17220
gatcatcctt agcttttgtt aagtgcattt ggtattgtga catgaaccag aggtatgctt 17280
cagtcaatga tttatagcaa caatcaaatc cttgagacgg tggtttggtg tcgataataa 17340
cgtacctcac tgtgagtcac tgacttactt cagattttct ttaattcaag agcatcaacc 17400
ttcaagaagt gaggaggact ctgtcttctc acaattctag ggaatgaatg tctgaaccag 17460
aatgattgtg tatcccatta acaaaagccc tagagaacct ggaatggctg gttcagccct 17520
aaatgctaca tctgacctaa agtgtgcaat catccgagag ctgtttcacc cttagccagg 17580
catgtgctaa aagcttgggg catcactttc tttcttttc ttgagatgga gtttcgctct 17640
```

FIG.4G tgttgcccag gctggagtgc aatggcatgg tcttggctca ctgcaacctc cacctcctgg 17700
gttcaagtga ttctcctccc tccgcttccc aagtagctgg gattacaggc acctgccacc 17760
atgcccagct aatttttgta tttttagtag agatggggtt tcaccatgtt ggccaagctg 17820
gtctcaaact cttgacctca ggcaatccac cggccttggc ctcccaaagt gctaggatta 17880
cagacgtgag ccaccgcgcc cagcctgggg caccactttc aaactgtcct tctcaagatc 17940
ttattgacag taaaactgta cccctacaac tgtcctatta aatgactaaa aacttttact 18000
attgaatcca cggcagcacc aaacaaatta atcaaaacgt tttggaatac attcctttct 18060
ttgaagctaa gttgatggct tgattcaatt attgtgtcca tttacacaac gtaggctaaa 18120
tgtttcctag aattggcaaa ggatcaaagg gttactttac ttattcatca tcttaaataa 18180
cccaagaaag cctttatatt attattatta ttattatttg agacagggcc cagctctgtc 18240
acctaggctg gagtgcagtg gcacaatctc agctcactgc aacctctgcc tccaaagcta 18300
aagtgatcct cctacctcaa gtgatcctcc tacctcagcc tcccgagagg cggggaccac 18360
aggcgcacca ccgcaaccgg ctaatttttg tattttttgt agagatgatg tcttgccaca 18420
ctgcccaggc tggtctcaaa ttcctgagct caagtgatcc acccacctca gcctcccaaa 18480
gtgctggcat tacaggagtg agcgccaggt ccaagaaatc ctttcaaagt aaaataccac 18540
aggacatggt ggctcacacc tgtaatccca acacttcagg aggccgaggt gggaggattg 18600
cttgagccca gagttccaga acctccccac ccactgcccc atgcaacata gcaagacctt 18660
gtcactacaa aaaatttaaa aattagctgg tgtggtgttg cgtgtaggtc ctagctactc 18720
aggaggctga gacaaaaaga ttgcttgagg ctaggcattc aagattacag tgaggtgctg 18780
ggtgcagtgt ctcaggcctg taatcccagc aattttggtg gccgaggcag gtgtatcact 18840
tgagctcagg agctcgagac cagcctggga agcatggtga aaccctgtct ctaccaaaaa 18900
tacaagaaat tagctgggca tggcagctca agcctgtggt ctcagctact caggaggcgg 18960
aggtggaagg atcacttgag cccaggacgc agagattgca atgagcctag atcccgccac 19020
tgcactccag gctgggtgac agagtgaaac cctgtctcta aaaaataata attaaaggta 19080
ccaaaaataa ataattgatg gtaatgccga cccaaattaa atttaacctt caaattactt 19140
atgaaaaatg tagtatatca taagaaagtc aatagtaaga aatttcatgt taagacagtg 19200
ttttcatata ttttaacatt ttacatataa atagtatgct aattgcaaat tcattttatt 19260
taatgtttaa tagtttatgt tatgaattca aggcattttc tatacttgtc aataatgaaa 19320
aggcatttct ccttttaaaa attctatgaa gtcagccttc ttattcctta ggaacatgaa 19380
ctagtgtggt ttggttttga atctgattgt tcaaacactt tacaaagtga ataggaaaat 19440
aatttgggaa catttatatt taaacttgtc aatctatgat tctgtttttc atgtgacagc 19500
caatcacaat gtgttctcta ctcaggaagt ttagctcagt atatggatta acacgtgttc 19560
tacttgtgtg atatttctta tgacaaccac agaaaacata tggggctggg cacagtggct 19620
tatgcctgta atcccagaac tttgggaggc caaggcgggt ggatcacttg agcgcagtaa 19680
tttgacacca gcctgggcag catgtcgaaa ctgcgtctct acaaaaaata ccaaaattaa 19740
ccaggtgtgg cggcacatgc ctgtaatcct agcttctcga gaagctgagg tgggaggatt 19800
acctgagccg gggaggtcaa ggttgcggtg agccgtgatg gtgccactgc actcaagcct 19860
gggtgacaga gtgagaccct gcctaaaaaa gaaaagaraa gaaarraaaa catatttgat 19920
gcattttaaa aagaatatac ctttgagata gagtctcact cttgttgccc aggctggagt 19980
gcagtggtgc aatctcggct cactgcaacc tctgcctcct gggttcaagc gattctcctg 20040
cctcagcctc ctgagtagct gggattacag gtgcgcacca ctgtgccctg ctaatttttg 20100
tattttcagt agagacaggg ttttgccatt ttggccagac tggtctggag ctcctcatct 20160

FIG.4H

```
caagtggtcc tcctgccgtg gcctcccaaa gtgttgagat tacaggcatg agccaccgcg 20220
cctggcctag atttaatttt ttcataaaac tttcacattt gtttgtttgt gatgttttca 20280
ggtgctaatt tcttgaccta gtatagaagc ataaacaaga gttcaatcct ttttaaatag 20340
ttgtctgtgc tgtgaatgcc ctcgcccacc atgtgctcaa caaggactca aggacattgt 20400
tggtgacttc agaggcttct ataggcagct cacaagtgat gggcagctca gatgggtaag 20460
ggacctattt tgtaaaatgc ttacataagt aatattacca aggtctgaga tgtcctttga 20520
gtgcaacgaa tgtgaaaata gagatgggtt tatttatttg tttatttatt tattttttga 20580
gatggagtct cactctgtca cccacgttgg agtgcagtga tgcaatcttg gctcactgca 20640
acctccgcct cctgggttca aacagttctc ctgcttcagc ctcctgagta gctgggacta 20700
caggcatgca ctagcacacc tggctaatgt ttgtaatttt agtagagatg ggtttgacc 20760
acgttggcca ggctggtctc gaactcctga cctcaagtga tccgccttcc tcagcctccc 20820
aaagtgctgg gattacaggt gtgagccacc atgcccatcc tagagatgtg tttataattt 20880
taaagtaaaa cattttattc agttaaattc aggcttgagt catttagatc atcagtattt 20940
tgaggtaaac aactcatttc tgtaagactg atgatctaaa tgactcaaga ctgaatttag 21000
ctgaataaaa tgttctacta aggagatgag gtcctgagat ttgggtccta agagctatct 21060
cttctctaag gacctcatct cctcctccct gaattggaaa gtgctctaga ggataaagta 21120
ctaaatgggc aatctcttta tggagaaata atgtgagtag tgttagagat gtaagagaag 21180
gtcaggccgg gcgcggtggc tcactcctgt aatcccagca ctttgggagg ccaaggcagg 21240
cagatcacga ggtcaggagg tcgagaccat cctggctaac atggtgaaac cccgtctcta 21300
ctaaaaatac aaaaaattag ccgggcatgg tggcgggcgc ctatagtccc agttactcag 21360
gaggctgagg caggagaacg gcgtgaacct gggaggcgga gcttgcagtg agccgagatc 21420
gcaccactgc actccagcct gggcaacaga gtgagactct gtctcaaaac aaaaaaaaaa 21480
aaaaaaaaaa aagagagaga tktaaaagaa ggkcattaaa gagaaaacat taagagaaga 21540
gcaaatttaa aaarrtggra gaccatggta ccttttatgg gtttgggatt tgacctataa 21600
attcaaggca tgaaaaagtt aggcyctgga gaaargrttc caacacaata aggtgaattc 21660
aataccctga cctttgcctt tgtcccgtga tactggattt tgtcttttcc taacccggct 21720
tagtctccca tccatgcact gagaarggca caagagaatg tactttcaat agtgcctggg 21780
atttcatctt ttactttata cagagaatat taaacttacc ttgaaagatg tcaccttgaa 21840
gaagttccca ttggctgaat ctgggacaat ttgaacatcc aaataaatat gatagtaatg 21900
gcttataacc cattgaataa aatccatgag tccattcaga taatgaacaa tcagctgggc 21960
acagtagctc acgcctataa tcccagcacc ttggggctga agcaggagaa tcacttaagg 22020
ccaggagttc aagaccagcc tgggcagcat agttgagacc cccgtctgta ctttttaaaa 22080
ataaaaataa tnaaatanaa natttttaag gaggtaataa acaacaaggt caagcccatt 22140
acagctgatt aanatctaat aantataaaa ggaatgataa catcagagaa tcaccataac 22200
tgtcatagct acaattaatt gaggcaagag tcatcaaggg atgcccaaat tttgggacaa 22260
taataacctc cttacttgga aaatgaaatg gtaacttcac agtggagaaa gcaaatggac 22320
actaagttac ccaagtggta aaagttaaca atcctaataa taaaacaaaa tgacataatc 22380
acttatgtag tattgatgcc aaaaaatgta ttacctgaat ctagtcatga aggaactcca 22440
gatcagccca gattgaggaa tgctgtacaa atcaagtggc ctgtactctt ttaaaatgct 22500
aataacattt aaaaaagaag aagaaaaatt attccaggta aaaagagact aaagaggcat 22560
ggcgactaaa tgtaatacgt gatcccagat gggatatgga ttagggtaaa ataaaataca 22620
ttattggaaa aaactggtga catttgatta tggactggcc tttagacagc aatattctat 22680
```

FIG. 4I caatgttata ttccctgagt gtgattattg tactacggtt atgtaagaaa atatccttgt 22740
tttcaggaac tatacactga tgtatttagg gttaagagag catgatattt gcaactttat 22800
tcaaatggtt cagaaaaaag aagtacatat gtgtgtgtgt tcatatgtat atacatacat 22860
atacttaaca tatatataga gagagagaaa gaagagagga aaacacaggt gtttttcctg 22920
ctattcttaa aactcttcaa taggttagca actgtttttt ttaaacttaa cctttaggtg 22980
ggtttctatt gctacctttt aattcttgag atgtgtccct ggacggaaga cctaaatatc 23040
tttctctctc tctctttttt tttttttttg agacagagtc ttgctctgtt gcccaggctg 23100
gagtgtagtg gtgcgatctt ggctcactgc aacctccgcc ttctgggttc gagagatcct 23160
cttgcctcag cctcctgagt agggactaca ggcacaaacc accacacctg gctcatttct 23220
ctgttttcag tagagacggg gtttcaccat gttggccagg ctggtcttgg tcccaaagtc 23280
ctgggtttac aggcatgagc catcacaccc agccctcttt ttcatttcta aaaagtgctt 23340
ttgtactttg cttcctaacc agattggtcc agaaaagggc gtggtgcacc tggcgacagc 23400
ggccgtccta aacgcggtgt gggacttgtg ggccaagcag gagggaaagg taacccctct 23460
cacaaacgct caggaggctc ctgggagctg cacgacactg actttcccta cgcacagagg 23520
aaagacagac acactgcagc ccccaaaagg aaatacagat aattgctttg gtgttttttt 23580
ctcctctgag aggttttggc agtaggtagg gaactgcagg aggaggagaa agaggagaca 23640
ggatggcgga aggcgcaggc agcagtagag gggggtgtgg ggacctggtg gctgacagcc 23700
agcattagct gccaacgtgt ttactgtcag gaaaaaatgg ggactttaca catatgtctt 23760
acaaatcctt tctttttttac ttcaagcctg tctggaagtt acttgtggac atggtgagta 23820
gcattgttaa tgttacaatt gtttctgtaa atgaaatgga tatcattgat gacatgcctt 23880
ttgatgatca gtaaatatat tcaggactat ctgttgatca ctatagcgat gataaagcaa 23940
aaagccaata aaatatgaca ttccttttct gatatctgac gtaacagatg gctgtgctca 24000
tgcaggcagg gtggcatgag gggaagcagt gagggggtcc tgcctccccc actgtgcatg 24060
tgtaacacac ggtgccagtt ctctgagcct ccattgcctg actatgacaa gaggatcatc 24120
ctaacttctc taggaacctc acaaaattaa agatcaatga gaaaagcacc tcataaactc 24180
tgaaaagcca gatgttataa tattatgaag atattatcca ggccaggcat ggtggctcaa 24240
gcctgtaatc ccaatacttt ggaaggctgg aggatggctt gagcccagga gtttcaggct 24300
gcagtgagct ataattgcac cactgcactc aggtgacaga gcaagaccct gtctcaaaaa 24360
aagaaaaaag aaaagatact atccagtcac tttgacacca agaataagat caggccattg 24420
tagcctctac tgtacaattc cagcagggaa ggagctcaac actgaattct aaagctatgc 24480
acttgactgt tttctttctc cttgaccttt tcatagcagg ggtgaacaac tggatgctga 24540
ggaggaaaaa actgggcaaa ttaaagggga atgagcttca gaccccatgc agagctggct 24600
gtgagtccgg gtttcactgc tcaccagctg catgaccttg agcatgtgac ttccccactc 24660
tgagctgcgg tggcctcagt gcaacacctg ggtggcggtt aaaaacctcg tgatccacaa 24720
atgaaggccc ttgttattag ttggcaaaaa attaaggaaa aacaaagaac accatggcct 24780
tgaagagtgt tgggcaggag actgctcctc ctccggagga aagtgaagac aggaggctgt 24840
cacatcgtct ctgacatgga gagtggcttc cgggccatcc gtaggggaag gacacagagc 24900
tcttgagccc ccttctagat tcaaggttgg cgttttacgg ggatggagga ggtagccacc 24960
aaaagggaat gatttgcagg ccaccagaaa tgtgcctgag gtcccacctg tggaccctcc 25020
atttttggat cctgttccct ttcaatgcca gtactctttt cttttttctt tttttctttc 25080
tttctttttt ttttttttag acggagtttt cttcttgttg cccaggctac agtacagtgg 25140
catgatctca gctcactgca actgattcaa gcgattctcc tgtctcagcc tcctgagtag 25200

FIG.4J ctgggattac aggcacccgc caccatgccc agctaatttt ttgtattttt agtgaaaacg 25260
gggtttcacc atgttggtca gtctgagctc gaactccgga cctcaggtga tccacccatc 25320
tcagcctccc aaagtgctgg gattacagat gtgagccacc gaacctggcc cagaactctt 25380
agaagtagaa tctcagggtt gaaagagttt ttcggatttt cgacagttat ggtagagtat 25440
tattggtcac tataagatgt tagtgggaat ggaactactg gctgttttcc aactgactgt 25500
tccgtcaggg tagggagagg tctcagcacg aggccccgcc gaaatgttgg taagtggtca 25560
gccaagtggg ccgctcactc ccggttcgcc cactgtgttc ctgtcagtga agcaaacatc 25620
cccatttggc aggagaagaa gctgccggag gtcacactgc tagtgattgg tggcccaggg 25680
gtagggcagc cttctttcct ctgcagttca ctgctccaga accatctcca gcctcatagc 25740
tcaccgtgga cagccctgcg gtgtggcgct gatgtacaga gtgatgccag gcgttcatct 25800
ccccactgag ctcctgctga gtgtttgcct ggggccaggt cctccttccg ggaagtcatt 25860
ttagctggaa agaacagggt gggggcgggt ggcaagggat cagagcatga gcgtttgagg 25920
gcttcgtcag gggcagtgag gagcctctaa aggactctac atttaggaat gacagagtca 25980
aacaatttaa caaagcccta aaggtccctg ccaggaaaga atgagcccca tgtatcacca 26040
taagcaactt cttagaaaca taacccaccc ctgtcatccc agcactttgg gaggccaagg 26100
agggaggatt gcttgaagcc aggagctcaa gatcaacctg gtcaacatag tgagacccca 26160
tctctacaaa aataaaaata aattagccgg gcatagtggc acatacctgg agtcccagct 26220
actcaggagg ctgaggcagg aggatcacat aagccgggga gactgaggct gcagtgagct 26280
atgatggcat cactgcactc cagcctgggc aacagagtga gaccttgtct ctaaaaaaag 26340
aataataaat tttaaaaaac aaaatataac ccaccttata attgattcag gcctcttccc 26400
ctcctgtcac gttgccagga tcccaggatg ctggtatcct gcatagattt caggtacatc 26460
actgatgtcc tgactgagga ggatgcccta ggtgagtttg gaagctttct gggatacacg 26520
atgtgcacac acagtagtgg catgctttgt ttcctaaaag agtgagtgat gctttttatt 26580
tcttccagaa atactgcaga aaggtcaaat tggtaaaaaa gaaagaggtg ggttgtaaga 26640
aaattttctt cattgttttt gctaacattg tccacttttg agtgcccctg tccttttggg 26700
gtacacattg tcttcccaaa tgccctgtgc tgagcagcta ggccctcaaa tcaacattca 26760
agtctgcatg gtgaagcctg ctgggtatga cctctgactg cagagtttgc ttcagccact 26820
gctgaaagga agtttggctt taggattaca ctgtagggag agccctgggg gagcagggca 26880
gtccgtgaga gtatcctgat cacctgggtt tgacatccta gtaatttgtg gctgggtgtg 26940
tgtgtgcagg gccggatcag gagaacagct ggactctcca ggggaaacag ctggactctc 27000
caggggaaac agcttagcta caggcacttc caattccgaa gggccctgga aagtgcaaaa 27060
tgttgacggc gctgtgtttt cacagagaag caaatgctgg cacaaggata ccctgcttac 27120
acgacatcgt gcgcctggct ggggtactca gatgacacgt tgaagcaggt gggcatttta 27180
acctggcttt gtagacagct gaatggggag aaaccaacct gtttttcctt ctgtcctcat 27240
accactactc tcagtacctc acttctgaca ccagatgtgt gtggttttcc ttctcacgcc 27300
aaccagttct ccacttctct gtggacacca actgggtgtc ctgctatttt actcaattct 27360
gacagcacat acctggaact agcctcagac cccacaggtt aagggctcag tcttacagga 27420
ctgccctatg gcagatgcca gtcacaagtc cacgttgtca cctgtgcttc tgactggctt 27480
tgcctcagat tagaggttcc cacaaacccc gctttgagtt gaatcatttg gtggaatggc 27540
tcacggaatt cagggaaaca ctacttatgt ttactcattt attataaagg atgcaactta 27600
agaacagcca aactgaagag acacacaggg caaggtgtga ggagggggta cagagcttcc 27660
atgtcccctc caggtgagcc acactcccag tacctccacg tgttcaccaa cctggaagct 27720

FIG.4K

```
ctctgaaccc tgttccttgg gggttttatg gaggcttcag tatttagatg tgattcatta 27780
tttggccatt ggccatcaat tcagccttca gccccctcgc ctccccagct atctgggaat 27840
aggctaaagt ttccaacccc accatcatgc ctttcaggtc tttctggtcc ccagccccat 27900
cctgaagcta cgtaggggac ctcagcaggg ctctctcgtt cacgtacaaa agacayycct 27960
atcactcagg agatgccmar ggktttwrgg gstgtgtgtt gtgtgttagg aaataggggg 28020
gcagcgatgg gggcagagac aaaatatata ttccttctta tgtcacatgg gcttttgatt 28080
ccagcctctc tgggagaaat ttaatacttt cctgttcacc tctctaaatc attttggctg 28140
agggcagtgg ctcacgccta taatcctagc attttgggag gctgaggtgg gtggatcacc 28200
tgaggtcaga agttcaaaac cagcctggcc aacatggtga aaccccgtct ctactaaaaa 28260
tacaaaaaat tatctgggcg tggtaatgcg tatctgtagt cccagccact caggaggctg 28320
aggcaggaga atcacttgaa cccaggaggc aggggttgca atgagccgag atcacgccac 28380
tgccctccaa cctgggtgac agaacaagag tccgtctcaa aaaacaacaa aaaaattatt 28440
ttggatccaa gccctcgttc tgaaagtaca caaggaaatg caaagccatt cattttgtgg 28500
accgcaggac tctgtgactt agtgagtcac cttgggctct ggaaggtgac agcctagggt 28560
aagattcctg ggcagcacca gcggtagacc cactgcgaga ttgagaagta atgcctattt 28620
catggggtgg ttttgaggat tcagatacat gctgtaagtt gcgtcatgct caaggcacca 28680
tggctggcac atggcatgca gtcggcacat ggtggattta ttactgtttc tccttacact 28740
gtgcccactt ctagagagtg gagagagagg ctggcttctg catgttactc ttatatccac 28800
tcattctatg gatgccacag aatattctag ctttaaaaag agagagatca gtgctatctt 28860
ccccttccgg gaaggttgtg accattaaaa aaatggttcc catagagatg aggaaagaaa 28920
gtcaccctac aagtaaaaag tgatctctgt cagccaggct gtttctgctg ttaatttcaa 28980
caacacatgg gtgttactct ggtctatgct ataaccgtaa tgcttgtgaa acagatcagc 29040
aatgactgac ttcctggtca gaccaagggg ctctctccag tgtgtgaccc tgtgctcctt 29100
tcccacagct ctgtgcccag gcgctgaagg atggctggac caggtgagtg tgatgatgga 29160
cctgactttc ccagttggcg gcaggagaga ctcaggcagt aagtctctcc tggcagggag 29220
ccaaggagta aaaggcaccc acgggctagg atcaccctgg ctcataggga tgcataagag 29280
aagtttcccc ttaggccagg ctctttctct aaaggcagga tgtgagtcct cattagaatt 29340
ataggccatc agagttgaaa gaggcttggg agattgttta tttcgggcac taacctagag 29400
tagaaatcca gtctttactg tcagtaacag cgttgattca gtttctgcat gaacatctcc 29460
agaggcagcg agcttaactt ggtgaggcac tttccattct ttgagggctt tgagtattag 29520
gtgggtcttt tcttctcttt tttttttttt tgagatgaag tttcactctc gtcacccaga 29580
ctggagtgca gtggcgcaat ctcggctcag tgcaacctcc acctcccgga ttcaagccat 29640
tctcctgcct cagcctccct agcagctggg attacagaca cccgccacca cacctggcta 29700
atttttgtat ttttaataga gacagggttt cgctatgttg atcaggctgg tcctgaactc 29760
ctgacctcag gtgatccgcc tgcctcagcc tcccaaagtg ctgggattat aggcgtgagc 29820
cactgcaccc agccaggtgg gtctttaata tcagcaaccc tttgcttcca tgtaatttcc 29880
agccagaggt cccagttccc aagagccagg ctgttcctct tccacttgag tgccctcctc 29940
tccctccagg ccacctcctt tccacactgc tcatctgcac ttctcccttc tgactctcgc 30000
ctgtgcaggt aaagacctct ggccatccta agaccttctc tggatgaacc tcgatggttg 30060
atgaccctgc atcctgaaac agggcaggat gcagagggac catcatctct tttgacccag 30120
tcactgtgtg tccctcagca cagctcacgg tggcactttt tgcctgtgac atgtcaccca 30180
ggcttcctat ctgacttgca gccactctgg tctctgagcc tcctgctact cagtgtgtcc 30240
```

FIG.4L

```
tgtggagcag gagctccagc atcacctggg agcttgtgag aaatgcagcc tgggcctctc 30300
cccagacccg ctgcctggga atctgcattg gaacaagatc ccctagtgak tcctatgcgt 30360
tcttaagttg gagaggcact gaattcttgt taatgcctca gctaaataaa ggcttgagga 30420
gtgagaactt gaaggaggca gcatgaagcs gcggaaagag gtgttggcat ctgatagaac 30480
tgaaatcaca tcttgccttt tcccctcatc cgctgcaagt acttgctgtg tgatcaatta 30540
ctcaacctct ctgaacttca ttttctctca gtagaaataa tatgagcttt ggtcctcctc 30600
caagttgcca tatctcagaa ggaccagcac agggcaggat tcagagcagc tgctgtaagt 30660
gctgtttgcc ctccctctgc atacccgggg gaggctgcag cagtgtatct ggtgagtcag 30720
agaaggctgt ggggagattt aaagggtctc ttcccagcac aggaagcctg gcacccagag 30780
cctaaggcca gccaccctct ctggagcatc acggatcatg tagttgaagc ctccagctgg 30840
tacagaagag aacagcaggt gcctgagaat gtgcggcact ctgcaagctg gggctctttg 30900
caaagcagca gggggacctc agccaaggag gcgcacaggg agggtaggct gctgttcgag 30960
ggggcagatg ctggcctccc cgtggtggtg tcccctcctc cacctgccag tgcccacact 31020
gaggccagca acacactctt ctgacagcag agtcataggg tgtggacata gagscccatg 31080
tctcaagaga acagctggac atccacagag attaaggagc tccctacaag tgtctggatg 31140
tggtgtaaag gagacctctg cacggaggct ccagccgcac tctgctattc cctagttacc 31200
tgatctcatc actttccctc ccggaacctc aggcccctgc actgcagggg acagaccatc 31260
cctgtggcct tcctctcact gagttaattc aagacaaagc tctcctttgt aaaccagacc 31320
ctttccattc agtctatcac agtgtggctt actcggcacc ccttttcagc cccgctctcc 31380
tcttcagttc tcactgtggc tttttttgttc ttaattcctt ttcatggccc ggcaaaaacg 31440
gagttaatta tattaaagac ctgacttccc tgtctagctc cttaactcca ggtcagcaga 31500
taattgagag tcattgccct gatactgaat gaagagataa agttcccagg tttatttcaa 31560
gtgacttatc tgaagatgag gaaagagcaa gaggttacta aaaaacatat ctgtgaattg 31620
ttgacagaga cggtcacttc tgcagaaact ccagatgccc ttgccaagtc caggtacagg 31680
tctaaactag caaaccaaat gcattttcta ggtttaaagt aaaggtgggt gctgatctcc 31740
aggatgacat gcgaagatgc caaatcatcc gagacatgat tggaccggaa aagactttgg 31800
taaatatcct ctcacaccac taagaagcag tagcctttgt ccagggctaa atacaactcg 31860
tttcaagatt aaagaacatt gggaatttaa aaagttaatt gtcagaggaa gtacacttct 31920
gtagtcttgc agtaggcgag ctcaaacaaa aataagcaaa gggactaata gttttacgtt 31980
ttttaattct gcagaactag ttaagtaagt ttggggttaa ggatcctttc ttactaacac 32040
agatgtacct gagcaaacag ttttcccatt ggtgctctgg tgtgtcaatc atgtaatctc 32100
ccctcctagc tcctcaggta ggagggtgtc agggggccat tactgaagaa atgttggaac 32160
ttcagctgag ataaatgtaa ggatcagtca tttctgattt gtatttttat aaaccagttc 32220
ttacgtgtaa aatattttca taaagtcaca gtaagatgtt tttatgaggc tttggaggct 32280
tttttgcata agttaaaata gaaattttga gttcttgacc caggatcact atttatacat 32340
gaattaatgc tgcttttttt ttttaatgaa gtcatctgta tccaaataac ttatgataaa 32400
aattgattct gggctggcca gatgctgtgg ctcatgcctg taatcctagc actttgggat 32460
gcctaggtga gtggattgcc ggagctcagg agtacaagat cagcctggca acatggaaaa 32520
accccatctg taccgaaaaa tacaagaaaa aaaagtgtta gcattatatg gctcatgcct 32580
ataatcctaa cactttggga ggctgaagca ggtggatcac ttgaggccag gagtttggga 32640
ccagcctggg ctacatagca agactctctc tctaaaagaa agaagaaaaa aaaattaacc 32700
aggtgtggtg gtgcatgtct gtaatccctc ctactttgga agatggggca agaggatcac 32760
```

FIG.4M

```
tgagctcagg agttggaggc tgcagtgagc tacaataata ccactgcact ccagcatggg 32820
caacagagtg agatccagcc tcttaaaaaa aaaaaatcca ttctgagcat actgtcctct 32880
ggttttcata gtgtcctggg agagagctct tatcacttag cacattctgt agagatgtcc 32940
atttctccaa gcacgataag atcagggatg aggggctgtc ccttaagctg ggcacagcca 33000
tcacctggct tccaagaagg atagtggtac acagagagcc agggcctagg agggagagga 33060
ctggacttga actcaccatt cactagattt attgttctta agcaagttac tgaatttctc 33120
tgcatgacag ttttcttatt tgtaaaatgg gttaatatga actgcctcat ggggttatta 33180
ttattatttt ttgagatagg gtctcactca gtcacccagg ctagagtaca gcagcatgat 33240
cacacctcac tgcagccttg acctcccctg gctcagggga tcctcccacc tcaacccccct 33300
gagtagctgg gactacaagt gagagccacc acacccagct amtttwkgta ttttttgtag 33360
agagaggatt ttgctatgtt gcccagcctg gtcttgaact cctgggctca agaaatccac 33420
aggctgggcc agatgcagtg gctcatggct gtaatcccag cactttggga ggccgaggcg 33480
ggcggatcac aaggtcagga gattgagacc atcctggcta acatggtgaa accccgtctc 33540
tactaaaaat acaaaaaaaa atagcctggt gtggtggtgg gcgcctgtag tcccagctac 33600
tcgggaggct gaggcaggag aatggcgtga acctgggagg cagaggttgc agtgagccga 33660
gatagcgcca ctacactcca gccttggtga cagagcgaga ctctgtctca aaaaaaaaaa 33720
agaaaaagaa aagaaatcca cgggcttcag cctcccagag tgttgagatt acaggcatga 33780
gccaccatgc ctggccagtt attataaata ttaaatggaa caaaatccat aaagtgccta 33840
gtggagtagg tgtgccatta tgggagagtt aaggctactt attattgtgc cagacacaca 33900
gtgggcaata gtcaataaat gactattgaa caaacaatgt tgattgtgca tgattcagaa 33960
tgtgacaaaa tggtttctac gaacagaacc aacactgcaa gacacatgta tttgggtggc 34020
atctagatgg agattggacc agagcccagg gccagcgagc acttctcatg gcccagccca 34080
gggcactgct ggacatccag tggctcctca agcaattcac ggctcctcct aaagactgta 34140
cctggagcca gagtccccgt ctcagcagct gctctctggc tctttttgtt agggccgtgt 34200
gctgggcctc agcagaggcg ttagggggtc tcactcagct gttggtggca ctgagtgaca 34260
gcatttcctc cctgggagcc gcagccctgc tgtgaggttg gctcagggct gacctccctg 34320
tgaagagtct ctttttgcag atgatggatg ccaaccagcg ctgggatgtg cctgaggcgg 34380
tggagtggat gtccaagctg gccaagttca agccattgtg gattgaggag ccaacctccc 34440
ctgatgacat tctggggcac gccaccattt ccaaggtagg aaaacggctg ctgctgctgt 34500
ggcagcttat ttttctgttt agttttccag agtgctgggg acagatccta aaatttcttc 34560
acttgttccc tcttgcattt cctgttgaag tagctgaaat aattgtaatg tgtgacaaat 34620
acaggggtta cagacctgac attccttttt ctacttcagc ttatactttg ccccttatttc 34680
tgtttgtttt agataaagta agctgctaaa agttgaaggg ctaccagcaa tttgaaggtt 34740
aatagacatg gttcctatgc tttgtaaata cagaaatgtg acagcatttt tttttttgt 34800
tttttggtgg ttttttttgt tttgttttgt tttgttttga gatagagtct tactctgttg 34860
cccaggctgg agtgcaatgg catgatctcg gctcactgca acctctgcct cccgagttca 34920
agcaattctt ctgcctcagc ctcctgagta gctgggacta cagatgtgtg ccaccatgcc 34980
tggctttttt tttttttttt tttttggtat ttttagtaga gatgaggttt caccacattg 35040
gccaggcctg tctcgaactc ctgacctcag accatctgcc cgccttggcc tcccaaagtg 35100
ctggattaca ggagtgagcc accgcgcccg gccttgtgtt ttcatctgat aatttttttt 35160
ctcctacacg ctaactggtt tggcacagtc atgtgcccca taacaatgtt tcagtcagtg 35220
aaagactgcc tatataatgg cgcagtatat ataatcccat aagcttataa tggagctgaa 35280
```

FIG.4N

```
aaactcattg cccagtgacg ttgtagagat tgtaatgtgg tgcaacgcat tacctttcct 35340
atgtttaagt atgtttagat actggccatt gtgttccaat tgcctgcagc gttcagaaca 35400
gtagcatgct gtacaggttt gtagcctggg agcaataggc catgccatat agcctagggc 35460
gtgtagtagt ctctaccatc tagggtcatg gacgtacact ctatgatgtt cacacaatga 35520
tgaaacagcc caacggcaca tttctcagag ggtaaccttg tcattcagtg acacgactgt 35580
acattcatgt ggcttatagc cacatcctgc ctgcctagga acattttttc ctgaggtgac 35640
tttgcatagc tatacactcc ccattttgtg ttgatcttac acctttaact ctgatggagc 35700
agtcttggtt ccagttctag gagggacacc ttgatgcatc ccacataaat tcatgggttg 35760
tactggaggt gtggagtcgg ggactcaggg accagttctc tgtttctctc agcaaatcag 35820
cacatgatct acattatgtg ggatactctg ccaaagcctg ggtttcagaa atgccctccc 35880
cttccacatt gcagcctcgc tggagagaac agccgagata tgtgaaacaa agaccggagg 35940
atactgggcc agggcactga atgccaagca cagtagaaaa gttcattgag gagaacgttg 36000
ggtgtgggct gggacgaggg agatggccag agctgactcc ataaggaaag ctaagcctca 36060
ggtgagggaa gggtgagcag gagccatgga gcgaccacag ccttcattat ttaaacagag 36120
cccaaatttt ctgaggaatc attccacaat aggaatctca ggtgaggagc cccgggggaaa 36180
caagactttt caccttgggt cccacttgct ttttcctcct tagggctctt tcaggttggc 36240
tgtgccctgc tgaatgccag ctggcctagc accaacctga tctctgccta cctgaagcat 36300
ctcacaggaa gctcctcagg gctctaaccc tcccaggttt tgcttacatg agggaggcca 36360
tccccttagg agtatctgag gaaggagcag ctgcagagcc tgcaggtcca ggcgggggca 36420
gtggagatgc cccagggagc acagggcaca tgccagggac aggctgccac gtggggctgg 36480
attatggggt ctgtccactc agaggatgca gccagtcaga gtgagccact gcagcttctc 36540
cgatgaaaga acggcatagt ggccaggcat agtggctcac acctgtaacc ccagcacttt 36600
gggaggccga ggtgggtgga tcacctgagg tcaggagttt gagaccagcc tggccaacat 36660
ggtgaaacct cgtctctact aaaaatacaa aaattagctg gtctcgatct tctgacctcg 36720
tgatccgccc acctatggtc ccagctactc ggagaggctg aggcaggaga atggcgtgaa 36780
cccaggagga ggagcttgca gtgagccaaa atcgcaccac tgcactccag cctgggtgac 36840
agagcgagac tccatctcag aaaaaaaaaa aaaattagca gggtgcggtg atgtgtgcct 36900
gtaatcccag ctactcagga ggctgaggca ggagaatggc ttgagcctgg gaagtggagg 36960
ttacggtaag ccaagtttgc gccattgcac tccagcctgg gcgacagagc aatactccat 37020
ctcaaaaaaa aaaaaaaaaa aaacacaaca gcatagtgac agctgaagca cagataatgt 37080
gactggtggc tacatgtaga gtccattgag acagagggtg tgtgggaggt gaggaatggg 37140
cagggagaaa cccaggcagg gatgggagcg aggaggcttt tccaggaatc tgagagagag 37200
aaagggagag ggcagcttga atagagcaga ttcaggaaat attgaaaagg aggaaaaaca 37260
tttggcccct agtctgccat atatgcttaa aatggtagaa caaataagtc aaatggcctt 37320
tcctcctccc ccttcctcca tttctccctt tctcttctct ttggagataa ataaccaaga 37380
gtacttaaat tagaaatttt aagaagcata aaatgttggc ttgaaaaggt gccttagaga 37440
ccatctgctc aaactaaggc cttctgcaga tgaggaggcc gaggctttgg gtggcacagg 37500
cggggcttgc ccaaggccac acatcccgtg agatgcgggg ccagcaccgg aatcagggat 37560
acttggctgc tgagtgaagg gatttttctg ctgagaagtt ggcttagtct gattattcag 37620
atgcctcctc tggctctgga atcagtggag ttccaaccca gtctctacca ctttctagct 37680
ttgtgatcca ggaacagttc aaacccggca cacagtttta tcattttttta taaaatgggg 37740
ataacgctgg ctcctctccc attggattga gaccaggaat catttaagtc agtgttttgc 37800
```

FIG.40 acagcacctg acaggtactc agagctccaa aaatgttagc tgtcagtgtg attactatta 37860
ccctaagcaa agggaaggga agccagggag gaaccaaggc tacctgtgcg gagtagctgt 37920
ggagtcgcag tcacagtaga ggatggatgg gagcgcccag agtccaggtg gcaggtgacg 37980
gaggtagtgt tcaggggcca ggtgagagga cagagagcag cagggctgtg ttcaggtgca 38040
gagtccagta cctcaccagg tgaggactct accaggtgag caatggtctc agcctaacct 38100
gcagattgag gtctgaggcc acccactgag ctggaaggaa gaggattttt ttttttcatg 38160
gatttttcct gccttaagga agaggatttt ggaatcaaca aagacatgag gccaggtgca 38220
gtggctcaca cctgtaatcc caacactttg ggaggccgag gcgggagggg atcatctgag 38280
gtcaggagtt tgagaccagc ctggccaaca tggcaaaacc ctgactctat taaaaataca 38340
aaaattagcc agcatggtgg cgtgcacctc taatcccagc tactcgggag gctgaggcac 38400
gagaatcgct tcagcctggg gggtggaggt tgcggtgarc taagatcatg ccactgcact 38460
ccagcttggg tgacagagca agactcggtc tcaaaaaaaa aaaaaaaaag atatgagagg 38520
gttctagaag gaggtttctc agggaggcaa gaagaaggga attgatggag tgatgaccca 38580
caggaaggag tcgtccaaag gttggaccct gtgagtccac aatgagccac tccgaatagc 38640
cctgtcctta tgccactgcg caggctggag agggaggtgc tgtccacgtt gggaggagcg 38700
cagctggagc atgggccggg acaccgcaga aggagatctg cagagccctg gtcaggaacg 38760
gggctggtgg yggcagctca gcagtgctca ccttctcctc tgcagataca cagagccctc 38820
ccgcacgcat gtgttcccct ggacatcctt tgccagtctt gagccttcac atggcttaac 38880
agcagggccg tttcctcctt cagctataaa tgtttttaaa cattaggagt tgcagttcaa 38940
aacttaggaa aataacacca ggctgccttc tattttatag gcactggtcc cattaggaat 39000
tggcattgcc acaggagaac aggtgagtga cgccccccaac aggtggatga cgtccccttg 39060
gggtcagtac acgctgacca gtgaccgagg acacagttgt gtgttaggct ccatcacctg 39120
ctgtactttg agttgggaaa ttttcatcat cttagaaact gggtcatttt atcagagtct 39180
agagtcagat atagaaaaag tttgtggcta tttctccaat ttatatgact aaggtcaggt 39240
atctttttca aagtgtctaa ttgaaattga aaaggcagca atttaaagtt gctattgcaa 39300
gggcagaaaa tggtcttaag aaagccagct ttcaaattga ataaacatga ctgcgttcac 39360
tttttgagct tataaatgaa gcccgagtgc ctgccaaaac ctgctgcagt cagcccacga 39420
gcagagcagc gtgaggagct gattctcagt tttcccggca aaaggagcaa tactgctctg 39480
ccgtggttcc gtgttgtcat ctgtgccacc tgctcatcac tgtcaccgta tttcatcctg 39540
atgcttcatc tcccacttat cagtcgctgt gacagtcatt ccctcataaa tggcgagcca 39600
gtgtgatttt gacctgactc acactgttgc attagcagat ttgtaaagaa gtgagcacaa 39660
ggtccctgcc cacgctataa aagctcgcct catgcccagc gagaacaaag aagaaataca 39720
gtctgggctt cctgacggcc actgatgaat aattattggc atagagtggc tgcgttgcca 39780
ggtttagaga tcctgaaggc caaggctgac tcttctgttg gtgttatttt caattctatt 39840
tccagtgcca caatagagtg atatttaagc aactcctaca ggcgaaggcc ctgcagttcc 39900
tccagattga cagttgcaga ctgggcagtg tcaatgagaa cctctcagta ttgctgatgg 39960
ccaaaaagtt tgaaagtaag cgtgctgcag cggctgcaga ccagaccttc atttccccac 40020
taatcagaca cctcccttga tggtttgcaa ttcacatgca tgggagtctg tagtttgcca 40080
tttcgatttt tttctaactc tcatttagct ttaatccggg aatttttgat gattttcatc 40140
ttggaatttc cttcctaaat attaataaat gatttaatca cctgtgggca ataagaaaaa 40200
ccagaaagtt ccctttcacc ccttcctctc cctgccctac tcttggtatt aaatagaaac 40260
gatttccttt tagttcctgt ttgcccccat gctggtggag ttggcctctg tgaactggtg 40320

FIG.4P

```
cagcacctga ttatatttga ctacatatca gtttctgcaa gccttgaaaa taggtcagta 40380
atgtggcatt aatactttct gtttcagtag ggtccytcaa tccaggccag agcttgtaaa 40440
ttctgccttc atgaccagaa cacactaaga ccttgtctgc tggcatgtcc tataactctc 40500
aggtggagtt ggttttgctt tcacagagac ccaccaatga acggtcattt tgcctcctaa 40560
gatagggtct ggtagctgac tcactttatt ttttaagtac attgaaggta agcttgcagc 40620
cacactactc ccttaaccag ctcctgtttt catcacgtgt attctgtact tctgtcccat 40680
ctcctcttcc cagtactgga gtcttccatg gtctagacac acatttattt catcttattt 40740
ctcagaacgc cccaggtggg cttttaaatt aggacaatct ccttccagtc atctgcacac 40800
gtagggtttt gcttattcca cttttcttgt ctcctggaat taaatgtctc acagaaagat 40860
cactgcaagt atatagcaaa ggcacaaaag cattcactgg gaaagggaaa caccaaattc 40920
aggactgaga gtgataaatg ggacccttga gggtacatag gaggcttcag taataatggt 40980
aaccgttttt ctcttcaggg gggtagtgag tagacaggtg ctgtctttta atatagccga 41040
actattttat actgtattag tctattcttg cactgctata aagaaatacc tgagactggg 41100
taatttataa mgaaaagagg tttaattggc ttacagttct gcaggctgca cgggaagcat 41160
agcggcttct gctcagcttc tggaaactta caatcatgat ggaaggtgaa gggggaacaa 41220
gcacttctta tggccaagag caggaggaag agagagtgag gggggaaggt gctacacact 41280
tttaaacaac agatcttgtg ataactatct cgaacagcac caaggaacgg gtgccaaacc 41340
attcatgaag gaccacttcc catgatccaa tcacctccca gcaggccctg ctgccaacac 41400
tggggattac agttcaacat gagatttggg cagggacaca aatccaaaac aaatccaaac 41460
catatcagcc tgcctgtcac agctgttcaa taacaggcga tggaagtcag gcagcagagc 41520
tcggtcactt gccccaagcc tcagaactac aaagtggctg acgcagaacc tgaacacaga 41580
ttgacctgat tctaaatcct ctgctcttca tctaaatcat ttgtatagct gaaaggaacc 41640
tcatttggtg attttatttt ttgggtgggg agtatggaat gtattttatt gttctgcatc 41700
tgggtttgct tccttagatg tcttggttct tggatggagg tgggtgtgtc ccacctccct 41760
cagttgtggt cccatggacc tgttcggatt gttttccagg tacaaagtgt accaagaaag 41820
cctcacagtg ctaatgcttc ctagatgccc agctgaggca gtgacaaaat ggccctccca 41880
accctacctg ctttttttaaa accccaagcc cctggcagct gctgcagcca tatgaaaaaa 41940
tacawacgct tcttgaaaaa tagatcacaa aatgtggtga ttttaatcta ttcatctgac 42000
ttttgaccag aggaacccaa ataattctgg atatttacag agtctgaatt gatccctttt 42060
aaagggcacc acaaaacctc tagagggact tcgtgtgttc atgtcatcaa agtccccacc 42120
tcacattgct atattttaga agaaaaggac ctgaggcaca gaggtttagg gacttgccta 42180
gaaacgcatg gtaacacagc taagccttgg ccaacactgt caattgagtg gtactcgctc 42240
cttctgcttt aagttagcac cacgtgaata atctgacttc aggcatcatt gccccgatct 42300
gattccctcc tcctagggtg tgtgagtatg ttgaccacct gcatgagcat ttcaagtatc 42360
ccgtgatgat ccagcgggct tcctacatgc ctcccaaggt aagctgtgcc tgagggcccc 42420
tgtgagaaga gatgctgcca gccactgcca cgcctgtctc gtgaactaga ctgtggagca 42480
ccaagctttg actcctgttt gtttgcaata tccactaaca aacggttctt cagtttgtct 42540
gtatcaaaat cctcaggcct gagggccagg gcttggaggt tcaattgcct ctgacaaggc 42600
ttctgtaata ctagcctttc ctcactagtg gagatcttaa catttgcact ccttgtgcaa 42660
aaaaacctgg caccatctag caagttagtg acctaaaaag tttggactac aattgtgtrg 42720
ctggggccat ttattctgat catgttcaag agatcatggc tcattttcac caacagaggt 42780
caaactatta tcaaagagtt tgatgagtta actaactctg gcaagtagcc agtaaaatat 42840
```

FIG.4Q gttcctctgc cctattattt ccaacagtct ccaaacttat tttaaaaata ttaattcagg 42900
gctgggcatg gtggcttacg cctgtaatcc caacactttg ggaggctgag gcaggtggat 42960
catttgaggt caggtgtttg agaccagcct ggccaacatg gtgaaaccct gtctctacaa 43020
aaaatacaaa aaattagccg ggcatggtgg caggtgcctg tgatcccagc tacatgggag 43080
gctgaggcag gagaatcact tgaacctggg aggtggaggt tgcagtgagc caagattgcg 43140
ccactgcact gcagcctggg caacggacag tgactccatg tcaraaaaaa aaaaattaat 43200
taattgcctc tggcttagac gtaaaagcat ttcttggagc agcataaatg cataaaatct 43260
gtttttgttc caggtggtkg ttaacaggac tcattttttt ggtctttgat aggatcccgg 43320
ctactcaaca gaaatgaagg aggaatctgt aaagaaacac cagtatccag atggtgaagt 43380
ttggaagaaa ctccttcctg ctcaagaaaa ttaagtgctc agccccaaca actttttttct 43440
ttctgaagtg aaagggctta aaatttcttg gaaatagttt tacaaaaatg gatttaaaaa 43500
atcctaccga tcaagatgag ttcagctaga agtcatacca ccctcaggaa tcagctaa*gt* 43560
*aattattact tgattctttt agcaaatcaa tgcacgttat cctacttaat ccttaaataa* 43620
*gtttagattt aactaaccca aagtccagga ggatgttctt acaaaaatag ctatatcaag* 43680
*ggctggcacc tagacattaa actgtaattt gaaaata*agc aacatgttgc ataacttgtt 43740
ggaataattc cttgttctgt ttaacacttg tcataaatta gcagaataaa aatagtcgtg 43800
caacaccggg ggtatctggt atgcaacgaa gggaaaaata tttcactgat taaccccgaa 43860
gtggttttgc atcttttcct tgcttaatct aagcatatta ttagagaagt cacaccatgc 43920
tgaagctaat gagggcaaaa tsgtagtcca tagattattt taaaataacc ctttaaggtt 43980
ataaaagttt aaaaaaaaaa aaaaaaaact ctatcctaaa tggtcattat attttgagga 44040
taagatgcag ttaaaatgag aaaaataggg caaaatatat tcactattat ttctaaaata 44100
tactctttta agtagcatcc aaaccagaat acagcacatg tttacttaag gagagttctt 44160
taatctattt taggaaggaa ctgagcagat aagtggcagt acagaatgaa caaagcgtgg 44220
acgaatgcag aacacttctt tattatagca acatataaaa caactataaa gttcataacc 44280
acactctaca tcatgatcga tggtgttact cagctccctc agatttgagg gaatagcttg 44340
tgaaattctt aaaatattct aaaaatattc caaaaatagc ttgtgaaatt caccaacctt 44400
ctttataagt acgtgggatt gaaatgcaca tacatgtttt tgctaagagc acatacattt 44460
cattctcctc actttgttca taacctcagc attgtcagat accctcagtg agttaactca 44520
aagcctttta ttatggaaag aactggcaca gttacatttg ccagtggcaa catccttaaa 44580
aattaataac tgataggtca cggacagatt tttgacctag ttcctttttc ttttagagca 44640
aaaagaactt ttacctcggc atccagccca acccctaaag actgacaata tccttcaagc 44700
tcctttgaaa gcaccctaaa cagccatttc cattttaata gttggatgcg gattgtaccc 44760
ttcaatctga aagtcttcag ctttgaagtc atcaattttc tcaacttttc gaagaatcct 44820
gagctttggg aaaggtctgg gttctcgctg aagctaaaaa caaaataagg ccattatttt 44880
gccataattg tacgacctgt tgtaattgct cctcatgtcc atgaaacaag tacacaggat 44940
gtgatcaaca aagttctatt ttacaggagt atgatcctgt cgataccttg ccgtaggtta 45000
tgtaacatga ttggagcgca accagctgtt ctcttgcaca gatcgagagt gaggggtatt 45060
ttgtgacatt acacagcatc aggagcctgg tgcctcatca ggtgtaagtt cttataacca 45120
ctyttggcaa atttattaaa gacaggaaca cagtcaatct gtaactcata gtagctctac 45180
gtttacttga attccacaat ccctaaccca tctgtccctg gcagaaagaa ggaaagatga 45240
catgcatgga cagtgaacag aaagggatga aagccaggat tcctgggatg aacagacagt 45300
ggcaattagg atgtgaagac aggtcacaac ctattactat gtctaaaaat gaccagagca 45360

FIG.4R gagagccaga gagaataagc ctgaagtcac ctccactcaa aagcagccaa actccctcaa 45420
aggaataact tttaaaacct ggatctaacc tggaaggggc taaaaagtgt ctggttctga 45480
gtttttttcc ttaaggctca tgaagcagat gaacttacat ttttattgcc atttcatatc 45540
aattgttggc tgctataact tcagggattt caacagactt ttgaagtttg gacctaaata 45600
ttgtacttaa tgtaaaatta acaaaaaata tttatggcca gggtggtggc ttatgcctgt 45660
aattccagaa ctttcggagg ctgaggcagg tggwwcactt gaagtcagga gtttgagayy 45720
agcctggcca acatgacgaa accccatctc tactaataat acaaaaatta gctgggtgtg 45780
gtggcatgtg cctgtaatcc cagctacctg ggaggctgag gcagaagaat tgcttgaacc 45840
cgggaggtgg aggttgcagt gagctgagat cgcaccacgg cacactccag cctggccgac 45900
agagaaagac tccatctcaa aaaaaaagaa aaggaaaaac atttgcactt caattctcct 45960
tcaagttaaa atgagttaaa atgcctcct

FIG.4S

METHODS AND COMPOSITIONS FOR THE DIAGNOSIS AND TREATMENT OF NEUROPSYCHIATRIC DISORDERS

STATEMENT AS TO RIGHTS TO INVENTIONS MADE UNDER FEDERALLY-SPONSORED RESEARCH AND DEVELOPMENT

Part of the work performed during development of this invention utilized U.S. Government funds. The U.S. Government has certain rights in this invention. This wordk was supported by National Institutes of Health Grants MH49499 and MH01375.

1. INTRODUCTION

The present invention relates to drug screening assays, and diagnostic and therapeutic methods for the treatment of neuropsychiatric disorders, mediated by the expression of the mutant form of the thymidylate synthase (rTS) gene or by aberrant levels of rTS expression. The invention is based on Applicant's discovery that the rTS gene is linked to the short arm of chromosome 18 in a region of the chromosome involved in mediating neuropsychiatric disorders such as bipolar-affected disorder (BAD). The invention relates to methods for the identification of compounds that modulate the expression, synthesis and activity of the rTS protein/gene and to using compounds such as those identified as therapeutic agents in the treatment of an rTS mediated disorder; a neuropsychiatric disorder, including, by way of example and not of limitation, bipolar affective disorder. The invention also relates to methods for the diagnostic evaluation, genetic testing and prognosis of rTS mediated disorders.

2. BACKGROUND OF THE INVENTION

2.1. Neuropsychiatric Disorder

There are only a few psychiatric disorders in which clinical manifestations of the disorder can be correlated with demonstrable defects in the structure and/or function of the nervous system. Well-known examples of such disorders include Huntington's disease, which can be traced to a mutation in a single gene and in which neurons in the striatum degenerate, and Parkinson's disease, in which dopaminergic neurons in the nigro-striatal pathway degenerate. The vast majority of psychiatric disorders, however, presumably involve subtle and/or undetectable changes, at the cellular and/or molecular levels, in nervous system structure and function. This lack of detectable neurological defects distinguishes "neuropsychiatric" disorders, such as schizophrenia, attention deficit disorders, schizoaffective disorder, bipolar affective disorders, or unipolar affective disorder, from neurological disorders, in which anatomical or biochemical pathologies are manifest. Hence, identification of the causative defects and the neuropathologies of neuropsychiatric disorders are needed in order to enable clinicians to evaluate and prescribe appropriate courses of treatment to cure or ameliorate the symptoms of these disorders.

One of the most prevalent and potentially devastating of neuropsychiatric disorders is bipolar affective disorder (BAD), also known as bipolar mood disorder (BP) or manic-depressive illness, which is characterized by episodes of elevated mood (mania) and depression (Goodwin, et al., 1990, *Manic Depressive Illness,* Oxford University Press, New York). The most severe and clinically distinctive forms of BAD are BP-I (severe bipolar affective (mood) disorder), which affects 2–3 million people in the United States, and SAD-M (schizoaffective disorder manic type). They are characterized by at least one full episode of mania, with or without episodes of major depression (defined by lowered mood, or depression, with associated disturbances in rhythmic behaviors such as sleeping, eating, and sexual activity). BP-I often co-segregates in families with more etiologically heterogeneous syndromes, such as with a unipolar affective disorder such as unipolar major depressive disorder (MDD), which is a more broadly defined phenotype (Freimer and Reus, 1992, in *The Molecular and Genetic Basis of Neurological Disease,* Rosenberg, et al., eds., Butterworths, New York, pp. 951–965; McInnes and Freimer, 1995, Curr. Opin. Genet. Develop., 5, 376–381). BP-I and SAD-M are severe mood disorders that are frequently difficult to distinguish from one another on a cross-sectional basis, follow similar clinical courses, and segregate together in family studies (Rosenthal, et al., 1980, Arch. General Psychiat. 37, 804–810; Levinson and Levitt, 1987, Am. J. Psychiat. 144, 415– 426; Goodwin, et al., 1990, *Manic Depressive Illness,* Oxford University Press, New York). Hence, methods for distinguishing neuropsychiatric disorders such as these are needed in order to effectively diagnose and treat afflicted individuals.

Currently, individuals are typically evaluated for BAD using the criteria set forth in the most current version of the American Psychiatric Association's Diagnostic and Statistical Manual of Mental Disorders (DSM). While many drugs have been used to treat individuals diagnosed with BAD, including lithium salts, carbamazepine and valproic acid, none of the currently available drugs are adequate. For example, drug treatments are effective in only approximately 60–70% of individuals diagnosed with BP-I. Moreover, it is currently impossible to predict which drug treatments will be effective in, for example, particular BP-I affected individuals. Commonly, upon diagnosis, affected individuals are prescribed one drug after another until one is found to be effective. Early prescription of an effective drug treatment, therefore, is critical for several reasons, including the avoidance of extremely dangerous manic episodes and the risk of progressive deterioration if effective treatments are not found.

The existence of a genetic component for BAD is strongly supported by segregation analyses and twin studies (Bertelson, et al., 1977, Br. J. Psychiat. 130, 330–351; Freimer and Reus, 1992, in *The Molecular and Genetic Basis of Neurological Disease,* Rosenberg, et al., eds., Butterworths, New York, pp. 951–965; Pauls, et al., 1992, Arch. Gen. Psychiat. 49, 703–708). Efforts to identify the chromosomal location of genes that might be involved in BP-I, however, have yielded disappointing results in that reports of linkage between BP-I and markers on chromosomes X and 11 could not be independently replicated nor confirmed in the re-analyses of the original pedigrees, indicating that with BAD linkage studies, even extremely high lod scores at a single locus, can be false positives (Baron, et al., 1987, Nature 326, 289 292; Egeland, et al., 1987, Nature 325, 783–787; Kelsoe, et al., 1989, Nature 342, 238–243; Baron, et al., 1993, Nature Genet. 3, 49–55).

Recent investigations have suggested possible localization of BAD genes on chromosomes 18p and 21q, but in both cases the proposed candidate region is not well defined and no unequivocal support exists for either location (Berrettini, et al., 1994, Proc. Natl. Acad. Sci. USA 91, 5918–5921; Murray, et al., 1994, Science 265, 2049–2054; Pauls, et al., 1995, Am. J. Hum. Genet. 57, 636–643; Maier, et al., 1995, Psych. Res. 59, 7–15; Straub, et al., 1994, Nature Genet. 8, 291–296).

Mapping genes for common diseases believed to be caused by multiple genes, such as BAD, may be complicated by the typically imprecise definition of phenotypes, by etiologic heterogeneity, and by uncertainty about the mode of genetic transmission of the disease trait. With neuropsychiatric disorders there is even greater ambiguity in distinguishing individuals who likely carry an affected genotype from those who are genetically unaffected. For example, one can define an affected phenotype for BAD by including one or more of the broad grouping of diagnostic classifications that constitute the mood disorders: BP-I, SAD-M, MDD, and bipolar affective (mood) disorder with hypomania and major depression (BP-II).

Thus, one of the greatest difficulties facing psychiatric geneticists is uncertainty regarding the validity of phenotype designations, since clinical diagnoses are based solely on clinical observation and subjective reports. Also, with complex traits such as neuropsychiatric disorders, it is difficult to genetically map the trait-causing genes because: (1) neuropsychiatric disorder phenotypes do not exhibit classic Mendelian recessive or dominant inheritance patterns attributable to a single genetic locus, (2) there may be incomplete penetrance, i.e., individuals who inherit a predisposing allele may not manifest disease; (3) a phenocopy phenomenon may occur, i.e., individuals who do not inherit a predisposing allele may nevertheless develop disease due to environmental or random causes; (4) genetic heterogeneity may exist, in which case mutations in any one of several genes may result in identical phenotypes.

Despite these difficulties, however, identification of the chromosomal location, sequence and function of genes and gene products responsible for causing neuropsychiatric disorders such as bipolar affective disorders is of great importance for genetic counseling, diagnosis and treatment of individuals in affected families.

2.2. The Human Gene rTHYMIDYLATE Synthase (rTS)

The rTS gene was previously identified from the isolation of a cDNA clone which had a region complementary to thymidylate synthase (TS) mRNA (Dolnick et al., 1993, Nucleic Acids Res. 21:1747–1752). The predicted protein encoded by the large ORF of rTS RNA, referred to as rTS$\alpha$, is 41 kd. As described in the examples, the deduced amino acid sequence of rTS$\alpha$ was found to have homology to a superfamily of proteins which includes mandelate racemase and muconate-lactonizing enzyme from *Pseudomonas putida.* These enzymes function to extract protons from the $\alpha$ carbons of carboxylic acids. However, their substrates and products are structurally similar to several types of neurotransmitters.

Previous studies on rTS found it to be overexpressed at both the RNA and protein levels in a human leukemic cell line (K562 B1A) which was selected for resistance to MTX (Dolnick et al., 1993, Nucleic Acids Res. 21:1747–1752; Black et al., 1996, Cancer Res. 56:700–705). The colocalization of the rTS gene with the TS gene and its overexpression in a cell line selected for resistance to MTX suggested to the authors the possibility that rTS function may be related to the enzymes TS and dihydrofolate reductase. rTS-overexpression in the K562 B1A cell line was also associated with a loss in the cells ability to down-regulate TS activity with cell growth, suggesting that rTS expression is related to TS activity.

A second mRNA referred to as rTS$\beta$ has also been isolated and characterized (Dolnick et al., 1996, Cancer Research 56:3207–3210). rTS$\beta$ mRNA is predicted to encode a protein larger than rTS$\alpha$ due to the presence of an extra exon retained in rTS$\beta$ mRNA as a result of alternative splicing. Immunoblot data indicate that rTS proteins of the predicted molecular weight for both rTS$\alpha$ and rTS$\beta$ are also expressed in a human colon tumor cell line.

Unexpectedly, the present inventors have found that alterations in the rTS gene is associated with neuropsychiatric disorders. This association provides a different mechanism or activity for rTS than what has previously been suggested.

3. SUMMARY OF THE INVENTION

It is an object of the present invention to identify genetic bases for neuropsychiatric disorders, provide methods of treating and diagnosing neuropsychiatric disorders, and provide methods for identifying compounds for use as part of therapeutic and/or diagnostic methods.

In particular, the present invention relates, first, to the identification of the association of the mammalian rTS gene with neuropsychiatric disorders in humans, e.g., bipolar affective disorder.

The invention further relates to methods for the treatment of rTS mediated neuropsychiatric disorders, wherein such methods comprise administering a compound which modulates the expression of a mammalian rTS gene and/or the synthesis or activity of a mammalian rTS gene product so symptoms of the disorder are ameliorated.

The invention further relates to methods for the treatment of mammalian rTS mediated neuropsychiatric disorders resulting from rTS gene mutations, wherein such methods comprise supplying the mammal with a nucleic acid molecule encoding an unimpaired rTS gene product such that an unimpaired rTS gene product is expressed and symptoms of the disorder are ameliorated.

The invention further relates to methods for the treatment of mammalian rTS mediated neuropsychiatric disorders resulting from rTS gene mutations, wherein such methods comprise supplying the mammal with a cell comprising a nucleic acid molecule that encodes an unimpaired rTS gene product such that the cell expresses the unimpaired rTS gene product and symptoms of the disorder are ameliorated.

In addition, the present invention is directed to methods that utilize the rTS gene and/or gene product sequences for the diagnostic evaluation, genetic testing and prognosis of an rTS mediated neuropsychiatric disorder. For example, the invention relates to methods for diagnosing rTS mediated neuropsychiatric disorders, wherein such methods comprise measuring rTS gene expression in a patient sample, or detecting an rTS mutation in the genome of the mammal suspected of exhibiting such a disorder.

The invention still further relates to methods for identifying compounds capable of modulating the expression of the mammalian rTS gene and/or the synthesis or activity of the mammalian rTS gene products, wherein such methods comprise contacting a compound to a cell that expresses an rTS gene, measuring the level of rTS gene expression, gene product expression or gene product activity, and comparing this level to the level of rTS gene expression, gene product expression or gene product activity produced by the cell in the absence of the compound, such that if the level obtained in the presence of the compound differs from that obtained in its absence, a compound capable of modulating the expression of the mammalian rTS gene and/or the synthesis or activity of the mammalian rTS gene products has been identified.

rTS gene and/or gene products can also be utilized as markers for fine structure mapping of the region of the short arm of human chromosome 18 between the telomere and D185481.

The rTS mediated neuropsychiatric disorders referred to herein include, but are not limited to, bipolar affective disorder, e.g., severe bipolar affective (mood) disorder (BP-I), bipolar affective (mood) disorder with hypomania and major depression (BP-II).

The term "rTS mediated neuropsychiatric disorder" as used herein refers to a disorder involving an aberrant level of rTS gene expression, gene product synthesis and/or gene product activity relative to levels found in normal, unaffected, unimpaired individuals, levels found in clinically normal individuals, and/or levels found in a population whose level represents a baseline, average rTS level.

3.1. DEFINITIONS

As used herein, the following terms shall have the abbreviations indicated.

BAC, bacterial artificial chromosomes

BAD, bipolar affective disorder(s)

BP, bipolar mood disorder

BP-I, severe bipolar affective (mood) disorder

BP-II, bipolar affective (mood) disorder with hypomania and major depression bp, base pair(s)

EST, expressed sequence tag lod, logarithm of odds

MDD, unipolar major depressive disorder

ROS, reactive oxygen species

RT-PCR, reverse transcriptase PCR

SSCP, single-stranded conformational polymorphism

SAD-M, schizoaffective disorder manic type

STS, short tag sequence

YAC, yeast artificial chromosome

4. BRIEF DESCRIPTION OF THE FIGURES

FIGS. 1A–B. Sequence of the human rTS-α gene (SEQ ID NO: 1). Amino acid sequences are indicated (SEQ ID NO:2).

FIGS. 2A–C. Sequence of the human rTS-β gene (SEQ ID NO: 3). Amino acid sequences are indicated (SEQ ID NO: 4).

FIG. 3A–3S. Genomic Sequence of the the human rTS-α gene (SEQ ID NO:5). Exons are in bold and the 3' UTR is underlined and italized.

FIGS. 4A–4S. Intron/Exon boundaries of the human rTS-β gene (SEQ ID NO:6).

5. DETAILED DESCRIPTION OF THE INVENTION

Described herein is the discovery that the rTS gene, is associated with neuropsychiatric disorders such as human bipolar affective disorder (BAD). This invention is based on the genetic and physical mapping of the rTS gene to a specific, narrow portion of chromosome 18, also described in the Example presented below in Section 6.

The invention described in the subsections below encompasses screening methods (e.g., assays) for the identification of compounds which can be used to treat individuals suffering from an rTS mediated neuropsychiatric disorder. The invention also encompasses agonists and antagonists of the rTS gene product, including small molecules, large molecules, and antibodies, as well as nucleotide sequences that can be used to inhibit rTS gene expression (e.g., antisense and ribozyme molecules), and gene or regulatory sequence replacement constructs designed to enhance rTS gene expression (e.g., expression constructs that place the rTS gene under the control of a strong promoter system).

In particular, cellular and non-cellular assays are described that can be used to identify compounds that interact with the rTS gene product, e.g., modulate the activity of the rTS and/or bind to the rTS gene product. Such cell-based assays of the invention utilize cells, cell lines, or engineered cells or cell lines that express the rTS gene product.

The invention also encompasses the use of cell-based assays or cell-lysate assays (e.g., in vitro transcription or translation assays) to screen for compounds or compositions that modulate rTS gene expression. To this end, constructs containing a reporter sequence linked to a regulatory element of the rTS gene can be used in engineered cells, or in cell lysate extracts, to screen for compounds that modulate the expression of the reporter gene product at the level of transcription. For example, such assays could be used to identify compounds that modulate the expression or activity of transcription factors involved in rTS gene expression, or to test the activity of triple helix polynucleotides. Alternatively, engineered cells or translation extracts can be used to screen for compounds (including antisense and ribozyme constructs) that modulate the translation of rTS mRNA transcripts, and therefore, affect expression of the rTS gene product.

The invention also encompasses rTS gene products, polypeptides (including soluble rTS polypeptides or peptides) and rTS fusion proteins for use in non-cell based screening assays, for use in generating antibodies, for diagnostics and therapeutics. Such peptides or polypeptides can be fused to a heterologous protein, e.g., reporter, an Ig Fc region, etc., to yield a fusion protein. Such peptides, polypeptides and fusion proteins can be used in the non-cell based assays for screening compounds that interact with, e.g., modulate the activity of the rTS gene product and/or bind to the rTS gene product.

rTS proteins can be used to treat neuropsychiatric disorders. Such rTS gene products include but are not limited to soluble derivatives such as peptides or polypeptides corresponding to one or more domains of the rTS gene product. Alternatively, antibodies to the rTS protein or anti-idiotypic antibodies that mimic the rTS gene product (including Fab fragments), antagonists or agonists can be used to treat neuropsychiatric disorders involving rTS. In yet another approach, nucleotide constructs encoding such rTS gene products can be used to genetically engineer host cells to express such rTS gene products in vivo; these genetically engineered cells can function as "bioreactors" in the body delivering a continuous supply of rTS gene product, rTS peptides, soluble rTS polypeptides.

In addition, this invention presents methods for the diagnostic evaluation and prognosis of neuropsychiatric disorders, including BAD. For example, nucleic acid molecules encoding rTS can be used as diagnostic hybridization probes or as primers for diagnostic PCR analysis for the identification of rTS gene mutations, allelic variations and regulatory defects in the rTS gene.

"Gene therapy" approaches for the modulation of rTS gene expression and/or activity in the treatment of neuropsychiatric disorders are within the scope of the invention. For example, nucleotide constructs encoding functional rTS gene, mutant rTS gene, as well as antisense and ribozyme molecules can be used to modulate rTS gene expression.

The invention also encompasses pharmaceutical formulations and methods for treating neuropsychiatric disorders involving the rTS gene. The present invention presents methods for selecting an effective drug to administer to an individual having an rTS medicated disorder. Such methods are based on the detection of genetic polymorphisms in the rTS gene or variations in rTS gene expression due to altered methylation, differential spinning, or post-transductional modification of the rTS gene product which can affect the safety and efficacy of a therapeutic agent.

5.1. The rTS Gene

With respect to rTS gene sequences as disclosed in FIGS. 1A–1B and FIGS. 2A–2C, such sequences can, for example, be obtained readily by utilizing standard sequencing and bacterial artificial chromosome (BAC) technologies in connection with BAC54 (Identification Reference EpHS996, ATCC Accession No. 98363).

For example, sheared libraries can be made from BAC54. Fragments of a convenient size, e.g., in the size range of approximately 1 kb, are cloned into a standard plasmid, and sequenced. Further rTS sequences can then readily be identified by alignment of the BAC sequences with the rTS sequences depicted in FIGS. 1A–1B or FIGS. 2A–2C. Alternatively, BAC subclones containing additional rTS sequences can be identified by identifying those subclones which hybridize to probes derived from the rTS sequences depicted in FIGS. 1A–1B or FIGS. 2A–2C.

With respect to the cloning of allelic variants of the human rTS gene and homologues from other species (e.g., mouse), the isolated rTS gene sequences disclosed herein may be labeled and used to screen a cDNA library constructed from mRNA obtained from appropriate cells or tissues (e.g., brain tissues) derived from the organism (e.g., mouse) of interest. The hybridization conditions used should be of a lower stringency when the cDNA library is derived from an organism different from the type of organism from which the labeled sequence was derived.

Alternatively, the labeled fragment may be used to screen a genomic library derived from the organism of interest, again, using appropriately stringent conditions. Low stringency conditions are well known to those of skill in the art, and will vary predictably depending on the specific organisms from which the library and the labeled sequences are derived. For guidance regarding such conditions see, for example, Sambrook, et al., 1989, Molecular Cloning, A Laboratory Manual, Second Edition, Cold Spring Harbor Press, N.Y.; and Ausubel, et al., 1989, Current Protocols in Molecular Biology, Green Publishing Associates and Wiley Interscience, N.Y.

Further, an rTS gene allelic variant may be isolated from, for example, human nucleic acid, by performing PCR using two degenerate oligonucleotide primer pools designed on the basis of amino acid sequences within the rTS gene product disclosed herein. The template for the reaction may be cDNA obtained by reverse transcription of mRNA prepared from, for example, human or non-human cell lines or tissue known or suspected to express an rTS gene allele (such as human leukemia cell lines e.g., K562 B1A, H630 and H630-1, e.g. Dolnick et al., 1996, Cancer Research 56:1207–3260; Dolnick et al., 1993, Nucleic Acids Res., 21:1747–1752; Black et al., 1996, Cancer Res. 56:700–705). Preferrably, the allelic variant will be isolated from an individual who has an rTS mediated neuropsychiatric disorder. One such variant is described in the examples below.

The PCR product may be subcloned and sequenced to ensure that the amplified sequences represent the sequences of an rTS gene nucleic acid sequence. The PCR fragment may then be used to isolate a full length cDNA clone by a variety of methods. For example, the amplified fragment may be labeled and used to screen a bacteriophage cDNA library. Alternatively, the labeled fragment may be used to isolate genomic clones via the screening of a genomic library.

PCR technology may also be utilized to isolate full length cDNA sequences. For example, RNA may be isolated, following standard procedures, from an appropriate cellular or tissue source (i.e., one known, or suspected, to express the rTS gene, such as, for example, brain tissue samples obtained through biopsy or post-mortem). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies that may be used, see e.g., Sambrook et al., 1989, supra.

As mentioned above, the rTS gene sequences may be used to isolate mutant rTS gene alleles, preferably from a human subject. Such mutant alleles may be isolated from individuals either known or proposed to have a genotype that contributes to the symptoms of an rTS mediated neuropsychiatric disorder, such as BAD. As described in the examples below, an allelic varient, the has been identified in an individual having BAD wherein the T at nucleotide 11 in exon 6 is replaced by a C. Mutant alleles and mutant allele products may then be utilized in the therapeutic and diagnostic systems described below. Additionally, such rTS gene sequences can be used to detect rTS gene regulatory (e.g., promoter) defects which can be associated with an rTS mediated neuropsychiatric disorder, a neuropsychiatric disorder such as BAD.

A cDNA of a mutant allelic variant of the rTS gene may be isolated, for example, by using PCR, a technique that is well known to those of skill in the art. In this case, the first cDNA strand may be synthesized by hybridizing an oligo-dT oligonucleotide to mRNA isolated from tissue known or suspected to be expressed in an individual putatively carrying the mutant rTS allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant rTS allele to that of the normal rTS allele, the mutation(s) responsible for the loss or alteration of function of the mutant rTS gene product can be ascertained.

Alternatively, a genomic library can be constructed using DNA obtained from an individual suspected of or known to carry a mutant rTS allele, or a cDNA library can be constructed using RNA from a tissue known, or suspected, to express a mutant rTS allele. An unimpaired rTS gene or any suitable fragment thereof may then be labeled and used as a probe to identify the corresponding mutant rTS allele in such libraries. Clones containing the mutant rTS gene sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant rTS allele in an individual suspected of or known to carry such a mutant allele. In this manner, gene products made by the putatively mutant tissue may be expressed and screened using standard antibody screening techniques in conjunction with antibodies raised against the normal rTS gene product, as described, below, in Section 5.3. (For screening techniques, see, for example, Harlow and Lane, eds., 1988, "Antibodies: A Laboratory Manual", Cold Spring Harbor Press, Cold Spring Harbor.)

In cases where an rTS mutation results in an expressed gene product with altered function (e.g., as a result of a missense or a frameshift mutation), a polyclonal set of anti-rTS gene product antibodies are likely to cross-react with the mutant rTS gene product. Library clones detected via their reaction with such labeled antibodies can be purified and subjected to sequence analysis according to methods well known to those of skill in the art.

rTS mutations can further be detected using PCR amplification techniques. Primers can routinely be designed to amplify overlapping regions of the whole rTS sequence including the promoter region. In one embodiment, primers are designed to cover the exon-intron boundaries such that, coding regions can be scanned for mutations (see, FIGS. 3A–S and FIGS. 4A–S). Several primers for analysing various rTS exons are provided in the Examples.

Genomic DNA isolated from lymphocytes of normal and affected individuals is used as PCR template. PCR products from normal and affected individuals are compared, either by single strand conformational polymorphism (SSCP) mutation detection techniques and/or by sequencing. The mutations responsible for the loss or alteration of function of the mutant rTS gene product can then be ascertained.

5.2. Protein Products of the rTS Gene rTS gene products, or peptide fragments thereof, can be prepared for a variety of uses. For example, such gene products, or peptide fragments thereof, can be used for the generation of antibodies, in diagnostic assays, or for the identification of other cellular or extracellular gene products involved in the regulation of rTS mediated neuropsychiatric disorders, such as BAD.

The amino acid sequence depicted in FIGS. 1A–1B and FIGS. 2A–2C represents an rTS gene product. The rTS gene product, sometimes referred to herein as an "rTS protein", includes those gene products encoded by the rTS gene sequences depicted in FIGS. 1A–1B or FIGS. 2A–2C, as well as other human allelic variants of rTS that can be identified by the methods herein described.

In addition, rTS gene products may include proteins that represent functionally equivalent gene products. Such an equivalent rTS gene product may contain deletions, including internal deletions, additions, including additions yielding fusion proteins, or substitutions of amino acid residues within and/or adjacent to the amino acid sequence encoded by the rTS gene sequences described, above, in Section 5.1, but that result in a "silent" change, in that the change produces a functionally equivalent rTS gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Alternatively, where alteration of function is desired, deletion or non-conservative alterations can be engineered to produce altered, including reduced rTS gene products. Such alterations can, for example, alter one or more of the biological functions of the rTS gene product. Further, such alterations can be selected so as to generate rTS gene products that are better suited for expression, scale up, etc. in the host cells chosen. For example, cysteine residues can be deleted or substituted with another amino acid residue in order to eliminate disulfide bridges.

The rTS gene products, peptide fragments thereof and fusion proteins thereof, may be produced by recombinant DNA technology using techniques well known in the art. Thus, methods for preparing the rTS gene products, polypeptides, peptides, fusion peptide and fusion polypeptides of the invention by expressing nucleic acid containing rTS gene sequences are described herein. Methods that are well known to those skilled in the art can be used to construct expression vectors containing rTS gene product coding sequences and appropriate transcriptional and translational control signals. These methods include, for example, in vitro recombinant DNA techniques, synthetic techniques, and in vivo genetic recombination. See, for example, the techniques described in Sambrook, et al., 1989, supra, and Ausubel, et al., 1989, supra. Alternatively, RNA capable of encoding rTS gene product sequences may be chemically synthesized using, for example, synthesizers. See, for example, the techniques described in "Oligonucleotide Synthesis", 1984, Gait, ed., IRL Press, Oxford.

A variety of host-expression vector systems may be utilized to express the rTS gene product coding sequences of the invention. Such host-expression systems represent vehicles by which the coding sequences of interest may be produced and subsequently purified, but also represent cells that may, when transformed or transfected with the appropriate nucleotide coding sequences, exhibit the rTS gene product of the invention in situ. These include but are not limited to microorganisms such as bacteria (e.g., *E. coli*, *B. subtilis*) transformed with recombinant bacteriophage DNA, plasmid DNA or cosmid DNA expression vectors containing rTS gene product coding sequences; yeast (e.g., Saccharomyces, Pichia) transformed with recombinant yeast expression vectors containing the rTS gene product coding sequences; insect cell systems infected with recombinant virus expression vectors (e.g., baculovirus) containing the rTS gene product coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing rTS gene product coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the rTS gene product being expressed. For example, when a large quantity of such a protein is to be produced, for the generation of pharmaceutical compositions of rTS gene product or for raising antibodies to rTS gene product, for example, vectors that direct the expression of high levels of fusion protein products that are readily purified may be desirable. Such vectors include, but are not limited, to the *E. coli* expression vector pUR278 (Ruther et al., 1983, EMBO J. 2, 1791), in which the rTS gene product coding sequence may be ligated individually into the vector in frame with the lac Z coding region so that a fusion protein is produced; pIN vectors (Inouye and Inouye, 1985, Nucleic Acids Res. 13, 3101–3109; Van Heeke and Schuster, 1.989, J. Biol. Chem. 264, 5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica,* nuclear polyhedrosis virus (AcNPV) is used as a vector to express foreign genes. The virus grows in *Spodoptera frugiperda* cells. The rTS gene product coding sequence may be cloned individually into non-essential regions (for example the polyhedrin gene) of the virus and placed under control of an AcNPV promoter (for example the polyhedrin promoter). Successful insertion of rTS gene product coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith, et al., 1983, J. Virol. 46, 584; Smith, U.S. Pat. No. 4,215,051).

In mammalian host cells, a number of viral-based expression systems may be utilized. In cases where an adenovirus is used as an expression vector, the rTS gene product coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing rTS gene product in infected hosts. (e.g., See Logan and Shenk, 1984, Proc. Natl. Acad. Sci. USA 81, 3655–3659). Specific initiation signals may also be required for efficient translation of inserted rTS gene product coding sequences. These signals include the ATG initiation codon and adjacent sequences. In cases where an entire rTS gene, including its own initiation codon and adjacent sequences, is inserted into the appropriate expression vector, no additional translational control signals may be needed. However, in cases where only a portion of the rTS gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner, et al., 1987, Methods in Enzymol. 153, 516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, and WI38.

For long-term, high-yield production of recombinant proteins, stable expression is preferred. For example, cell lines that stably express the rTS gene product may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method may advantageously be used to engineer cell lines that express the rTS gene product. Such engineered cell lines may be particularly useful in screening and evaluation of compounds that affect the endogenous activity of the rTS gene product.

A number of selection systems may be used, including but not limited to the herpes simplex virus thymidine kinase (Wigler, et al., 1977, Cell 11, 223), hypoxanthine-guanine phosphoribosyltransferase (Szybalska and Szybalski, 1962, Proc. Natl. Acad. Sci. USA 48, 2026), and adenine phosphoribosyltransferase (Lowy, et al., 1980, Cell 22, 817) genes can be employed in $tk^-$, $hgprt^-$ or $aprt^-$ cells, respectively. Also, antimetabolite resistance can be used as the basis of selection for the following genes: dhfr, which confers resistance to methotrexate (Wigler, et al., 1980, Natl. Acad. Sci. USA 77, 3567; O'Hare, et al., 1981, Proc. Natl. Acad. Sci. USA 78, 1527); gpt, which confers resistance to mycophenolic acid (Mulligan and Berg, 1981, Proc. Natl. Acad. Sci. USA 78, 2072); neo, which confers resistance to the aminoglycoside G-418 (Colberre-Garapin, et al., 1981, J. Mol. Biol. 150, 1); and hygro, which confers resistance to hygromycin (Santerre, et al., 1984, Gene 30, 147).

Alternatively, any fusion protein may be readily purified by utilizing an antibody specific for the fusion protein being expressed. For example, a system described by Janknecht, et al. allows for the ready purification of non-denatured fusion proteins expressed in human cell lines (Janknecht, et al., 1991, Proc. Natl. Acad. Sci. USA 88, 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$.nitriloacetic acid-agarose columns and histidine-tagged proteins are selectively eluted with imidazole-containing buffers.

The rTS gene products can also be expressed in transgenic animals. Animals of any species, including, but not limited to, mice, rats, rabbits, guinea pigs, pigs, micro-pigs, goats, sheep, and non-human primates, e.g., baboons, monkeys, and chimpanzees may be used to generate rTS transgenic animals. The term "transgenic," as used herein, refers to animals expressing rTS gene sequences from a different species (e.g., mice expressing human rTS gene sequences), as well as animals that have been genetically engineered to overexpress endogenous (i.e., same species) rTS sequences or animals that have been genetically engineered to no longer express endogenous rTS gene sequences (i.e., "knock-out" animals), and their progeny.

Any technique known in the art may be used to introduce an rTS gene transgene into animals to produce the founder lines of transgenic animals. Such techniques include, but are not limited to pronuclear microinjection (Hoppe and Wagner, 1989, U.S. Pat. No. 4,873,191); retrovirus mediated gene transfer into germ lines (Van der Putten, et al., 1985, Proc. Natl. Acad. Sci., USA 82, 6148–6152); gene targeting in embryonic stem cells (Thompson, et al., 1989, Cell 56, 313–321); electroporation of embryos (Lo, 1983, Mol. Cell. Biol. 3, 1803–1814); and sperm-mediated gene transfer (Lavitrano et al., 1989, Cell 57, 717–723) (For a review of such techniques, see Gordon, 1989, Transgenic Animals, Intl. Rev. Cytol. 115, 171–229)

Any technique known in the art may be used to produce transgenic animal clones containing an rTS transgene, for example, nuclear transfer into enucleated oocytes of nuclei from cultured embryonic, fetal or adult cells induced to quiescence (Campbell, et al., 1996, Nature 380, 64–66; Wilmut, et al., Nature 385, 810–813).

The present invention provides for transgenic animals that carry an rTS transgene in all their cells, as well as animals that carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, et al., 1992, Proc. Natl. Acad. Sci. USA 89, 6232–6236). The regulatory sequences required for such a cell-type specific activation will depend upon the particular cell type of interest, and will be apparent to those of skill in the art. When it is desired that the rTS transgene be integrated into the chromosomal site of the endogenous rTS gene, gene targeting is preferred. Briefly, when such a technique is to be utilized, vectors containing some nucleotide sequences homologous to the endogenous rTS gene are designed for the purpose of integrating, via homologous recombination with chromosomal sequences, into and disrupting the function of the nucleotide sequence of the endogenous rTS gene. The transgene may also be selectively introduced into a particular cell type, thus inactivating the endogenous rTS gene in only that cell type, by following, for example, the teaching of Gu, et al. (Gu, et al., 1994, Science 265, 103–106). The regulatory sequences required for such a cell-type specific inactivation will depend upon the particular cell type of interest, and will be apparent to those of skill in the art.

Once transgenic animals have been generated, the expression of the recombinant rTS gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques that include but are not limited to Northern blot analysis of tissue samples obtained from the animal, in situ hybridization analysis, and RT-PCR (reverse transcriptase PCR). Samples of rTS gene-expressing tissue, may also be evaluated immunocytochemically using antibodies specific for the rTS transgene product.

5.3. Antibodies to rTS Gene Products

Described herein are methods for the production of antibodies capable of specifically recognizing one or more rTS gene product epitopes or epitopes of conserved variants or peptide fragments of the rTS gene products. Further, antibodies that specifically recognize mutant forms of rTS, are encompassed by the invention.

Such antibodies may include, but are not limited to, polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above. Such antibodies may be used, for example, in the detection of an rTS gene product in an biological sample and may, therefore, be utilized as part of a diagnostic or prognostic technique whereby patients may be tested for abnormal levels of rTS gene products, and/or for the presence of abnormal forms of such gene products. Such antibodies may also be utilized in conjunction with, for example, compound screening schemes, as described, below, in Section 5.8, for the evaluation of the effect of test compounds on rTS gene product levels and/or activity. Additionally, such antibodies can be used in conjunction with the gene therapy techniques described, below, in Section 5.9.2 to, for example, evaluate the normal and/or engineered rTS-expressing cells prior to their introduction into the patient.

Anti-rTS gene product antibodies may additionally be used in methods for inhibiting abnormal rTS gene product activity. Thus, such antibodies may, therefore, be utilized as part of treatment methods for an rTS mediated neuropsychiatric disorder, such as BAD.

For the production of antibodies against an rTS gene product, various host animals may be immunized by injection with an rTS gene product, or a portion thereof. Such host animals may include, but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.*

Polyclonal antibodies are heterogeneous populations of antibody molecules derived from the sera of animals immunized with an antigen, such as an rTS gene product, or an antigenic functional derivative thereof. For the production of polyclonal antibodies, host animals such as these described above, may be immunized by injection with rTS gene product supplemented with adjuvants as also described above.

Monoclonal antibodies, which are homogeneous populations of antibodies to a particular antigen, may be obtained by any technique that provides for the production of antibody molecules by continuous cell lines in culture. These include, but are not limited to, the hybridoma technique of Kohler and Milstein, (1975, Nature 256, 495–497; and U.S. Pat. No. 4,376,110), the human B-cell hybridoma technique (Kosbor et al., 1983, Immunology Today 4, 72; Cole et al., 1983, Proc. Natl. Acad. Sci. USA 80, 2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison, et al., 1984, Proc. Natl. Acad. Sci., 81, 6851–6855; Neuberger, et al., 1984, Nature 312, 604–608; Takeda, et al., 1985, Nature, 314, 452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816397, which are incorporated herein by reference in their entirety,)

In addition, techniques have been developed for the production of humanized antibodies. (See, e.g., Queen, U.S. Pat. No. 5,585,089, which is incorporated herein by reference in its entirety.) An immunoglobulin light or heavy chain variable region consists of a "framework" region interrupted by three hypervariable regions, referred to as complementarily determining regions (CDRs). The extent of the framework region and CDRs have been precisely defined (see, "Sequences of Proteins of Immunological Interest", Kabat, E. et al., U.S. Department of Health and Human Services (1983). Briefly, humanized antibodies are antibody molecules from non-human species having one or more CDRs from the non-human species and a framework region from a human immunoglobulin molecule.

Alternatively, techniques described for the production of single chain antibodies (U.S. Pat. No. 4,946,778; Bird, 1988, Science 242, 423–426; Huston, et al., 1988, Proc. Natl. Acad. Sci. USA 85, 5879–5883; and Ward, et al., 1989, Nature 334, 544–546) can be adapted to produce single chain antibodies against rTS gene products. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the $F(ab')_2$ fragments, which can be produced by pepsin digestion of the antibody molecule and the Fab fragments, which can be generated by reducing the disulfide bridges of the $F(ab')_2$ fragments. Alternatively, Fab expression libraries may be constructed (Huse, et al., 1989, Science, 246, 1275–1281) to allow rapid and easy identification of monoclonal Fab fragments with the desired specificity.

5.4. Uses of rTS Gene Sequences Gene Products, and Antibodies

Described herein are various applications of rTS gene sequences, rTS gene products, including peptide fragments and fusion proteins thereof, and of antibodies directed against rTS gene products and peptide fragments thereof. Such applications include, for example, prognostic and diagnostic evaluation of an rTS mediated neuropsychiatric disorder, such as BAD, and the identification of subjects with a predisposition to such disorders, as described, below, in Section 5.5. Additionally, such applications include methods for the treatment of an rTS mediated neuropsychiatric disorder, such as BAD as described, below, in Section 5.9, and for the identification of compounds that modulate the expression of the rTS gene and/or the synthesis or activity of the rTS gene product, as described below, in Section 5.8. Such compounds can include, for example, other cellular products that are involved in mood regulation and in rTS mediated neuropsychiatric disorders, such as BAD. These compounds can be used, for example, in the amelioration of rTS mediated neuropsychiatric disorders, such as BAD.

5.5. Diagnosis of Abnormalities of an rTS Mediated Neuropsychiatric Disorder A variety of methods can be employed for the diagnostic and prognostic evaluation of rTS mediated neuropsychiatric disorders and for the identification of subjects having a predisposition to such disorders.

Such methods may, for example, utilize reagents such as the rTS gene nucleotide sequences described in Sections 5.1, and antibodies directed against rTS gene products, including peptide fragments thereof, as described, above, in Section 5.3. Specifically, such reagents may be used, for example, for:

(1) the detection of the presence of rTS gene mutations, or the detection of either over- or under-expression of neuropsychiatric disorder rTS protein mutations of the detection of;

(2) the detection of over- or under-abundance of rTS gene product relative; and (3) the detection of an aberrant level of rTS gene product activity.

rTS gene nucleotide sequences can, for example, be used to diagnose an rTS mediated neuropsychiatric disorder using, for example, the techniques for rTS mutation detection described above in Section 5.1.

Mutations at a number of different genetic loci may lead to phenotypes related to neuropsychiatric disorders. Ideally, the treatment of patients suffering from such neuropsychiatric disorder will be designed to target the particular genetic loci containing the mutation mediating the disorder. Genetic polymorphisms have been linked to differences in drug effectiveness. Thus, identification of alterations in the rTS gene or protein can be utilized to optimize therapeutic drug treatments.

In an embodiment of the present invention, polymorphisms in the rTS gene sequence, or variations in rTS gene expression due to altered methylation, differential splicing, or post-translational modification of the rTS gene product, may be utilized to identify an individual having a disease or condition resulting from an rTS mediated disorder and thus define the most effective and safest drug treatment. Assays such as those described herein may be used to identify such polymorphisms or variations in rTS gene expression activity. Once a polymorphism in the rTS gene, or a variation in rTS gene expression has been identified in an individual, an appropriate drug treatment can be prescribed to the individual.

The methods described herein may be performed, for example, by utilizing pre-packaged diagnostic kits comprising at least one specific rTS gene nucleic acid or anti-rTS gene product antibody reagent described herein, which may be conveniently used, e.g., in clinical settings, to diagnose patients exhibiting abnormalities of an rTS mediated neuropsychiatric disorder, such as BAD.

For the detection of rTS gene mutations, any nucleated cell can be used as a starting source for genomic nucleic acid. For the detection of rTS gene expression or rTS gene products, any cell type or tissue in which the rTS gene is expressed may be utilized.

Nucleic acid-based detection techniques are described, below, in Section 5.6. Peptide detection techniques are described, below, in Section 5.7.

5.6. Detection of rTS Nucleic Acid Molecules

A variety of methods can be employed to screen for the presence of rTS gene-specific mutations and to detect and/or assay levels of rTS nucleic acid sequences.

Mutations within the rTS gene can be detected by utilizing a number of techniques. Nucleic acid from any nucleated cell can be used as the starting point for such assay techniques, and may be isolated according to standard nucleic acid preparation procedures that are well known to those of skill in the art.

rTS nucleic acid sequences may be used in hybridization or amplification assays of biological samples to detect abnormalities involving rTS gene structure, including point mutations, insertions, deletions, inversions, translocations and chromosomal rearrangements. Such assays may include, but are not limited to, Southern analyses, single-stranded conformational polymorphism analyses (SSCP), and PCR analyses.

Diagnostic methods for the detection of rTS gene-specific mutations can involve for example, contacting and incubating nucleic acids including recombinant DNA molecules, cloned genes or degenerate variants thereof, obtained from a sample, e.g., derived from a patient sample or other appropriate cellular source, such as lymphocytes, with one or more labeled nucleic acid reagents including recombinant DNA molecules, cloned genes or degenerate variants thereof, as described in Section 5.1, under conditions favorable for the specific annealing of these reagents to their complementary sequences within the rTS gene. The diagnostic methods of the present invention further encompass contacting and incubating nucleic acids for the detection of single nucleotide mutations or polymorphisms of the rTS gene. Preferably, the lengths of these nucleic acid reagents are at least 15 to 30 nucleotides. After incubation, all non-annealed nucleic acids are removed from the nucleic acid: rTS molecule hybrid. The presence of nucleic acids that have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents of the type described in Section 5.1 are easily removed. Detection of the remaining, annealed, labeled rTS nucleic acid reagents is accomplished using standard techniques well-known to those in the art. The rTS gene sequences to which the nucleic acid reagents have annealed can be compared to the annealing pattern expected from a normal rTS gene sequence in order to determine whether an rTS gene mutation is present.

In a preferred embodiment, rTS mutations or polymorphisms can be detected by using a microassay of rTS nucleic acid sequences immobilized to a substrate or "gene chip" (see, e.g. Cronin, et al., 1996, Human Mutation 7:244–255).

Alternative diagnostic methods for the detection of rTS gene specific nucleic acid molecules, in patient samples or other appropriate cell sources, may involve their amplification, e.g., by PCR (the experimental embodiment set forth in Mullis, 1987, U.S. Pat. No. 4,683,202), followed by the detection of the amplified molecules using techniques well known to those of skill in the art. The resulting amplified sequences can be compared to those that would be expected if the nucleic acid being amplified contained only normal copies of the rTS gene in order to determine whether an rTS gene mutation exists.

Additionally, well-known genotyping techniques can be performed to identify individuals carrying rTS gene mutations. Such techniques include, for example, the use of restriction fragment length polymorphisms (RFLPs), which involve sequence variations in one of the recognition sites for the specific restriction enzyme used.

Additionally, improved methods for analyzing DNA polymorphisms, which can be utilized for the identification of rTS gene-specific mutations, have been described that capitalize on the presence of variable numbers of short, tandemly repeated DNA sequences between the restriction enzyme sites. For example, Weber (U.S. Pat. No. 5,075,217) describes a DNA marker based on length polymorphisms in blocks of (dC-dA)n-(dG-dT)n short tandem repeats. The average separation of (dC-dA)n-(dG-dT)n blocks is estimated to be 30,000–60,000 bp. Markers that are so closely spaced exhibit a high frequency co-inheritance, and are extremely useful in the identification of genetic mutations, such as, for example, mutations within the rTS gene, and the diagnosis of diseases and disorders related to rTS mutations.

Also, Caskey et al. (U.S. Pat. No. 5,364,759) describe a DNA profiling assay for detecting short tri and tetra nucleotide repeat sequences. The process includes extracting the DNA of interest, such as the rTS gene, amplifying the extracted DNA, and labelling the repeat sequences to form a genotypic map of the individual's DNA.

The level of rTS gene expression can also be assayed. For example, RNA from a cell type or tissue known, or suspected, to express the rTS gene, such as brain, may be isolated and tested utilizing hybridization or PCR techniques such as are described, above. The isolated cells can be derived from cell culture or from a patient. The analysis of cells taken from culture may be a necessary step in the assessment of cells to be used as part of a cell-based gene therapy technique or, alternatively, to test the effect of compounds on the expression of the rTS gene. Such analyses may reveal both quantitative and qualitative aspects of the expression pattern of the rTS gene, including activation or inactivation of rTS gene expression.

In one embodiment of such a detection scheme, a cDNA molecule is synthesized from an RNA molecule of interest (e.g., by reverse transcription of the RNA molecule into cDNA). A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the rTS gene nucleic acid reagents described in Section 5.1. The preferred lengths of such nucleic acid reagents are at least 9–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Additionally, it is possible to perform such rTS gene expression assays "in situ", i.e., directly upon tissue sections (fixed and/or frozen) of patient tissue obtained from biopsies or resections, such that no nucleic acid purification is necessary. Nucleic acid reagents such as those described in Section 5.1 may be used as probes and/or primers for such in situ procedures (see, for example, Nuovo, G. J., 1992, "PCR In Situ Hybridization: Protocols And Applications", Raven Press, N.Y.).

Alternatively, if a sufficient quantity of the appropriate cells can be obtained, standard Northern analysis can be performed to determine the level of mRNA expression of the rTS gene.

5.7. Detection of rTS Gene Products

Antibodies directed against unimpaired or mutant rTS gene products or conserved variants or peptide fragments thereof, which are discussed, above, in Section 5.3, may also be used as diagnostics and prognostics for an rTS mediated neuropsychiatric disorder, such as BAD. Such methods may be used to detect abnormalities in the level of rTS gene product synthesis or expression, or abnormalities in the structure, temporal expression, and/or physical location of rTS gene product. The antibodies and immunoassay methods described herein have, for example, important in vitro applications in assessing the efficacy of treatments for rTS mediated neuropsychiatric disorders, such as BAD. Antibodies, or fragments of antibodies, such as those described below, may be used to screen potentially therapeutic compounds in vitro to determine their effects on rTS gene expression and rTS gene product production. The compounds that have beneficial effects on an rTS mediated neuropsychiatric disorder, such as BAD.

In vitro immunoassays may also be used, for example, to assess the efficacy of cell-based gene therapy for an rTS mediated neuropsychiatric disorder, such as BAD. Antibodies directed against rTS gene products may be used in vitro to determine, for example, the level of rTS gene expression achieved in cells genetically engineered to produce rTS gene product. In the case of intracellular rTS gene products, such an assessment is done, preferably, using cell lysates or extracts. Such analysis will allow for a determination of the number of transformed cells necessary to achieve therapeutic efficacy in vivo, as well as optimization of the gene replacement protocol.

The tissue or cell type to be analyzed will generally include those that are known, or suspected, to express the rTS gene. The protein isolation methods employed herein may, for example, be such as those described in Harlow and Lane (1988, "Antibodies: A Laboratory Manual", Cold Spring Harbor Laboratory Press, Cold Spring Harbor, N.Y.). The isolated cells can be derived from cell culture or from a patient. The analysis of cells taken from culture may be a necessary step in the assessment of cells to be used as part of a cell-based gene therapy technique or, alternatively, to test the effect of compounds on the expression of the rTS gene.

Preferred diagnostic methods for the detection of rTS gene products, conserved variants or peptide fragments thereof, may involve, for example, immunoassays wherein the rTS gene products or conserved variants or peptide fragments are detected by their interaction with an anti-rTS gene product-specific antibody.

For example, antibodies, or fragments of antibodies, such as those described, above, in Section 5.3, may be used to quantitatively or qualitatively detect the presence of rTS gene products or conserved variants or peptide fragments thereof. This can be accomplished, for example, by immunofluorescence techniques employing a fluorescently labeled antibody (see below, this Section) coupled with light microscopic, flow cytometric, or fluorimetric detection. Such techniques are especially preferred for rTS gene products that are expressed on the cell surface.

The antibodies (or fragments thereof) useful in the present invention may, additionally, be employed histologically, as in immunofluorescence or immunoelectron microscopy, for in situ detection of rTS gene products, conserved variants or peptide fragments thereof. In situ detection may be accomplished by removing a histological specimen from a patient, and applying thereto a labeled antibody that binds to an rTS polypeptide. The antibody (or fragment) is preferably applied by overlaying the labeled antibody (or fragment) onto a biological sample. Through the use of such a procedure, it is possible to determine not only the presence of the rTS gene product, conserved variants or peptide fragments, but also its distribution in the examined tissue. Using the present invention, those of ordinary skill will readily recognize that any of a wide variety of histological methods (such as staining procedures) can be modified in order to achieve in situ detection of an rTS gene product.

Immunoassays for rTS gene products, conserved variants, or peptide fragments thereof will typically comprise incubating a sample, such as a biological fluid, a tissue extract, freshly harvested cells, or lysates of cells in the presence of a detectably labeled antibody capable of identifying rTS gene product, conserved variants or peptide fragments thereof, and detecting the bound antibody by any of a number of techniques well-known in the art.

The biological sample may be brought in contact with and immobilized onto a solid phase support or carrier, such as nitrocellulose, that is capable of immobilizing cells, cell particles or soluble proteins. The support may then be washed with suitable buffers followed by treatment with the detectably labeled rTS gene product specific antibody. The solid phase support may then be washed with the buffer a second time to remove unbound antibody. The amount of bound label on the solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

One of the ways in which the rTS gene product-specific antibody can be detectably labeled is by linking the same to an enzyme, such as for use in an enzyme immunoassay (EIA) (Voller, A., "The Enzyme Linked Immunosorbent Assay (ELISA)", 1978, Diagnostic Horizons 2, 1–7, Microbiological Associates Quarterly Publication, Walkersville, Md.); Voller, A. et al., 1978, J. Clin. Pathol. 31, 507–520; Butler, J. E., 1981, Meth. Enzymol. 73, 482–523; Maggio, E. (ed.), 1980, Enzyme Immunoassay, CRC Press, Boca Raton, Fla.,; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety that can be detected, for example, by spectrophotometric, fluorimetric or by visual means. Enzymes that can be used to detectably label the antibody include, but are not limited to, malate dehydrogenase, staphylococcal nuclease, delta-5-steroid isomerase, yeast alcohol dehydrogenase, α-glycerophosphate, dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase and acetylcholinesterase. The detection can be accomplished by colorimetric methods that employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect rTS gene products through the use of a radioimmunoassay (RIA) (see, for example, Weintraub, B., Principles of Radioimmunoassays, Seventh Training Course on Radioligand Assay Techniques, The Endocrine Society, March, 1986). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

5.8. Screening Assays for Compounds that Modulate rTS Gene Activity

The following assays are designed to identify compounds that bind to an rTS gene product, compounds that bind to intracellular proteins, or portions of proteins that interact with an rTS gene product, compounds that interfere with the interaction of an rTS gene product with intracellular proteins and compounds that modulate the activity of the rTS gene (i.e., modulate the level of rTS gene expression and/or modulate the level of rTS gene product activity). Assays may additionally be utilized that identify compounds that bind to rTS gene regulatory sequences (e.g., promoter sequences; see e.g., Platt, 1994, J. Biol. Chem. 269, 28558–28562), and that can modulate the level of rTS gene expression. Such compounds may include, but are not limited to, small organic molecules, such as ones that are able to cross the blood-brain barrier, gain entry into an appropriate cell and affect expression of the rTS gene or some other gene involved in an rTS regulatory pathway, or intracellular proteins.

Methods for the identification of such intracellular proteins are described, below, in Section 5.8.2. Such intracellular proteins may be involved in the control and/or regulation of mood. Further, among these compounds are compounds that affect the level of rTS gene expression and/or rTS gene product activity and that can be used in the therapeutic treatment of rTS mediated neuropsychiatric disorders such as BAD as described, below, in Section 5.9.

Compounds may include, but are not limited to, peptides such as, for example, soluble peptides, including but not limited to, Ig-tailed fusion peptides, and members of random peptide libraries; (see, e.g., Lam, et al., 1991, Nature 354, 82–84; Houghten, et al., 1991, Nature 354, 84–86), and combinatorial chemistry-derived molecular library made of D- and/or L-configuration amino acids, phosphopeptides (including, but not limited to members of random or partially degenerate, directed phosphopeptide libraries; see, e.g., Songyang, et al., 1993, Cell 72, 767–778), antibodies (including, but not limited to, polyclonal, monoclonal, humanized, anti-idiotypic, chimeric or single chain antibodies, and FAb, $F(ab')_2$ and FAb expression library fragments, and epitope-binding fragments thereof), and small organic or inorganic molecules.

Such compounds may further comprise compounds, in particular drugs or members of classes or families of drugs, known to ameliorate or exacerbate the symptoms of a neuropsychiatric disorder such as BAD. Such compounds include antidepressants such as lithium salts, carbamazepine, valproic acid, lysergic acid diethylamide (LSD), p-chlorophenylalanine, p-propyldopacetamide dithiocarbamate derivatives e.g., FLA 63; anti-anxiety drugs, e.g., diazepam; monoamine oxidase (MAO) inhibitors, e.g., iproniazid, clorgyline, phenelzine and isocarboxazid; biogenic amine uptake blockers, e.g., tricyclic antidepressants such as desipramine, imipramine arid amitriptyline; serotonin reuptake inhibitors e.g., fluoxetine; antipsychotic drugs such as phenothiazine derivatives (e.g., chlorpromazine (thorazine) and trifluopromazine)), butyrophenones (e.g., haloperidol (Haldol)), thioxanthene derivatives (e.g., chlorprothixene), and dibenzodiazepines (e.g., clozapine); benzodiazepines; dopaminergic agonists and antagonists e.g., L-DOPA, cocaine, amphetamine, α-methyl-tyrosine, reserpine, tetrabenazine, benzotropine, pargyline; noradrenergic agonists and antagonists e.g., clonidine, phenoxybenzamine, phentolamine, tropolone.

Compounds identified via assays such as those described herein may be useful, for example, in elaborating the biological function of the rTS gene product and for ameliorating rTS mediated neuropsychiatric disorders, such as BAD. Assays for testing the effectiveness of compounds identified by, for example, techniques such as those described in Sections 5.8.1–5.8.3, are discussed, below, in Section 5.8.4.

5.8.1. In Vitro Screening Assay for Compounds that Bind to the rTS Gene Product In vitro systems may be designed to identify compounds capable of binding the rTS gene products of the invention.

Compounds identified may be useful, for example, in modulating the activity of unimpaired and/or mutant rTS gene products, may be useful in elaborating the biological function of the rTS gene product, may be utilized in screens for identifying compounds that disrupt normal rTS gene product interactions, or may in themselves disrupt such interactions.

The principle of the assays used to identify compounds that bind to the rTS gene product involves preparing a reaction mixture of the rTS gene product and the test compound under conditions and for a time sufficient to allow the two components to interact and bind, thus forming a complex that can be removed and/or detected in the reaction mixture. These assays can be conducted in a variety of ways. For example, one method to conduct such an assay involves anchoring an rTS gene product or a test substance onto a solid support and detecting rTS gene product/test compound complexes formed on the solid support at the end of the reaction. In one embodiment of such a method, the rTS gene product may be anchored onto a solid support, and the test compound, which is not anchored, may be labeled, either directly or indirectly.

In practice, microtiter plates are conveniently utilized as the solid support. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the previously non-immobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for rTS gene product or the test compound to anchor any complexes formed in solution, and a labeled antibody specific for the other component of the possible complex to detect anchored complexes.

5.8.2. Assays for Intracellular Proteins that Interact with rTS Gene Products

Any method suitable for detecting protein-protein interactions may be employed for identifying rTS gene product-protein interactions.

Among the traditional methods that may be employed are co-immunoprecipitation, cross-linking and co-purification through gradients or chromatographic columns. Utilizing procedures such as these allows for the identification of proteins, including intracellular proteins, that interact with rTS gene products. Once isolated, such a protein can be identified and can be used in conjunction with standard techniques, to identify proteins it interacts with. For example, at least a portion of the amino acid sequence of a protein that interacts with the rTS gene product can be ascertained using techniques well known to those of skill in the art, such as via the Edman degradation technique (see, e.g., Creighton, 1983, "Proteins: Structures and Molecular Principles," W.H. Freeman & Co., N.Y., pp.34–49). The amino acid sequence obtained may be used as a guide for the generation of oligonucleotide mixtures that can be used to screen for gene sequences encoding such proteins. Screening made be accomplished, for example, by standard hybridization or PCR techniques. Techniques for the generation of oligonucleotide mixtures and the screening are well-known. (See, e.g., Ausubel, supra, and 1990, "PCR Protocols: A Guide to Methods and Applications," Innis, et al., eds. Academic Press, Inc., New York).

Additionally, methods may be employed that result in the simultaneous identification of genes that encode a protein which interacts with an rTS gene product. These methods include, for example, probing expression libraries with labeled rTS gene product, using rTS gene product in a manner similar to the well known technique of antibody probing of λgt11 libraries.

One method that detects protein interactions in vivo, the two-hybrid system, is described in detail for illustration only and not by way of limitation. One version of this system has been described (Chien, et al., 1991, Proc. Natl. Acad. Sci. USA, 88, 9578–9582) and is commercially available from Clontech (Palo Alto, Calif.).

Briefly, utilizing such a system, plasmids are constructed that encode two hybrid proteins: one consists of the DNA-binding domain of a transcription activator protein fused to the rTS gene product and the other consists of the transcription activator protein's activation domain fused to an unknown protein that is encoded by a cDNA that has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodologies may be used to screen activation domain libraries for proteins that interact with the "bait" gene product. By way of example, and not by way of limitation, rTS gene products may be used as the bait gene product. Total genomic or cDNA sequences are fused to the DNA encoding an activation domain. This library and a plasmid encoding a hybrid of a bait rTS gene product fused to the DNA-binding domain are co-transformed into a yeast reporter strain, and the resulting transformants are screened for those that express the reporter gene. For example, a bait rTS gene sequence, such as the open reading frame of the rTS gene, can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait rTS gene product are to be detected can be made using methods routinely practiced in the art. According to the particular system described herein, for example, the cDNA fragments can be inserted into a vector such that they are translationally fused to the transcriptional activation domain of GAL4. Such a library can be co-transformed along with the bait rTS gene-GAL4 fusion plasmid into a yeast strain that contains a lacZ gene driven by a promoter that contains GAL4 activation sequence. A cDNA encoded protein, fused to a GAL4 transcriptional activation domain that interacts with bait rTS gene product will reconstitute an active GAL4 protein and thereby drive expression of the HIS3 gene. Colonies that express HIS3 can be detected by their growth on petri dishes containing semi-solid agar based media lacking histidine. The cDNA can then be purified from these strains, and used to produce and isolate the bait rTS gene product-interacting protein using techniques routinely practiced in the art.

5.8.3. Assays for Compounds that Interfere with rTS Gene Product Macromolecule Interaction The rTS gene products may, in vivo, interact with one or more macromolecules, including intracellular macromolecules, such as proteins. Such macromolecules may include, but are not limited to, nucleic acid molecules and those proteins identified via methods such as those described, above, in Sections 5.8.1–5.8.2. For purposes of this discussion, the macromolecules are referred to herein as "binding partners". Compounds that disrupt rTS gene product binding to a binding partner may be useful in regulating the activity of the rTS gene product, especially mutant rTS gene products. Such compounds may include, but are not limited to molecules such as peptides, and the like, as described, for example, in Section 5.8.2 above.

The basic principle of an assay system used to identify compounds that interfere with the interaction between the rTS gene product and a binding partner or partners involves preparing a reaction mixture containing the rTS gene product and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of rTS gene product and its binding partner. Control reaction mixtures are incubated without the test compound or with a compound which is known not to block complex formation. The formation of any complexes between the rTS gene product and the binding partner is then detected. The formation of a complex in the control reaction, but not in the reaction mixture containing the test compound, indicates that the compound interferes with the interaction of the rTS gene product and the binding partner. Additionally, complex formation within reaction mixtures containing the test compound and normal rTS gene product may also be compared to complex formation within reaction mixtures containing the test compound and a mutant rTS gene product. This comparison may be important in those cases wherein it is desirable to identify compounds that disrupt interactions of mutant but not normal rTS gene product.

The assay for compounds that interfere with the interaction of the rTS gene products and binding partners can be conducted in a heterogeneous or homogeneous format. Heterogeneous assays involve anchoring either the rTS gene product or the binding partner onto a solid support and detecting complexes formed on the solid support at the end of the reaction. In homogeneous assays, the entire reaction is carried out in a liquid phase. In either approach, the order of addition of reactants can be varied to obtain different information about the compounds being tested. For example, test compounds that interfere with the interaction between the rTS gene products and the binding partners, e.g., by competition, can be identified by conducting the reaction in the presence of the test substance; i.e., by adding the test substance to the reaction mixture prior to or simultaneously with the rTS gene product and interactive intracellular binding partner. Alternatively, test compounds that disrupt preformed complexes, e.g., compounds with higher binding constants that displace one of the components from the complex, can be tested by adding the test compound to the reaction mixture after complexes have been formed. The various formats are described briefly below.

In a heterogeneous assay system, either the rTS gene product or the interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the rTS gene product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex formation or that disrupt preformed complexes can be identified.

In an alternate embodiment of the invention, a homogeneous assay can be used. In this approach, a preformed complex of the rTS gene product and the interactive binding partner is prepared in which either the rTS gene product or its binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances that disrupt rTS gene product/binding partner interaction can be identified.

In another embodiment of the invention, these same techniques can be employed using peptide fragments that correspond to the binding domains of the rTS product and/or the binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described in this Section above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the segments is engineered to express peptide fragments of the protein, it can then be tested for binding activity and purified or synthesized.

For example, and not by way of limitation, an rTS gene product can be anchored to a solid material as described, above, in this Section by making a GST-rTS fusion protein and allowing it to bind to glutathione agarose beads. The binding partner can be labeled with a radioactive isotope, such as $^{35}S$, and cleaved with a proteolytic enzyme such as trypsin. Cleavage products can then be added to the anchored GST-rTS fusion protein and allowed to bind. After washing away unbound peptides, labeled bound material, representing the binding partner binding domain, can be eluted, purified, and analyzed for amino acid sequence by well-known methods. Peptides so identified can be produced synthetically or produced using recombinant DNA technology.

5.8.4. Assays for Identification of Compounds that Ameliorate an rTS Mediated Neuropsychiatric Disorder Compounds, including but not limited to binding compounds identified via assay techniques such as those described, above, in Sections 5.8.1–5.8.4, can be tested for the ability to ameliorate symptoms of an rTS mediated neuropsychiatric disorder, bipolar affective (mood) disorders, such as severe bipolar affective (mood) disorder (BP-I), bipolar affective (mood) disorder with hypomania and major depression (BP-II).

It should be noted that the assays described herein can identify compounds that affect rTS activity by either affecting rTS gene expression or by affecting the level of rTS gene product activity. For example, compounds may be identified that are involved in another step in the pathway in which the rTS gene and/or rTS gene product is involved and, by affecting this same pathway may modulate the effect of rTS on the development of an rTS mediated neuropsychiatric disorder, such as BAD. Such compounds can be used as part of a therapeutic method for the treatment of the disorder.

Described below are cell-based and animal model-based assays for the identification of compounds exhibiting such an ability to ameliorate symptoms of an rTS mediated neuropsychiatric disorder, such as BAD.

First, cell-based systems can be used to identify compounds that may act to ameliorate symptoms of an rTS mediated neuropsychiatric disorder, such as BAD. Such cell systems can include, for example, recombinant or non-recombinant cell, such as cell lines, that express the rTS gene.

In utilizing such cell systems, cells that express rTS may be exposed to a compound suspected of exhibiting an ability to ameliorate symptoms of an rTS mediated neuropsychiatric disorder, such as BAD, at a sufficient concentration and for a sufficient time to elicit such an amelioration of such symptoms in the exposed cells. After exposure, the cells can be assayed to measure alterations in the expression of the rTS gene, e.g., by assaying cell lysates for rTS mRNA transcripts (e.g., by Northern analysis) or for rTS gene products expressed by the cell; compounds that modulate expression of the rTS gene are good candidates as therapeutics.

In addition, animal-based systems or models for an rTS mediated neuropsychiatric disorder, for example, transgenic mice containing a human or altered form of rTS gene, may be used to identify compounds capable of ameliorating symptoms of the disorder. Such animal models may be used as test substrates for the identification of drugs, pharmaceuticals, therapies and interventions. For example, animal models may be exposed to a compound suspected of exhibiting an ability to ameliorate symptoms, at a sufficient concentration and for a sufficient time to elicit such an amelioration of symptoms of an rTS neuropsychiatric disorder. The response of the animals to the exposure may be monitored by assessing the reversal of the symptoms of the disorder.

With regard to intervention, any treatments that reverse any aspect of symptoms of an rTS mediated neuropsychiatric disorder, should be considered as candidates for human therapeutic intervention in such a disorder. Dosages of test agents may be determined by deriving dose-response curves, as discussed in Section 5.10.1, below.

5.9. Compounds and Methods for the Treatment of rTS Mediated Neuropsychiatric Disorders Described below are methods and compositions whereby an rTS mediated neuropsychiatric disorder, such as BAD, may be treated. For example, such methods can comprise administering compounds which modulate the expression of a mammalian rTS gene and/or the synthesis or activity of a mammalian rTS gene product so symptoms of the disorder are ameliorated.

Alternatively, in those instances whereby the mammalian rTS mediated neuropsychiatric disorders result from rTS gene mutations, such methods can comprise supplying the mammal with a nucleic acid molecule encoding an unimpaired rTS gene product such that an unimpaired rTS gene product is expressed and symptoms of the disorder are ameliorated.

In another embodiment of methods for the treatment of mammalian rTS mediated neuropsychiatric disorders resulting from rTS gene mutations, such methods can comprise supplying the mammal with a cell comprising a nucleic acid molecule that encodes an unimpaired rTS gene product such that the cell expresses the unimpaired rTS gene product and symptoms of the disorder are ameliorated.

In cases in which a loss of normal rTS gene product function results in the development of a rTS mediated neuropsychiatric disorder an increase in rTS gene product activity would facilitate progress towards an asymptomatic state in individuals exhibiting a deficient level of rTS gene expression and/or rTS gene product activity. Methods for enhancing the expression or synthesis of rTS can include, for example, methods such as those described below, in Section 5.9.2.

Alternatively, symptoms of rTS mediated neuropsychiatric disorders, may be ameliorated by administering a compound that decreases the level of rTS gene expression and/or rTS gene product activity. Methods for inhibiting or reducing the level of rTS gene product synthesis or expression can include, for example, methods such as those described in Section 5.9.1.

In one embodiment of treatment methods, the compounds administered comprise compounds, in particular drugs, reported to ameliorate or exacerbate the symptoms of a neuropsychiatric disorder, such as BAD. Such compounds include antidepressants such as lithium salts, carbamazepine, valproic acid, lysergic acid diethylamide (LSD), p-chlorophenylalanine, p-propyldopacetamide dithiocarbamate derivatives e.g., FLA 63; anti-anxiety drugs, e.g., diazepam; monoamine oxidase (MAO) inhibitors, e.g., iproniazid, clorgyline, phenelzine and isocarboxazid; biogenic amine uptake blockers, e.g., tricyclic antidepressants such as desipramine, imipramine and amitriptyline; serotonin reuptake inhibitors e.g., fluoxetine; antipsychotic drugs such as phenothiazine derivatives (e.g., chlorpromazine (thorazine) and trifluopromazine)), butyrophenones (e.g., haloperidol (Haldol)), thioxanthene derivatives (e.g., chlorprothixene), and dibenzodiazepines (e.g., clozapine); benzodiazepines; dopaminergic agonists and antagonists e.g., L-DOPA, cocaine, amphetamine, α-methyl-tyrosine, reserpine, tetrabenazine, benzotropine, pargyline; noradrenergic agonists and antagonists e.g., clonidine, phenoxybenzamine, phentolamine tropolone.

5.9.1. Inhibitory Antisense, Ribozyme and Triple Helix Approaches

In another embodiment, symptoms of rTS mediated neuropsychiatric disorders may be ameliorated by decreasing the level of rTS gene expression and/or rTS gene product activity by using rTS gene sequences in conjunction with well-known antisense, gene "knock-out," ribozyme and/or triple helix methods to decrease the level of rTS gene expression. Among the compounds that may exhibit the ability to modulate the activity, expression or synthesis of the rTS gene, including the ability to ameliorate the symptoms of a rTS mediated neuropsychiatric disorder, such as BAD, are antisense, ribozyme, and triple helix molecules. Such molecules may be designed to reduce or inhibit either unimpaired, or if appropriate, mutant target gene activity. Techniques for the production and use of such molecules are well known to those of skill in the art.

Antisense RNA and DNA molecules act to directly block the translation of mRNA by hybridizing to targeted mRNA and preventing protein translation. Antisense approaches involve the design of oligonucleotides that are complementary to a target gene mRNA. The antisense oligonucleotides will bind to the complementary target gene mRNA transcripts and prevent translation. Absolute complementarity, although preferred, is not required.

A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

In one embodiment, oligonucleotides complementary to non-coding regions of the rTS gene could be used in an antisense approach to inhibit translation of endogenous rTS mRNA. Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and nonspecific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger, et al., 1989, Proc. Natl. Acad. Sci. U.S.A. 86, 6553–6556; Lemaitre, et al., 1987, Proc. Natl. Acad. Sci. U.S.A. 84, 648–652; PCT Publication No. WO88/09810, published Dec. 15, 1988) or the blood-brain barrier (see, e.g., PCT Publication No. WO89/10134, published Apr. 25, 1988), hybridization-triggered cleavage agents (see, e.g., Krol et al., 1988, BioTechniques 6, 958–976) or intercalating agents (see, e.g., Zon, 1988, Pharm. Res. 5, 539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine; N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier, et al., 1987, Nucl. Acids Res. 15, 6625–6641). The oligonucleotide is a 2'-O-methylribonucleotide (Inoue, et al., 1987, Nucl. Acids Res. 15, 6131–6148), or a chimeric RNA-DNA analogue (Inoue, et al., 1987, FEBS Lett. 215, 327–330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein, et al. (1988, Nucl. Acids Res. 16, 3209), methylphosphonate oligonucleotides can be prepared by use of controlled pore glass polymer supports (Sarin, et al., 1988, Proc. Natl. Acad. Sci. U.S.A. 85, 7448–7451), etc.

While antisense nucleotides complementary to the target gene coding region sequence could be used, those complementary to the transcribed, untranslated region are most preferred.

Antisense molecules should be delivered to cells that express the target gene in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced e.g., such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA care be by any promoter known in the art to act in mammalian, preferably human cells. Such promoters can be inducible or constitutive. Such promoters include but are not limited to: the SV40 early promoter region (Bernoist and Chambon, 1981, Nature 290, 304–310), the promoter contained in the 3' long terminal repeat of Rous sarcoma virus (Yamamoto, et al., 1980, Cell 22, 787–797), the herpes thymidine kinase promoter (Wagner, et al., 1981, Proc. Natl. Acad. Sci. U.S.A. 78, 1441–1445), the regulatory sequences of the metallothionein gene (Brinster, et al., 1982, Nature 296, 39–42), etc. Any type of plasmid, cosmid, YAC or viral vector can be used to prepare the recombinant DNA construct which can be introduced directly into the tissue site. Alternatively, viral vectors can be used that selectively infect the desired tissue, in which case administration may be accomplished by another route (e.g., systemically).

Ribozyme molecules designed to catalytically cleave target gene mRNA transcripts can also be used to prevent translation of target gene mRNA and, therefore, expression of target gene product. (See, e.g., PCT International Publication W090/11364, published Oct. 4, 1990; Sarver, et: al., 1990, Science 247, 1222–1225).

Ribozymes are enzymatic RNA molecules capable of catalyzing the specific cleavage of RNA. (For a review, see Rossi, 1994, Current Biology 4, 469–471). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246, which is incorporated herein by reference in its entirety.

While ribozymes that cleave mRNA at site specific recognition sequences can be used to destroy target gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Myers, 1995, *Molecular Biology and Biotechnology: A Comprehensive Desk Reference,* VCH Publishers, New York, (see especially FIG. 4, page 833) and in Haseloff and Gerlach, 1988, Nature, 334, 585–591, which is incorporated herein by reference in its entirety.

Preferably the ribozyme is engineered so that the cleavage recognition site is located near the 5' end of the target gene mRNA, i.e., to increase efficiency and minimize the intracellular accumulation of non-functional mRNA transcripts.

The ribozymes of the present invention also include RNA endoribonucleases (hereinafter "Cech-type ribozymes") such as the one that occurs naturally in *Tetrahymena thermophila* (known as the IVS, or L-19 IVS RNA) and that has been extensively described by Thomas Cech and collaborators (Zaug, et al., 1984, Science, 224, 574–578; Zaug and Cech, 1986, Science, 231, 470–475; Zaug, et al., 1986, Nature, 324, 429–433; published International patent application No. WO 88/04300 by University Patents Inc.; Been and Cech, 1986, Cell, 47, 207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in the target gene.

As in the antisense approach, the ribozymes can be composed of modified oligonucleotides (e.g., for improved stability, targeting, etc.) and should be delivered to cells that express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target gene messages and inhibit translation. Because ribozymes unlike antisense molecules, are catalytic, a lower intracellular concentration is required for efficiency.

Endogenous target gene expression can also be reduced by inactivating or "knocking out" the target gene or its promoter using targeted homologous recombination (e.g., see Smithies, et al., 1985, Nature 317, 230–234; Thomas and Capecchi, 1987, Cell 51, 503–512; Thompson, et al., 1989, Cell 5, 313–321; each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene (e.g., see Thomas and Capecchi, 1987 and Thompson, 1989, supra). However this approach can be adapted for use in humans provided the recombinant DNA constructs are directly administered or targeted to the required site in vivo using appropriate viral vectors.

Alternatively, endogenous target gene expression can be reduced by targeting deoxyribonucleotide sequences complementary to the regulatory region of the target gene (i.e., the target gene promoter and/or enhancers) to form triple helical structures that prevent transcription of the target gene in target cells in the body. (See generally, Helene, 1991, Anticancer Drug Des., 6(6), 569–584; Helene, et al., 1992, Ann. N.Y. Acad. Sci., 660, 27–36; and Maher, 1992, Bioassays 14(12), 807–815).

Nucleic acid molecules to be used in triplex helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and $CGC^+$ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to inhibit mutant gene expression, it is possible that the technique may so efficiently reduce or inhibit the transcription (triple helix) and/or translation (antisense, ribozyme) of mRNA produced by normal target gene alleles that the possibility may arise wherein the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may, be introduced into cells via gene therapy methods such as those described, below, in Section 5.9.2 that do not contain sequences susceptible to whatever antisense, ribozyme, or triple helix treatments are being utilized. Alternatively, in instances whereby the target gene encodes an extracellular protein, it may be preferable to co-administer normal target gene protein in order to maintain the requisite level of target gene activity.

Anti-sense RNA and DNA, ribozyme, and triple helix molecules of the invention may be prepared by any method known in the art for the synthesis of DNA and RNA molecules, as discussed above. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

5.9.2. Gene Replacement Therapy rTS gene nucleic acid sequences, described above in Section 5.1, can be utilized for the treatment of an rTS mediated neuropsychiatric disorder. Such treatment can be in the form of gene replacement therapy. Specifically, one or more copies of a normal rTS gene or a portion of the rTS gene that directs the production of an rTS gene product exhibiting normal rTS gene function, may be inserted into the appropriate cells within a patient, using vectors that include, but are not limited to edenovirus, adeno-associated virus, and retrovirus vectors, in addition to other particles that introduce DNA into cells, such as liposomes.

Because the rTS gene is expressed in the brain, such gene replacement therapy techniques should be capable delivering rTS gene sequences to these cell types within patients. Thus, in one embodiment, techniques that are well known to those of skill in the art (see, e.g., PCT Publication No. WO89/10134, published Apr. 25, 1988) can be used to enable rTS gene sequences to cross the blood-brain barrier readily and to deliver the sequences to cells in the brain. With respect to delivery that is capable of crossing the blood-brain barrier, viral vectors such as, for example, those described above, are preferable.

In another embodiment, techniques for delivery involve direct administration of such rTS gene sequences to the site of the cells in which the rTS gene sequences are to be expressed.

Additional methods that may be utilized to increase the overall level of rTS gene expression and/or rTS gene product activity include the introduction of appropriate rTS-expressing cells, preferably autologous cells, into a patient at positions and in numbers that are sufficient to ameliorate the symptoms of an rTS mediated neuropsychiatric disorder. Such cells may be either recombinant or non-recombinant.

Among the cells that can be administered to increase the overall level of rTS gene expression in a patient are normal cells, preferably brain cells, that express the rTS gene. Alternatively, cells, preferably autologous cells, can be engineered to express rTS gene sequences, and may then be introduced into a patient in positions appropriate for the amelioration of the symptoms of an rTS mediated neuropsychiatric disorder. Alternately, cells that express an unimpaired rTS gene and that are from a MHC matched individual can be utilized, and may include, for example, brain cells. The expression of the rTS gene sequences is controlled by the appropriate gene regulatory sequences to allow such expression in the necessary cell types. Such gene regulatory sequences are well known to the skilled artisan. Such cell-based gene therapy techniques are well known to those skilled in the art, see, e.g., Anderson, U.S. Pat. No. 5,399,349.

When the cells to be administered are non-autologous cells, they can be administered using well known techniques that prevent a host immune response against the introduced cells from developing. For example, the cells may be introduced in an encapsulated form which, while allowing for an exchange of components with the immediate extracellular environment, does not allow the introduced cells to be recognized by the host immune system.

Additionally, compounds, such as those identified via techniques such as those described, above, in Section 5.8, that are capable of modulating rTS gene product activity can be administered using standard techniques that are well known to those of skill in the art. In instances in which the compounds to be administered are to involve an interaction with brain cells, the administration techniques should include well known ones that allow for a crossing of the blood-brain barrier.

5.10. Pharmaceutical Preparations and Methods of Administration

The compounds that are determined to affect rTS gene expression or gene product activity can be administered to a patient at therapeutically effective doses to treat or ameliorate an rTS mediated neuropsychiatric disorder. A therapeutically effective dose refers to that amount of the compound sufficient to result in amelioration of symptoms of such a disorder.

5.10.1. Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

5.10.2. Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

6. EXAMPLE

Localization of the rTS Gene to Chromosome 18

In the Example presented in this Section, studies are described that, first, define an interval approximately 310 kb on the short arm of human chromosome 18 within which a region associated with a neuropsychiatric disorder is located and, second, to the identification of the rTS gene, as mapping within this region and which is involved in mediating BAD.

6.1. Materials and Methods

6.1.1. Linkage Disequilibrium

Linkage disequilibrium (LD) studies were performed using DNA from a population sample of neuropsychiatric disorder (BP-I) patients. The population sample and LD techniques were as described in Freimer et al., 1996, Nature Genetics 12:436–441. The present LD study took advantage of the additional physical markers identified via the physical mapping techniques described below.

6.1.2. Yeast Artificial Chromosome (YAC) Mapping

For physical mapping, yeast artificial chromosomes (YACs) containing human sequences were mapped to the region being analyzed based on publicly available maps (Cohen et al., 1993, C.R. Acad. Sci. 316, 1484–1488). The YACs were then ordered and contig reconstructed by performing standard short tag sequence (STS)-content mapping with microsatellite markers and non-polymorphic STSs available from databases that surround the genetically defined candidate region.

6.1.3. Bacterial Artificial Chromosome (BAC) Mapping

STSs from the short arm of human chromosome 18 were used to screen a human BAC library (Research Genetics, Huntsville, Ala.). The ends of the BACs were cloned or directly sequenced. The end sequences were used to amplify the next overlapping BACs. From each BAC, additional microsatellites were identified. Specifically, random sheared libraries were prepared from overlapping BACs within the defined genetic interval. BAC DNA was sheared with a nebulizer (CIS-US Inc., Bedford, Mass.). Fragments in the size range of 600 to 1,000 bp were utilized for the sublibrary production. Microsatellite sequences from the sublibraries were identified by corresponding microsatellite probes. Sequences around such repeats were obtained to enable development of PCR primers for genomic DNA.

6.1.4. Radiation Hybrid (RH) Mapping

Standard RH mapping techniques were applied to a Stanford G3 RH mapping panel (Research Genetics, Huntsville, Ala.) to order all microsatellite markers and non-polymorphic STSs in the region being analyzed.

6.1.5. Sample Sequencing

Random sheared libraries were made from all the BACs within the defined genetic region. Approximately 9,000 subclones within the approximately 310 kb region were sequenced with vector primers in order to achieve an 8-fold sequence coverage of the region. All sequences were processed through an automated sequence analysis pipeline that assessed quality, removed vector sequences and masked repetitive sequences. The resulting sequences were then compared to public DNA and protein databases using BLAST algorithms (Altschul, et al., 1990, J. Molec. Biol., 215, 403–410).

6.2. Results

Genetic regions involved in bipolar affective disorder (BAD) human genes had previously been reported to map to portions of the long (18q) and short (18p) arms of human chromosome 18, including a broad 18q genetic region of about 6–7 cM between markers D18S469 and D18S554 (U.S. Provisional Applications Ser. Nos. 60/014,498 and 60/023,438, filed on Mar. 28, 1996 and Aug. 23, 1996, respectively, the entire contents of each of which are incorporated herein by reference; Freimer, et al., 1996, Neuropsychiat. Genet. 67, 254–263; Freimer, et al., 1996, Nature Genetics 12, 436–441), the entire contents of each of which are incorporated herein by reference.

Linkage Disequilibrium. Prior to attempting to identify gene sequences, studies were performed to further narrow the neuropsychiatric disorder region. Specifically, a linkage disequilibrium (LD) analysis was performed using population samples and techniques as described in Section 6.1, above, which took advantage of the additional physical markers identified via the physical mapping techniques described below.

High resolution physical mapping using YAC. BAC and RH techniques. In order to provide the precise order of genetic markers necessary for linkage and LD mapping, and to guide new microsatellite marker development for finer mapping, a high resolution physical map of the 18q23 candidate region was developed using YAC, BAC and RH techniques.

For such physical mapping, first, YACs were mapped to the chromosome 18 region being analyzed. Using the mapped YAC contig as a framework, the region from publicly available markers D18S1161 and D18S554, which spans most of the D18S469-D18S554 region described above, was also mapped and contiged with BACs. Sublibraries from the contiged BACs were constructed, from which microsatellite marker sequences were identified and sequenced.

To ensure development of an accurate physical map, the radiation hybrid (RH) mapping technique was independently applied to the region being analyzed. RH was used to order all microsatellite markers and non-polymorphic STSs in the region. Thus, the high resolution physical map ultimately constructed was obtained using data from RH mapping and STS-content mapping.

BAC clones within the newly identified 310 kb neuropsychiatric disorder region were analyzed to identify specific genes within the region. A combination of sample sequencing, cDNA selection and transcription mapping analyses were combined to arrange sequences into tentative transcription units, that is, tentatively delineating the coding sequences of genes within this genomic region of interest.

One of the transcription units identified was termed rTS. The position of the rTS gene within the disease associate chromosomal interval identifies the rTS gene as mediating BAD.

7. EXAMPLE

Screening Affect Individuals for Alternations in rTS

Forward and reverse primers were designed to amplify each exon. One primer set 5'ACCCACCTTATAATTGATTCAGGC3 (SEQ ID NO:7) and 5'GAAACAAAGCATGCCACTACTG3' (SEQ ID NO:8) was used to amplify exon 6 of the rTS gene. Analysis of multiple samples from individuals having BAD identified a T to C base substitution at nucelotide 11 in exon 6. This alteration, which cosegregates with BAD, alters the codon ATG to ACG.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference.

What is claimed is:

1. A method of treating a rTS-mediated neuropsychiatric disorder comprising identifying a compound that can be used to treat a rTS-mediated neuropsychiatric disorder, comprising the steps of:

a) contacting a small molecule test compound with an rTS protein;

b) determining whether said small molecule test compound binds to said rTS protein;

c) selecting a small molecule test compound that binds to said rTS protein as being a compound that can be used to treat an rTS-mediated neuropsychiatric disorder; and d) administering said compound to a patient in need thereof.

2. The method of claim 1, wherein the rTS protein comprises the amino acid sequence of SEQ ID NO: 2.

3. The method of claim 1, wherein the rTS protein comprises the amino acid sequence of SEQ ID NO: 4.

4. The method of claim 1, wherein said test compound interferes with rTS gene product macromolecular interactions.

* * * * *

```
                              SEQUENCE LISTING


<160> NUMBER OF SEQ ID NOS: 8

<210> SEQ ID NO 1
<211> LENGTH: 1817
<212> TYPE: DNA
<213> ORGANISM: Homo sapiens
<220> FEATURE:
<221> NAME/KEY: CDS
<222> LOCATION: (67)..(1149)

<400> SEQUENCE: 1

gccacggcgc ggacgccatg cacacggacc ctgactactc ggctgcctat gtcgtcatag      60

aaactg atg cag aag atg gaa tca agg ggt gtg gaa tta cct tca ctc       108
       Met Gln Lys Met Glu Ser Arg Gly Val Glu Leu Pro Ser Leu
         1               5                  10

tgg gaa aag gca ctg aag ttg att ggt cca gaa aag ggc gtg gtg cac      156
Trp Glu Lys Ala Leu Lys Leu Ile Gly Pro Glu Lys Gly Val Val His
 15                  20                  25                  30

ctg gcg aca gcg gcc gtc cta aac gcg gtg tgg gac ttg tgg gcc aag      204
Leu Ala Thr Ala Ala Val Leu Asn Ala Val Trp Asp Leu Trp Ala Lys
                 35                  40                  45

cag gag gga aag cct gtc tgg aag tta ctt gtg gac atg gat ccc agg      252
Gln Glu Gly Lys Pro Val Trp Lys Leu Leu Val Asp Met Asp Pro Arg
             50                  55                  60

atg ctg gta tcc tgc ata gat ttc agg tac atc act gat gtc ctg act      300
Met Leu Val Ser Cys Ile Asp Phe Arg Tyr Ile Thr Asp Val Leu Thr
         65                  70                  75

gag gag gat gcc cta gaa ata ctg cag aaa ggt caa att ggt aaa aaa      348
Glu Glu Asp Ala Leu Glu Ile Leu Gln Lys Gly Gln Ile Gly Lys Lys
```

-continued

```
    80                  85                  90

gaa aga gag aag caa atg ctg gca caa gga tac cct gct tac acg aca      396
Glu Arg Glu Lys Gln Met Leu Ala Gln Gly Tyr Pro Ala Tyr Thr Thr
 95                 100                 105                 110

tcg tgc gcc tgg ctg ggg tac tca gat gac acg ttg aag cag ctc tgt      444
Ser Cys Ala Trp Leu Gly Tyr Ser Asp Asp Thr Leu Lys Gln Leu Cys
                115                 120                 125

gcc cag gcg ctg aag gat ggc tgg acc agg ttt aaa gta aag gtg ggt      492
Ala Gln Ala Leu Lys Asp Gly Trp Thr Arg Phe Lys Val Lys Val Gly
            130                 135                 140

gct gat ctc cag gat gac atg cga aga tgc caa atc atc cga gac atg      540
Ala Asp Leu Gln Asp Asp Met Arg Arg Cys Gln Ile Ile Arg Asp Met
        145                 150                 155

att gga ccg gaa aag act ttg atg atg gat gcc aac cag cgc tgg gat      588
Ile Gly Pro Glu Lys Thr Leu Met Met Asp Ala Asn Gln Arg Trp Asp
    160                 165                 170

gtg cct gag gcg gtg gag tgg atg tcc aag ctg gcc aag ttc aag cca      636
Val Pro Glu Ala Val Glu Trp Met Ser Lys Leu Ala Lys Phe Lys Pro
175                 180                 185                 190

ttg tgg att gag gag cca acc tcc cct gat gac att ctg ggg cac gcc      684
Leu Trp Ile Glu Glu Pro Thr Ser Pro Asp Asp Ile Leu Gly His Ala
                195                 200                 205

acc att tcc aag gca ctg gtc cca tta gga att ggc att gcc aca gga      732
Thr Ile Ser Lys Ala Leu Val Pro Leu Gly Ile Gly Ile Ala Thr Gly
            210                 215                 220

gaa cag tgc cac aat aga gtg ata ttt aag caa ctc cta cag gcg aag      780
Glu Gln Cys His Asn Arg Val Ile Phe Lys Gln Leu Leu Gln Ala Lys
        225                 230                 235

gcc ctg cag ttc ctc cag att gac agt tgc aga ctg ggc agt gtc aat      828
Ala Leu Gln Phe Leu Gln Ile Asp Ser Cys Arg Leu Gly Ser Val Asn
    240                 245                 250

gag aac ctc tca gta ttg ctg atg gcc aaa aag ttt gaa att cct gtt      876
Glu Asn Leu Ser Val Leu Leu Met Ala Lys Lys Phe Glu Ile Pro Val
255                 260                 265                 270

tgc ccc cat gct ggt gga gtt ggc ctc tgt gaa ctg gtg cag cac ctg      924
Cys Pro His Ala Gly Gly Val Gly Leu Cys Glu Leu Val Gln His Leu
                275                 280                 285

att ata ttt gac tac ata tca gtt tct gca agc ctt gaa aat agg gtg     972
Ile Ile Phe Asp Tyr Ile Ser Val Ser Ala Ser Leu Glu Asn Arg Val
            290                 295                 300

tgt gag tat gtt gac cac ctg cat gag cat ttc aag tat ccc gtg atg     1020
Cys Glu Tyr Val Asp His Leu His Glu His Phe Lys Tyr Pro Val Met
        305                 310                 315

atc cag cgg gct tcc tac atg cct ccc aag gat ccc ggc tac tca aca     1068
Ile Gln Arg Ala Ser Tyr Met Pro Pro Lys Asp Pro Gly Tyr Ser Thr
    320                 325                 330

gaa atg aag gag gaa tct gta aag aaa cac cag tat cca gat ggt gaa     1116
Glu Met Lys Glu Glu Ser Val Lys Lys His Gln Tyr Pro Asp Gly Glu
335                 340                 345                 350

gtt tgg aag aaa ctc ctt cct gct caa gaa aat taagtgctca gccccaacaa   1169
Val Trp Lys Lys Leu Leu Pro Ala Gln Glu Asn
                355                 360

ctttttcttt tctgaagtga aagggcttaa aatttcttgg aaatagtttt acaaaaatgg   1229

atttaaaaaa tcctaccgat caagatgagt tcagctagaa gtcataccac cctcaggaat   1289

cagctaaagc aaaaagaact tttacctcgg catccagccc aacccctaaa gactgacaat   1349

atccttcaag ctcctttgaa agcaccctaa acagccattt ccattttaat agttggatgc   1409

ggattgtacc cttcaatctg aaagtcttca gctttgaagt catcaatttt ctcaactttt   1469
```

```
cgaagaatcc tgagctttgg gaaaggtctg ggttctcgct gaagctaaaa acaaaataag   1529

gccattattt tgccataatt gtacgacctg ttgtaattgc tcctcatgtc catgaaacaa   1589

gtacacagga tgtgatcaac aaagttctat tttacaggag tatgatcctg tcgatacctt   1649

gccgtagtta tgtaacatga ttggagcgca accagctgtt ctcttgacca cagatcgaga   1709

gtgaggggta ttttgtgaca ttacacagca tcaggagcct ggtgcctcat caggtgtaag   1769

ttcttataac cactcttggc aaatttatta aagacaggaa cacagtca                 1817


<210> SEQ ID NO 2
<211> LENGTH: 361
<212> TYPE: PRT
<213> ORGANISM: Homo sapiens

<400> SEQUENCE: 2

Met Gln Lys Met Glu Ser Arg Gly Val Glu Leu Pro Ser Leu Trp Glu
  1               5                  10                  15

Lys Ala Leu Lys Leu Ile Gly Pro Glu Lys Gly Val Val His Leu Ala
             20                  25                  30

Thr Ala Ala Val Leu Asn Ala Val Trp Asp Leu Trp Ala Lys Gln Glu
         35                  40                  45

Gly Lys Pro Val Trp Lys Leu Leu Val Asp Met Asp Pro Arg Met Leu
     50                  55                  60

Val Ser Cys Ile Asp Phe Arg Tyr Ile Thr Asp Val Leu Thr Glu Glu
 65                  70                  75                  80

Asp Ala Leu Glu Ile Leu Gln Lys Gly Gln Ile Gly Lys Lys Glu Arg
                 85                  90                  95

Glu Lys Gln Met Leu Ala Gln Gly Tyr Pro Ala Tyr Thr Thr Ser Cys
            100                 105                 110

Ala Trp Leu Gly Tyr Ser Asp Asp Thr Leu Lys Gln Leu Cys Ala Gln
        115                 120                 125

Ala Leu Lys Asp Gly Trp Thr Arg Phe Lys Val Lys Val Gly Ala Asp
    130                 135                 140

Leu Gln Asp Asp Met Arg Arg Cys Gln Ile Ile Arg Asp Met Ile Gly
145                 150                 155                 160

Pro Glu Lys Thr Leu Met Met Asp Ala Asn Gln Arg Trp Asp Val Pro
                165                 170                 175

Glu Ala Val Glu Trp Met Ser Lys Leu Ala Lys Phe Lys Pro Leu Trp
            180                 185                 190

Ile Glu Glu Pro Thr Ser Pro Asp Asp Ile Leu Gly His Ala Thr Ile
        195                 200                 205

Ser Lys Ala Leu Val Pro Leu Gly Ile Gly Ile Ala Thr Gly Glu Gln
    210                 215                 220

Cys His Asn Arg Val Ile Phe Lys Gln Leu Leu Gln Ala Lys Ala Leu
225                 230                 235                 240

Gln Phe Leu Gln Ile Asp Ser Cys Arg Leu Gly Ser Val Asn Glu Asn
                245                 250                 255

Leu Ser Val Leu Leu Met Ala Lys Lys Phe Glu Ile Pro Val Cys Pro
            260                 265                 270

His Ala Gly Gly Val Gly Leu Cys Glu Leu Val Gln His Leu Ile Ile
        275                 280                 285

Phe Asp Tyr Ile Ser Val Ser Ala Ser Leu Glu Asn Arg Val Cys Glu
    290                 295                 300

Tyr Val Asp His Leu His Glu His Phe Lys Tyr Pro Val Met Ile Gln
```

-continued 305 310 315 320

Arg Ala Ser Tyr Met Pro Pro Lys Asp Pro Gly Tyr Ser Thr Glu Met
325 330 335

Lys Glu Glu Ser Val Lys Lys His Gln Tyr Pro Asp Gly Glu Val Trp
340 345 350

Lys Lys Leu Leu Pro Ala Gln Glu Asn
355 360

<210> SEQ ID NO 3
<211> LENGTH: 1613
<212> TYPE: DNA
<213> ORGANISM: Homo sapiens
<220> FEATURE:
<221> NAME/KEY: CDS
<222> LOCATION: (18)..(1265)

<400> SEQUENCE: 3
gccacggcgc ggacgcc atg cac acg gac cct gac tac tcg gct gcc tat 50
Met His Thr Asp Pro Asp Tyr Ser Ala Ala Tyr
1 5 10 gtc gtc ata gaa act gat gca gaa gat gga atc aag ggg tgt gga att 98
Val Val Ile Glu Thr Asp Ala Glu Asp Gly Ile Lys Gly Cys Gly Ile
15 20 25 acc ttc act ctg gga aaa ggc act gaa gtt gtt gtc tgt gct gtg aat 146
Thr Phe Thr Leu Gly Lys Gly Thr Glu Val Val Val Cys Ala Val Asn
30 35 40 gcc ctc gcc cac cat gtg ctc aac aag gac ctc aag gac att gtt ggt 194
Ala Leu Ala His His Val Leu Asn Lys Asp Leu Lys Asp Ile Val Gly
45 50 55 gac ttc aga ggc ttc tat agg cag ctc aca agt gat ggg cag ctc aga 242
Asp Phe Arg Gly Phe Tyr Arg Gln Leu Thr Ser Asp Gly Gln Leu Arg
60 65 70 75 tgg att ggt cca gaa aag ggc gtg gtg cac ctg gcg aca gcg gcc gtc 290
Trp Ile Gly Pro Glu Lys Gly Val Val His Leu Ala Thr Ala Ala Val
80 85 90 cta aac gcg gtg tgg gac ttg tgg gcc aag cag gag gga aag cct gtc 338
Leu Asn Ala Val Trp Asp Leu Trp Ala Lys Gln Glu Gly Lys Pro Val
95 100 105 tgg aag tta ctt gtg gac atg gat ccc agg atg ctg gta tcc tgc ata 386
Trp Lys Leu Leu Val Asp Met Asp Pro Arg Met Leu Val Ser Cys Ile
110 115 120 gat ttc agg tac atc act gat gtc ctg act gag gag gat gcc cta gaa 434
Asp Phe Arg Tyr Ile Thr Asp Val Leu Thr Glu Glu Asp Ala Leu Glu
125 130 135 ata ctg cag aaa ggt caa att ggt aaa aaa gaa aga gag aag caa atg 482
Ile Leu Gln Lys Gly Gln Ile Gly Lys Lys Glu Arg Glu Lys Gln Met
140 145 150 155 ctg gca caa gga tac cct gct tac acg aca tcg tgc gcc tgg ctg ggg 530
Leu Ala Gln Gly Tyr Pro Ala Tyr Thr Thr Ser Cys Ala Trp Leu Gly
160 165 170 tac tca gat gac acg ttg aag cag ctc tgt gcc cag gcg ctg aag gat 578
Tyr Ser Asp Asp Thr Leu Lys Gln Leu Cys Ala Gln Ala Leu Lys Asp
175 180 185 ggc tgg acc agg ttt aaa gta aag gtg ggt gct gat ctc cag gat gac 626
Gly Trp Thr Arg Phe Lys Val Lys Val Gly Ala Asp Leu Gln Asp Asp
190 195 200 atg cga aga tgc caa atc atc cga gac atg att gga ccg gaa aag act 674
Met Arg Arg Cys Gln Ile Ile Arg Asp Met Ile Gly Pro Glu Lys Thr
205 210 215 ttg atg atg gat gcc aac cag cgc tgg gat gtg cct gag gcg gtg gag 722

-continued

```
Leu Met Met Asp Ala Asn Gln Arg Trp Asp Val Pro Glu Ala Val Glu
220                 225                 230                 235

tgg atg tcc aag ctg gcc aag ttc aag cca ttg tgg att gag gag cca      770
Trp Met Ser Lys Leu Ala Lys Phe Lys Pro Leu Trp Ile Glu Glu Pro
                240                 245                 250

acc tcc cct gat gac att ctg ggg cac gcc acc att tcc aag gca ctg      818
Thr Ser Pro Asp Asp Ile Leu Gly His Ala Thr Ile Ser Lys Ala Leu
            255                 260                 265

gtc cca tta gga att ggc att gcc aca gga gaa cag tgc cac aat aga      866
Val Pro Leu Gly Ile Gly Ile Ala Thr Gly Glu Gln Cys His Asn Arg
        270                 275                 280

gtg ata ttt aag caa ctc cta cag gcg aag gcc ctg cag ttc ctc cag      914
Val Ile Phe Lys Gln Leu Leu Gln Ala Lys Ala Leu Gln Phe Leu Gln
    285                 290                 295

att gac agt tgc aga ctg ggc agt gtc aat gag aac ctc tca gta ttg      962
Ile Asp Ser Cys Arg Leu Gly Ser Val Asn Glu Asn Leu Ser Val Leu
300                 305                 310                 315

ctg atg gcc aaa aag ttt gaa att cct gtt tgc ccc cat gct ggt gga     1010
Leu Met Ala Lys Lys Phe Glu Ile Pro Val Cys Pro His Ala Gly Gly
                320                 325                 330

gtt ggc ctc tgt gaa ctg gtg cag cac ctg att ata ttt gac tac ata     1058
Val Gly Leu Cys Glu Leu Val Gln His Leu Ile Ile Phe Asp Tyr Ile
            335                 340                 345

tca gtt tct gca agc ctt gaa aat agg gtg tgt gag tat gtt gac cac     1106
Ser Val Ser Ala Ser Leu Glu Asn Arg Val Cys Glu Tyr Val Asp His
        350                 355                 360

ctg cat gag cat ttc aag tat ccc gtg atg atc cag cgg gct tcc tac     1154
Leu His Glu His Phe Lys Tyr Pro Val Met Ile Gln Arg Ala Ser Tyr
    365                 370                 375

atg cct ccc aag gat ccc ggc tac tca aca gaa atg aag gag gaa tct     1202
Met Pro Pro Lys Asp Pro Gly Tyr Ser Thr Glu Met Lys Glu Glu Ser
380                 385                 390                 395

gta aag aaa cac cag tat cca gat ggt gaa gtt tgg aag aaa ctc ctt     1250
Val Lys Lys His Gln Tyr Pro Asp Gly Glu Val Trp Lys Lys Leu Leu
                400                 405                 410

cct gct caa gaa aat taagtgctca gccccaacaa ctttttctt tctgaagtga     1305
Pro Ala Gln Glu Asn
            415

aagggcttaa aatttcttgg aaatagtttt acaaaaatgg atttaaaaaa tcctaccgat   1365

caagatgagt tcagctagaa gtcataccac cctcaggaat cagctaagta attattactt   1425

gattctttta gcaaatcaat gcacgttatc ctacttaatc cttaaataag tttagattta   1485

actaacccaa agtccaggag gatgttctta caaaaatagc tatatcaagg gctggcacct   1545

agacattaaa ctgtactttg aaaataaaaa aaaaaaaaaa aaaaaaaaaa aaaaaaaaaa   1605

aaaaaaaa                                                            1613


<210> SEQ ID NO 4
<211> LENGTH: 416
<212> TYPE: PRT
<213> ORGANISM: Homo sapiens

<400> SEQUENCE: 4

Met His Thr Asp Pro Asp Tyr Ser Ala Ala Tyr Val Val Ile Glu Thr
  1               5                  10                  15

Asp Ala Glu Asp Gly Ile Lys Gly Cys Gly Ile Thr Phe Thr Leu Gly
             20                  25                  30

Lys Gly Thr Glu Val Val Val Cys Ala Val Asn Ala Leu Ala His His
         35                  40                  45
```

```
Val Leu Asn Lys Asp Leu Lys Asp Ile Val Gly Asp Phe Arg Gly Phe
     50                  55                  60

Tyr Arg Gln Leu Thr Ser Asp Gly Gln Leu Arg Trp Ile Gly Pro Glu
 65                  70                  75                  80

Lys Gly Val Val His Leu Ala Thr Ala Ala Val Leu Asn Ala Val Trp
                 85                  90                  95

Asp Leu Trp Ala Lys Gln Glu Gly Lys Pro Val Trp Lys Leu Leu Val
            100                 105                 110

Asp Met Asp Pro Arg Met Leu Val Ser Cys Ile Asp Phe Arg Tyr Ile
        115                 120                 125

Thr Asp Val Leu Thr Glu Glu Asp Ala Leu Glu Ile Leu Gln Lys Gly
    130                 135                 140

Gln Ile Gly Lys Lys Glu Arg Glu Lys Gln Met Leu Ala Gln Gly Tyr
145                 150                 155                 160

Pro Ala Tyr Thr Thr Ser Cys Ala Trp Leu Gly Tyr Ser Asp Asp Thr
                165                 170                 175

Leu Lys Gln Leu Cys Ala Gln Ala Leu Lys Asp Gly Trp Thr Arg Phe
            180                 185                 190

Lys Val Lys Val Gly Ala Asp Leu Gln Asp Asp Met Arg Arg Cys Gln
        195                 200                 205

Ile Ile Arg Asp Met Ile Gly Pro Glu Lys Thr Leu Met Met Asp Ala
    210                 215                 220

Asn Gln Arg Trp Asp Val Pro Glu Ala Val Glu Trp Met Ser Lys Leu
225                 230                 235                 240

Ala Lys Phe Lys Pro Leu Trp Ile Glu Glu Pro Thr Ser Pro Asp Asp
                245                 250                 255

Ile Leu Gly His Ala Thr Ile Ser Lys Ala Leu Val Pro Leu Gly Ile
            260                 265                 270

Gly Ile Ala Thr Gly Glu Gln Cys His Asn Arg Val Ile Phe Lys Gln
        275                 280                 285

Leu Leu Gln Ala Lys Ala Leu Gln Phe Leu Gln Ile Asp Ser Cys Arg
    290                 295                 300

Leu Gly Ser Val Asn Glu Asn Leu Ser Val Leu Leu Met Ala Lys Lys
305                 310                 315                 320

Phe Glu Ile Pro Val Cys Pro His Ala Gly Gly Val Gly Leu Cys Glu
                325                 330                 335

Leu Val Gln His Leu Ile Ile Phe Asp Tyr Ile Ser Val Ser Ala Ser
            340                 345                 350

Leu Glu Asn Arg Val Cys Glu Tyr Val Asp His Leu His Glu His Phe
        355                 360                 365

Lys Tyr Pro Val Met Ile Gln Arg Ala Ser Tyr Met Pro Pro Lys Asp
    370                 375                 380

Pro Gly Tyr Ser Thr Glu Met Lys Glu Glu Ser Val Lys Lys His Gln
385                 390                 395                 400

Tyr Pro Asp Gly Glu Val Trp Lys Lys Leu Leu Pro Ala Gln Glu Asn
                405                 410                 415
```

<210> SEQ ID NO 5
<211> LENGTH: 45716
<212> TYPE: DNA
<213> ORGANISM: Homo sapiens

<400> SEQUENCE: 5
ctgggtgcag tggctcatgc ctgtaatccc aacactttgg gagcctggtc tggaggatcg     60

-continued

```
cttgagccca ggagttcaag ataagcctgg gcagcaagac gaaaccccat ctgtacaaaa    120
attagctggg catggtggtg cgtacctgtg gtcccaacta ctaaggaggc tgaggtggga    180
taactgtttg agtccaggag gtagaaactg cagtgaactg tgattgcacc actgcactcc    240
aatctgggtg acagaatgag accctgtctc aaaaaaaaaa ttagaaataa gacttagtaa    300
aacaataaaa gctaaataga taatatgtga aatttatcca gtagcaggaa tggtccctgg    360
gacctttaag aagcagatgg cggtattcaa ttttaagttg cttgcagagt ccttgctacc    420
ccaaaccttc ctgcaaatca gctacacata acggtgagtc agtgaccttt aggaaagaaa    480
agggattggg gtcacggcca gaggtacaat gacaaggtac aaacaaggat agggatggat    540
ttcataacct agtttaaacg cagtggggaa ataaattcag gaaataaatc aggtaagtag    600
gagaaaagtt caccaagtac ttggagagac actggatttc acagggacat ggcgtagggg    660
ttcaatccag cttcacttct atcttaaagg tcaagttaac gagtaagttg gaggactttg    720
aaaatccaag taaaaaattg tcactagcct gtgacaatag ggatgagaga aataaaaact    780
tcgcagttgg ccaaaaaggt tgacagtgat tctaataact gaattaaagt ggtgtggccc    840
ttaaagttta tcaaattcca tttattcact cataattgca ctattttcat ggaaagtctt    900
agtctcctaa aacattgaga ggatatacca cggaactaga tggcaaactt ggtttggttg    960
gtttttgtaa tctttaccat tgctagaaag ttagaaaagg gtggcttcac ttcagcagaa   1020
attttgaaaa attcgtggaa ccagaagaaa cccaatctaa aagaaataca agagaacatt   1080
ttcgcagagt tttaagtgca atttcaaaga aaattcaaac ttagaatcaa attcaaagag   1140
gaggcagcac cccaaagcaa catttttttgt tttattgagg tataatttac atacaacaaa   1200
gctcaccatt ttaagtgtac cactagatga gttgttgaca aatgtagaca gccatgaaac   1260
caccatgaaa ccagaatcat agaacatttc catcatttca gaaaattcca ttatgccctt   1320
ttacagtcaa tctcttccat tcacccctga cctctgtcaa ccactgagtg ttttctgtca   1380
ctataattgt acatttctag ggctttatat aaatggaatc atatgtagtc actgtgtctg   1440
atgtctttcg tttagcataa tgcttttgag atctttttat ggctcagtaa tattccattg   1500
tgtggatgtg tactacatct tggttttgtc ctttaccaat tgatggatgt ttaggttgtt   1560
actagtttta ggctatcaca aataaagctg ctatgaacat tcaaatacaa gtttttattt   1620
taaacatagg ttttaaattc tcttggataa ttacctatga gtaggattac tgagttgtat   1680
gatacatgaa tgcttaactt tctaagaaac tgataaccta tttccaaaga agatgtaccc   1740
tttcataccc ctccagcaat gtatgagagt tccagctgct tcacatcctt gccaatactt   1800
ggtattgcca gtcactttaa ttgcagccat cctggtgcgt gttagtagta catcattgtg   1860
gttttagtgt gcatttccct aatgactaat aatgttgagt cttttcataa gcttatttca   1920
aattcatatg tctgcttagg tggaatgtct attagaaagt cttttgccca ttttttatat   1980
caagttgcca tcttactgag ttgtaatttt ttcagtattc tgcatacaag tccttttaac   2040
agatatgttt tgcaaatatt tttcttccaa tctgcagctt gcattttcat ttctttaatg   2100
gttttcatca aagagaaaac atttttaatg ttgataattt aattggcaat gtttttcttt   2160
tatgattcat gcttttagtg tcctaagaaa gtttgcttta tccaagtaca aaaagatttt   2220
ctcctgtgtt ttctttagaa gttttgtaat tctagctctt aaaatttaga tctatattcc   2280
acttcgagat gatttttgtg tatgatataa ggtaatgatc caggattgtt ctgtttgttc   2340
ttatggatat tcaattgttc gagcaccagt tgttggaaag actagcttac tcgttgaatt   2400
```

-continued

```
ttcttggccc ctgttttttt tttgttgttt ttattttgta gacggagtct cgctttgtcg   2460
cccagcctgg agggcagtgg cgcgatctca gctcaccgca acctccgcct cccgggttca   2520
aatgattctc ctgcctcagc ctcccgagta gctgggacta caggcgcgtg ctaccacgcc   2580
tggctaattt tttgtatttt tactatttca agacctcttc tgttccattg atctacttgt   2640
ctgtctttat gtcaatttca cattgactcg attagtgtat agcaagtctt aaaaccaagt   2700
agtttaagtt cttcagcctt gttctttttt aggattattt tggctattca aatttccata   2760
taaattttag aatcaacttg gtccaatttc ttcaaaaaaa tcctgctagt gatttagatt   2820
agattgcatt gaatttgtag ttcgatttgg gaagaactgc tattttaaca atattgagtc   2880
ttccaatcca agaatatgaa tttctctaca tttctacatt tctttagatc ttttttctc    2940
agcaatgttt tatagttcag tgtgcaaatc ttgcatattt ttgttaaact tgtcctgttt   3000
tatattttca atgcaattgt tttaagagat acngttttct aatttgtttc caatttttta   3060
ttactagcac atcaactata gattttaaat tgaccttgta tcctacaaac ttgctaagct   3120
caatattagt tccagtagct tttttcgtta agtccaatga agacagtttt caacaaagat   3180
gaataatcat gtcatccaag aataaacagg tttacttcct tttcaatctg cctttttattt  3240
cttttcttat tatattaccc taactagaac ctgcagtact atgttgaata gaagtggtgg   3300
aagcagacat cctttccttg ttccaaatct taaggagaaa gcatcaatca ttcaccataa   3360
agtcagtttg tggctgtttc tatcttctga aatagattat agagaattgt tgtaatttct   3420
tccttaaatg tttggtgtaa aattcaccag tgaaaccatg gacctggtgc tttttgtttt   3480
tggaaggcta ttatttattc aagttattta atagatatag gcctattcag attgtccatt   3540
tcttctcgtg tgaattttgg cagattgtgt ctttcaagga attggtttat ttcatcncag   3600
gttatcaaat ttgtggacat agaattcata gtattccttt attatcattt taatgtccgt   3660
cggatctgta gtaatgttcc ttattncact tttgatatta gttatttgcg ttctcttttc   3720
ttgcctggnt agaggcttat tgattttatc aatgttttca aagaaccagc tttkgttttc   3780
attgattttt ctttgttgct ttcctgtttt caatttcaca ggtttctgct ttaattttta   3840
ttatttcttc tcttctgctt actttggatt ttctttttat ttctttttat ttatttattt   3900
ttgagacaca gtctcactct gtcgcccagg ctggagtgca gtggtgcgat ctcggctcac   3960
tgcaacctcc gcctcctggg ttgaagcgat tctcctgcct cagcctcccg agtagctggg   4020
actgcaggcg cccgccacca cgcccggcta atttttgta tttttagtag agacggggtt    4080
tcaccgtgtt agccaggatg gtctcgatct cctgactcgc catctgcccg ccttggcctc   4140
ccaaactgct gggattacag gcgtgagccg cccagcatyt tttttttttt gagtcggagt   4200
cttgctctgt cgcccggggct gcagtgcagt ggcgcgatct cagttcactg caagctccac  4260
ctcccgggtt caggcagttc tgcctcagcc tcccgagtag ccgggactac gggcgcgcac   4320
caccacgccc tgctaatttt tgtttttagt agaggcggga tttcgccgta ttggccaggc   4380
tgatttcaaa cgcctgacct caggtgatcc gcccgcctcg gcctcccgaa ktctggatta   4440
caggctgagg cacggtacgg gacctcatct gcatcagtac gggtgtaatc aatgatgacc   4500
tgcctcttaa tttatcaggt ggcaaactga ggctgtgggc actgaaagag acctagcatt   4560
ttctagggca ccgctctcct gggtacgctg gcgacaacca gcggcctcgg cttgggagct   4620
gagccactgg ccggaatctg ccgctgagcg aatgcactcg ctcagacccg acttctccct   4680
ctagggcgcg gctcccgggc aggtcccttc acgagtcttc catccgagca gagcagggtc   4740
ccgcggaggc gccgaccggg cgcgaggcct cctgcctgcc caggttcccc ggcgaccctg   4800
```

-continued

```
agcgaaccct ctcggggtca gctccgtcta ggctgagaag ggaacggcgg aaggcggagt   4860
gcgcccccgg gagcccggag ctgggactgc agctcccatg ggccaagtt cacggggtgc   4920
ggccgcgcgg ccaatgagcg ccctctatgc cctgacggtg ccccgcctcg cggcgctgcc   4980
ggctcccgcc ctcccgccct cccgccgcgc gctcgggatc ccgaccagtc ctgaccgcac   5040
gggggccgcg gccacggggc gcaggggcca tggtgcgcgg caggatctcc cggctctcgg   5100
tccgggacgt gcgcttcccc acgtcgcttg ggggccacgg cgcggacgcc atggtaagcg   5160
cggacgccat ggtaagcgcg gacgccatgg taagcgcgga cgccatggta agcgcggacg   5220
ccatggtaag cgcggacgcc atggtaagcg cggacgccat ggtaagcgcg gacgccatgg   5280
taagcgcgga cgccatggta agcgcggacg ccatggtaag cgcggacgcc atggtaagcg   5340
cggcttgcgg cccgggtccc tcccgccccg actgcagctc tgcgggcccc gggcagcttc   5400
ccgacttcga acccattgct tctgtaaagt gggaggcgcg cctgggggag acactcgctt   5460
ttcatgcctt ggagcaattg tataagtatc cagaaacttt ccactctcct gggtttttc    5520
tttgctggag tttagaatat cctggtttta cttttacgac tcacattttg ctggaaatgg   5580
tagaatgcat aataggcaat agcagcaaaa tgattttgtt gggttcccgc cagtggaaac   5640
cctagagcac agtgctcgct ggcttcctct gtaccctgaa cgcgacgggg ttggcgctga   5700
gggagaacgg gaagcccggg gctgggagtt ttgagtggtg atcccgcttc cacaacttgc   5760
tgtgtgactt ggagaagttc cagacctctc tgggtctctt ggacccgtct gtgtaatgaa   5820
ggtgtcacag tcgggttgag aaaccaagcg cgtgctaact gcgtcacatg agagggcgct   5880
ctcgtgaaat tacccgcaaa cacgcttaga aaggactgat gcaaatgtca gttcgtctta   5940
agagatgtaa taaagtaagg gcaggaactc tgactcctac ctaaatattg aaggtctttt   6000
ttgcttactg agggtgttag aatgtcaggc cttccctccc ctgccccgt ctagagcggt    6060
gtttcccaaa tacagtgggt tctgtgcagg gttttcaggg agcctgttcc ccactgggtc   6120
ctcactgccc gtcgtagtcc actgatgaga ttggccgcgc tagaaaagca gagttgtatg   6180
ggtatgtagt gaatgtgtga aagtatgctg ggaagtgagg aacggcaatg ttaggaaaat   6240
ggttaccagt agggagggaa ggaaatgggg tcacggaggg gaccacgagg tctctaattc   6300
ccattgtaat gttttacttc ctaaattggg tggatggcaa gctggtgtcc attacattat   6360
ctatactctt tttgtacctg aaatgtttta taaaaataga tctctcgtta aagttattaa   6420
atgcaaaaca atgtcctttt tgagattaag ttcatcctgc atttttaaat ttttatttta   6480
ttctatttta tgttttaaat ttatttattt atttattttg aggcagggtc tcttatctgt   6540
tgcccaagct ggagtgcagt ggtactatca tggctcacag cagccttgac ctccctgact   6600
caaccaatcc tcccacctca gcctcccaag tagctgggac tacaggtgtg caccatgatg   6660
cccagctact ttctgtattt tttgtagaga cagggcccag gctgtcatcc tctttaaaat   6720
cttcatgttt cctttcttac atgatgttgg taaataactt aaacacccag caggcaatcc   6780
tttatggaac tcaaaataaa tgttggaaat tttactggct tatagaatcc aaacactcga   6840
tctcatgcaa ctgcctttgc ctctgtgaag ctttagcagc tgtggctaag tcacacaatc   6900
tttctaagcc taggtttctc atctgtaaaa tgggtataat aatattcact ttatacatgt   6960
aaatgagata cctgtaaaga gcctggctca gagaaggccg tcagtaaagt tggctatagg   7020
ccaggcatga gggctcacac ctctaatcct aagtggaggc ctaggcaggg ggatcacttg   7080
agcccaggaa ttcaattaca tgagctatga tcatgccact gcattccagc ctgggcactg   7140
```

-continued

```
gatgacacag tgagaccctg tttctaaaga aaaaaggagg ggtggctgta attactattc   7200

actctgagga aactgaagca gaaggaatcc ctaatctaga cttgactttg aatttgtgaa   7260

atgttaagac agcctggttt ggctgagacg tggtggttca agcctataat cccagcactt   7320

tggaaggcca aggcaggtgg atcgcttgag cccaggagtt cgagaccagc ctgagcaaca   7380

tagtgagacc tcgtctcaac aaaaaaatac aaaaattagc tgggcgtagt tgcatgcacc   7440

tgtggtccca gccactcagg aggctgagkt gggaggatct cttgagtcca ggaggtcgag   7500

gctgcagtga gctgtaattg tgtcactgca ctccagcctg ggtgagagag agagaccctg   7560

tctcaaaaga cagcctggtt tactgtagaa taattcaaga aatggaattt gcctctgggc   7620

ctgagtgatg tctaacacag ggtaaggaga cattatctaa cacctgtatt gcaagctcat   7680

aaatacttaa gcattttatc ttggggagat agggtgtatg ttgtgtgcca gctctcaagt   7740

gccttcttat tagaatgagc tgttttgcag ttcaccatgg agatggcttc acatgccctc   7800

gaggcatgct ggaccatcag cacttagcaa agtgagcctc cctgatcaga agtaggatat   7860

tttcaagaaa gagcaataaa gctgtcctcc aaaatctgct aaagactcct gctttttttt   7920

tttagacaga gtctcgcttg ttgcnccagc ctggagtgca gtggtgcaat ctcatctcac   7980

tgcaacctct gcctcccata tgcaaatgat tstsgtacct cagmctctgg agtagctgtg   8040

attacaggtg tgcaccacca cacctggcta atttttgtat ttttggtaga gacggggttt   8100

caacatgttg tccaggctgg tctcgaactc ctgagctcag gtgatccacc tgcctcggcc   8160

tcccaaagtg ccggattaca ggcatgagcc actactccgg gcttacctcc ttcttaatct   8220

gaaatctact tctgttcctt tcttctctgt gaattgccct tgttatttct ccttcagctg   8280

tccttaccct cagatacgtt ttccgctgtc ggccgcctct tcttcgtgtg ctctctcccc   8340

tcgtggcctc ctgcctttct gacagctcct tcttcctcca ctggcccctt cttccctctc   8400

tgaggctcag gcctcagtgt ctttccggtc tccctacaca ctcccatgaa gaccctctcc   8460

acattctgac ttcggtgcca ccctttatgc cggagactcc cagatctcat ttccggatct   8520

gcctccttaa cttataggtc tggatacttc ctgtttggtt tttcaccttc atgctaaacg   8580

cagtttgtct aaatcggaag tcaacttcca ttctctgccg cccctccctc ctgacccatg   8640

ttggatcatt ccgctaatca cagggaccca aaagcttcga gtcacttttg gctcatctcg   8700

tcctgttgac cctcatctga ggcttcagtg caaggtttcc tttttccatt gcttcctctt   8760

cttggaaccc agaaactgcc gatgggtctt taattcttgg agtctccttc tcagcctcat   8820

cgctcaactc cttcaggaac ccaatggctc agccaaccca ggtgggcacc aacacttgaa   8880

tacactccag tctctccctc ttctgacccc tttactttct gcactgctgc tgctgctacc   8940

ttgcctgaga tattcctccc tcccagactc ttcactcccc ttcccactgc tgaggagctc   9000

cccttccttg accggccagc tcacattctg tcttcatcat aaagcgctct ccctcttcaa   9060

gaagcacatt cagctaacag cgctctctgc cagtcgttca tagtttgcat ccctcccagg   9120

ccttagcatt ttctgcctta tattattaag gttttttttt aaccatgtct ttttatttat   9180

ttattttaga gatggggtct cgctttgttg cccaggctag tctcgaactc ctgggctcaa   9240

acaatcctcc tgtcttggcc tcccaaagtg ttgggattac aggtatgagc cagcatgccc   9300

gttctataag caggtcttct caaatgtaac ctcctcaagg gcagacgtat ctgtaacccc   9360

ctagcaagct gcaccagctc tgacacgtac ttggtgctca gcgatgcatc acactgattt   9420

cctgccactg gactgtgata ccagactcag ggctcccagc catcacatac agctccctca   9480

gccacgacac cccaatacag ggatttaaaa tctgccttca taatttactt gtggccgggc   9540
```

-continued

```
gtggtggctc acacctgtaa tcctagcact ttgggaggcc gaggcaagtg gatcacctga   9600
ggtcaggagt tcaagaccag cctggccaac atggcaaaat cccatcttta ctaaaaaaaa   9660
aaaaaaagct ggtcatagtg gtgggtgcct gtaatcccag ctacttggga ggctgaggca   9720
gaagaatcgc ttgaatccag gaggcagagg ttgcagtgag ccaagatcat gccactgcac   9780
tccagcctgg agaacagagt gagagtcagt ctcaaaaata ataataataa taataaaaca   9840
ttatttactt gtggtgtgac cttttgtaaa ttactaaagc tccttaaaac ttcatttcct   9900
ctttaataag gataagagca cctactttat aatattgtta taagattaaa ttaaaccatg   9960
tggagctctt agaatatagt gtgtctggca caataaatat tatagaataa taacagtaat  10020
aaattttcat agccttatgc acaattcttc tttatgaatg cattcacatc ttctgcctgg  10080
ctttttggag tctccattat tccatgacat agaacaaaac aaaaaatgag tgaattaatc  10140
tcgaagcttt acttcttcat tttcccccac tggtgtctga acttttgcca gtgtattttc  10200
agccctgcta taaactgcta taagtgagat cactccaatt ttatgcaaca gttttctgaa  10260
cctttggctt gttcaatttg aagctgcttg tgaatgtaac tttgttcaaa aagctgacag  10320
agatagctgc gagtgaaaac tccttggctt aaaattgagc cccttccggg catgatggct  10380
catgcctgta atcccagcac tttaagaggc ccaagcgggt ggatcactag agctctggag  10440
tttgagacca gcctgggtaa catgcaagac tccatctcta ttttttttatt taaaaaaataa  10500
ataagtaaat aaaattgagc ctcatttttt aacctaattg aaaatgggtg ataaaaatgt  10560
atacattgcg accaggtgcg gtggctcaca cttgtaatcc cagcactttg ggaggccaag  10620
gcaggtggat cacctgaggt caggagttca agaccagcct ggccaacatg gtgaaacttc  10680
gtctctatta aaaatacaaa aatcagccaa gtgtggtggc acatgcctgt aatcccagct  10740
acccgggagg ctgaggcagg agaatcgctt gaacttggga ggctgcagtt gcagtgagct  10800
gagatcgcac cattgcactc ctgcctaggt gacagagcaa gactctgtct caaaaaagaa  10860
aaaaaaaaaa atatatatat atatatatat atacatacat tgctcttgtt gaaacatttt  10920
ggatctttca ggaggacatt ccttttctcc attcagagcc ctttgttttc tttggggtat  10980
agcaacagtt ccttctatgg gagctcttgt ggcacggccc ctgtggcatt gtctgtcctc  11040
atgtgacatc attctcatgg ttcttttcgg gtttctcaca ctggcattgt ttcggcgggg  11100
aactcctctc ctgcagcaca cggaccctga ctactcggct gcctatgtcg tcatagaaac  11160
tgatgcagaa gatggaatca aggggtgtgg aattaccttc actctgggaa aaggcactga  11220
agttggtgag ttgaagattc tctcgaggtt ccagaatgct taattttcag atgagattct  11280
aatttagatt cttagattca ttagaatctt gatttagatt gagttctgat cttgttttta  11340
tctgtattta cactgctcaa agtgagtaaa aacagtgttt catggtttgt tacttgtttc  11400
actgggagaa atttaaaagt gacagaattt ggcctctctc cttgcaatca tctctagcct  11460
gttagaaaat ccttggctgt tagtctgttt ctctgtgtca aatgacagct acaagagtgc  11520
ttttcacctg cctttcaccc ggggccactg tcgagctttg acaacctgta gtgggcgagt  11580
aaccaagggc aatgagaggg aggagacatg agttcccata gcaaaaaagg ctcattgtga  11640
tgtgcacagc aagtctactc gcttttcaat atatatatgt atatattttt gagacagagt  11700
ctcactctgt cgcccaggct ggagtgcagt ggcacaatct cagctcactg caacctctgc  11760
ctcctgggtt caagcaattc tcctgcctca gcctcccgag aagctaggat tacaggctcc  11820
caccaccatg cccagccaat ttttgtattt ttagtagaga cagggtttca ccatgttggc  11880
```

-continued

```
caggctggtc tcgaactcct gacctcaaat gatccgcctg tctcagcctc gcaaagtgct  11940
gggattacag gtgtgagcca tcacacccgg ccttttcaaa atatttcaca ccaaatcggt  12000
ttcaagttca ctattttcat ggcgaaaagg gctttggccc cgcccaatct cggaggtctc  12060
ccttggggaa gagcagattc tttaagatgc atactgagcc gtgtatacgt cattcttttt  12120
ttatttgcat tttctatttt cttaaacaga agacacagaa cataactttt ttcagagctg  12180
gatgtgatct caaatggtga tcttgagccg tctcattttt tagagagaag aaaactgagg  12240
cacagacagc tacccagcaa gtcatggcag aaccacctga ctgcccagag cactttctct  12300
tcagaacttt taaatgcaac tctttttgaa tacataatac ttacacatgg tacaaaattc  12360
aagaagtcca aaacagtggc cttcgccaga tcaatttcag tggattatta gagcctgaag  12420
ccaaattatg atagattgaa gggtaagggt ctagaaggag ggaaaagagt ttctctaact  12480
tcggtggtag tgtgatacct ctcccttgga tatttgcacc atcagcgctc tcagtagttg  12540
tagaaaaaaa tcttggccca ttgagagatt ttaaattgtt aagcatataa aagaagtgtg  12600
tgagtttgtg aatgtgtgta tgtgcgaatg gcaagggaac cttccttgaa ctttcaatgg  12660
acactgccca ggtggctgct gttactgctc ttcacagggc tggcggtcag ttgtccagca  12720
agtcagtcct tctgcagact tctcctgagt gctgccatgt atcaggcacc aaagtaattt  12780
taaaaagaga aagataggcc gggcgtggtg attcaggcct gtaatcccag cactttggga  12840
ggctgaggcg ggcagattgc ttgagtcaag cagttcgaga ccagcctggt caacatgctg  12900
aaaccctgtc tttactaaaa atacaaaaat tacctggccg tggtgatgca tggctgtaat  12960
ctcagctact caggaggctg aagcacgaga attgcttgaa cctgggagtt ggagtttgca  13020
gtgagccgag attgcgccgc tgcactccag cctgggtgaa aaagcgagac tccatcccaa  13080
aaaaaaaaaa aaaaaaagat acagaagaca gaatcccaca tacaaggagc acacgaactt  13140
attggggaag tagacataaa agaaatgatc atagtgcagt ctgagaatta ctgtttttta  13200
aaactatgta caagttttac agagagagga tatattaggc tgttcttttt tttttttttt  13260
ttttttcttt ttctttttgg aaacaagagt cttgctctgt cgcccagcct ggagtgcagt  13320
ggcgcaatct cgctcactac aacctccacc tcccgggttc aagcaattct tatgcctcag  13380
cctcccgagt agctgggatt acaggcacac accaccacgc ccggctagkt tttatatttt  13440
tagtaaagat gaggtttcac cgtgtttsgt caggctggtc tcctgacttc aaatgatctg  13500
cccaccttgg cctctcaaag tgctaagatt ataggcatga accaccactc tgagccaggc  13560
tatttttgca ttgctataaa ggagtacgag agactggata atttataaag aaaaagaggt  13620
ttaattgcct catggttctg caggttttac agaaagcatg atgccagcta ctcagcttct  13680
agggaggctt caggacactt acaatcatgg tagaaggtga agggggagca ggcacgtcct  13740
atgtcgaaag gatcaagaga aagggaatgg ggaggtgcta cacactttta agtcaccaga  13800
tctcacgaga actcactcac tatctcaaag acagtaccaa tgggatagtg ctaaaccatt  13860
caggagaaat ccacctccaa gatctaataa tcacctccca ccaggcccca cctccaacac  13920
tggggattac acttcaacat gaaatttgtg cagaatgtct aaaccatctc agggggtaac  13980
ttcactctgt ccaaaaggct cagggaaggc ttcagagcag aagtaatgct ttgaggtgag  14040
tctcgaagag caaacaggaa tttgccaggc agagaaagac catgctgtga gtcagtcccg  14100
cttttctcca ttaagtaaac aatttactgt taaagttttc cccagagtag taaccactta  14160
ctaagacaga gctgtgagct gtttctgctt cttctgcaac tctaattgtc ccttgtttgt  14220
aagttgagta ctttatgaag ccgctgcctt tctccatact gcaaatccta cagcacagcc  14280
```

-continued

```
cccaaaggtt gcataaaact cagcgagctt acaagatatg ttaggccatt ggacccactc  14340
tctgttaaca gcccagactt taaactttgc tgacttgggc acacgtggag gggccctggg  14400
cactaagata gataagaagc ccttctggga tgggtgctga gctcagtgtt tagggccttc  14460
acttcccctc tcctcctcca ttcccagccc cacaccgctg tcttggtgga tgtctcaggc  14520
acggataaat caacttccat ctctccatga ctttaattaa tgactctttt gtgctaaggg  14580
ttttggcttc ctccttttc agaccacaac atgacagaac ccattttaac tttaaccttg  14640
ctacatattt caggtgactc actgcagtct cactaaatgt gttacacagc actcacacta  14700
aagatgaaaa attccattag ctcatcctgg ttcttctgct tacttaccta atcatctgtt  14760
tatgatttaa aaaaataggg ttactgtgaa gagagtgctt gtgtgtgaga cagagaggga  14820
gggttgtttt tcaaatgtat agaatatacc aatgtagttt ttggttgggt atttttttaa  14880
atcatgactt tattaaattt acttaattaa tattcatttt tatccttttt ttatgttttt  14940
aaagttttta ttatttatta atttatttga gataaggtct tgctctgtca cccaggctgg  15000
agtgcagtgg tgcaatcacg gctcatacag ccttgacctt ccagactcaa atgattgtcc  15060
cacctcacct tcccgagtag ctgggcccac aggcacaagc caccatgcct agctaatgtt  15120
tctttttttt gagagacaga gtctcgctct gttgcccagg ctggagtgga gtggcacatt  15180
cttggctcac tgcaacctcc acctccaagg ttcaaacgat tctcctgcct cagtttccca  15240
agtagctggg actacagatg tgtgccacca tgcccagcta atttttgtat ttttaggaga  15300
gacagggttt cactatatgt tggccaggct ggtctcaaac tcctgacctc aggtgatcca  15360
cccactttgg cctcccaaag tggtaggatt gcagatgtaa gccaccamac ctgacykggg  15420
tttttttttt tttttttttt gagatgtagt ttcgctcttg ttgcccaggc tggagtgcag  15480
tagcacaatc tctgctcact gcaacaacca cctcccaggt tcaagcgatt ctcctgcctc  15540
agcctcccag gtagctggga ctataggtgc ctgccaccat gctgggctga tttttgtatt  15600
ttttgtagag acaggatttc atcattttgc ccagactggt cttgaactcc tgagctcaag  15660
caatccgcct gcctcagcct cccaaagtga tgggattgca ggcataagct ataagccacc  15720
atgcctggcc tgtttctgtt tttatttatt tatttattta tttatctatg tatttattta  15780
tttttgagat agagtcccac tctgttgccc aggctggagt gcagtggtgt gatctcggct  15840
cactgcaacc tctgcctcct aggttcaagc aattctcctg cctcagcctc ccgagtagct  15900
gggattacag gtgcccacta tcacgccagc taattttttt tttttttgag atggagtctc  15960
gctctgtcac ccaggctgga gtacagtggc gcgatctcag ctcactgcaa gctctgcttc  16020
ctgggttcac gccattctcc tgcctcagcc tctccagtag ctggactaca ggcacctgcc  16080
accacgcccg gctaattttt tttttatttt tagtagagat ggggtttcac cgtgttagcc  16140
aggatggtct cgaactcctg acctcaggtg atccacccgc cttgacctcc caaagtgctg  16200
ggattacagg cgtgagccac cgtggccagc cttttttttt tttaagactt tatttttta  16260
gagtagtttt aggttcacag caaaactgaa tggaagttac aaagatttcc cacatacccc  16320
tgtccccaca caggcacagc ctccttcatt atcaacattc tgcccagagt ggcccacttg  16380
gtacaactga tgaacctgca ttggcacatc atgatcaccc aaagtctgta gtttacaata  16440
ggggtcactc ttaggtttgg acacatgtat aataatatgt acaatgtaga ctaagttagt  16500
tttttaaaaa atagaaaaag atgtacaaag aaagaatttt taaatagaca aaatttttaa  16560
aaatccagcc ttaagagttt atgacaccac tcttacttca gacacccaca agtcacccac  16620
```

-continued

```
agactttact caatgtcctt ccagtgctag aggctccaga gaattgaagt ccctgagcag  16680
atagaatcac aagagaaaac cccccgggtt tagttgccaa gaagctgctt tcaagggcct  16740
tttttttctt ttccaagtca atttcctgcc acagccaaaa tttctctcgt tttttttttt  16800
tttttttttt ttgaggcaga gtttcgctct tgtcgcccag actggagtgc gatggcgtga  16860
tcttggctgg ctcactgcaa cctctgcctc ccaggttcaa gcgattctca tacctcagcc  16920
cccacaagta gctgggatta caggcatgtg ccaccacacc cagctaattt ttgtattttt  16980
agtagagaca gggtttcacc atgttgatca ggttggtctc atactcctga cctcaggtga  17040
tccgcccgcc tcagcctccc aaagtgctgg gattacaggc atgagccacc gtgcctggcc  17100
tcacaaccca aatttctatt gaatgcgaca aattctagtc tcctgttgag caagaaaaat  17160
ccatacactg tagatgaata cataagtgct gcttgtgcac tctgagagtc ataaaaatga  17220
gatcatcctt agcttttgtt aagtgcattt ggtattgtga catgaaccag aggtatgctt  17280
cagtcaatga tttatagcaa caatcaaatc cttgagacgg tggtttggtg tcgataataa  17340
cgtacctcac tgtgagtcac tgacttactt cagattttct ttaattcaag agcatcaacc  17400
ttcaagaagt gaggaggact ctgtcttctc acaattctag ggaatgaatg tctgaaccag  17460
aatgattgtg tatcccatta acaaaagccc tagagaacct ggaatggctg gttcagccct  17520
aaatgctaca tctgacctaa agtgtgcaat catccgagag ctgtttcacc cttagccagg  17580
catgtgctaa aagcttgggg catcactttc tttctttttc ttgagatgga gtttcgctct  17640
tgttgcccag gctggagtgc aatggcatgg tcttggctca ctgcaacctc cacctcctgg  17700
gttcaagtga ttctcctccc tccgcttccc aagtagctgg gattacaggc acctgccacc  17760
atgcccagct aatttttgta tttttagtag agatggggtt tcaccatgtt ggccaagctg  17820
gtctcaaact cttgacctca ggcaatccac cggccttggc ctcccaaagt gctaggatta  17880
cagacgtgag ccaccgcgcc cagcctgggg caccactttc aaactgtcct tctcaagatc  17940
ttattgacag taaaactgta cccctacaac tgtcctatta aatgactaaa aacttttact  18000
attgaatcca cggcagcacc aaacaaatta atcaaaacgt tttggaatac attcctttct  18060
ttgaagctaa gttgatggct tgattcaatt attgtgtcca tttacacaac gtaggctaaa  18120
tgtttcctag aattggcaaa ggatcaaagg gttactttac ttattcatca tcttaaataa  18180
cccaagaaag cctttatatt attattatta ttattatttg agacagggcc cagctctgtc  18240
acctaggctg gagtgcagtg gcacaatctc agctcactgc aacctctgcc tccaaagcta  18300
aagtgatcct cctacctcaa gtgatcctcc tacctcagcc tcccgagagg cggggaccac  18360
aggcgcacca ccgcaaccgg ctaatttttg tattttttgt agagatgatg tcttgccaca  18420
ctgcccaggc tggtctcaaa ttcctgagct caagtgatcc acccacctca gcctcccaaa  18480
gtgctggcat tacaggagtg agcgccaggt ccaagaaatc ctttcaaagt aaaataccac  18540
aggacatggt ggctcacacc tgtaatccca acacttcagg aggccgaggt gggaggattg  18600
cttgagccca gagttccaga acctccccac ccactgcccc atgcaacata gcaagacctt  18660
gtcactacaa aaaatttaaa aattagctgg tgtggtgttg cgtgtaggtc ctagctactc  18720
aggaggctga gacaaaaaga ttgcttgagg ctaggcattc aagattacag tgaggtgctg  18780
ggtgcagtgt ctcaggcctg taatcccagc aattttggtg gccgaggcag gtgtatcact  18840
tgagctcagg agctcgagac cagcctggga agcatggtga aaccctgtct ctaccaaaaa  18900
tacaagaaat tagctgggca tggcagctca agcctgtggt ctcagctact caggaggcgg  18960
aggtggaagg atcacttgag cccaggacgc agagattgca atgagcctag atcccgccac  19020
```

-continued

```
tgcactccag gctgggtgac agagtgaaac cctgtctcta aaaaataata attaaaggta  19080
ccaaaaataa ataattgatg gtaatgccga cccaaattaa atttaacctt caaattactt  19140
atgaaaaatg tagtatatca taagaaagtc aatagtaaga aatttcatgt taagacagtg  19200
ttttcatata ttttaacatt ttacatataa atagtatgct aattgcaaat tcattttatt  19260
taatgtttaa tagtttatgt tatgaattca aggcattttc tatacttgtc aataatgaaa  19320
aggcatttct ccttttaaaa attctatgaa gtcagccttc ttattcctta ggaacatgaa  19380
ctagtgtggt ttggttttga atctgattgt tcaaacactt tacaaagtga ataggaaaat  19440
aatttgggaa catttatatt taaacttgtc aatctatgat tctgtttttc atgtgacagc  19500
caatcacaat gtgttctcta ctcaggaagt ttagctcagt atatggatta acacgtgttc  19560
tacttgtgtg atatttctta tgacaaccac agaaaacata tggggctggg cacagtggct  19620
tatgcctgta atcccagaac tttgggaggc caaggcgggt ggatcacttg agcgcagtaa  19680
tttgacacca gcctgggcag catgtcgaaa ctgcgtctct acaaaaaata ccaaaattaa  19740
ccaggtgtgg cggcacatgc ctgtaatcct agcttctcga gaagctgagg tgggaggatt  19800
acctgagccg gggaggtcaa ggttgcggtg agccgtgatg gtgccactgc actcaagcct  19860
gggtgacaga gtgagaccct gcctaaaaaa gaaaagaraa gaaarraaaa catatttgat  19920
gcattttaaa aagaatatac ctttgagata gagtctcact cttgttgccc aggctggagt  19980
gcagtggtgc aatctcggct cactgcaacc tctgcctcct gggttcaagc gattctcctg  20040
cctcagcctc ctgagtagct gggattacag gtgcgcacca ctgtgccctg ctaatttttg  20100
tattttcagt agagacaggg ttttgccatt ttggccagac tggtctggag ctcctcatct  20160
caagtggtcc tcctgccgtg gcctcccaaa gtgttgagat tacaggcatg agccaccgcg  20220
cctggcctag atttaatttt ttcataaaac tttcacattt gtttgtttgt gatgttttca  20280
ggtgctaatt tcttgaccta gtatagaagc ataaacaaga gttcaatcct ttttaaatag  20340
ggtaagggac ctattttgta aaatgcttac ataagtaata ttaccaaggt ctgagatgtc  20400
ctttgagtgc aacgaatgtg aaaatagaga tgggtttatt tatttgttta tttatttatt  20460
ttttgagatg gagtctcact ctgtcaccca cgttggagtg cagtgatgca atcttggctc  20520
actgcaacct ccgcctcctg ggttcaaaca gttctcctgc ttcagcctcc tgagtagctg  20580
ggactacagg catgcactag cacacctggc taatgtttgt aattttagta gagatggggt  20640
ttgaccacgt tggccaggct ggtctcgaac tcctgacctc aagtgatccg ccttcctcag  20700
cctcccaaag tgctgggatt acaggtgtga gccaccatgc ccatcctaga gatgtgttta  20760
taattttaaa gtaaaacatt ttattcagtt aaattcaggc ttgagtcatt tagatcatca  20820
gtattttgag gtaaacaact catttctgta agactgatga tctaaatgac tcaagactga  20880
atttagctga ataaaatgtt ctactaagga gatgaggtcc tgagatttgg gtcctaagag  20940
ctatctcttc tctaaggacc tcatctcctc ctccctgaat tggaaagtgc tctagaggat  21000
aaagtactaa atgggcaatc tctttatgga gaaataatgt gagtagtgtt agagatgtaa  21060
gagaaggtca ggccgggcgc ggtggctcac tcctgtaatc ccagcacttt gggaggccaa  21120
ggcaggcaga tcacgaggtc aggaggtcga gaccatcctg gctaacatgg tgaaaccccg  21180
tctctactaa aaatacaaaa aattagccgg gcatggtggc gggcgcctat agtcccagtt  21240
actcaggagg ctgaggcagg agaacggcgt gaacctggga ggcggagctt gcagtgagcc  21300
gagatcgcac cactgcactc cagcctgggc aacagagtga gactctgtct caaaacaaaa  21360
```

-continued

```
aaaaaaaaaa aaaaaaaaga gagagatkta aaagaaggkc attaaagaga aaacattaag  21420
agaagagcaa atttaaaaar rtggragacc atggtacctt ttatgggttt gggatttgac  21480
ctataaattc aaggcatgaa aaagttaggc yctggagaaa rgrttccaac acaataaggt  21540
gaattcaata ccctgacctt tgcctttgtc ccgtgatact ggattttgtc ttttcctaac  21600
ccggcttagt ctcccatcca tgcactgaga arggcacaag agaatgtact ttcaatagtg  21660
cctgggattt catcttttac tttatacaga gaatattaaa cttaccttga aagatgtcac  21720
cttgaagaag ttcccattgg ctgaatctgg gacaatttga acatccaaat aaatatgata  21780
gtaatggctt ataacccatt gaataaaatc catgagtcca ttcagataat gaacaatcag  21840
ctgggcacag tagctcacgc ctataatccc agcaccttgg ggctgaagca ggagaatcac  21900
ttaaggccag gagttcaaga ccagcctggg cagcatagtt gagacccccg tctgtacttt  21960
ttaaaaataa aaataatnaa atanaanatt tttaaggagg taataaacaa caaggtcaag  22020
cccattacag ctgattaana tctaataant ataaaaggaa tgataacatc agagaatcac  22080
cataactgtc atagctacaa ttaattgagg caagagtcat caagggatgc ccaaattttg  22140
ggacaataat aacctcctta cttggaaaat gaaatggtaa cttcacagtg gagaaagcaa  22200
atggacacta agttacccaa gtggtaaaag ttaacaatcc taataataaa acaaaatgac  22260
ataatcactt atgtagtatt gatgccaaaa aatgtattac ctgaatctag tcatgaagga  22320
actccagatc agcccagatt gaggaatgct gtacaaatca agtggcctgt actcttttaa  22380
aatgctaata acatttaaaa aagaagaaga aaaattattc caggtaaaaa gagactaaag  22440
aggcatggcg actaaatgta atacgtgatc ccagatggga tatggattag ggtaaaataa  22500
aatacattat tggaaaaaac tggtgacatt tgattatgga ctggccttta gacagcaata  22560
ttctatcaat gttatattcc ctgagtgtga ttattgtact acggttatgt aagaaaatat  22620
ccttgttttc aggaactata cactgatgta tttagggtta agagagcatg atatttgcaa  22680
ctttattcaa atggttcaga aaaaagaagt acatatgtgt gtgtgttcat atgtatatac  22740
atacatatac ttaacatata tatagagaga gagaaagaag agaggaaaac acaggtgttt  22800
ttcctgctat tcttaaaact cttcaatagg ttagcaactg tttttttaa acttaacctt  22860
taggtgggtt tctattgcta ccttttaatt cttgagatgt gtccctggac ggaagaccta  22920
aatatctttc tctctctctc tttttttttt tttttgagac agagtcttgc tctgttgccc  22980
aggctggagt gtagtggtgc gatcttggct cactgcaacc tccgccttct gggttcgaga  23040
gatcctcttg cctcagcctc ctgagtaggg actacaggca caaaccacca cacctggctc  23100
atttctctgt tttcagtaga gacggggttt caccatgttg gccaggctgg tcttggtccc  23160
aaagtcctgg gtttacaggc atgagccatc acacccagcc ctctttttca tttctaaaaa  23220
gtgcttttgt actttgcttc ctaaccagat tggtccagaa aagggcgtgg tgcacctggc  23280
gacagcggcc gtcctaaacg cggtgtggga cttgtgggcc aagcaggagg gaaaggtaac  23340
ccctctcaca aacgctcagg aggctcctgg gagctgcacg acactgactt tccctacgca  23400
cagaggaaag acagacacac tgcagccccc aaaaggaaat acagataatt gctttggtgt  23460
ttttttctcc tctgagaggt tttggcagta ggtagggaac tgcaggagga ggagaaagag  23520
gagacaggat ggcggaaggc gcaggcagca gtagaggggg gtgtggggac ctggtggctg  23580
acagccagca ttagctgcca acgtgtttac tgtcaggaaa aaatggggac tttacacata  23640
tgtcttacaa atcctttctt ttttacttca agcctgtctg gaagttactt gtggacatgg  23700
tgagtagcat tgttaatgtt acaattgttt ctgtaaatga aatggatatc attgatgaca  23760
```

-continued

```
tgccttttga tgatcagtaa atatattcag gactatctgt tgatcactat agcgatgata  23820
aagcaaaaag ccaataaaat atgacattcc ttttctgata tctgacgtaa cagatggctg  23880
tgctcatgca ggcagggtgg catgagggga agcagtgagg gggtcctgcc tcccccactg  23940
tgcatgtgta acacacggtg ccagttctct gagcctccat tgcctgacta tgacaagagg  24000
atcatcctaa cttctctagg aacctcacaa aattaaagat caatgagaaa agcacctcat  24060
aaactctgaa aagccagatg ttataatatt atgaagatat tatccaggcc aggcatggtg  24120
gctcaagcct gtaatcccaa tactttggaa ggctggagga tggcttgagc ccaggagttt  24180
caggctgcag tgagctataa ttgcaccact gcactcaggt gacagagcaa gaccctgtct  24240
caaaaaaaga aaaaagaaaa gatactatcc agtcactttg acaccaagaa taagatcagg  24300
ccattgtagc ctctactgta caattccagc agggaaggag ctcaacactg aattctaaag  24360
ctatgcactt gactgttttc tttctccttg accttttcat agcaggggtg aacaactgga  24420
tgctgaggag gaaaaaactg ggcaaattaa aggggaatga gcttcagacc ccatgcagag  24480
ctggctgtga gtccgggttt cactgctcac cagctgcatg accttgagca tgtgacttcc  24540
ccactctgag ctgcggtggc ctcagtgcaa cacctgggtg gcggttaaaa acctcgtgat  24600
ccacaaatga aggcccttgt tattagttgg caaaaaatta aggaaaaaca aagaacacca  24660
tggccttgaa gagtgttggg caggagactg ctcctcctcc ggaggaaagt gaagacagga  24720
ggctgtcaca tcgtctctga catggagagt ggcttccggg ccatccgtag gggaaggaca  24780
cagagctctt gagccccctt ctagattcaa ggttggcgtt ttacggggat ggaggaggta  24840
gccaccaaaa gggaatgatt tgcaggccac cagaaatgtg cctgaggtcc cacctgtgga  24900
ccctccattt ttggatcctg ttccctttca atgccagtac tcttttcttt tttcttttt  24960
tctttctttc tttttttttt ttttagacgg agttttcttc ttgttgccca ggctacagta  25020
cagtggcatg atctcagctc actgcaactg attcaagcga ttctcctgtc tcagcctcct  25080
gagtagctgg gattacaggc acccgccacc atgcccagct aattttttgt atttttagtg  25140
aaaacggggt ttcaccatgt tggtcagtct gagctcgaac tccggacctc aggtgatcca  25200
cccatctcag cctcccaaag tgctgggatt acagatgtga gccaccgaac ctggcccaga  25260
actcttagaa gtagaatctc agggttgaaa gagtttttcg gattttcgac agttatggta  25320
gagtattatt ggtcactata agatgttagt gggaatggaa ctactggctg ttttccaact  25380
gactgttccg tcagggtagg gagaggtctc agcacgaggc cccgccgaaa tgttggtaag  25440
tggtcagcca agtgggccgc tcactcccgg ttcgcccact gtgttcctgt cagtgaagca  25500
aacatcccca tttggcagga gaagaagctg ccggaggtca cactgctagt gattggtggc  25560
ccaggggtag ggcagccttc tttcctctgc agttcactgc tccagaacca tctccagcct  25620
catagctcac cgtggacagc cctgcggtgt ggcgctgatg tacagagtga tgccaggcgt  25680
tcatctcccc actgagctcc tgctgagtgt ttgcctgggg ccaggtcctc cttccgggaa  25740
gtcattttag ctggaaagaa cagggtgggg gcgggtggca agggatcaga gcatgagcgt  25800
ttgagggctt cgtcaggggc agtgaggagc ctctaaagga ctctacattt aggaatgaca  25860
gagtcaaaca atttaacaaa gccctaaagg tccctgccag gaaagaatga gccccatgta  25920
tcaccataag caacttctta gaaacataac ccacccctgt catcccagca ctttgggagg  25980
ccaaggaggg aggattgctt gaagccagga gctcaagatc aacctggtca acatagtgag  26040
accccatctc tacaaaaata aaaataaatt agccgggcat agtggcacat acctggagtc  26100
```

-continued

```
ccagctactc aggaggctga ggcaggagga tcacataagc cggggagact gaggctgcag  26160
tgagctatga tggcatcact gcactccagc ctgggcaaca gagtgagacc ttgtctctaa  26220
aaaaagaata ataaatttta aaaaacaaaa tataacccac cttataattg attcaggcct  26280
cttcccctcc tgtcacgttg ccaggatccc aggatgctgg tatcctgcat agatttcagg  26340
tacatcactg atgtcctgac tgaggaggat gccctaggtg agtttggaag ctttctggga  26400
tacacgatgt gcacacacag tagtggcatg ctttgtttcc taaaagagtg agtgatgctt  26460
tttatttctt ccagaaatac tgcagaaagg tcaaattggt aaaaaagaaa gaggtgggtt  26520
gtaagaaaat tttcttcatt gtttttgcta acattgtcca cttttgagtg cccctgtcct  26580
tttggggtac acattgtctt cccaaatgcc ctgtgctgag cagctaggcc ctcaaatcaa  26640
cattcaagtc tgcatggtga agcctgctgg gtatgacctc tgactgcaga gtttgcttca  26700
gccactgctg aaaggaagtt tggctttagg attacactgt agggagagcc ctgggggagc  26760
agggcagtcc gtgagagtat cctgatcacc tgggtttgac atcctagtaa tttgtggctg  26820
ggtgtgtgtg tgcagggccg gatcaggaga acagctggac tctccagggg aaacagctgg  26880
actctccagg ggaaacagct tagctacagg cacttccaat tccgaagggc cctggaaagt  26940
gcaaaatgtt gacggcgctg tgttttcaca gagaagcaaa tgctggcaca aggataccct  27000
gcttacacga catcgtgcgc ctggctgggg tactcagatg acacgttgaa gcaggtgggc  27060
attttaacct ggctttgtag acagctgaat ggggagaaac caacctgttt ttccttctgt  27120
cctcatacca ctactctcag tacctcactt ctgacaccag atgtgtgtgg ttttccttct  27180
cacgccaacc agttctccac ttctctgtgg acaccaactg ggtgtcctgc tattttactc  27240
aattctgaca gcacatacct ggaactagcc tcagacccca caggttaagg gctcagtctt  27300
acaggactgc cctatggcag atgccagtca caagtccacg ttgtcacctg tgcttctgac  27360
tggctttgcc tcagattaga ggttcccaca aaccccgctt tgagttgaat catttggtgg  27420
aatggctcac ggaattcagg gaaacactac ttatgtttac tcatttatta taaaggatgc  27480
aacttaagaa cagccaaact gaagagacac acagggcaag gtgtgaggag ggggtacaga  27540
gcttccatgt cccctccagg tgagccacac tcccagtacc tccacgtgtt caccaacctg  27600
gaagctctct gaaccctgtt ccttggggggt tttatggagg cttcagtatt tagatgtgat  27660
tcattatttg gccattggcc atcaattcag ccttcagccc cctcgcctcc ccagctatct  27720
gggaataggc taaagtttcc aaccccacca tcatgccttt caggtctttc tggtccccag  27780
ccccatcctg aagctacgta ggggacctca gcagggctct ctcgttcacg tacaaaagac  27840
ayycctatca ctcaggagat gccmarggkt ttwrgggstg tgtgttgtgt gttaggaaat  27900
aggggggcag cgatgggggc agagacaaaa tatatattcc ttcttatgtc acatgggctt  27960
ttgattccag cctctctggg agaaatttaa tactttcctg ttcacctctc taaatcattt  28020
tggctgaggg cagtggctca cgcctataat cctagcattt tgggaggctg aggtgggtgg  28080
atcacctgag gtcagaagtt caaaaccagc ctggccaaca tggtgaaacc ccgtctctac  28140
taaaaataca aaaaattatc tgggcgtggt aatgcgtatc tgtagtccca gccactcagg  28200
aggctgaggc aggagaatca cttgaaccca ggaggcaggg gttgcaatga gccgagatca  28260
cgccactgcc ctccaacctg ggtgacagaa caagagtccg tctcaaaaaa caacaaaaaa  28320
attattttgg atccaagccc tcgttctgaa agtacacaag gaaatgcaaa gccattcatt  28380
ttgtggaccg caggactctg tgacttagtg agtcaccttg ggctctggaa ggtgacagcc  28440
tagggtaaga ttcctgggca gcaccagcgg tagacccact gcgagattga gaagtaatgc  28500
```

-continued

```
ctatttcatg gggtggtttt gaggattcag atacatgctg taagttgcgt catgctcaag  28560
gcaccatggc tggcacatgg catgcagtcg gcacatggtg gatttattac tgtttctcct  28620
tacactgtgc ccacttctag agagtggaga gagaggctgg cttctgcatg ttactcttat  28680
atccactcat tctatggatg ccacagaata ttctagcttt aaaaagagag agatcagtgc  28740
tatcttcccc ttccgggaag gttgtgacca ttaaaaaaat ggttcccata gagatgagga  28800
aagaaagtca ccctacaagt aaaaagtgat ctctgtcagc caggctgttt ctgctgttaa  28860
tttcaacaac acatgggtgt tactctggtc tatgctataa ccgtaatgct tgtgaaacag  28920
atcagcaatg actgacttcc tggtcagacc aaggggctct ctccagtgtg tgaccctgtg  28980
ctcctttccc acagctctgt gcccaggcgc tgaaggatgg ctggaccagg tgagtgtgat  29040
gatggacctg actttcccag ttggcggcag gagagactca ggcagtaagt ctctcctggc  29100
agggagccaa ggagtaaaag gcacccacgg gctaggatca ccctggctca tagggatgca  29160
taagagaagt ttccccttag gccaggctct ttctctaaag gcaggatgtg agtcctcatt  29220
agaattatag gccatcagag ttgaaagagg cttgggagat tgtttatttc gggcactaac  29280
ctagagtaga aatccagtct ttactgtcag taacagcgtt gattcagttt ctgcatgaac  29340
atctccagag gcagcgagct taacttggtg aggcactttc cattctttga gggctttgag  29400
tattaggtgg gtcttttctt ctcttttttt tttttttgag atgaagtttc actctcgtca  29460
cccagactgg agtgcagtgg cgcaatctcg gctcagtgca acctccacct cccggattca  29520
agccattctc ctgcctcagc ctccctagca gctgggatta cagacacccg ccaccacacc  29580
tggctaattt ttgtattttt aatagagaca gggtttcgct atgttgatca ggctggtcct  29640
gaactcctga cctcaggtga tccgcctgcc tcagcctccc aaagtgctgg gattataggc  29700
gtgagccact gcacccagcc aggtgggtct ttaatatcag caaccctttg cttccatgta  29760
atttccagcc agaggtccca gttcccaaga gccaggctgt tcctcttcca cttgagtgcc  29820
ctcctctccc tccaggccac ctcctttcca cactgctcat ctgcacttct cccttctgac  29880
tctcgcctgt gcaggtaaag acctctggcc atcctaagac cttctctgga tgaacctcga  29940
tggttgatga ccctgcatcc tgaaacaggg caggatgcag agggaccatc atctcttttg  30000
acccagtcac tgtgtgtccc tcagcacagc tcacggtggc actttttgcc tgtgacatgt  30060
cacccaggct tcctatctga cttgcagcca ctctggtctc tgagcctcct gctactcagt  30120
gtgtcctgtg gagcaggagc tccagcatca cctgggagct tgtgagaaat gcagcctggg  30180
cctctcccca gacccgctgc ctgggaatct gcattggaac aagatcccct agtgaktcct  30240
atgcgttctt aagttggaga ggcactgaat tcttgttaat gcctcagcta aataaaggct  30300
tgaggagtga gaacttgaag gaggcagcat gaagcsgcgg aaagaggtgt tggcatctga  30360
tagaactgaa atcacatctt gccttttccc ctcatccgct gcaagtactt gctgtgtgat  30420
caattactca acctctctga acttcatttt ctctcagtag aaataatatg agctttggtc  30480
ctcctccaag ttgccatatc tcagaaggac cagcacaggg caggattcag agcagctgct  30540
gtaagtgctg tttgccctcc ctctgcatac ccgggggagg ctgcagcagt gtatctggtg  30600
agtcagagaa ggctgtgggg agatttaaag ggtctcttcc cagcacagga agcctggcac  30660
ccagagccta aggccagcca ccctctctgg agcatcacgg atcatgtagt tgaagcctcc  30720
agctggtaca gaagagaaca gcaggtgcct gagaatgtgc ggcactctgc aagctggggc  30780
tctttgcaaa gcagcagggg gacctcagcc aaggaggcgc acagggaggg taggctgctg  30840
```

-continued

```
ttcgaggggg cagatgctgg cctccccgtg gtggtgtccc ctcctccacc tgccagtgcc  30900
cacactgagg ccagcaacac actcttctga cagcagagtc atagggtgtg gacatagags  30960
cccatgtctc aagagaacag ctggacatcc acagagatta aggagctccc tacaagtgtc  31020
tggatgtggt gtaaaggaga cctctgcacg gaggctccag ccgcactctg ctattcccta  31080
gttacctgat ctcatcactt tccctcccgg aacctcaggc ccctgcactg caggggacag  31140
accatccctg tggccttcct ctcactgagt taattcaaga caaagctctc ctttgtaaac  31200
cagacccttt ccattcagtc tatcacagtg tggcttactc ggcacccctt ttcagccccg  31260
ctctcctctt cagttctcac tgtggctttt ttgttcttaa ttccttttca tggcccggca  31320
aaaacggagt taattatatt aaagacctga cttccctgtc tagctcctta actccaggtc  31380
agcagataat tgagagtcat tgccctgata ctgaatgaag agataaagtt cccaggttta  31440
tttcaagtga cttatctgaa gatgaggaaa gagcaagagg ttactaaaaa acatatctgt  31500
gaattgttga cagagacggt cacttctgca gaaactccag atgcccttgc caagtccagg  31560
tacaggtcta aactagcaaa ccaaatgcat tttctaggtt taaagtaaag gtgggtgctg  31620
atctccagga tgacatgcga agatgccaaa tcatccgaga catgattgga ccggaaaaga  31680
ctttggtaaa tatcctctca caccactaag aagcagtagc ctttgtccag ggctaaatac  31740
aactcgtttc aagattaaag aacattggga atttaaaaag ttaattgtca gaggaagtac  31800
acttctgtag tcttgcagta ggcgagctca aacaaaaata agcaaaggga ctaatagttt  31860
tacgtttttt aattctgcag aactagttaa gtaagtttgg ggttaaggat cctttcttac  31920
taacacagat gtacctgagc aaacagtttt cccattggtg ctctggtgtg tcaatcatgt  31980
aatctcccct cctagctcct caggtaggag ggtgtcaggg ggccattact gaagaaatgt  32040
tggaacttca gctgagataa atgtaaggat cagtcatttc tgatttgtat ttttataaac  32100
cagttcttac gtgtaaaata ttttcataaa gtcacagtaa gatgttttta tgaggctttg  32160
gaggcttttt tgcataagtt aaaatagaaa ttttgagttc ttgacccagg atcactattt  32220
atacatgaat taatgctgct tttttttttt aatgaagtca tctgtatcca aataacttat  32280
gataaaaatt gattctgggc tggccagatg ctgtggctca tgcctgtaat cctagcactt  32340
tgggatgcct aggtgagtgg attgccggag ctcaggagta caagatcagc ctggcaacat  32400
ggaaaaaccc catctgtacc gaaaaataca agaaaaaaaa gtgttagcat tatatggctc  32460
atgcctataa tcctaacact ttgggaggct gaagcaggtg gatcacttga ggccaggagt  32520
ttgggaccag cctgggctac atagcaagac tctctctcta aaagaaagaa gaaaaaaaaa  32580
ttaaccaggt gtggtggtgc atgtctgtaa tccctcctac tttggaagat ggggcaagag  32640
gatcactgag ctcaggagtt ggaggctgca gtgagctaca ataataccac tgcactccag  32700
catgggcaac agagtgagat ccagcctctt aaaaaaaaaa aatccattct gagcatactg  32760
tcctctggtt ttcatagtgt cctgggagag agctcttatc acttagcaca ttctgtagag  32820
atgtccattt ctccaagcac gataagatca gggatgaggg gctgtccctt aagctgggca  32880
cagccatcac ctggcttcca agaaggatag tggtacacag agagccaggg cctaggaggg  32940
agaggactgg acttgaactc accattcact agatttattg ttcttaagca agttactgaa  33000
tttctctgca tgacagtttt cttatttgta aaatgggtta atatgaactg cctcatgggg  33060
ttattattat tattttttga gatagggtct cactcagtca cccaggctag agtacagcag  33120
catgatcaca cctcactgca gccttgacct cccctggctc aggggatcct cccacctcaa  33180
ccccctgagt agctgggact acaagtgaga gccaccacac ccagctamtt twkgtatttt  33240
```

-continued

```
ttgtagagag aggattttgc tatgttgccc agcctggtct tgaactcctg ggctcaagaa  33300
atccacaggc tgggccagat gcagtggctc atggctgtaa tcccagcact ttgggaggcc  33360
gaggcgggcg gatcacaagg tcaggagatt gagaccatcc tggctaacat ggtgaaaccc  33420
cgtctctact aaaaatacaa aaaaaaatag cctggtgtgg tggtgggcgc ctgtagtccc  33480
agctactcgg gaggctgagg caggagaatg gcgtgaacct gggaggcaga ggttgcagtg  33540
agccgagata gcgccactac actccagcct tggtgacaga gcgagactct gtctcaaaaa  33600
aaaaaaagaa aaagaaaaga aatccacggg cttcagcctc ccagagtgtt gagattacag  33660
gcatgagcca ccatgcctgg ccagttatta taaatattaa atggaacaaa atccataaag  33720
tgcctagtgg agtaggtgtg ccattatggg agagttaagg ctacttatta ttgtgccaga  33780
cacacagtgg gcaatagtca ataaatgact attgaacaaa caatgttgat tgtgcatgat  33840
tcagaatgtg acaaaatggt ttctacgaac agaaccaaca ctgcaagaca catgtatttg  33900
ggtggcatct agatggagat tggaccagag cccagggcca gcgagcactt ctcatggccc  33960
agcccagggc actgctggac atccagtggc tcctcaagca attcacggct cctcctaaag  34020
actgtacctg gagccagagt ccccgtctca gcagctgctc tctggctctt tttgttaggg  34080
ccgtgtgctg ggcctcagca gaggcgttag gggtctcac tcagctgttg gtggcactga  34140
gtgacagcat ttcctccctg ggagccgcag ccctgctgtg aggttggctc agggctgacc  34200
tccctgtgaa gagtctcttt ttgcagatga tggatgccaa ccagcgctgg gatgtgcctg  34260
aggcggtgga gtggatgtcc aagctggcca agttcaagcc attgtggatt gaggagccaa  34320
cctcccctga tgacattctg ggcacgccca ccatttccaa ggtaggaaaa cggctgctgc  34380
tgctgtggca gcttattttt ctgtttagtt ttccagagtg ctggggacag atcctaaaat  34440
ttcttcactt gttccctctt gcatttcctg ttgaagtagc tgaaataatt gtaatgtgtg  34500
acaaatacag gggttacaga cctgacattc ctttttctac ttcagcttat actttgccct  34560
tatttctgtt tgttttagat aaagtaagct gctaaaagtt gaagggctac cagcaatttg  34620
aaggttaata gacatggttc ctatgctttg taaatacaga aatgtgacag cattttttt  34680
ttttgttttt tggtggtttt ttttgttttg ttttgttttg ttttgagata gagtcttact  34740
ctgttgccca ggctggagtg caatggcatg atctcggctc actgcaacct ctgcctcccg  34800
agttcaagca attcttctgc ctcagcctcc tgagtagctg ggactacaga tgtgtgccac  34860
catgcctggc tttttttttt tttttttttt tggtattttt agtagagatg aggtttcacc  34920
acattggcca ggcctgtctc gaactcctga cctcagacca tctgcccgcc ttggcctccc  34980
aaagtgctgg attacaggag tgagccaccg cgcccggcct tgtgttttca tctgataatt  35040
tttttctcc tacacgctaa ctggtttggc acagtcatgt gccccataac aatgtttcag  35100
tcagtgaaag actgcctata taatggcgca gtatatataa tcccataagc ttataatgga  35160
gctgaaaaac tcattgccca gtgacgttgt agagattgta atgtggtgca acgcattacc  35220
tttcctatgt ttaagtatgt ttagatactg gccattgtgt tccaattgcc tgcagcgttc  35280
agaacagtag catgctgtac aggtttgtag cctgggagca ataggccatg ccatatagcc  35340
tagggcgtgt agtagtctct accatctagg gtcatggacg tacactctat gatgttcaca  35400
caatgatgaa acagcccaac ggcacatttc tcagagggta accttgtcat tcagtgacac  35460
gactgtacat tcatgtggct tatagccaca tcctgcctgc ctaggaacat tttttcctga  35520
ggtgactttg catagctata cactccccat tttgtgttga tcttacacct ttaactctga  35580
```

-continued

```
tggagcagtc ttggttccag ttctaggagg gacaccttga tgcatcccac ataaattcat  35640
gggttgtact ggaggtgtgg agtcggggac tcagggacca gttctctgtt tctctcagca  35700
aatcagcaca tgatctacat tatgtgggat actctgccaa agcctgggtt tcagaaatgc  35760
cctcccctte cacattgcag cctcgctgga gagaacagcc gagatatgtg aaacaaagac  35820
cggaggatac tgggccaggg cactgaatgc caagcacagt agaaaagttc attgaggaga  35880
acgttgggtg tgggctggga cgagggagat ggccagagct gactccataa ggaaagctaa  35940
gcctcaggtg agggaagggt gagcaggagc catggagcga ccacagcctt cattatttaa  36000
acagagccca aattttctga ggaatcattc cacaatagga atctcaggtg aggagccccg  36060
gggaaacaag acttttcacc ttgggtccca cttgcttttt cctccttagg gctctttcag  36120
gttggctgtg ccctgctgaa tgccagctgg cctagcacca acctgatctc tgcctacctg  36180
aagcatctca caggaagctc ctcagggctc taaccctccc aggttttgct tacatgaggg  36240
aggccatccc cttaggagta tctgaggaag gagcagctgc agagcctgca ggtccaggcg  36300
ggggcagtgg agatgcccca gggagcacag ggcacatgcc agggacaggc tgccacgtgg  36360
ggctggatta tggggtctgt ccactcagag gatgcagcca gtcagagtga gccactgcag  36420
cttctccgat gaaagaacgg catagtggcc aggcatagtg gctcacacct gtaaccccag  36480
cactttggga ggccgaggtg ggtggatcac ctgaggtcag gagtttgaga ccagcctggc  36540
caacatggtg aaacctcgtc tctactaaaa atacaaaaat tagctggtct cgatcttctg  36600
acctcgtgat ccgcccacct atggtcccag ctactcggag aggctgaggc aggagaatgg  36660
cgtgaaccca ggaggaggag cttgcagtga gccaaaatcg caccactgca ctccagcctg  36720
ggtgacagag cgagactcca tctcagaaaa aaaaaaaaaa ttagcagggt gcggtgatgt  36780
gtgcctgtaa tcccagctac tcaggaggct gaggcaggag aatggcttga gcctgggaag  36840
tggaggttac ggtaagccaa gtttgcgcca ttgcactcca gcctgggcga cagagcaata  36900
ctccatctca aaaaaaaaaa aaaaaaaaac acaacagcat agtgacagct gaagcacaga  36960
taatgtgact ggtggctaca tgtagagtcc attgagacag agggtgtgtg ggaggtgagg  37020
aatgggcagg gagaaaccca ggcagggatg ggagcgagga ggcttttcca ggaatctgag  37080
agagagaaag ggagagggca gcttgaatag agcagattca ggaaatattg aaaaggagga  37140
aaaacatttg gcccctagtc tgccatatat gcttaaaatg gtagaacaaa taagtcaaat  37200
ggcctttcct cctcccctt cctccatttc tccctttctc ttctctttgg agataaataa  37260
ccaagagtac ttaaattaga aattttaaga agcataaaat gttggcttga aaaggtgcct  37320
tagagaccat ctgctcaaac taaggccttc tgcagatgag gaggccgagg ctttgggtgg  37380
cacaggcggg gcttgcccaa ggccacacat cccgtgagat gcggggccag caccggaatc  37440
agggatactt ggctgctgag tgaagggatt tttctgctga gaagttggct tagtctgatt  37500
attcagatgc ctcctctggc tctggaatca gtggagttcc aacccagtct ctaccacttt  37560
ctagctttgt gatccaggaa cagttcaaac ccggcacaca gttttatcat tttttataaa  37620
atggggataa cgctggctcc tctcccattg gattgagacc aggaatcatt taagtcagtg  37680
ttttgcacag cacctgacag gtactcagag ctccaaaaat gttagctgtc agtgtgatta  37740
ctattaccct aagcaaaggg aagggaagcc agggaggaac caaggctacc tgtgcggagt  37800
agctgtggag tcgcagtcac agtagaggat ggatgggagc gcccagagtc caggtggcag  37860
gtgacggagg tagtgttcag gggccaggtg agaggacaga gagcagcagg gctgtgttca  37920
ggtgcagagt ccagtacctc accaggtgag gactctacca ggtgagcaat ggtctcagcc  37980
```

-continued

```
taacctgcag attgaggtct gaggccaccc actgagctgg aaggaagagg attttttttt  38040
ttcatggatt tttcctgcct taaggaagag gattttggaa tcaacaaaga catgaggcca  38100
ggtgcagtgg ctcacacctg taatcccaac actttgggag gccgaggcgg gaggggatca  38160
tctgaggtca ggagtttgag accagcctgg ccaacatggc aaaaccctga ctctattaaa  38220
aatacaaaaa ttagccagca tggtggcgtg cacctctaat cccagctact cgggaggctg  38280
aggcacgaga atcgcttcag cctggggggt ggaggttgcg gtgarctaag atcatgccac  38340
tgcactccag cttgggtgac agagcaagac tcggtctcaa aaaaaaaaaa aaaaagatat  38400
gagagggttc tagaaggagg tttctcaggg aggcaagaag aagggaattg atggagtgat  38460
gacccacagg aaggagtcgt ccaaaggttg gaccctgtga gtccacaatg agccactccg  38520
aatagccctg tccttatgcc actgcgcagg ctggagaggg aggtgctgtc cacgttggga  38580
ggagcgcagc tggagcatgg gccgggacac cgcagaagga gatctgcaga gccctggtca  38640
ggaacggggc tggtggyggc agctcagcag tgctcacctt ctcctctgca gatacacaga  38700
gccctcccgc acgcatgtgt tcccctggac atcctttgcc agtcttgagc cttcacatgg  38760
cttaacagca gggccgtttc ctccttcagc tataaatgtt tttaaacatt aggagttgca  38820
gttcaaaact taggaaaata acaccaggct gccttctatt ttataggcac tggtcccatt  38880
aggaattggc attgccacag gagaacaggt gagtgacgcc cccaacaggt ggatgacgtc  38940
cccttggggt cagtacacgc tgaccagtga ccgaggacac agttgtgtgt taggctccat  39000
cacctgctgt actttgagtt gggaaatttt catcatctta gaaactgggt cattttatca  39060
gagtctagag tcagatatag aaaaagtttg tggctatttc tccaatttat atgactaagg  39120
tcaggtatct ttttcaaagt gtctaattga aattgaaaag gcagcaattt aaagttgcta  39180
ttgcaagggc agaaaatggt cttaagaaag ccagctttca aattgaataa acatgactgc  39240
gttcactttt tgagcttata aatgaagccc gagtgcctgc caaaacctgc tgcagtcagc  39300
ccacgagcag agcagcgtga ggagctgatt ctcagttttc ccggcaaaag gagcaatact  39360
gctctgccgt ggttccgtgt tgtcatctgt gccacctgct catcactgtc accgtatttc  39420
atcctgatgc ttcatctccc acttatcagt cgctgtgaca gtcattccct cataaatggc  39480
gagccagtgt gattttgacc tgactcacac tgttgcatta gcagatttgt aaagaagtga  39540
gcacaaggtc cctgcccacg ctataaaagc tcgcctcatg cccagcgaga acaaagaaga  39600
aatacagtct gggcttcctg acggccactg atgaataatt attggcatag agtggctgcg  39660
ttgccaggtt tagagatcct gaaggccaag gctgactctt ctgttggtgt tattttcaat  39720
tctatttcca gtgccacaat agagtgatat ttaagcaact cctacaggcg aaggccctgc  39780
agttcctcca gattgacagt tgcagactgg gcagtgtcaa tgagaacctc tcagtattgc  39840
tgatggccaa aaagtttgaa agtaagcgtg ctgcagcggc tgcagaccag accttcattt  39900
ccccactaat cagacacctc ccttgatggt ttgcaattca catgcatggg agtctgtagt  39960
ttgccatttc gatttttttc taactctcat ttagctttaa tccgggaatt tttgatgatt  40020
ttcatcttgg aatttccttc ctaaatatta ataaatgatt taatcacctg tgggcaataa  40080
gaaaaaccag aaagttccct ttcacccctt cctctccctg ccctactctt ggtattaaat  40140
agaaacgatt tccttttagt tcctgtttgc ccccatgctg gtggagttgg cctctgtgaa  40200
ctggtgcagc acctgattat atttgactac atatcagttt ctgcaagcct tgaaaatagg  40260
tcagtaatgt ggcattaata ctttctgttt cagtagggtc cytcaatcca ggccagagct  40320
```

-continued

```
tgtaaattct gccttcatga ccagaacaca ctaagacctt gtctgctggc atgtcctata  40380
actctcaggt ggagttggtt ttgctttcac agagacccac caatgaacgg tcattttgcc  40440
tcctaagata gggtctggta gctgactcac tttatttttt aagtacattg aaggtaagct  40500
tgcagccaca ctactccctt aaccagctcc tgttttcatc acgtgtattc tgtacttctg  40560
tcccatctcc tcttcccagt actggagtct tccatggtct agacacacat ttatttcatc  40620
ttatttctca gaacgcccca ggtgggcttt taaattagga caatctcctt ccagtcatct  40680
gcacacgtag ggttttgctt attccacttt tcttgtctcc tggaattaaa tgtctcacag  40740
aaagatcact gcaagtatat agcaaaggca caaaagcatt cactgggaaa gggaaacacc  40800
aaattcagga ctgagagtga taaatgggac ccttgagggt acataggagg cttcagtaat  40860
aatggtaacc gtttttctct tcaggggggt agtgagtaga caggtgctgt cttttaatat  40920
agccgaacta ttttatactg tattagtcta ttcttgcact gctataaaga aatacctgag  40980
actgggtaat ttataamgaa aagaggttta attggcttac agttctgcag gctgcacggg  41040
aagcatagcg gcttctgctc agcttctgga aacttacaat catgatggaa ggtgaagggg  41100
gaacaagcac ttcttatggc caagagcagg aggaagagag agtgaggggg gaaggtgcta  41160
cacactttta aacaacagat cttgtgataa ctatctcgaa cagcaccaag gaacgggtgc  41220
caaaccattc atgaaggacc acttcccatg atccaatcac ctcccagcag gccctgctgc  41280
caacactggg gattacagtt caacatgaga tttgggcagg gacacaaatc caaaacaaat  41340
ccaaaccata tcagcctgcc tgtcacagct gttcaataac aggcgatgga agtcaggcag  41400
cagagctcgg tcacttgccc caagcctcag aactacaaag tggctgacgc agaacctgaa  41460
cacagattga cctgattcta aatcctctgc tcttcatcta aatcatttgt atagctgaaa  41520
ggaacctcat ttggtgattt tattttttgg gtggggagta tggaatgtat tttattgttc  41580
tgcatctggg tttgcttcct tagatgtctt ggttcttgga tggaggtggg tgtgtcccac  41640
ctccctcagt tgtggtccca tggacctgtt cggattgttt tccaggtaca aagtgtacca  41700
agaaagcctc acagtgctaa tgcttcctag atgcccagct gaggcagtga caaaatggcc  41760
ctcccaaccc tacctgcttt tttaaaaccc caagcccctg gcagctgctg cagccatatg  41820
aaaaaataca wacgcttctt gaaaaataga tcacaaaatg tggtgatttt aatctattca  41880
tctgactttt gaccagagga acccaaataa ttctggatat ttacagagtc tgaattgatc  41940
ccttttaaag ggcaccacaa aacctctaga gggacttcgt gtgttcatgt catcaaagtc  42000
cccacctcac attgctatat tttagaagaa aaggacctga ggcacagagg tttagggact  42060
tgcctagaaa cgcatggtaa cacagctaag ccttggccaa cactgtcaat tgagtggtac  42120
tcgctccttc tgctttaagt tagcaccacg tgaataatct gacttcaggc atcattgccc  42180
cgatctgatt ccctcctcct agggtgtgtg agtatgttga ccacctgcat gagcatttca  42240
agtatcccgt gatgatccag cgggcttcct acatgcctcc caaggtaagc tgtgcctgag  42300
ggcccctgtg agaagagatg ctgccagcca ctgccacgcc tgtctcgtga actagactgt  42360
ggagcaccaa gctttgactc ctgtttgttt gcaatatcca ctaacaaacg gttcttcagt  42420
ttgtctgtat caaaatcctc aggcctgagg gccagggctt ggaggttcaa ttgcctctga  42480
caaggcttct gtaatactag cctttcctca ctagtggaga tcttaacatt tgcactcctt  42540
gtgcaaaaaa acctggcacc atctagcaag ttagtgacct aaaaagtttg gactacaatt  42600
gtgtrgctgg ggccatttat tctgatcatg ttcaagagat catggctcat tttcaccaac  42660
agaggtcaaa ctattatcaa agagtttgat gagttaacta actctggcaa gtagccagta  42720
```

-continued

```
aaatatgttc ctctgcccta ttatttccaa cagtctccaa acttatttta aaaatattaa 42780
ttcagggctg ggcatggtgg cttacgcctg taatcccaac actttgggag gctgaggcag 42840
gtggatcatt tgaggtcagg tgtttgagac cagcctggcc aacatggtga aaccctgtct 42900
ctacaaaaaa tacaaaaaat tagccgggca tggtggcagg tgcctgtgat cccagctaca 42960
tgggaggctg aggcaggaga atcacttgaa cctgggaggt ggaggttgca gtgagccaag 43020
attgcgccac tgcactgcag cctgggcaac ggacagtgac tccatgtcar aaaaaaaaaa 43080
attaattaat tgcctctggc ttagacgtaa aagcatttct tggagcagca taaatgcata 43140
aaatctgttt ttgttccagg tggtkgttaa caggactcat ttttttggtc tttgatagga 43200
tcccggctac tcaacagaaa tgaaggagga atctgtaaag aaacaccagt atccagatgg 43260
tgaagtttgg aagaaactcc ttcctgctca agaaaattaa gtgctcagcc ccaacaactt 43320
ttttctttct gaagtgaaag ggcttaaaat ttcttggaaa tagttttaca aaaatggatt 43380
taaaaaatcc taccgatcaa gatgagttca gctagaagtc ataccaccct caggaatcag 43440
ctaaagcaac atgttgcata acttgttgga ataattcctt gttctgttta acacttgtca 43500
taaattagca gaataaaaat agtcgtgcaa caccgggggt atctggtatg caacgaaggg 43560
aaaaatattt cactgattaa ccccgaagtg gttttgcatc ttttccttgc ttaatctaag 43620
catattatta gagaagtcac accatgctga agctaatgag ggcaaaatsg tagtccatag 43680
attattttaa aataaccctt taaggttata aaagtttaaa aaaaaaaaaa aaaaactcta 43740
tcctaaatgg tcattatatt ttgaggataa gatgcagtta aaatgagaaa aatagggcaa 43800
aatatattca ctattatttc taaaatatac tcttttaagt agcatccaaa ccagaataca 43860
gcacatgttt acttaaggag agttctttaa tctattttag gaaggaactg agcagataag 43920
tggcagtaca gaatgaacaa agcgtggacg aatgcagaac acttctttat tatagcaaca 43980
tataaaacaa ctataaagtt cataaccaca ctctacatca tgatcgatgg tgttactcag 44040
ctccctcaga tttgagggaa tagcttgtga aattcttaaa atattctaaa aatattccaa 44100
aaatagcttg tgaaattcac caaccttctt tataagtacg tgggattgaa atgcacatac 44160
atgtttttgc taagagcaca tacatttcat tctcctcact ttgttcataa cctcagcatt 44220
gtcagatacc ctcagtgagt taactcaaag ccttttatta tggaaagaac tggcacagtt 44280
acatttgcca gtggcaacat ccttaaaaat taataactga taggtcacgg acagattttt 44340
gacctagttc ctttttcttt tagagcaaaa agaactttta cctcggcatc cagcccaacc 44400
cctaaagact gacaatatcc ttcaagctcc tttgaaagca ccctaaacag ccatttccat 44460
tttaatagtt ggatgcggat tgtacccttc aatctgaaag tcttcagctt tgaagtcatc 44520
aattttctca acttttcgaa gaatcctgag ctttgggaaa ggtctgggtt ctcgctgaag 44580
ctaaaaacaa aataaggcca ttattttgcc ataattgtac gacctgttgt aattgctcct 44640
catgtccatg aaacaagtac acaggatgtg atcaacaaag ttctatttta caggagtatg 44700
atcctgtcga taccttgccg taggttatgt aacatgattg gagcgcaacc agctgttctc 44760
ttgcacagat cgagagtgag gggtattttg tgacattaca cagcatcagg agcctggtgc 44820
ctcatcaggt gtaagttctt ataaccacty ttggcaaatt tattaaagac aggaacacag 44880
tcaatctgta actcatagta gctctacgtt tacttgaatt ccacaatccc taacccatct 44940
gtccctggca gaaagaagga aagatgacat gcatggacag tgaacagaaa gggatgaaag 45000
ccaggattcc tgggatgaac agacagtggc aattaggatg tgaagacagg tcacaaccta 45060
```

-continued

```
ttactatgtc taaaaatgac cagagcagag agccagagag aataagcctg aagtcacctc  45120
cactcaaaag cagccaaact ccctcaaagg aataactttt aaaacctgga tctaacctgg  45180
aaggggctaa aaagtgtctg gttctgagtt tttttcctta aggctcatga agcagatgaa  45240
cttacatttt tattgccatt tcatatcaat tgttggctgc tataacttca gggatttcaa  45300
cagacttttg aagtttggac ctaaatattg tacttaatgt aaaattaaca aaaaatattt  45360
atggccaggg tggtggctta tgcctgtaat tccagaactt tcggaggctg aggcaggtgg  45420
wwcacttgaa gtcaggagtt tgagayyagc ctggccaaca tgacgaaacc ccatctctac  45480
taataataca aaaattagct gggtgtggtg gcatgtgcct gtaatcccag ctacctggga  45540
ggctgaggca gaagaattgc ttgaacccgg gaggtggagg ttgcagtgag ctgagatcgc  45600
accacggcac actccagcct ggccgacaga gaaagactcc atctcaaaaa aaaagaaaag  45660
gaaaaacatt tgcacttcaa ttctccttca agttaaaatg agttaaaatg cctcct      45716
```

<210> SEQ ID NO 6
<211> LENGTH: 45989
<212> TYPE: DNA
<213> ORGANISM: Homo sapiens

<400> SEQUENCE: 6

```
ctgggtgcag tggctcatgc ctgtaatccc aacactttgg gagcctggtc tggaggatcg     60
cttgagccca ggagttcaag ataagcctgg gcagcaagac gaaaccccat ctgtacaaaa    120
attagctggg catggtggtg cgtacctgtg gtcccaacta ctaaggaggc tgaggtggga    180
taactgtttg agtccaggag gtagaaactg cagtgaactg tgattgcacc actgcactcc    240
aatctgggtg acagaatgag accctgtctc aaaaaaaaaa ttagaaataa gacttagtaa    300
aacaataaaa gctaaataga taatatgtga aatttatcca gtagcaggaa tggtccctgg    360
gacctttaag aagcagatgg cggtattcaa ttttaagttg cttgcagagt ccttgctacc    420
ccaaaccttc ctgcaaatca gctacacata acggtgagtc agtgaccttt aggaaagaaa    480
agggattggg gtcacggcca gaggtacaat gacaaggtac aaacaaggat agggatggat    540
ttcataacct agtttaaacg cagtggggaa ataaattcag gaaataaatc aggtaagtag    600
gagaaaagtt caccaagtac ttggagagac actggatttc acagggacat ggcgtagggg    660
ttcaatccag cttcacttct atcttaaagg tcaagttaac gagtaagttg gaggactttg    720
aaaatccaag taaaaaattg tcactagcct gtgacaatag ggatgagaga aataaaaact    780
tcgcagttgg ccaaaaaggt tgacagtgat tctaataact gaattaaagt ggtgtggccc    840
ttaaagttta tcaaattcca tttattcact cataattgca ctattttcat ggaaagtctt    900
agtctcctaa aacattgaga ggatatacca cggaactaga tggcaaactt ggtttggttg    960
gtttttgtaa tctttaccat tgctagaaag ttagaaaagg gtggcttcac ttcagcagaa   1020
attttgaaaa attcgtggaa ccagaagaaa cccaatctaa aagaaataca agagaacatt   1080
ttcgcagagt tttaagtgca atttcaaaga aaattcaaac ttagaatcaa attcaaagag   1140
gaggcagcac cccaaagcaa catttttgt tttattgagg tataatttac atacaacaaa    1200
gctcaccatt ttaagtgtac cactagatga gttgttgaca aatgtagaca gccatgaaac   1260
caccatgaaa ccagaatcat agaacatttc catcatttca gaaaattcca ttatgccctt   1320
ttacagtcaa tctcttccat tcacccctga cctctgtcaa ccactgagtg ttttctgtca   1380
ctataattgt acatttctag ggctttatat aaatggaatc atatgtagtc actgtgtctg   1440
atgtctttcg tttagcataa tgcttttgag atctttttat ggctcagtaa tattccattg   1500
```

-continued

```
tgtggatgtg tactacatct tggttttgtc ctttaccaat tgatggatgt ttaggttgtt   1560

actagtttta ggctatcaca aataaagctg ctatgaacat tcaaatacaa gtttttattt   1620

taaacatagg ttttaaattc tcttggataa ttacctatga gtaggattac tgagttgtat   1680

gatacatgaa tgcttaactt tctaagaaac tgataaccta tttccaaaga agatgtaccc   1740

tttcataccc ctccagcaat gtatgagagt tccagctgct tcacatcctt gccaatactt   1800

ggtattgcca gtcactttaa ttgcagccat cctggtgcgt gttagtagta catcattgtg   1860

gttttagtgt gcatttccct aatgactaat aatgttgagt cttttcataa gcttatttca   1920

aattcatatg tctgcttagg tggaatgtct attagaaagt cttttgccca ttttttatat   1980

caagttgcca tcttactgag ttgtaatttt ttcagtattc tgcatacaag tccttttaac   2040

agatatgttt tgcaaatatt tttcttccaa tctgcagctt gcattttcat ttctttaatg   2100

gttttcatca aagagaaaac atttttaatg ttgataattt aattggcaat gtttttcttt   2160

tatgattcat gcttttagtg tcctaagaaa gtttgcttta tccaagtaca aaaagatttt   2220

ctcctgtgtt ttctttagaa gttttgtaat tctagctctt aaaatttaga tctatattcc   2280

acttcgagat gatttttgtg tatgatataa ggtaatgatc caggattgtt ctgtttgttc   2340

ttatggatat tcaattgttc gagcaccagt tgttggaaag actagcttac tcgttgaatt   2400

ttcttggccc ctgttttttt tttgttgttt ttattttgta gacggagtct cgctttgtcg   2460

cccagcctgg agggcagtgg cgcgatctca gctcaccgca acctccgcct cccgggttca   2520

aatgattctc ctgcctcagc ctcccgagta gctgggacta caggcgcgtg ctaccacgcc   2580

tggctaattt tttgtatttt tactatttca agacctcttc tgttccattg atctacttgt   2640

ctgtctttat gtcaatttca cattgactcg attagtgtat agcaagtctt aaaaccaagt   2700

agtttaagtt cttcagcctt gttctttttt aggattattt tggctattca aatttccata   2760

taaattttag aatcaacttg gtccaatttc ttcaaaaaaa tcctgctagt gatttagatt   2820

agattgcatt gaatttgtag ttcgatttgg gaagaactgc tattttaaca atattgagtc   2880

ttccaatcca agaatatgaa tttctctaca tttctacatt tctttagatc tttttttctc   2940

agcaatgttt tatagttcag tgtgcaaatc ttgcatattt ttgttaaact tgtcctgttt   3000

tatattttca atgcaattgt tttaagagat acngttttct aatttgtttc caatttttta   3060

ttactagcac atcaactata gattttaaat tgaccttgta tcctacaaac ttgctaagct   3120

caatattagt tccagtagct tttttcgtta agtccaatga agacagtttt caacaaagat   3180

gaataatcat gtcatccaag aataaacagg tttacttcct tttcaatctg ccttttattt   3240

cttttcttat tatattaccc taactagaac ctgcagtact atgttgaata gaagtggtgg   3300

aagcagacat cctttccttg ttccaaatct taaggagaaa gcatcaatca ttcaccataa   3360

agtcagtttg tggctgtttc tatcttctga aatagattat agagaattgt tgtaatttct   3420

tccttaaatg tttggtgtaa aattcaccag tgaaaccatg gacctggtgc tttttgtttt   3480

tggaaggcta ttatttattc aagttattta atagatatag gcctattcag attgtccatt   3540

tcttctcgtg tgaattttgg cagattgtgt ctttcaagga attggtttat ttcatcncag   3600

gttatcaaat ttgtggacat agaattcata gtattccttt attatcattt taatgtccgt   3660

cggatctgta gtaatgttcc ttattncact tttgatatta gttatttgcg ttctcttttc   3720

ttgcctggnt agaggcttat tgattttatc aatgttttca aagaaccagc tttkgttttc   3780

attgattttt ctttgttgct ttcctgtttt caatttcaca ggtttctgct ttaattttta   3840
```

-continued

```
ttatttcttc tcttctgctt actttggatt ttctttttat ttctttttat ttatttattt   3900
ttgagacaca gtctcactct gtcgcccagg ctggagtgca gtggtgcgat ctcggctcac   3960
tgcaacctcc gcctcctggg ttgaagcgat tctcctgcct cagcctcccg agtagctggg   4020
actgcaggcg cccgccacca cgcccggcta atttttgta tttttagtag agacggggtt    4080
tcaccgtgtt agccaggatg gtctcgatct cctgactcgc catctgcccg ccttggcctc   4140
ccaaactgct gggattacag gcgtgagccg cccagcatyt tttttttttt gagtcggagt   4200
cttgctctgt cgcccgggct gcagtgcagt ggcgcgatct cagttcactg caagctccac   4260
ctcccgggtt caggcagttc tgcctcagcc tcccgagtag ccgggactac gggcgcgcac   4320
caccacgccc tgctaatttt tgtttttagt agaggcggga tttcgccgta ttggccaggc   4380
tgatttcaaa cgcctgacct caggtgatcc gcccgcctcg gcctcccgaa ktctggatta   4440
caggctgagg cacggtacgg gacctcatct gcatcagtac gggtgtaatc aatgatgacc   4500
tgcctcttaa tttatcaggt ggcaaactga ggctgtgggc actgaaagag acctagcatt   4560
ttctagggca ccgctctcct gggtacgctg gcgacaacca gcggcctcgg cttgggagct   4620
gagccactgg ccggaatctg ccgctgagcg aatgcactcg ctcagacccg acttctccct   4680
ctagggcgcg gctcccgggc aggtcccttc acgagtcttc catccgagca gagcagggtc   4740
ccgcggaggc gccgaccggg cgcgaggcct cctgcctgcc caggttcccc ggcgaccctg   4800
agcgaaccct ctcggggtca gctccgtcta ggctgagaag ggaacggcgg aaggcggagt   4860
gcgcccccgg gagcccggag ctgggactgc agctcccatg ggccaagtt cacggggtgc    4920
ggccgcgcgg ccaatgagcg ccctctatgc cctgacggtg ccccgcctcg cggcgctgcc   4980
ggctcccgcc ctcccgccct cccgccgcgc gctcgggatc ccgaccagtc ctgaccgcac   5040
gggggccgcg gccacggggc gcaggggcca tggtgcgcgg caggatctcc cggctctcgg   5100
tccgggacgt gcgcttcccc acgtcgcttg gggccacgg cgcggacgcc atggtaagcg    5160
cggacgccat ggtaagcgcg gacgccatgg taagcgcgga cgccatggta agcgcggacg   5220
ccatggtaag cgcggacgcc atggtaagcg cggacgccat ggtaagcgcg gacgccatgg   5280
taagcgcgga cgccatggta agcgcggacg ccatggtaag cgcggacgcc atggtaagcg   5340
cggcttgcgg cccgggtccc tcccgccccg actgcagctc tgcgggcccc gggcagcttc   5400
ccgacttcga acccattgct tctgtaaagt gggaggcgcg cctgggggag acactcgctt   5460
ttcatgcctt ggagcaattg tataagtatc cagaaacttt ccactctcct gggtttttc    5520
tttgctggag tttagaatat cctggtttta cttttacgac tcacattttg ctggaaatgg   5580
tagaatgcat aataggcaat agcagcaaaa tgattttgtt gggttcccgc cagtggaaac   5640
cctagagcac agtgctcgct ggcttcctct gtaccctgaa cgcgacgggg ttggcgctga   5700
gggagaacgg gaagcccggg gctgggagtt ttgagtggtg atcccgcttc cacaacttgc   5760
tgtgtgactt ggagaagttc cagacctctc tgggtctctt ggacccgtct gtgtaatgaa   5820
ggtgtcacag tcgggttgag aaaccaagcg cgtgctaact gcgtcacatg agagggcgct   5880
ctcgtgaaat tacccgcaaa cacgcttaga aaggactgat gcaaatgtca gttcgtctta   5940
agagatgtaa taaagtaagg gcaggaactc tgactcctac ctaaatattg aaggtctttt   6000
ttgcttactg agggtgttag aatgtcaggc cttccctccc ctgcccccgt ctagagcggt   6060
gtttcccaaa tacagtgggt tctgtgcagg gttttcaggg agcctgttcc ccactgggtc   6120
ctcactgccc gtcgtagtcc actgatgaga ttggccgcgc tagaaaagca gagttgtatg   6180
ggtatgtagt gaatgtgtga aagtatgctg ggaagtgagg aacggcaatg ttaggaaaat   6240
```

-continued

```
ggttaccagt agggagggaa ggaaatgggg tcacggaggg gaccacgagg tctctaattc   6300
ccattgtaat gttttacttc ctaaattggg tggatggcaa gctggtgtcc attacattat   6360
ctatactctt tttgtacctg aaatgtttta taaaaataga tctctcgtta aagttattaa   6420
atgcaaaaca atgtcctttt tgagattaag ttcatcctgc atttttaaat ttttatttta   6480
ttctatttta tgttttaaat ttatttattt atttattttg aggcagggtc tcttatctgt   6540
tgcccaagct ggagtgcagt ggtactatca tggctcacag cagccttgac ctccctgact   6600
caaccaatcc tcccacctca gcctcccaag tagctgggac tacaggtgtg caccatgatg   6660
cccagctact ttctgtattt tttgtagaga cagggcccag gctgtcatcc tctttaaaat   6720
cttcatgttt cctttcttac atgatgttgg taaataactt aaacacccag caggcaatcc   6780
tttatggaac tcaaaataaa tgttggaaat tttactggct tatagaatcc aaacactcga   6840
tctcatgcaa ctgcctttgc ctctgtgaag ctttagcagc tgtggctaag tcacacaatc   6900
tttctaagcc taggtttctc atctgtaaaa tgggtataat aatattcact ttatacatgt   6960
aaatgagata cctgtaaaga gcctggctca gagaaggccg tcagtaaagt tggctatagg   7020
ccaggcatga gggctcacac ctctaatcct aagtggaggc ctaggcaggg ggatcacttg   7080
agcccaggaa ttcaattaca tgagctatga tcatgccact gcattccagc ctgggcactg   7140
gatgacacag tgagaccctg tttctaaaga aaaaaggagg ggtggctgta attactattc   7200
actctgagga aactgaagca gaaggaatcc ctaatctaga cttgactttg aatttgtgaa   7260
atgttaagac agcctggttt ggctgagacg tggtggttca agcctataat cccagcactt   7320
tggaaggcca aggcaggtgg atcgcttgag cccaggagtt cgagaccagc ctgagcaaca   7380
tagtgagacc tcgtctcaac aaaaaaatac aaaaattagc tgggcgtagt tgcatgcacc   7440
tgtggtccca gccactcagg aggctgagkt gggaggatct cttgagtcca ggaggtcgag   7500
gctgcagtga gctgtaattg tgtcactgca ctccagcctg ggtgagagag agagaccctg   7560
tctcaaaaga cagcctggtt tactgtagaa taattcaaga aatggaattt gcctctgggc   7620
ctgagtgatg tctaacacag ggtaaggaga cattatctaa cacctgtatt gcaagctcat   7680
aaatacttaa gcattttatc ttggggagat agggtgtatg ttgtgtgcca gctctcaagt   7740
gccttcttat tagaatgagc tgttttgcag ttcaccatgg agatggcttc acatgccctc   7800
gaggcatgct ggaccatcag cacttagcaa agtgagcctc cctgatcaga agtaggatat   7860
tttcaagaaa gagcaataaa gctgtcctcc aaaatctgct aaagactcct gctttttttt   7920
tttagacaga gtctcgcttg ttgcnccagc ctggagtgca gtggtgcaat ctcatctcac   7980
tgcaacctct gcctcccata tgcaaatgat tstsgtacct cagmctctgg agtagctgtg   8040
attacaggtg tgcaccacca cacctggcta atttttgtat ttttggtaga gacggggttt   8100
caacatgttg tccaggctgg tctcgaactc ctgagctcag gtgatccacc tgcctcggcc   8160
tcccaaagtg ccggattaca ggcatgagcc actactccgg gcttacctcc ttcttaatct   8220
gaaatctact tctgttcctt tcttctctgt gaattgccct tgttatttct ccttcagctg   8280
tccttaccct cagatacgtt ttccgctgtc ggccgcctct tcttcgtgtg ctctctcccc   8340
tcgtggcctc ctgcctttct gacagctcct tcttcctcca ctggcccctt cttccctctc   8400
tgaggctcag gcctcagtgt ctttccggtc tccctacaca ctcccatgaa gaccctctcc   8460
acattctgac ttcggtgcca ccctttatgc cggagactcc cagatctcat ttccggatct   8520
gcctccttaa cttataggtc tggatacttc ctgtttggtt tttcaccttc atgctaaacg   8580
```

-continued

```
cagtttgtct aaatcggaag tcaacttcca ttctctgccg cccctccctc ctgacccatg   8640
ttggatcatt ccgctaatca cagggaccca aaagcttcga gtcacttttg gctcatctcg   8700
tcctgttgac cctcatctga ggcttcagtg caaggtttcc tttttccatt gcttcctctt   8760
cttggaaccc agaaactgcc gatgggtctt taattcttgg agtctccttc tcagcctcat   8820
cgctcaactc cttcaggaac ccaatggctc agccaaccca ggtgggcacc aacacttgaa   8880
tacactccag tctctccctc ttctgacccc tttactttct gcactgctgc tgctgctacc   8940
ttgcctgaga tattcctccc tcccagactc ttcactcccc ttcccactgc tgaggagctc   9000
cccttccttg accggccagc tcacattctg tcttcatcat aaagcgctct ccctcttcaa   9060
gaagcacatt cagctaacag cgctctctgc cagtcgttca tagtttgcat ccctcccagg   9120
ccttagcatt ttctgcctta tattattaag gttttttttt aaccatgtct ttttatttat   9180
ttattttaga gatggggtct cgctttgttg cccaggctag tctcgaactc ctgggctcaa   9240
acaatcctcc tgtcttggcc tcccaaagtg ttgggattac aggtatgagc cagcatgccc   9300
gttctataag caggtcttct caaatgtaac ctcctcaagg gcagacgtat ctgtaacccc   9360
ctagcaagct gcaccagctc tgacacgtac ttggtgctca gcgatgcatc acactgattt   9420
cctgccactg gactgtgata ccagactcag ggctcccagc catcacatac agctccctca   9480
gccacgacac cccaatacag ggatttaaaa tctgccttca taatttactt gtggccgggc   9540
gtggtggctc acacctgtaa tcctagcact ttgggaggcc gaggcaagtg gatcacctga   9600
ggtcaggagt tcaagaccag cctggccaac atggcaaaat cccatcttta ctaaaaaaaa   9660
aaaaaaagct ggtcatagtg gtgggtgcct gtaatcccag ctacttggga ggctgaggca   9720
gaagaatcgc ttgaatccag gaggcagagg ttgcagtgag ccaagatcat gccactgcac   9780
tccagcctgg agaacagagt gagagtcagt ctcaaaaata ataataataa taataaaaca   9840
ttatttactt gtggtgtgac cttttgtaaa ttactaaagc tccttaaaac ttcatttcct   9900
ctttaataag gataagagca cctactttat aatattgtta taagattaaa ttaaaccatg   9960
tggagctctt agaatatagt gtgtctggca caataaatat tatagaataa taacagtaat  10020
aaattttcat agccttatgc acaattcttc tttatgaatg cattcacatc ttctgcctgg  10080
ctttttggag tctccattat tccatgacat agaacaaaac aaaaaatgag tgaattaatc  10140
tcgaagcttt acttcttcat tttcccccac tggtgtctga acttttgcca gtgtattttc  10200
agccctgcta taaactgcta taagtgagat cactccaatt ttatgcaaca gttttctgaa  10260
cctttggctt gttcaatttg aagctgcttg tgaatgtaac tttgttcaaa aagctgacag  10320
agatagctgc gagtgaaaac tccttggctt aaaattgagc cccttccggg catgatggct  10380
catgcctgta atcccagcac tttaagaggc ccaagcgggt ggatcactag agctctggag  10440
tttgagacca gcctgggtaa catgcaagac tccatctcta ttttttttatt taaaaaataa  10500
ataagtaaat aaaattgagc ctcatttttt aacctaattg aaaatgggtg ataaaaatgt  10560
atacattgcg accaggtgcg gtggctcaca cttgtaatcc cagcactttg ggaggccaag  10620
gcaggtggat cacctgaggt caggagttca agaccagcct ggccaacatg gtgaaacttc  10680
gtctctatta aaaatacaaa aatcagccaa gtgtggtggc acatgcctgt aatcccagct  10740
acccgggagg ctgaggcagg agaatcgctt gaacttggga ggctgcagtt gcagtgagct  10800
gagatcgcac cattgcactc ctgcctaggt gacagagcaa gactctgtct caaaaaagaa  10860
aaaaaaaaaa atatatatat atatatatat atacatacat tgctcttgtt gaaacatttt  10920
ggatctttca ggaggacatt ccttttctcc attcagagcc ctttgttttc tttggggtat  10980
```

-continued

```
agcaacagtt ccttctatgg gagctcttgt ggcacggccc ctgtggcatt gtctgtcctc  11040
atgtgacatc attctcatgg ttcttttcgg gtttctcaca ctggcattgt ttcggcgggg  11100
aactcctctc ctgcagcaca cggaccctga ctactcggct gcctatgtcg tcatagaaac  11160
tgatgcagaa gatggaatca aggggtgtgg aattaccttc actctgggaa aaggcactga  11220
agttggtgag ttgaagattc tctcgaggtt ccagaatgct taattttcag atgagattct  11280
aatttagatt cttagattca ttagaatctt gatttagatt gagttctgat cttgttttta  11340
tctgtattta cactgctcaa agtgagtaaa aacagtgttt catggtttgt tacttgtttc  11400
actgggagaa atttaaaagt gacagaattt ggcctctctc cttgcaatca tctctagcct  11460
gttagaaaat ccttggctgt tagtctgttt ctctgtgtca aatgacagct acaagagtgc  11520
ttttcacctg cctttcaccc ggggccactg tcgagctttg acaacctgta gtgggcgagt  11580
aaccaagggc aatgagaggg aggagacatg agttcccata gcaaaaaagg ctcattgtga  11640
tgtgcacagc aagtctactc gcttttcaat atatatatgt atatattttt gagacagagt  11700
ctcactctgt cgcccaggct ggagtgcagt ggcacaatct cagctcactg caacctctgc  11760
ctcctgggtt caagcaattc tcctgcctca gcctcccgag aagctaggat tacaggctcc  11820
caccaccatg cccagccaat ttttgtattt ttagtagaga cagggtttca ccatgttggc  11880
caggctggtc tcgaactcct gacctcaaat gatccgcctg tctcagcctc gcaaagtgct  11940
gggattacag gtgtgagcca tcacacccgg ccttttcaaa atatttcaca ccaaatcggt  12000
ttcaagttca ctattttcat ggcgaaaagg gctttggccc cgcccaatct cggaggtctc  12060
ccttggggaa gagcagattc tttaagatgc atactgagcc gtgtatacgt cattcttttt  12120
ttatttgcat tttctatttt cttaaacaga agacacagaa cataactttt ttcagagctg  12180
gatgtgatct caaatggtga tcttgagccg tctcattttt tagagagaag aaaactgagg  12240
cacagacagc tacccagcaa gtcatggcag aaccacctga ctgcccagag cactttctct  12300
tcagaacttt taaatgcaac tctttttgaa tacataatac ttacacatgg tacaaaattc  12360
aagaagtcca aaacagtggc cttcgccaga tcaatttcag tggattatta gagcctgaag  12420
ccaaattatg atagattgaa gggtaagggt ctagaaggag ggaaaagagt ttctctaact  12480
tcggtggtag tgtgatacct ctcccttgga tatttgcacc atcagcgctc tcagtagttg  12540
tagaaaaaaa tcttggccca ttgagagatt ttaaattgtt aagcatataa aagaagtgtg  12600
tgagtttgtg aatgtgtgta tgtgcgaatg gcaagggaac cttccttgaa ctttcaatgg  12660
acactgccca ggtggctgct gttactgctc ttcacagggc tggcggtcag ttgtccagca  12720
agtcagtcct tctgcagact tctcctgagt gctgccatgt atcaggcacc aaagtaattt  12780
taaaaagaga aagataggcc gggcgtggtg attcaggcct gtaatcccag cactttggga  12840
ggctgaggcg ggcagattgc ttgagtcaag cagttcgaga ccagcctggt caacatgctg  12900
aaaccctgtc tttactaaaa atacaaaaat tacctggccg tggtgatgca tggctgtaat  12960
ctcagctact caggaggctg aagcacgaga attgcttgaa cctgggagtt ggagtttgca  13020
gtgagccgag attgcgccgc tgcactccag cctgggtgaa aaagcgagac tccatcccaa  13080
aaaaaaaaaa aaaaaaagat acagaagaca gaatcccaca tacaaggagc acacgaactt  13140
attggggaag tagacataaa agaaatgatc atagtgcagt ctgagaatta ctgtttttta  13200
aaactatgta caagttttac agagagagga tatattaggc tgttcttttt tttttttttt  13260
ttttttttctt ttctttttgg aaacaagagt cttgctctgt cgcccagcct ggagtgcagt  13320
```

-continued

```
ggcgcaatct cgctcactac aacctccacc tcccgggttc aagcaattct tatgcctcag  13380
cctcccgagt agctgggatt acaggcacac accaccacgc ccggctagkt tttatatttt  13440
tagtaaagat gaggtttcac cgtgtttsgt caggctggtc tcctgacttc aaatgatctg  13500
cccaccttgg cctctcaaag tgctaagatt ataggcatga accaccactc tgagccaggc  13560
tattttttgca ttgctataaa ggagtacgag agactggata atttataaag aaaaagaggt  13620
ttaattgcct catggttctg caggttttac agaaagcatg atgccagcta ctcagcttct  13680
agggaggctt caggacactt acaatcatgg tagaaggtga agggggagca ggcacgtcct  13740
atgtcgaaag gatcaagaga aagggaatgg ggaggtgcta cacactttta agtcaccaga  13800
tctcacgaga actcactcac tatctcaaag acagtaccaa tgggatagtg ctaaaccatt  13860
caggagaaat ccacctccaa gatctaataa tcacctccca ccaggcccca cctccaacac  13920
tggggattac acttcaacat gaaatttgtg cagaatgtct aaaccatctc agggggtaac  13980
ttcactctgt ccaaaaggct cagggaaggc ttcagagcag aagtaatgct ttgaggtgag  14040
tctcgaagag caaacaggaa tttgccaggc agagaaagac catgctgtga gtcagtcccg  14100
cttttctcca ttaagtaaac aatttactgt taaagttttc cccagagtag taaccactta  14160
ctaagacaga gctgtgagct gtttctgctt cttctgcaac tctaattgtc ccttgtttgt  14220
aagttgagta ctttatgaag ccgctgcctt tctccatact gcaaatccta cagcacagcc  14280
cccaaaggtt gcataaaact cagcgagctt acaagatatg ttaggccatt ggacccactc  14340
tctgttaaca gcccagactt taaactttgc tgacttgggc acacgtggag gggccctggg  14400
cactaagata gataagaagc ccttctggga tgggtgctga gctcagtgtt tagggccttc  14460
acttcccctc tcctcctcca ttcccagccc cacaccgctg tcttggtgga tgtctcaggc  14520
acggataaat caacttccat ctctccatga ctttaattaa tgactctttt gtgctaaggg  14580
ttttggcttc ctccttttc agaccacaac atgacagaac ccattttaac tttaaccttg  14640
ctacatattt caggtgactc actgcagtct cactaaatgt gttacacagc actcacacta  14700
aagatgaaaa attccattag ctcatcctgg ttcttctgct tacttaccta atcatctgtt  14760
tatgatttaa aaaaataggg ttactgtgaa gagagtgctt gtgtgtgaga cagagaggga  14820
gggttgtttt tcaaatgtat agaatatacc aatgtagttt ttggttgggt attttttttaa  14880
atcatgactt tattaaattt acttaattaa tattcatttt tatccttttt ttatgttttt  14940
aaagttttta ttatttatta atttatttga gataaggtct tgctctgtca cccaggctgg  15000
agtgcagtgg tgcaatcacg gctcatacag ccttgacctt ccagactcaa atgattgtcc  15060
cacctcacct tcccgagtag ctgggcccac aggcacaagc caccatgcct agctaatgtt  15120
tctttttttt gagagacaga gtctcgctct gttgcccagg ctggagtgga gtggcacatt  15180
cttggctcac tgcaacctcc acctccaagg ttcaaacgat tctcctgcct cagtttccca  15240
agtagctggg actacagatg tgtgccacca tgcccagcta atttttgtat ttttaggaga  15300
gacagggttt cactatatgt tggccaggct ggtctcaaac tcctgacctc aggtgatcca  15360
cccactttgg cctcccaaag tggtaggatt gcagatgtaa gccaccamac ctgacykggg  15420
tttttttttt tttttttttt gagatgtagt ttcgctcttg ttgcccaggc tggagtgcag  15480
tagcacaatc tctgctcact gcaacaacca cctcccaggt tcaagcgatt ctcctgcctc  15540
agcctcccag gtagctggga ctataggtgc ctgccaccat gctgggctga tttttgtatt  15600
ttttgtagag acaggatttc atcattttgc ccagactggt cttgaactcc tgagctcaag  15660
caatccgcct gcctcagcct cccaaagtga tgggattgca ggcataagct ataagccacc  15720
```

-continued

```
atgcctggcc tgtttctgtt tttatttatt tatttattta tttatctatg tatttattta  15780
tttttgagat agagtcccac tctgttgccc aggctggagt gcagtggtgt gatctcggct  15840
cactgcaacc tctgcctcct aggttcaagc aattctcctg cctcagcctc ccgagtagct  15900
gggattacag gtgcccacta tcacgccagc taattttttt tttttttgag atggagtctc  15960
gctctgtcac ccaggctgga gtacagtggc gcgatctcag ctcactgcaa gctctgcttc  16020
ctgggttcac gccattctcc tgcctcagcc tctccagtag ctggactaca ggcacctgcc  16080
accacgcccg gctaattttt tttttatttt tagtagagat ggggtttcac cgtgttagcc  16140
aggatggtct cgaactcctg acctcaggtg atccacccgc cttgacctcc caaagtgctg  16200
ggattacagg cgtgagccac cgtggccagc cttttttttt tttaagactt tattttttta  16260
gagtagtttt aggttcacag caaaactgaa tggaagttac aaagatttcc cacatacccc  16320
tgtccccaca caggcacagc ctccttcatt atcaacattc tgcccagagt ggcccacttg  16380
gtacaactga tgaacctgca ttggcacatc atgatcaccc aaagtctgta gtttacaata  16440
ggggtcactc ttaggtttgg acacatgtat aataatatgt acaatgtaga ctaagttagt  16500
tttttaaaaa atagaaaaag atgtacaaag aaagaatttt taaatagaca aaatttttaa  16560
aaatccagcc ttaagagttt atgacaccac tcttacttca gacacccaca agtcacccac  16620
agactttact caatgtcctt ccagtgctag aggctccaga gaattgaagt ccctgagcag  16680
atagaatcac aagagaaaac cccccgggtt tagttgccaa gaagctgctt tcaagggcct  16740
tttttttctt ttccaagtca atttcctgcc acagccaaaa tttctctcgt tttttttttt  16800
tttttttttt ttgaggcaga gtttcgctct tgtcgcccag actggagtgc gatggcgtga  16860
tcttggctgg ctcactgcaa cctctgcctc ccaggttcaa gcgattctca tacctcagcc  16920
cccacaagta gctgggatta caggcatgtg ccaccacacc cagctaattt ttgtattttt  16980
agtagagaca gggtttcacc atgttgatca ggttggtctc atactcctga cctcaggtga  17040
tccgcccgcc tcagcctccc aaagtgctgg gattacaggc atgagccacc gtgcctggcc  17100
tcacaaccca aatttctatt gaatgcgaca aattctagtc tcctgttgag caagaaaaat  17160
ccatacactg tagatgaata cataagtgct gcttgtgcac tctgagagtc ataaaaatga  17220
gatcatcctt agcttttgtt aagtgcattt ggtattgtga catgaaccag aggtatgctt  17280
cagtcaatga tttatagcaa caatcaaatc cttgagacgg tggtttggtg tcgataataa  17340
cgtacctcac tgtgagtcac tgacttactt cagattttct ttaattcaag agcatcaacc  17400
ttcaagaagt gaggaggact ctgtcttctc acaattctag ggaatgaatg tctgaaccag  17460
aatgattgtg tatcccatta acaaaagccc tagagaacct ggaatggctg gttcagccct  17520
aaatgctaca tctgacctaa agtgtgcaat catccgagag ctgtttcacc cttagccagg  17580
catgtgctaa aagcttgggg catcactttc tttctttttc ttgagatgga gtttcgctct  17640
tgttgcccag gctggagtgc aatggcatgg tcttggctca ctgcaacctc cacctcctgg  17700
gttcaagtga ttctcctccc tccgcttccc aagtagctgg gattacaggc acctgccacc  17760
atgcccagct aatttttgta tttttagtag agatggggtt tcaccatgtt ggccaagctg  17820
gtctcaaact cttgacctca ggcaatccac cggccttggc ctcccaaagt gctaggatta  17880
cagacgtgag ccaccgcgcc cagcctgggg caccactttc aaactgtcct tctcaagatc  17940
ttattgacag taaaactgta cccctacaac tgtcctatta aatgactaaa aacttttact  18000
attgaatcca cggcagcacc aaacaaatta atcaaaacgt tttggaatac attcctttct  18060
```

-continued

```
ttgaagctaa gttgatggct tgattcaatt attgtgtcca tttacacaac gtaggctaaa  18120
tgtttcctag aattggcaaa ggatcaaagg gttactttac ttattcatca tcttaaataa  18180
cccaagaaag cctttatatt attattatta ttattatttg agacagggcc cagctctgtc  18240
acctaggctg gagtgcagtg gcacaatctc agctcactgc aacctctgcc tccaaagcta  18300
aagtgatcct cctacctcaa gtgatcctcc tacctcagcc tcccgagagg cggggaccac  18360
aggcgcacca ccgcaaccgg ctaatttttg tatttttttgt agagatgatg tcttgccaca  18420
ctgcccaggc tggtctcaaa ttcctgagct caagtgatcc acccacctca gcctcccaaa  18480
gtgctggcat tacaggagtg agcgccaggt ccaagaaatc ctttcaaagt aaaataccac  18540
aggacatggt ggctcacacc tgtaatccca acacttcagg aggccgaggt gggaggattg  18600
cttgagccca gagttccaga acctccccac ccactgcccc atgcaacata gcaagacctt  18660
gtcactacaa aaaatttaaa aattagctgg tgtggtgttg cgtgtaggtc ctagctactc  18720
aggaggctga gacaaaaaga ttgcttgagg ctaggcattc aagattacag tgaggtgctg  18780
ggtgcagtgt ctcaggcctg taatcccagc aattttggtg gccgaggcag gtgtatcact  18840
tgagctcagg agctcgagac cagcctggga agcatggtga aaccctgtct ctaccaaaaa  18900
tacaagaaat tagctgggca tggcagctca agcctgtggt ctcagctact caggaggcgg  18960
aggtggaagg atcacttgag cccaggacgc agagattgca atgagcctag atcccgccac  19020
tgcactccag gctgggtgac agagtgaaac cctgtctcta aaaaataata attaaaggta  19080
ccaaaaataa ataattgatg gtaatgccga cccaaattaa atttaacctt caaattactt  19140
atgaaaaatg tagtatatca taagaaagtc aatagtaaga aatttcatgt taagacagtg  19200
ttttcatata ttttaacatt ttacatataa atagtatgct aattgcaaat tcattttatt  19260
taatgtttaa tagtttatgt tatgaattca aggcattttc tatacttgtc aataatgaaa  19320
aggcatttct ccttttaaaa attctatgaa gtcagccttc ttattcctta ggaacatgaa  19380
ctagtgtggt ttggttttga atctgattgt tcaaacactt tacaaagtga ataggaaaat  19440
aatttgggaa catttatatt taaacttgtc aatctatgat tctgtttttc atgtgacagc  19500
caatcacaat gtgttctcta ctcaggaagt ttagctcagt atatggatta acacgtgttc  19560
tacttgtgtg atatttctta tgacaaccac agaaaacata tggggctggg cacagtggct  19620
tatgcctgta atcccagaac tttgggaggc caaggcgggt ggatcacttg agcgcagtaa  19680
tttgacacca gcctgggcag catgtcgaaa ctgcgtctct acaaaaaata ccaaaattaa  19740
ccaggtgtgg cggcacatgc ctgtaatcct agcttctcga gaagctgagg tgggaggatt  19800
acctgagccg gggaggtcaa ggttgcggtg agccgtgatg gtgccactgc actcaagcct  19860
gggtgacaga gtgagaccct gcctaaaaaa gaaaagaraa gaaarraaaa catatttgat  19920
gcattttaaa aagaatatac ctttgagata gagtctcact cttgttgccc aggctggagt  19980
gcagtggtgc aatctcggct cactgcaacc tctgcctcct gggttcaagc gattctcctg  20040
cctcagcctc ctgagtagct gggattacag gtgcgcacca ctgtgccctg ctaatttttg  20100
tattttcagt agagacaggg ttttgccatt ttggccagac tggtctggag ctcctcatct  20160
caagtggtcc tcctgccgtg gcctcccaaa gtgttgagat tacaggcatg agccaccgcg  20220
cctggcctag atttaatttt ttcataaaac tttcacattt gtttgtttgt gatgttttca  20280
ggtgctaatt tcttgaccta gtatagaagc ataaacaaga gttcaatcct ttttaaatag  20340
ttgtctgtgc tgtgaatgcc ctcgcccacc atgtgctcaa caaggactca aggacattgt  20400
tggtgacttc agaggcttct ataggcagct cacaagtgat gggcagctca gatgggtaag  20460
```

-continued

```
ggacctattt tgtaaaatgc ttacataagt aatattacca aggtctgaga tgtcctttga 20520
gtgcaacgaa tgtgaaaata gagatgggtt tatttatttg tttatttatt tattttttga 20580
gatggagtct cactctgtca cccacgttgg agtgcagtga tgcaatcttg gctcactgca 20640
acctccgcct cctgggttca aacagttctc ctgcttcagc ctcctgagta gctgggacta 20700
caggcatgca ctagcacacc tggctaatgt ttgtaatttt agtagagatg gggtttgacc 20760
acgttggcca ggctggtctc gaactcctga cctcaagtga tccgccttcc tcagcctccc 20820
aaagtgctgg gattacaggt gtgagccacc atgcccatcc tagagatgtg tttataattt 20880
taaagtaaaa cattttattc agttaaattc aggcttgagt catttagatc atcagtattt 20940
tgaggtaaac aactcatttc tgtaagactg atgatctaaa tgactcaaga ctgaatttag 21000
ctgaataaaa tgttctacta aggagatgag gtcctgagat ttgggtccta agagctatct 21060
cttctctaag gacctcatct cctcctccct gaattggaaa gtgctctaga ggataaagta 21120
ctaaatgggc aatctcttta tggagaaata atgtgagtag tgttagagat gtaagagaag 21180
gtcaggccgg gcgcggtggc tcactcctgt aatcccagca ctttgggagg ccaaggcagg 21240
cagatcacga ggtcaggagg tcgagaccat cctggctaac atggtgaaac cccgtctcta 21300
ctaaaaatac aaaaaattag ccgggcatgg tggcgggcgc ctatagtccc agttactcag 21360
gaggctgagg caggagaacg gcgtgaacct gggaggcgga gcttgcagtg agccgagatc 21420
gcaccactgc actccagcct gggcaacaga gtgagactct gtctcaaaac aaaaaaaaaa 21480
aaaaaaaaaa aagagagaga tktaaaagaa ggkcattaaa gagaaaacat taagagaaga 21540
gcaaatttaa aaarrtggra gaccatggta ccttttatgg gtttgggatt tgacctataa 21600
attcaaggca tgaaaaagtt aggcyctgga gaaargrttc caacacaata aggtgaattc 21660
aataccctga cctttgcctt tgtcccgtga tactggattt tgtcttttcc taacccggct 21720
tagtctccca tccatgcact gagaarggca caagagaatg tactttcaat agtgcctggg 21780
atttcatctt ttactttata cagagaatat taaacttacc ttgaaagatg tcaccttgaa 21840
gaagttccca ttggctgaat ctgggacaat ttgaacatcc aaataaatat gatagtaatg 21900
gcttataacc cattgaataa aatccatgag tccattcaga taatgaacaa tcagctgggc 21960
acagtagctc acgcctataa tcccagcacc ttggggctga agcaggagaa tcacttaagg 22020
ccaggagttc aagaccagcc tggcagcat agttgagacc cccgtctgta ctttttaaaa 22080
ataaaaataa tnaaatanaa nattttaag gaggtaataa acaacaaggt caagcccatt 22140
acagctgatt aanatctaat aantataaaa ggaatgataa catcagagaa tcaccataac 22200
tgtcatagct acaattaatt gaggcaagag tcatcaaggg atgcccaaat tttgggacaa 22260
taataacctc cttacttgga aaatgaaatg gtaacttcac agtggagaaa gcaaatggac 22320
actaagttac ccaagtggta aaagttaaca atcctaataa taaaacaaaa tgacataatc 22380
acttatgtag tattgatgcc aaaaaatgta ttacctgaat ctagtcatga aggaactcca 22440
gatcagccca gattgaggaa tgctgtacaa atcaagtggc ctgtactctt ttaaaatgct 22500
aataacattt aaaaaagaag aagaaaaatt attccaggta aaaagagact aaagaggcat 22560
ggcgactaaa tgtaatacgt gatcccagat gggatatgga ttagggtaaa ataaaataca 22620
ttattggaaa aaactggtga catttgatta tggactggcc tttagacagc aatattctat 22680
caatgttata ttccctgagt gtgattattg tactacggtt atgtaagaaa atatccttgt 22740
tttcaggaac tatacactga tgtatttagg gttaagagag catgatattt gcaactttat 22800
```

-continued

```
tcaaatggtt cagaaaaaag aagtacatat gtgtgtgtgt tcatatgtat atacatacat  22860
atacttaaca tatatataga gagagagaaa gaagagagga aaacacaggt gtttttcctg  22920
ctattcttaa aactcttcaa taggttagca actgtttttt ttaaacttaa cctttaggtg  22980
ggtttctatt gctacctttt aattcttgag atgtgtccct ggacggaaga cctaaatatc  23040
tttctctctc tctctttttt tttttttttg agacagagtc ttgctctgtt gcccaggctg  23100
gagtgtagtg gtgcgatctt ggctcactgc aacctccgcc ttctgggttc gagagatcct  23160
cttgcctcag cctcctgagt agggactaca ggcacaaacc accacacctg gctcatttct  23220
ctgttttcag tagagacggg gtttcaccat gttggccagg ctggtcttgg tcccaaagtc  23280
ctgggtttac aggcatgagc catcacaccc agccctcttt ttcatttcta aaaagtgctt  23340
ttgtactttg cttcctaacc agattggtcc agaaaagggc gtggtgcacc tggcgacagc  23400
ggccgtccta aacgcggtgt gggacttgtg ggccaagcag gagggaaagg taacccctct  23460
cacaaacgct caggaggctc ctgggagctg cacgacactg actttcccta cgcacagagg  23520
aaagacagac acactgcagc cccaaaaagg aaatacagat aattgctttg gtgttttttt  23580
ctcctctgag aggttttggc agtaggtagg gaactgcagg aggaggagaa agaggagaca  23640
ggatggcgga aggcgcaggc agcagtagag gggggtgtgg ggacctggtg gctgacagcc  23700
agcattagct gccaacgtgt ttactgtcag gaaaaaatgg ggactttaca catatgtctt  23760
acaaatcctt tctttttttac ttcaagcctg tctggaagtt acttgtggac atggtgagta  23820
gcattgttaa tgttacaatt gtttctgtaa atgaaatgga tatcattgat gacatgcctt  23880
ttgatgatca gtaaatatat tcaggactat ctgttgatca ctatagcgat gataaagcaa  23940
aaagccaata aaatatgaca ttcctttctt gatatctgac gtaacagatg gctgtgctca  24000
tgcaggcagg gtggcatgag gggaagcagt gagggggtcc tgcctccccc actgtgcatg  24060
tgtaacacac ggtgccagtt ctctgagcct ccattgcctg actatgacaa gaggatcatc  24120
ctaacttctc taggaacctc acaaaattaa agatcaatga gaaaagcacc tcataaactc  24180
tgaaaagcca gatgttataa tattatgaag atattatcca ggccaggcat ggtggctcaa  24240
gcctgtaatc ccaatacttt ggaaggctgg aggatggctt gagcccagga gtttcaggct  24300
gcagtgagct ataattgcac cactgcactc aggtgacaga gcaagaccct gtctcaaaaa  24360
aagaaaaaag aaaagatact atccagtcac tttgacacca agaataagat caggccattg  24420
tagcctctac tgtacaattc cagcagggaa ggagctcaac actgaattct aaagctatgc  24480
acttgactgt tttctttctc cttgaccttt tcatagcagg ggtgaacaac tggatgctga  24540
ggaggaaaaa actgggcaaa ttaaagggga atgagcttca gaccccatgc agagctggct  24600
gtgagtccgg gtttcactgc tcaccagctg catgaccttg agcatgtgac ttccccactc  24660
tgagctgcgg tggcctcagt gcaacacctg ggtggcggtt aaaaacctcg tgatccacaa  24720
atgaaggccc ttgttattag ttggcaaaaa attaaggaaa aacaaagaac accatggcct  24780
tgaagagtgt tgggcaggag actgctcctc ctccggagga aagtgaagac aggaggctgt  24840
cacatcgtct ctgacatgga gagtggcttc cgggccatcc gtaggggaag gacacagagc  24900
tcttgagccc ccttctagat tcaaggttgg cgttttacgg ggatggagga ggtagccacc  24960
aaaagggaat gatttgcagg ccaccagaaa tgtgcctgag gtcccacctg tggaccctcc  25020
atttttggat cctgttccct ttcaatgcca gtactctttt cttttttctt tttttctttc  25080
tttctttttt tttttttttag acggagtttt cttcttgttg cccaggctac agtacagtgg  25140
catgatctca gctcactgca actgattcaa gcgattctcc tgtctcagcc tcctgagtag  25200
```

-continued

```
ctgggattac aggcacccgc caccatgccc agctaatttt ttgtattttt agtgaaaacg  25260
gggtttcacc atgttggtca gtctgagctc gaactccgga cctcaggtga tccacccatc  25320
tcagcctccc aaagtgctgg gattacagat gtgagccacc gaacctggcc cagaactctt  25380
agaagtagaa tctcagggtt gaaagagttt ttcggatttt cgacagttat ggtagagtat  25440
tattggtcac tataagatgt tagtgggaat ggaactactg gctgttttcc aactgactgt  25500
tccgtcaggg tagggagagg tctcagcacg aggccccgcc gaaatgttgg taagtggtca  25560
gccaagtggg ccgctcactc ccggttcgcc cactgtgttc ctgtcagtga agcaaacatc  25620
cccatttggc aggagaagaa gctgccggag gtcacactgc tagtgattgg tggcccaggg  25680
gtagggcagc cttctttcct ctgcagttca ctgctccaga accatctcca gcctcatagc  25740
tcaccgtgga cagccctgcg gtgtggcgct gatgtacaga gtgatgccag gcgttcatct  25800
ccccactgag ctcctgctga gtgtttgcct ggggccaggt cctccttccg ggaagtcatt  25860
ttagctggaa agaacagggt gggggcgggt ggcaagggat cagagcatga gcgtttgagg  25920
gcttcgtcag gggcagtgag gagcctctaa aggactctac atttaggaat gacagagtca  25980
aacaatttaa caaagcccta aaggtccctg ccaggaaaga atgagcccca tgtatcacca  26040
taagcaactt cttagaaaca taacccaccc ctgtcatccc agcactttgg gaggccaagg  26100
agggaggatt gcttgaagcc aggagctcaa gatcaacctg gtcaacatag tgagacccca  26160
tctctacaaa aataaaaata aattagccgg gcatagtggc acatacctgg agtcccagct  26220
actcaggagg ctgaggcagg aggatcacat aagccgggga gactgaggct gcagtgagct  26280
atgatggcat cactgcactc cagcctgggc aacagagtga gaccttgtct ctaaaaaaag  26340
aataataaat tttaaaaaac aaaatataac ccaccttata attgattcag gcctcttccc  26400
ctcctgtcac gttgccagga tcccaggatg ctggtatcct gcatagattt caggtacatc  26460
actgatgtcc tgactgagga ggatgcccta ggtgagtttg gaagctttct gggatacacg  26520
atgtgcacac acagtagtgg catgctttgt ttcctaaaag agtgagtgat gctttttatt  26580
tcttccagaa atactgcaga aaggtcaaat tggtaaaaaa gaaagaggtg ggttgtaaga  26640
aaattttctt cattgttttt gctaacattg tccacttttg agtgcccctg tccttttggg  26700
gtacacattg tcttcccaaa tgccctgtgc tgagcagcta ggccctcaaa tcaacattca  26760
agtctgcatg gtgaagcctg ctgggtatga cctctgactg cagagtttgc ttcagccact  26820
gctgaaagga agtttggctt taggattaca ctgtagggag agccctgggg gagcagggca  26880
gtccgtgaga gtatcctgat cacctgggtt tgacatccta gtaatttgtg gctgggtgtg  26940
tgtgtgcagg gccggatcag gagaacagct ggactctcca ggggaaacag ctggactctc  27000
caggggaaac agcttagcta caggcacttc caattccgaa gggccctgga aagtgcaaaa  27060
tgttgacggc gctgtgtttt cacagagaag caaatgctgg cacaaggata ccctgcttac  27120
acgacatcgt gcgcctggct ggggtactca gatgacacgt tgaagcaggt gggcatttta  27180
acctggcttt gtagacagct gaatggggag aaaccaacct gtttttcctt ctgtcctcat  27240
accactactc tcagtacctc acttctgaca ccagatgtgt gtggttttcc ttctcacgcc  27300
aaccagttct ccacttctct gtggacacca actgggtgtc ctgctatttt actcaattct  27360
gacagcacat acctggaact agcctcagac cccacaggtt aagggctcag tcttacagga  27420
ctgccctatg gcagatgcca gtcacaagtc cacgttgtca cctgtgcttc tgactggctt  27480
tgcctcagat tagaggttcc cacaaacccc gctttgagtt gaatcatttg gtggaatggc  27540
```

-continued

```
tcacggaatt cagggaaaca ctacttatgt ttactcattt attataaagg atgcaactta  27600
agaacagcca aactgaagag acacacaggg caaggtgtga ggagggggta cagagcttcc  27660
atgtcccctc caggtgagcc acactcccag tacctccacg tgttcaccaa cctggaagct  27720
ctctgaaccc tgttccttgg gggttttatg gaggcttcag tatttagatg tgattcatta  27780
tttggccatt ggccatcaat tcagccttca gccccctcgc ctccccagct atctgggaat  27840
aggctaaagt ttccaacccc accatcatgc ctttcaggtc tttctggtcc ccagccccat  27900
cctgaagcta cgtaggggac ctcagcaggg ctctctcgtt cacgtacaaa agacayycct  27960
atcactcagg agatgccmar ggktttwrgg gstgtgtgtt gtgtgttagg aaataggggg  28020
gcagcgatgg gggcagagac aaaatatata ttccttctta tgtcacatgg gcttttgatt  28080
ccagcctctc tgggagaaat ttaatacttt cctgttcacc tctctaaatc attttggctg  28140
agggcagtgg ctcacgccta taatcctagc attttgggag gctgaggtgg gtggatcacc  28200
tgaggtcaga agttcaaaac cagcctggcc aacatggtga aaccccgtct ctactaaaaa  28260
tacaaaaaat tatctgggcg tggtaatgcg tatctgtagt cccagccact caggaggctg  28320
aggcaggaga atcacttgaa cccaggaggc aggggttgca atgagccgag atcacgccac  28380
tgccctccaa cctgggtgac agaacaagag tccgtctcaa aaaacaacaa aaaaattatt  28440
ttggatccaa gccctcgttc tgaaagtaca caaggaaatg caaagccatt cattttgtgg  28500
accgcaggac tctgtgactt agtgagtcac cttgggctct ggaaggtgac agcctagggt  28560
aagattcctg ggcagcacca gcggtagacc cactgcgaga ttgagaagta atgcctattt  28620
catggggtgg ttttgaggat tcagatacat gctgtaagtt gcgtcatgct caaggcacca  28680
tggctggcac atggcatgca gtcggcacat ggtggattta ttactgtttc tccttacact  28740
gtgcccactt ctagagagtg gagagagagg ctggcttctg catgttactc ttatatccac  28800
tcattctatg gatgccacag aatattctag ctttaaaaag agagagatca gtgctatctt  28860
ccccttccgg gaaggttgtg accattaaaa aaatggttcc catagagatg aggaaagaaa  28920
gtcaccctac aagtaaaaag tgatctctgt cagccaggct gtttctgctg ttaatttcaa  28980
caacacatgg gtgttactct ggtctatgct ataaccgtaa tgcttgtgaa acagatcagc  29040
aatgactgac ttcctggtca gaccaagggg ctctctccag tgtgtgaccc tgtgctcctt  29100
tcccacagct ctgtgcccag gcgctgaagg atggctggac caggtgagtg tgatgatgga  29160
cctgactttc ccagttggcg gcaggagaga ctcaggcagt aagtctctcc tggcagggag  29220
ccaaggagta aaaggcaccc acgggctagg atcaccctgg ctcataggga tgcataagag  29280
aagtttcccc ttaggccagg ctctttctct aaaggcagga tgtgagtcct cattagaatt  29340
ataggccatc agagttgaaa gaggcttggg agattgttta tttcgggcac taacctagag  29400
tagaaatcca gtctttactg tcagtaacag cgttgattca gtttctgcat gaacatctcc  29460
agaggcagcg agcttaactt ggtgaggcac tttccattct ttgagggctt tgagtattag  29520
gtgggtcttt tcttctcttt tttttttttt tgagatgaag tttcactctc gtcacccaga  29580
ctggagtgca gtggcgcaat ctcggctcag tgcaacctcc acctcccgga ttcaagccat  29640
tctcctgcct cagcctccct agcagctggg attacagaca cccgccacca cacctggcta  29700
atttttgtat ttttaataga gacagggttt cgctatgttg atcaggctgg tcctgaactc  29760
ctgacctcag gtgatccgcc tgcctcagcc tcccaaagtg ctgggattat aggcgtgagc  29820
cactgcaccc agccaggtgg gtctttaata tcagcaaccc tttgcttcca tgtaatttcc  29880
agccagaggt cccagttccc aagagccagg ctgttcctct tccacttgag tgccctcctc  29940
```

-continued

```
tccctccagg ccacctcctt tccacactgc tcatctgcac ttctcccttc tgactctcgc  30000
ctgtgcaggt aaagacctct ggccatccta agaccttctc tggatgaacc tcgatggttg  30060
atgaccctgc atcctgaaac agggcaggat gcagagggac catcatctct tttgacccag  30120
tcactgtgtg tccctcagca cagctcacgg tggcactttt tgcctgtgac atgtcaccca  30180
ggcttcctat ctgacttgca gccactctgg tctctgagcc tcctgctact cagtgtgtcc  30240
tgtggagcag gagctccagc atcacctggg agcttgtgag aaatgcagcc tgggcctctc  30300
cccagacccg ctgcctggga atctgcattg gaacaagatc ccctagtgak tcctatgcgt  30360
tcttaagttg gagaggcact gaattcttgt taatgcctca gctaaataaa ggcttgagga  30420
gtgagaactt gaaggaggca gcatgaagcs gcggaaagag gtgttggcat ctgatagaac  30480
tgaaatcaca tcttgccttt tcccctcatc cgctgcaagt acttgctgtg tgatcaatta  30540
ctcaacctct ctgaacttca ttttctctca gtagaaataa tatgagcttt ggtcctcctc  30600
caagttgcca tatctcagaa ggaccagcac agggcaggat tcagagcagc tgctgtaagt  30660
gctgtttgcc ctccctctgc atacccgggg gaggctgcag cagtgtatct ggtgagtcag  30720
agaaggctgt ggggagattt aaagggtctc ttcccagcac aggaagcctg gcacccagag  30780
cctaaggcca gccaccctct ctggagcatc acggatcatg tagttgaagc ctccagctgg  30840
tacagaagag aacagcaggt gcctgagaat gtgcggcact ctgcaagctg ggctctttg   30900
caaagcagca gggggacctc agccaaggag gcgcacaggg agggtaggct gctgttcgag  30960
ggggcagatg ctggcctccc cgtggtggtg tcccctcctc cacctgccag tgcccacact  31020
gaggccagca acacactctt ctgacagcag agtcataggg tgtggacata gagscccatg  31080
tctcaagaga acagctggac atccacagag attaaggagc tccctacaag tgtctggatg  31140
tggtgtaaag gagacctctg cacggaggct ccagccgcac tctgctattc cctagttacc  31200
tgatctcatc actttccctc ccggaacctc aggcccctgc actgcagggg acagaccatc  31260
cctgtggcct tcctctcact gagttaattc aagacaaagc tctcctttgt aaaccagacc  31320
ctttccattc agtctatcac agtgtggctt actcggcacc ccttttcagc cccgctctcc  31380
tcttcagttc tcactgtggc ttttttgttc ttaattcctt ttcatggccc ggcaaaaacg  31440
gagttaatta tattaaagac ctgacttccc tgtctagctc cttaactcca ggtcagcaga  31500
taattgagag tcattgccct gatactgaat gaagagataa agttcccagg tttatttcaa  31560
gtgacttatc tgaagatgag gaaagagcaa gaggttacta aaaaacatat ctgtgaattg  31620
ttgacagaga cggtcacttc tgcagaaact ccagatgccc ttgccaagtc caggtacagg  31680
tctaaactag caaaccaaat gcattttcta ggtttaaagt aaaggtgggt gctgatctcc  31740
aggatgacat gcgaagatgc caaatcatcc gagacatgat tggaccggaa aagactttgg  31800
taaatatcct ctcacaccac taagaagcag tagcctttgt ccagggctaa atacaactcg  31860
tttcaagatt aaagaacatt gggaatttaa aaagttaatt gtcagaggaa gtacacttct  31920
gtagtcttgc agtaggcgag ctcaaacaaa aataagcaaa gggactaata gttttacgtt  31980
ttttaattct gcagaactag ttaagtaagt ttggggttaa ggatcctttc ttactaacac  32040
agatgtacct gagcaaacag ttttcccatt ggtgctctgg tgtgtcaatc atgtaatctc  32100
ccctcctagc tcctcaggta ggagggtgtc agggggccat tactgaagaa atgttggaac  32160
ttcagctgag ataaatgtaa ggatcagtca tttctgattt gtatttttat aaaccagttc  32220
ttacgtgtaa aatattttca taaagtcaca gtaagatgtt tttatgaggc tttggaggct  32280
```

-continued

```
tttttgcata agttaaaata gaaattttga gttcttgacc caggatcact atttatacat  32340
gaattaatgc tgcttttttt ttttaatgaa gtcatctgta tccaaataac ttatgataaa  32400
aattgattct gggctggcca gatgctgtgg ctcatgcctg taatcctagc actttgggat  32460
gcctaggtga gtggattgcc ggagctcagg agtacaagat cagcctggca acatggaaaa  32520
accccatctg taccgaaaaa tacaagaaaa aaaagtgtta gcattatatg gctcatgcct  32580
ataatcctaa cactttggga ggctgaagca ggtggatcac ttgaggccag gagtttggga  32640
ccagcctggg ctacatagca agactctctc tctaaaagaa agaagaaaaa aaaattaacc  32700
aggtgtggtg gtgcatgtct gtaatccctc ctactttgga agatggggca agaggatcac  32760
tgagctcagg agttggaggc tgcagtgagc tacaataaata ccactgcact ccagcatggg  32820
caacagagtg agatccagcc tcttaaaaaa aaaaaatcca ttctgagcat actgtcctct  32880
ggttttcata gtgtcctggg agagagctct tatcacttag cacattctgt agagatgtcc  32940
atttctccaa gcacgataag atcagggatg aggggctgtc ccttaagctg ggcacagcca  33000
tcacctggct tccaagaagg atagtggtac acagagagcc agggcctagg agggagagga  33060
ctggacttga actcaccatt cactagattt attgttctta agcaagttac tgaatttctc  33120
tgcatgacag ttttcttatt tgtaaaatgg gttaatatga actgcctcat ggggttatta  33180
ttattatttt ttgagatagg gtctcactca gtcacccagg ctagagtaca gcagcatgat  33240
cacacctcac tgcagccttg acctcccctg gctcagggga tcctcccacc tcaaccccct  33300
gagtagctgg gactacaagt gagagccacc acacccagct amtttwkgta ttttttgtag  33360
agagaggatt ttgctatgtt gcccagcctg gtcttgaact cctgggctca agaaatccac  33420
aggctgggcc agatgcagtg gctcatggct gtaatcccag cactttggga ggccgaggcg  33480
ggcggatcac aaggtcagga gattgagacc atcctggcta acatggtgaa accccgtctc  33540
tactaaaaat acaaaaaaaa atagcctggt gtggtggtgg gcgcctgtag tcccagctac  33600
tcgggaggct gaggcaggag aatggcgtga acctgggagg cagaggttgc agtgagccga  33660
gatagcgcca ctacactcca gccttggtga cagagcgaga ctctgtctca aaaaaaaaaa  33720
agaaaaagaa aagaaatcca cgggcttcag cctcccagag tgttgagatt acaggcatga  33780
gccaccatgc ctggccagtt attataaata ttaaatggaa caaaatccat aaagtgccta  33840
gtggagtagg tgtgccatta tgggagagtt aaggctactt attattgtgc cagacacaca  33900
gtgggcaata gtcaataaat gactattgaa caaacaatgt tgattgtgca tgattcagaa  33960
tgtgacaaaa tggtttctac gaacagaacc aacactgcaa gacacatgta tttgggtggc  34020
atctagatgg agattggacc agagcccagg gccagcgagc acttctcatg gcccagccca  34080
gggcactgct ggacatccag tggctcctca agcaattcac ggctcctcct aaagactgta  34140
cctggagcca gagtccccgt ctcagcagct gctctctggc tctttttgtt agggccgtgt  34200
gctgggcctc agcagaggcg ttagggggtc tcactcagct gttggtggca ctgagtgaca  34260
gcatttcctc cctgggagcc gcagccctgc tgtgaggttg gctcagggct gacctccctg  34320
tgaagagtct ctttttgcag atgatggatg ccaaccagcg ctgggatgtg cctgaggcgg  34380
tggagtggat gtccaagctg gccaagttca agccattgtg gattgaggag ccaacctccc  34440
ctgatgacat tctggggcac gccaccattt ccaaggtagg aaaacggctg ctgctgctgt  34500
ggcagcttat ttttctgttt agttttccag agtgctgggg acagatccta aaatttcttc  34560
acttgttccc tcttgcattt cctgttgaag tagctgaaat aattgtaatg tgtgacaaat  34620
acaggggtta cagacctgac attccttttt ctacttcagc ttatactttg cccttatttc  34680
```

-continued tgtttgtttt agataaagta agctgctaaa agttgaaggg ctaccagcaa tttgaaggtt 34740
aatagacatg gttcctatgc tttgtaaata cagaaatgtg acagcatttt tttttttgt 34800 tttttggtgg tttttttgt tttgttttgt tttgttttga gatagagtct tactctgttg 34860
cccaggctgg agtgcaatgg catgatctcg gctcactgca acctctgcct cccgagttca 34920
agcaattctt ctgcctcagc ctcctgagta gctgggacta cagatgtgtg ccaccatgcc 34980
tggctttttt tttttttttt tttttggtat ttttagtaga gatgaggttt caccacattg 35040
gccaggcctg tctcgaactc ctgacctcag accatctgcc cgccttggcc tcccaaagtg 35100
ctggattaca ggagtgagcc accgcgcccg gccttgtgtt ttcatctgat aattttttt 35160 ctcctacacg ctaactggtt tggcacagtc atgtgcccca taacaatgtt tcagtcagtg 35220
aaagactgcc tatataatgg cgcagtatat ataatcccat aagcttataa tggagctgaa 35280
aaactcattg cccagtgacg ttgtagagat tgtaatgtgg tgcaacgcat tacctttcct 35340
atgtttaagt atgtttagat actggccatt gtgttccaat tgcctgcagc gttcagaaca 35400
gtagcatgct gtacaggttt gtagcctggg agcaataggc catgccatat agcctagggc 35460
gtgtagtagt ctctaccatc tagggtcatg gacgtacact ctatgatgtt cacacaatga 35520
tgaaacagcc caacggcaca tttctcagag ggtaaccttg tcattcagtg acacgactgt 35580
acattcatgt ggcttatagc cacatcctgc ctgcctagga acattttttc ctgaggtgac 35640
tttgcatagc tatacactcc ccattttgtg ttgatcttac acctttaact ctgatggagc 35700
agtcttggtt ccagttctag gagggacacc ttgatgcatc ccacataaat tcatgggttg 35760
tactggaggt gtggagtcgg ggactcaggg accagttctc tgtttctctc agcaaatcag 35820
cacatgatct acattatgtg ggatactctg ccaaagcctg ggtttcagaa atgccctccc 35880
cttccacatt gcagcctcgc tggagagaac agccgagata tgtgaaacaa agaccggagg 35940
atactgggcc agggcactga atgccaagca cagtagaaaa gttcattgag gagaacgttg 36000
ggtgtgggct gggacgaggg agatggccag agctgactcc ataaggaaag ctaagcctca 36060
ggtgagggaa gggtgagcag gagccatgga gcgaccacag ccttcattat ttaaacagag 36120
cccaaatttt ctgaggaatc attccacaat aggaatctca ggtgaggagc cccggggaaa 36180
caagactttt caccttgggt cccacttgct ttttcctcct tagggctctt tcaggttggc 36240
tgtgccctgc tgaatgccag ctggcctagc accaacctga tctctgccta cctgaagcat 36300
ctcacaggaa gctcctcagg gctctaaccc tcccaggttt tgcttacatg agggaggcca 36360
tccccttagg agtatctgag gaaggagcag ctgcagagcc tgcaggtcca ggcgggggca 36420
gtggagatgc cccagggagc acagggcaca tgccagggac aggctgccac gtggggctgg 36480
attatggggt ctgtccactc agaggatgca gccagtcaga gtgagccact gcagcttctc 36540
cgatgaaaga acggcatagt ggccaggcat agtggctcac acctgtaacc ccagcacttt 36600
gggaggccga ggtgggtgga tcacctgagg tcaggagttt gagaccagcc tggccaacat 36660
ggtgaaacct cgtctctact aaaaatacaa aaattagctg gtctcgatct tctgacctcg 36720
tgatccgccc acctatggtc ccagctactc ggagaggctg aggcaggaga atggcgtgaa 36780
cccaggagga ggagcttgca gtgagccaaa atcgcaccac tgcactccag cctgggtgac 36840
agagcgagac tccatctcag aaaaaaaaaa aaaattagca gggtgcggtg atgtgtgcct 36900
gtaatcccag ctactcagga ggctgaggca ggagaatggc ttgagcctgg gaagtggagg 36960
ttacggtaag ccaagtttgc gccattgcac tccagcctgg gcgacagagc aatactccat 37020

-continued

```
ctcaaaaaaa aaaaaaaaaa aaacacaaca gcatagtgac agctgaagca cagataatgt  37080
gactggtggc tacatgtaga gtccattgag acagagggtg tgtgggaggt gaggaatggg  37140
cagggagaaa cccaggcagg gatgggagcg aggaggcttt tccaggaatc tgagagagag  37200
aaagggagag ggcagcttga atagagcaga ttcaggaaat attgaaaagg aggaaaaaca  37260
tttggcccct agtctgccat atatgcttaa aatggtagaa caaataagtc aaatggcctt  37320
tcctcctccc ccttcctcca tttctccctt tctcttctct ttggagataa ataaccaaga  37380
gtacttaaat tagaaatttt aagaagcata aaatgttggc ttgaaaaggt gccttagaga  37440
ccatctgctc aaactaaggc cttctgcaga tgaggaggcc gaggctttgg gtggcacagg  37500
cggggcttgc ccaaggccac acatcccgtg agatgcgggg ccagcaccgg aatcagggat  37560
acttggctgc tgagtgaagg gatttttctg ctgagaagtt ggcttagtct gattattcag  37620
atgcctcctc tggctctgga atcagtggag ttccaaccca gtctctacca ctttctagct  37680
ttgtgatcca ggaacagttc aaacccggca cacagtttta tcattttttta taaaatgggg  37740
ataacgctgg ctcctctccc attggattga gaccaggaat catttaagtc agtgttttgc  37800
acagcacctg acaggtactc agagctccaa aaatgttagc tgtcagtgtg attactatta  37860
ccctaagcaa agggaaggga agccagggag gaaccaaggc tacctgtgcg gagtagctgt  37920
ggagtcgcag tcacagtaga ggatggatgg gagcgcccag agtccaggtg gcaggtgacg  37980
gaggtagtgt tcaggggcca ggtgagagga cagagagcag cagggctgtg ttcaggtgca  38040
gagtccagta cctcaccagg tgaggactct accaggtgag caatggtctc agcctaacct  38100
gcagattgag gtctgaggcc acccactgag ctggaaggaa gaggattttt tttttcatg  38160
gatttttcct gccttaagga agaggatttt ggaatcaaca aagacatgag gccaggtgca  38220
gtggctcaca cctgtaatcc caacactttg ggaggccgag gcgggagggg atcatctgag  38280
gtcaggagtt tgagaccagc ctggccaaca tggcaaaacc ctgactctat taaaaataca  38340
aaaattagcc agcatggtgg cgtgcacctc taatcccagc tactcgggag gctgaggcac  38400
gagaatcgct tcagcctggg gggtggaggt tgcggtgarc taagatcatg ccactgcact  38460
ccagcttggg tgacagagca agactcggtc tcaaaaaaaa aaaaaaaaag atatgagagg  38520
gttctagaag gaggtttctc agggaggcaa gaagaaggga attgatggag tgatgaccca  38580
caggaaggag tcgtccaaag gttggaccct gtgagtccac aatgagccac tccgaatagc  38640
cctgtcctta tgccactgcg caggctggag agggaggtgc tgtccacgtt gggaggagcg  38700
cagctggagc atgggccggg acaccgcaga aggagatctg cagagccctg gtcaggaacg  38760
gggctggtgg yggcagctca gcagtgctca ccttctcctc tgcagataca cagagccctc  38820
ccgcacgcat gtgttcccct ggacatcctt tgccagtctt gagccttcac atggcttaac  38880
agcagggccg tttcctcctt cagctataaa tgtttttaaa cattaggagt tgcagttcaa  38940
aacttaggaa aataacacca ggctgccttc tattttatag gcactggtcc cattaggaat  39000
tggcattgcc acaggagaac aggtgagtga cgcccccaac aggtggatga cgtccccttg  39060
gggtcagtac acgctgacca gtgaccgagg acacagttgt gtgttaggct ccatcacctg  39120
ctgtactttg agttgggaaa ttttcatcat cttagaaact gggtcatttt atcagagtct  39180
agagtcagat atagaaaaag tttgtggcta tttctccaat ttatatgact aaggtcaggt  39240
atctttttca aagtgtctaa ttgaaattga aaaggcagca atttaaagtt gctattgcaa  39300
gggcagaaaa tggtcttaag aaagccagct ttcaaattga ataaacatga ctgcgttcac  39360
tttttgagct tataaatgaa gcccgagtgc ctgccaaaac ctgctgcagt cagcccacga  39420
```

gcagagcagc gtgaggagct gattctcagt tttcccggca aaaggagcaa tactgctctg 39480
ccgtggttcc gtgttgtcat ctgtgccacc tgctcatcac tgtcaccgta tttcatcctg 39540
atgcttcatc tcccacttat cagtcgctgt gacagtcatt ccctcataaa tggcgagcca 39600
gtgtgatttt gacctgactc acactgttgc attagcagat ttgtaaagaa gtgagcacaa 39660
ggtccctgcc cacgctataa aagctcgcct catgcccagc gagaacaaag aagaaataca 39720
gtctgggctt cctgacggcc actgatgaat aattattggc atagagtggc tgcgttgcca 39780
ggtttagaga tcctgaaggc caaggctgac tcttctgttg gtgttatttt caattctatt 39840
tccagtgcca caatagagtg atatttaagc aactcctaca ggcgaaggcc ctgcagttcc 39900
tccagattga cagttgcaga ctgggcagtg tcaatgagaa cctctcagta ttgctgatgg 39960
ccaaaaagtt tgaaagtaag cgtgctgcag cggctgcaga ccagaccttc atttccccac 40020
taatcagaca cctcccttga tggtttgcaa ttcacatgca tgggagtctg tagtttgcca 40080
tttcgatttt tttctaactc tcatttagct ttaatccggg aatttttgat gattttcatc 40140
ttggaatttc cttcctaaat attaataaat gatttaatca cctgtgggca ataagaaaaa 40200
ccagaaagtt ccctttcacc ccttcctctc cctgccctac tcttggtatt aaatagaaac 40260
gatttccttt tagttcctgt ttgcccccat gctggtggag ttggcctctg tgaactggtg 40320
cagcacctga ttatatttga ctacatatca gtttctgcaa gccttgaaaa taggtcagta 40380
atgtggcatt aatactttct gtttcagtag ggtccytcaa tccaggccag agcttgtaaa 40440
ttctgccttc atgaccagaa cacactaaga ccttgtctgc tggcatgtcc tataactctc 40500
aggtggagtt ggttttgctt tcacagagac ccaccaatga acggtcattt tgcctcctaa 40560
gatagggtct ggtagctgac tcactttatt ttttaagtac attgaaggta agcttgcagc 40620
cacactactc ccttaaccag ctcctgtttt catcacgtgt attctgtact tctgtcccat 40680
ctcctcttcc cagtactgga gtcttccatg gtctagacac acatttattt catcttattt 40740
ctcagaacgc cccaggtggg cttttaaatt aggacaatct ccttccagtc atctgcacac 40800
gtagggtttt gcttattcca cttttcttgt ctcctggaat taaatgtctc acagaaagat 40860
cactgcaagt atatagcaaa ggcacaaaag cattcactgg gaaagggaaa caccaaattc 40920
aggactgaga gtgataaatg ggacccttga gggtacatag gaggcttcag taataatggt 40980
aaccgttttt ctcttcaggg gggtagtgag tagacaggtg ctgtctttta atatagccga 41040
actattttat actgtattag tctattcttg cactgctata aagaaatacc tgagactggg 41100
taatttataa mgaaaagagg tttaattggc ttacagttct gcaggctgca cgggaagcat 41160
agcggcttct gctcagcttc tggaaactta caatcatgat ggaaggtgaa gggggaacaa 41220
gcacttctta tggccaagag caggaggaag agagagtgag gggggaaggt gctacacact 41280
tttaaacaac agatcttgtg ataactatct cgaacagcac caaggaacgg gtgccaaacc 41340
attcatgaag gaccacttcc catgatccaa tcacctccca gcaggccctg ctgccaacac 41400
tggggattac agttcaacat gagatttggg cagggacaca aatccaaaac aaatccaaac 41460
catatcagcc tgcctgtcac agctgttcaa taacaggcga tggaagtcag gcagcagagc 41520
tcggtcactt gccccaagcc tcagaactac aaagtggctg acgcagaacc tgaacacaga 41580
ttgacctgat tctaaatcct ctgctcttca tctaaatcat ttgtatagct gaaaggaacc 41640
tcatttggtg attttatttt ttgggtgggg agtatggaat gtattttatt gttctgcatc 41700
tgggtttgct tccttagatg tcttggttct tggatggagg tgggtgtgtc ccacctccct 41760

-continued

```
cagttgtggt cccatggacc tgttcggatt gttttccagg tacaaagtgt accaagaaag  41820
cctcacagtg ctaatgcttc ctagatgccc agctgaggca gtgacaaaat ggccctccca  41880
accctacctg ctttttaaa accccaagcc cctggcagct gctgcagcca tatgaaaaaa  41940
tacawacgct tcttgaaaaa tagatcacaa aatgtggtga ttttaatcta ttcatctgac  42000
ttttgaccag aggaacccaa ataattctgg atatttacag agtctgaatt gatccctttt  42060
aaagggcacc acaaaacctc tagagggact tcgtgtgttc atgtcatcaa agtccccacc  42120
tcacattgct atattttaga agaaaaggac ctgaggcaca gaggtttagg gacttgccta  42180
gaaacgcatg gtaacacagc taagccttgg ccaacactgt caattgagtg gtactcgctc  42240
cttctgcttt aagttagcac cacgtgaata atctgacttc aggcatcatt gccccgatct  42300
gattccctcc tcctagggtg tgtgagtatg ttgaccacct gcatgagcat ttcaagtatc  42360
ccgtgatgat ccagcgggct tcctacatgc ctcccaaggt aagctgtgcc tgagggcccc  42420
tgtgagaaga gatgctgcca gccactgcca cgcctgtctc gtgaactaga ctgtggagca  42480
ccaagctttg actcctgttt gtttgcaata tccactaaca aacggttctt cagtttgtct  42540
gtatcaaaat cctcaggcct gagggccagg gcttggaggt tcaattgcct ctgacaaggc  42600
ttctgtaata ctagcctttc ctcactagtg gagatcttaa catttgcact ccttgtgcaa  42660
aaaaacctgg caccatctag caagttagtg acctaaaaag tttggactac aattgtgtrg  42720
ctggggccat ttattctgat catgttcaag agatcatggc tcattttcac caacagaggt  42780
caaactatta tcaaagagtt tgatgagtta actaactctg gcaagtagcc agtaaaatat  42840
gttcctctgc cctattattt ccaacagtct ccaaacttat tttaaaaata ttaattcagg  42900
gctgggcatg gtggcttacg cctgtaatcc caacactttg ggaggctgag gcaggtggat  42960
catttgaggt caggtgtttg agaccagcct ggccaacatg gtgaaaccct gtctctacaa  43020
aaaatacaaa aaattagccg ggcatggtgg caggtgcctg tgatcccagc tacatgggag  43080
gctgaggcag gagaatcact tgaacctggg aggtggaggt tgcagtgagc caagattgcg  43140
ccactgcact gcagcctggg caacggacag tgactccatg tcaraaaaaa aaaaaattaat  43200
taattgcctc tggcttagac gtaaaagcat ttcttggagc agcataaatg cataaaatct  43260
gtttttgttc caggtggtkg ttaacaggac tcattttttt ggtctttgat aggatcccgg  43320
ctactcaaca gaaatgaagg aggaatctgt aaagaaacac cagtatccag atggtgaagt  43380
ttggaagaaa ctccttcctg ctcaagaaaa ttaagtgctc agccccaaca actttttttct  43440
ttctgaagtg aaagggctta aaatttcttg gaaatagttt tacaaaaatg gatttaaaaa  43500
atcctaccga tcaagatgag ttcagctaga agtcatacca ccctcaggaa tcagctaagt  43560
aattattact tgattctttt agcaaatcaa tgcacgttat cctacttaat ccttaaataa  43620
gtttagattt aactaaccca aagtccagga ggatgttctt acaaaaatag ctatatcaag  43680
ggctggcacc tagacattaa actgtaattt gaaaataagc aacatgttgc ataacttgtt  43740
ggaataattc cttgttctgt ttaacacttg tcataaatta gcagaataaa aatagtcgtg  43800
caacaccggg ggtatctggt atgcaacgaa gggaaaaata tttcactgat taaccccgaa  43860
gtggttttgc atcttttcct tgcttaatct aagcatatta ttagagaagt cacaccatgc  43920
tgaagctaat gagggcaaaa tsgtagtcca tagattattt taaaataacc ctttaaggtt  43980
ataaaagttt aaaaaaaaaa aaaaaaaact ctatcctaaa tggtcattat attttgagga  44040
taagatgcag ttaaaatgag aaaaataggg caaaatatat tcactattat ttctaaaata  44100
tactctttta agtagcatcc aaaccagaat acagcacatg tttacttaag gagagttctt  44160
```

```
taatctattt taggaaggaa ctgagcagat aagtggcagt acagaatgaa caaagcgtgg  44220

acgaatgcag aacacttctt tattatagca acatataaaa caactataaa gttcataacc  44280

acactctaca tcatgatcga tggtgttact cagctccctc agatttgagg gaatagcttg  44340

tgaaattctt aaaatattct aaaaatattc caaaaatagc ttgtgaaatt caccaacctt  44400

ctttataagt acgtgggatt gaaatgcaca tacatgtttt tgctaagagc acatacattt  44460

cattctcctc actttgttca taacctcagc attgtcagat accctcagtg agttaactca  44520

aagcctttta ttatggaaag aactggcaca gttacatttg ccagtggcaa catccttaaa  44580

aattaataac tgataggtca cggacagatt tttgacctag ttcctttttc ttttagagca  44640

aaaagaactt ttacctcggc atccagccca acccctaaag actgacaata tccttcaagc  44700

tcctttgaaa gcaccctaaa cagccatttc cattttaata gttggatgcg gattgtaccc  44760

ttcaatctga aagtcttcag ctttgaagtc atcaattttc tcaacttttc gaagaatcct  44820

gagctttggg aaaggtctgg gttctcgctg aagctaaaaa caaaataagg ccattatttt  44880

gccataattg tacgacctgt tgtaattgct cctcatgtcc atgaaacaag tacacaggat  44940

gtgatcaaca aagttctatt ttacaggagt atgatcctgt cgataccttg ccgtaggtta  45000

tgtaacatga ttggagcgca accagctgtt ctcttgcaca gatcgagagt gaggggtatt  45060

ttgtgacatt acacagcatc aggagcctgg tgcctcatca ggtgtaagtt cttataacca  45120

ctyttggcaa atttattaaa gacaggaaca cagtcaatct gtaactcata gtagctctac  45180

gtttacttga attccacaat ccctaaccca tctgtccctg gcagaaagaa ggaaagatga  45240

catgcatgga cagtgaacag aaagggatga aagccaggat tcctgggatg aacagacagt  45300

ggcaattagg atgtgaagac aggtcacaac ctattactat gtctaaaaat gaccagagca  45360

gagagccaga gagaataagc ctgaagtcac ctccactcaa aagcagccaa actccctcaa  45420

aggaataact tttaaaacct ggatctaacc tggaaggggc taaaaagtgt ctggttctga  45480

gttttttttcc ttaaggctca tgaagcagat gaacttacat ttttattgcc atttcatatc  45540

aattgttggc tgctataact tcagggattt caacagactt ttgaagtttg gacctaaata  45600

ttgtacttaa tgtaaaatta acaaaaaata tttatggcca gggtggtggc ttatgcctgt  45660

aattccagaa ctttcggagg ctgaggcagg tggwwcactt gaagtcagga gtttgagayy  45720

agcctggcca acatgacgaa accccatctc tactaataat acaaaaatta gctgggtgtg  45780

gtggcatgtg cctgtaatcc cagctacctg ggaggctgag gcagaagaat tgcttgaacc  45840

cgggaggtgg aggttgcagt gagctgagat cgcaccacgg cacactccag cctggccgac  45900

agagaaagac tccatctcaa aaaaaaagaa aaggaaaaac atttgcactt caattctcct  45960

tcaagttaaa atgagttaaa atgcctcct                                    45989
```

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 7

```
acccacctta taattgattc aggc                                         24
```

<210> SEQ ID NO 8
<211> LENGTH: 22
<212> TYPE: DNA

-continued

```
<213> ORGANISM: Artificial Sequence
<220> FEATURE:
<223> OTHER INFORMATION: Description of Artificial Sequence: primer

<400> SEQUENCE: 8

gaaacaaagc atgccactac tg                                            22
```